US010556892B2

(12) United States Patent
Piomelli et al.

(10) Patent No.: US 10,556,892 B2
(45) Date of Patent: Feb. 11, 2020

(54) PIPERAZINYL METHANONE NAAA INHIBITORS

(71) Applicants: The Regents of the University of California, Oakland, CA (US); Fondazione Istituto Italiano Di Tecnologia, Genoa (IT)

(72) Inventors: Daniele Piomelli, Irvine, CA (US); Rita Scarpelli, Rome (IT); Marco Migliore, Genoa (IT); Roger Heim, San Diego, CA (US); Miguel Garcia-Guzmàn, San Diego, CA (US)

(73) Assignees: The Regents of the University of California, Oakland, CA (US); Fondazione Istituto Italiano di Technologia, Genoa (IT)

( * ) Notice: Subject to any disclaimer, the term of this patent is extended or adjusted under 35 U.S.C. 154(b) by 0 days.

(21) Appl. No.: 16/301,200

(22) PCT Filed: May 16, 2017

(86) PCT No.: PCT/US2017/032981
§ 371 (c)(1),
(2) Date: Nov. 13, 2018

(87) PCT Pub. No.: WO2017/201103
PCT Pub. Date: Nov. 23, 2017

(65) Prior Publication Data
US 2019/0177313 A1    Jun. 13, 2019

Related U.S. Application Data

(60) Provisional application No. 62/337,744, filed on May 17, 2016.

(51) Int. Cl.
*C07D 417/04* (2006.01)
*C07D 413/04* (2006.01)
*C07D 417/14* (2006.01)
*A61P 25/28* (2006.01)
*A61P 25/16* (2006.01)

(52) U.S. Cl.
CPC ............ *C07D 417/04* (2013.01); *A61P 25/16* (2018.01); *A61P 25/28* (2018.01); *C07D 413/04* (2013.01); *C07D 417/14* (2013.01)

(58) Field of Classification Search
CPC .. C07D 417/04; C07D 413/04; C07D 417/14; A61P 25/28; A61P 25/16
USPC .................................................... 514/253.1
See application file for complete search history.

(56) References Cited

U.S. PATENT DOCUMENTS

| 5,189,224 | A | 2/1993 | Baba et al. |
|---|---|---|---|
| 2006/0128712 | A1 | 6/2006 | Jolidon et al. |
| 2010/0311711 | A1 | 12/2010 | Piomelli et al. |
| 2016/0068483 | A1 | 3/2016 | Piomelli et al. |

FOREIGN PATENT DOCUMENTS

| WO | WO-2009/049238 A1 | 4/2009 |
|---|---|---|
| WO | WO-2012/020567 A1 | 2/2012 |
| WO | WO-2013/078430 A1 | 5/2013 |
| WO | WO-2015/179190 A1 | 11/2015 |
| WO | WO-2017/201103 A1 | 11/2017 |

OTHER PUBLICATIONS

Angewandte Chemie, International Edition (2016), 55(37). 11193-11197 (Year: 2016).*
International Preliminary Report on Patentability received for PCT International Application No. PCT/US17/32981, dated Nov. 29, 2018, 6 pages.
International Search Report received for PCT Patent International Application No. PCT/US17/32981, dated Sep. 27, 2017, 4 pages.
Ahn, K. et al. (May 2008) "Enzymatic Pathways That Regulate Endocannabinoid Signaling in the Nervous System," Chemical reviews, 108(5):1687-1707.
Armirotti, A. et al. (2012) "β-Lactones Inhibit N-acylethanolamine Acid Amidase by S-Acylation of the Catalytic N-Terminal Cysteine," ACS Medicinal Chemistry, 3(5):422-426.
Baker, D. et al. (Feb. 2001) "Endocannabinoids Control Spasticity in a Multiple Sclerosis Model," FASEB Journal, 15(2):300-302.
Bandiera, T. et al. (2014) "Advances in the Discovery of N-acylethanolamine Acid Amidase Inhibitors," Pharmacological Research, 86:11-17.
Berge, S. M. et al. (Jan. 1977) "Pharmaceutical Salts," Journal of Pharmaceutical Sciences, 66(1):1-19.
Blankman, J. L. et al. (Dec. 26, 2007) "A Comprehensive Profile of Brain Enzymes that Hydrolyze the Endocannabinoid2-Arachidonoylglycerol," Chemistry and Biology, 14(12):1347-1356.
Filippo, M.D. et al. (2008) "Abnormalities in the Cerebrospinal Fluid Levels of Endocannabinoids in Multiple Sclerosis," Journal of Neurology, Neurosurgery and Psychiatry, 79(11):1224-1229.
Jean-Gilles, L. et al. (Dec. 15, 2009) "Plasma Endocannabinoid Levels in Multiple Sclerosis," Journal of the Neurological Sciences, 287(1-2):212-215.
Karlsson, I. et al. (2016) "Peptide Reactivity of Isothiocyanates Implications for Skin Allergy," Science Reports, 6:21203:12 pages.
Lassmann, H. (Nov. 2014) "Mechanisms of White Matter Damage in Multiple Sclerosis," Glia, 62(11):1816-1830.
Piomelli, D. et al. (Feb. 2014) "Peripheral Gating of Pain Signals by Endogenous Lipid Mediators," Nature Neuroscience, 17(2):164-174.
Pontis, S. et al. (2016) "Macrophage-Derived Lipid Agonists of PPAR-α as Intrinsic Controllers of Inflammation," Journal of Critical Reviews in Biochemistry and Molecular Biology, 51(1):7-14.

(Continued)

*Primary Examiner* — Kahsay Habte
(74) *Attorney, Agent, or Firm* — Edward D. Grieff; Mintz, Levin, Cohn, Ferris, Glovsky and Popeo, P.C.

(57) ABSTRACT

Disclosed herein, inter alia, are compositions and methods for modulating the activity of N-acylethanolamine acid amidase for the treatment of a pathological state, including pain, an inflammatory condition, or a neurodegenerative disorder.

18 Claims, 31 Drawing Sheets

(56) References Cited

OTHER PUBLICATIONS

Ponzano, S. et al. (Aug. 30, 2013) "Synthesis and Structure-Activity Relationship (SAR) of 2-methyl-4-oxo-3-oxetanylcarbamic Acid Esters, a Class of Potent N-acylethanolamine Acid Amidase (NAAA) Inhibitors," Journal of Medicinal Chemistry, 56(17):6917-6934.

Pubchem (Jul. 29, 2006) "Pubchem CID 7565632," National Center for Biotechnology Information, 11 pages.

Ribeiro, A. et al. (2015) "A Potent Systemically Active N-Acylethanolamine Acid Amidase Inhibitor that Suppresses Inflammation and Human Macrophage Activation," ACS Chemical Biology, 10(8):1838-1846.

Romeo, E. et al. (Sep. 18, 2015) "An Activity-Based Probe for N-Acylethanolamine Acid Amidasem," American Chemical Society, 10(9):2057-2064.

Speers, A. E. et al. (Dec. 2009) "Activity-Based Protein Profiling (ABPP) and Click Chemistry (CC) ABPP by MudPIT Mass Spectrometry," Current Protocols in Chemical Biology, 1(1):29-41.

Tsuboi, K. et al. (Mar. 25, 2005) "Molecular Characterization of N-Acylethanolamine-hydrolyzing Acid Amidase, a Novel Member of the Choloylglycine Hydrolase Family with Structural and Functional Similarity to Acid Ceramidase," The Journal of Biological Chemistry, 280(12):11082-11092.

Tsuboi, K. et al. (Aug. 2007) "The N-Acylethanolamine-Hydrolyzing Acid Amidase (NAAA)," Chemistry and Biodiversity, 4(8):1914-1925.

Ueda, N. et al. (Oct. 2010) "N-Acylethanolamine Metabolism with Special Reference to N-Acylethanolamine-Hydrolyzing Acid Amidase (NAAA)," Progress in Lipid Research, 49(4):299-315.

Uniprot, "*Homo sapiens* N-acylethanolamine Acid Amidase (NAAA), Transcript Variant 1, mRNA," Uniprot Accession No. NM_014435.4, 5 pages.

Uniprot, "N-acylethanolamine-Hydrolyzing Acid Amidase Isoform 1 Precursor [*Homo sapiens*]," Uniprot Accession No. NP_055250.2, 3 pages.

Written Opinion received for PCT Patent International Application No. PCT/US17/32981, dated Sep. 27, 2017, 5 pages.

Extended European Search Report dated Sep. 26, 2019, for European Patent Application No. 17800051.9, 12 pages.

STN Database (Aug. 2, 2009) "Methanone, (4-(5,6-dimethyl-2-benzothiazolyl)-1-piperazinyl][2-(ethylsulfonyl)phenyl]", Accession No. 1171601-75-4, 1 page.

STN Database (Aug. 4, 2009) "Methanone, (4-(5,6-dimethyl-2-benzothiazolyI)-1-piperazinyl][2-(methylsulfonyl)phenyl]-", Accession No. 1172451-98-7, 1 page.

STN Database (Nov. 23, 2007) "Methanone, [2-(ethylsulfonyl)phenyl][4-[4-(1-methylethyl)-2-benzothiazolyl]-1-piperazinyl]-", Accession No. 955743-02-9, 1 page.

STN Database (Jan. 24, 2010) "Methanone, [2-(methylsulfonyl)phenyl][446-(trifluoromethoxy)-2-benzothiazolyl]-1-piperazinyl]", Accession No. 1203182-12-0, 1 page.

STN Database (Jul. 27, 2006) "Methanone, [4-(2-benzothiazolyl)-1-piperazinyl] [2-(methylsulfonyl)phenyl]-", Accession No. 896367-51-4, 1 page.

STN Database (Jun. 6, 2006) "Methanone, [4-(7-chloro-4-rnethoxy-2-benzothiazolyl)-1-piperazinyl]-[2-(ethylsulfonyl)phenyl]-", Accession No. 886956-42-9, 17 pages.

\* cited by examiner

Probe 5 µM
Compounds 100 µM

PIPERAZINYL METHANONE NAAA INHIBITORS

This application is a Section 371 US National Phase of International Application No. PCT/US2017/032981 filed May 16, 2017, which claims the benefit of U.S. Provisional Application No. 62/337,744, filed May 17, 2016, which is incorporated by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant no. NS092123 awarded by the National Institutes of Health. The government has certain rights in the invention.

BACKGROUND

N-acylethanolamine acid amidase (NAAA) is a cysteine amidase that plays a central role in the catabolism of saturated or monounsaturated fatty acid ethanolamides (FAEs), such as palmitoylethanolamide (PEA) and oleoylethanolamide (OEA). NAAA exhibits a preference for PEA over other FAEs. PEA is a lipid produced by most of mammalian cells. PEA is involved in the regulation of inflammatory and pain processes, reduces peripheral inflammation, and exerts antinociceptive effects. Local and systemic administration of PEA alleviates pain behaviors elicited by chemical irritants, nerve damage, or inflammation. NAAA is highly expressed in inflammatory cells. NAAA inhibition offers the advantage of sustaining endogenous PEA and OEA levels under inflammatory stress conditions by blocking their degradation.

There exists an ongoing need for compounds that show proper pharmacological and pharmacokinetic profiles to be suitable for systemic administration and that are useful in treating disorders such as pain, inflammation, and neurodegenerative disorders and disease states. This invention is directed to these as well as others problems by providing, inter alia, small molecule inhibitors of NAAA as well as methods for treating pain, inflammation and neuro degenerative disorders for which there is no current and valuable pharmacological treatment.

BRIEF SUMMARY OF THE INVENTION

In an aspect, provided herein is a compound having the formula:

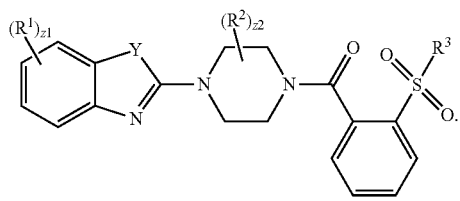

(I)

$R^1$ is independently halogen, —$CF_3$, —$Cl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently halogen, —$CF_3$, —$Cl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently halogen, —$CF_3$, —$Cl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol Y is S or O. The symbol z1 is independently an integer from 0 to 4. The symbol z2 is independently an integer from 0 to 8.

In another aspect, provided herein is a compound of formula (I), wherein the compound does not have the formula:

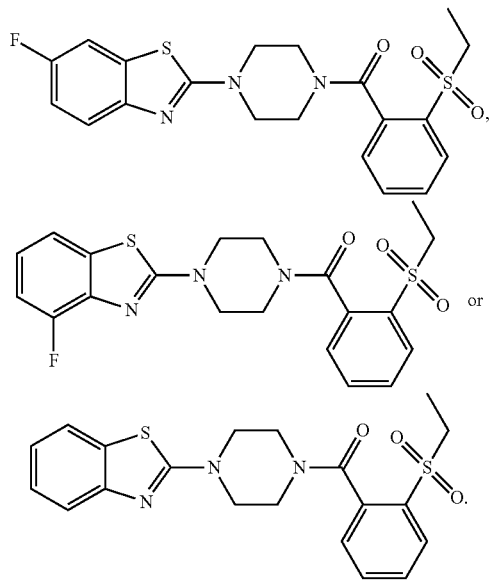

In an aspect is provided a pharmaceutical composition including a pharmaceutically acceptable excipient and a compound, or pharmaceutically acceptable salt thereof, as described herein.

In an aspect is provided a method of inhibiting N-acylethanolamine acid amidase, the method including contacting the N-acylethanolamine acid amidase with a compound, or pharmaceutically acceptable salt thereof, as described herein.

In another aspect are provided methods of treating a pathological state, an inflammatory condition, or a neurodegenerative disorder, the methods including administering to a subject in need thereof an effective amount of a compound, or pharmaceutically acceptable salt thereof, as described herein.

In another aspect is provided methods of treating a pathological state, an inflammatory condition, or a neurodegenerative disorder, the methods including administering to a subject in need thereof an effective amount of a NAAA inhibitor and an additional agent, as described herein.

BRIEF DESCRIPTION OF THE DRAWINGS

FIG. 3A is a graph illustrating LC-MS tracings (top tracing) showing that the covalent inhibitor 4 forms an adduct with a peptide containing NAAA's catalytic C126 (C126TSIVAQDSR), as illustrated in the inset, whereas compound 8 or its vehicle (DMSO) have no such effect (bottom tracing). FIG. 3B are histograms illustrating results of covalent inhibitor 4 (top histogram) or compound 8 (bottom histogram) incubated with NAAA (shaded bin) or buffer alone (unshaded bin) and quantified in supernatant after protein precipitation. Bars: mean±SEM, n=3.

FIG. 4A is a graph illustrating levels of compound 8 in plasma (black circles) or brain (gray triangles) after oral administration (10 mg/kg). FIG. 4B is a histogram illustrating time course of the effects of compound 8 (30 mg/kg) on PEA, OEA and anandamide (AEA) levels in brain. Results are expressed as mean±SEM, n=3. * $P<0.05$; $P<0.01$; *$P<0.001$, one-way ANOVA.

FIG. 10A: Compound 16261 refers to compound 1 in Table 9. Compound 19658 refers to compound 11 in Table 9. Compound 19666 refers to compound 12 in Table 9. Compound 19685 refers to compound 35 in Table 9. Compound 19719 refers to compound 36 in Table 9.

FIGS. 10B-10D: Compound 19666 refers to compound 12 in Table 9. Compound 19702 refers to compound 19 in Table 9. Compound 19719 refers to compound 36 in Table 9. Compound 19732 refers to compound 22 in Table 9. Compound 19802 refers to compound 43 in Table 2. The inhibitors compete for the same active site as the covalent fluo-probe.

FIGS. 14A-14C illustrate the effects of compound 19702 and gabapentin over the course of seven (7) days. FIGS. 14D-F illustrate the effects of compound 19702 and gabapentin over the course of (14) days. * or # P<0.05;  or ## P<0.01; * or ### P<0.001.

DETAILED DESCRIPTION

Figure 1:
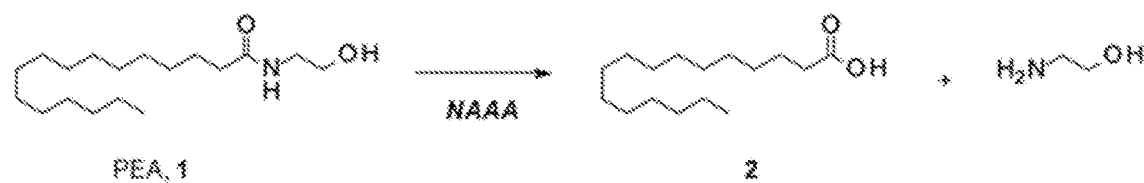
FIG. 1. Chemical scheme illustrating that NAAA hydrolyzes saturated and monounsaturated fatty acid ethanolamides (e.g., PEA, 1) into fatty acid (e.g., palmitic acid, 2) and ethanolamine.

Described herein are novel NAAA inhibitors comprised of a piperazine benzothiazole or benzoxazole scaffold.

In embodiments, the compounds of the present disclosure are potent, selective for NAAA, and orally available.

In embodiments, the compounds of the present disclosure inhibit NAAA activity through a non-covalent and uncompetitive mechanism.

In embodiments, compounds described herein cross the blood-brain barrier, elevate palmitoylethanolamide (PEA) and oleoylethanolamide (OEA) levels in the central nervous system, and produce marked therapeutic effects in treating a pathological state such as, for example, inflammatory conditions, neurodegenerative disorders, pain, a corneal neovascularization, diabetic retinopathy, dry macular degeneration, migraine, neuropathy, post herpetic neuralgia, trigeminal neuralgia, causalgia, diabetic neuropathy, chronic pain, nociceptive pain, complex regional pain syndrome (CRPS), neurogenic pain (including, but not limited to neuropathic pain, central pain and deafferentation pain), peripheral or polyneuropathic pain, toxic neuropathy, chronic neuropathy caused by chemotherapeutic and antiviral agents, nociceptive pain, or pruritus induced by uremia, pain associated with cancers, malignancies of various origin, polycythemia, jaundice or cholestasis, iron deficiency, athlete's foot, xerosis, wound healing, thyroid illness, hyperparathyroidism, or menopause, glossopharyngeal neuralgia, occipital neuralgia, pain, postherpetic neuralgia, retinopathy of prematurity, sinus headache, trigeminal neuralgia, or wet macular degeneration.

In embodiments, provided herein are methods of treating chronic pain conditions, including neuropathic pain, nociceptive pain and chronic or intermittent pain associated with chronic health conditions (as such conditions are often substantial stressors), and neuroinflammatory or neurodegenerative disorders (e.g., multiple sclerosis and Parkinson's disease).

I. Definitions

In this disclosure, "comprises," "comprising," "containing" and "having" and the like can have the meaning ascribed to them in U.S. Patent law and can mean "includes," "including," and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, S, B, As, or Si), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, P, S, B, As, or Si). A heteroalkyl moiety may include two optionally different heteroatoms (e.g., O, N, P, S, B, As, or Si). A heteroalkyl moiety may include three optionally different heteroatoms (e.g., O, N, P, S, B, As, or Si). A heteroalkyl moiety may include four optionally different heteroatoms (e.g., O, N, P, S, B, As, or Si). A heteroalkyl moiety may include five optionally different heteroatoms (e.g., O, N, P, S, B, As, or Si). A heteroalkyl moiety may include up to 8 optionally different heteroatoms (e.g., O, N, P, S, B, As, or Si).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ⁓ " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

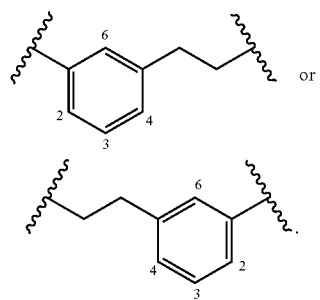

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cyclalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), boron (B), arsenic (As) and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it.

Similarly, cachets and lozenges are included. Tablets, powders, capsules, pills, cachets, and lozenges can be used as solid dosage forms suitable for oral administration.

The terms "polypeptide," "peptide" and "protein" are used interchangeably herein to refer to a polymer of amino acid residues, wherein the polymer may optionally be conjugated to a moiety that does not consist of amino acids (e.g., a block copolymer). The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme.

In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "treating", or "treatment" refers to any indicia of success in the therapy or amelioration of an injury, disease, pathology or condition (e.g., pathological state, an inflammatory condition, or a neurodegenerative disorder) including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease (e.g., pathological state, an inflammatory condition, or a neurodegenerative disorder). In embodiments, treating is preventing. In embodiments, treating does not include preventing. In embodiments, treatment results in increased levels of a biomarker (e.g., a protein, PEA, or OEA) relative to a control.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of an injury or disease (e.g., pathological state, an inflammatory condition, or a neurodegenerative disorder), which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms (e.g., pathological state, an inflammatory condition, or a neurodegenerative disorder). The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, severity of symptom or symptoms of an injury or disease (e.g., infarct size and location), and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

"Co-administer" it is meant that a composition described herein is administered at the same time, just prior to, or just after the administration of one or more additional therapies.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. PEA, corticosteroids, anti-inflammatory agents). The compositions of the present invention can be delivered transdermally, by a topical route, or formulated as applicator sticks, solutions, suspensions, emulsions, gels, creams, ointments, pastes, jellies, paints, powders, and aerosols.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Disease" or "condition" refer to a state of being or health status of a patient or subject capable of being treated with the compounds or methods provided herein. In embodiments, the disease is a pathological state, an inflammatory condition, or a neurodegenerative disorder.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring.

Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

As used herein, a "pathological state" refers to inflammatory conditions, neurodegenerative disorders, pain, a corneal neovascularization, diabetic retinopathy, dry macular degeneration, migraine, neuropathy, post herpetic neuralgia, trigeminal neuralgia, causalgia, diabetic neuropathy, chronic pain, nociceptive pain, complex regional pain syndrome (CRPS), neurogenic pain (including, but not limited to neuropathic pain, central pain and deafferentation pain), peripheral or polyneuropathic pain, toxic neuropathy, chronic neuropathy caused by chemotherapeutic and antiviral agents, nociceptive pain, or pruritus induced by uremia, pain associated with cancers, malignancies of various origin, polycythemia, jaundice or cholestasis, iron deficiency, athlete's foot, xerosis, wound healing, thyroid illness, hyperparathyroidism, or menopause, glossopharyngeal neuralgia, occipital neuralgia, pain, postherpetic neuralgia, retinopathy of prematurity, sinus headache, trigeminal neuralgia, or wet macular degeneration. In embodiments, pain, particularly severe pain, can be a stressor. In embodiments, provided herein are methods of treating chronic pain conditions, including neuropathic pain, and chronic or intermittent pain associated with chronic health conditions as such conditions are often substantial stressors.

In embodiments, "neuropathic pain" may include pain caused by a primary lesion or dysfunction of the nervous system. Such pain may be chronic and involve a maintained abnormal state of increased pain sensation, in which a reduction of pain threshold and the like are continued, due to persistent functional abnormalities ensuing from an injury or degeneration of a nerve, plexus or perineural soft tissue. Such injury or degeneration may be caused by wound, compression, infection, cancer, ischemia, or a metabolic or nutritional disorder such as diabetes mellitus. Neuropathic pain may include, but is not limited to, neuropathic allodynia wherein a pain sensation is induced by mechanical, thermal or another stimulus that does not normally provoke pain, neuropathic hyperalgesia wherein an excessive pain occurs in response to a stimulus that is normally less painful than experienced. Examples of neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine. In embodiments, the neuropathic pain includes the pain caused by either central or peripheral nerve damage. In embodiments, it includes the pain caused by either mononeuropathy or polyneuropathy (e.g., familial amyloid polyneuropathy). In embodiments, as compared to inflammatory pain, neuropathic pain is resistant to therapy with nonsteroidal anti-inflammatory agents and opioid substances (e.g., morphine). Neuropathic pain may be bilateral in mirror image sites, or may be distributed approximately according to the innervation of the injured nerve, it may persist for months or years, and be experienced as burning, stabbing shooting, throbbing, piercing electric shock, or other unpleasant sensation.

As used herein, the term "inflammatory condition" refers to a disease or condition characterized by aberrant inflammation (e.g. an increased level of inflammation compared to a control such as a healthy person not suffering from a disease). Examples of inflammatory condition include postoperative cognitive dysfunction, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barré syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

As used herein, the term "neurodegenerative disorder" refers to a disease or condition in which the function of a subject's nervous system becomes impaired. Examples of neurodegenerative diseases that may be treated with a compound, pharmaceutical composition, or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, chronic fatigue syndrome, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, myalgic encephalomyelitis, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, progressive supranuclear palsy, or Tabes *dorsalis*.

The terms "N-acylethanolamine acid amidase", "NAAA", and "hNAAA" are used according to the plain and ordinary meaning in the art and refer to a 31 kDa enzyme by the same name involved in the hydrolysis of non-peptidic amides. The term "NAAA" may refer to the nucleotide sequence or protein sequence of human NAAA (e.g., Entrez 27163, Uniprot Q02083, RefSeq NM_014435, or RefSeq NP_055250). The term "NAAA" includes both the wild-type form of the nucleotide sequences or proteins as well as any mutants thereof. In some embodiments, "NAAA" is wild-type NAAA receptor. In some embodiments, "NAAA" is one or more mutant forms. The term "NAAA" XYZ refers to a nucleotide sequence or protein of a mutant NAAA wherein the Y numbered amino acid of NAAA that normally has an X amino acid in the wildtype, instead has a Z amino acid in the mutant. In embodiments, an NAAA is the human NAAA. In embodiments, the NAAA has the nucleotide sequence corresponding to reference number GI: 109148549. In embodiments, the NAAA has the nucleotide sequence corresponding to RefSeq NM_014435.3. In embodiments, the NAAA has the protein sequence corresponding to reference number GI: 109148550. In embodiments, the NAAA has the protein sequence corresponding to RefSeq NP_055250.2. In embodiments, NAAA functions in acidic conditions (e.g., pH about 4.5-5.0).

II. Compounds

In an aspect, provided herein is a compound having the formula (I):

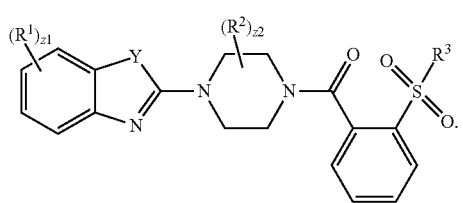

$R^1$ is independently
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is independently
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is independently
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol Y is S or O. The symbol z1 is independently an integer from 0 to 4. The symbol z2 is independently an integer from 0 to 8.

In embodiments, $R^1$ is independently
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^1$ is
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^4$-substituted or unsubstituted alkyl (e.g., $C_1$-$C_8$ alkyl, $C_1$-$C_6$ alkyl, or $C_1$-$C_4$ alkyl), $R^4$-substituted or unsubstituted heteroalkyl (e.g., 2 to 8 membered heteroalkyl, 2 to 6 membered heteroalkyl, or 2 to 4 membered heteroalkyl), $R^4$-substituted or unsubstituted cycloalkyl (e.g., $C_3$-$C_8$ cycloalkyl, $C_3$-$C_6$ cycloalkyl, or $C_5$-$C_6$ cycloalkyl), $R^4$-substituted or unsubstituted heterocycloalkyl (e.g., 3 to 8 membered heterocycloalkyl, 3 to 6 membered heterocycloalkyl, or 5 to 6 membered heterocycloalkyl), $R^4$-substituted or unsubstituted aryl (e.g., $C_6$-$C_{10}$ aryl, $C_{10}$ aryl, or phenyl), or $R^4$-substituted or unsubstituted heteroaryl (e.g., 5 to 10 membered heteroaryl, 5 to 9 membered heteroaryl, or 5 to 6 membered heteroaryl).

In embodiments, $R^1$ is halogen. In embodiments, $R^1$ is —F. In embodiments, $R^1$ is —Cl. In embodiments, $R^1$ is —Br. In embodiments, $R^1$ is —I. In embodiments, $R^1$ is —F, —Cl, —Br, —$CH_3$, —$CF_3$, —CN, —$OCH_3$, —$NO_2$, —$NH_2$, —$N(CH_3)_2$, —NHC(O)$CH_3$, or phenyl. In embodiments, $R^1$ is —$CH_3$. In embodiments, $R^1$ is —$CF_3$. In embodiments, $R^1$ is —CN. In embodiments, $R^1$ is —$OCH_3$. In embodiments, $R^1$ is —$NO_2$. In embodiments, $R^1$ is —$NH_2$. In embodiments, $R^1$ is —$N(CH_3)_2$. In embodiments, $R^1$ is —NHC(O)$CH_3$. In embodiments, $R^1$ is unsubstituted phenyl.

In embodiments, $R^2$ is independently
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^2$ is
halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^5$-substituted or unsubstituted alkyl (e.g., $C_1$-$C_8$ alkyl, $C_1$-$C_6$ alkyl, or $C_1$-$C_4$ alkyl), $R^5$-substituted or unsubstituted heteroalkyl (e.g., 2 to 8 membered heteroalkyl, 2 to 6 membered heteroalkyl, or 2 to 4 membered heteroalkyl), $R^s$-substituted or unsubstituted cycloalkyl (e.g., $C_3$-$C_8$ cycloalkyl, $C_3$-$C_6$ cycloalkyl, or $C_5$-$C_6$ cycloalkyl), $R^s$-substituted or unsubstituted heterocycloalkyl (e.g., 3 to 8 membered heterocycloalkyl, 3 to 6 membered heterocycloalkyl, or 5 to 6 membered heterocycloalkyl), $R^s$-substituted or unsubstituted aryl (e.g., $C_6$-$C_{10}$ aryl, $C_{10}$ aryl, or phenyl), or $R^s$-substituted or unsubstituted heteroaryl (e.g., 5 to 10 membered heteroaryl, 5 to 9 membered heteroaryl, or 5 to 6 membered heteroaryl).

In embodiments, $R^2$ is substituted or unsubstituted alkyl, substituted or unsubstituted heteroalkyl. In embodiments, $R^2$ is substituted or unsubstituted $C_1$-$C_8$ alkyl, substituted or unsubstituted 2 to 8 membered heteroalkyl. In embodiments, $R^2$ is substituted or unsubstituted $C_1$-$C_4$ alkyl. In embodiments, $R^2$ is unsubstituted $C_1$-$C_4$ alkyl. In embodiments, $R^2$ is unsubstituted methylene. In embodiments, $R^2$ is $R^5$-substituted or unsubstituted alkyl, $R^{5}$-substituted or unsubstituted heteroalkyl. In embodiments, $R^2$ is $R^5$-substituted or unsubstituted $C_1$-$C_8$ alkyl, $R^s$-substituted or unsubstituted 2 to 8 membered heteroalkyl. In embodiments, $R^2$ is $R^5$-substituted or unsubstituted $C_1$-$C_4$ alkyl. In embodiments, $R^2$ is unsubstituted $C_1$-$C_3$ alkyl. In embodiments, $R^2$ is unsubstituted $C_1$-$C_2$ alkyl. In embodiments, $R^2$ is unsubstituted methyl. In embodiments, $R^2$ is —OH substituted methyl. In embodiments, $R^2$ is —OH substituted ethyl.

In embodiments, $R^3$ is halogen, —$CCl_3$, —$CBr_3$, —$CF_3$, —$CI_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, $R^6$-substituted or unsubstituted alkyl (e.g., $C_1$-$C_8$ alkyl, $C_1$-$C_6$ alkyl, or $C_1$-$C_4$ alkyl), $R^6$-substituted or unsubstituted heteroalkyl (e.g., 2 to 8 membered heteroalkyl, 2 to 6 membered heteroalkyl, or 2 to 4 membered heteroalkyl), $R^6$-substituted or unsubstituted cycloalkyl (e.g., $C_3$-$C_8$ cycloalkyl, $C_3$-$C_6$ cycloalkyl, or $C_5$-$C_6$ cycloalkyl), $R^6$-substituted or unsubstituted heterocycloalkyl (e.g., 3 to 8 membered heterocycloalkyl, 3 to 6 membered heterocycloalkyl, or 5 to 6 membered heterocycloalkyl), $R^6$-substituted or unsubstituted aryl (e.g., $C_6$-$C_{10}$ aryl, $C_{10}$ aryl, or phenyl), or $R^6$-substituted or unsubstituted heteroaryl (e.g., 5 to 10 membered heteroaryl, 5 to 9 membered heteroaryl, or 5 to 6 membered heteroaryl).

In embodiments, $R^3$ is
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^6$-substituted or unsubstituted $C_1$-$C_8$ alkyl, $R^6$-substituted or unsubstituted 2 to 8 membered heteroalkyl, $R^6$-substituted or unsubstituted $C_3$-$C_8$ cycloalkyl, $R^6$-substituted or unsubstituted 3 to 6 membered heterocycloalkyl, $R^6$-substituted or unsubstituted phenyl, or $R^6$-substituted or unsubstituted 5 to 6 membered heteroaryl.

In embodiments, $R^3$ is a $R^6$-substituted or unsubstituted $C_1$-$C_8$ alkyl, $R^6$-substituted or unsubstituted 2 to 8 membered heteroalkyl, $R^6$-substituted or unsubstituted $C_3$-$C_8$ cycloalkyl, $R^6$-substituted or unsubstituted 3 to 6 membered heterocycloalkyl, $R^6$-substituted or unsubstituted phenyl, or $R^6$-substituted or unsubstituted 5 to 6 membered heteroaryl. In embodiments, $R^3$ is $R^6$-substituted or unsubstituted $C_1$-$C_8$ alkyl. In embodiments, $R^3$ is $R^6$-substituted or unsubstituted $C_1$-$C_4$ alkyl. In embodiments, $R^3$ is $R^6$-substituted or unsubstituted $C_1$-$C_4$ alkyl. In embodiments, $R^3$ is $R^6$-substituted or unsubstituted $C_3$-$C_8$ cycloalkyl, or $R^6$-substituted or unsubstituted 3 to 6 membered heterocycloalkyl. In embodiments, $R^3$ is $R^6$-substituted or unsubstituted $C_3$-$C_8$ cycloalkyl.

In embodiments, $R^3$ is $R^6$-substituted or unsubstituted alkyl (e.g., $C_1$-$C_8$ alkyl, $C_1$-$C_6$ alkyl, or $C_1$-$C_4$ alkyl). In embodiments, $R^3$ is $R^6$-substituted alkyl (e.g., $C_1$-$C_8$ alkyl, $C_1$-$C_6$ alkyl, or $C_1$-$C_4$ alkyl). In embodiments, $R^3$ is an unsubstituted alkyl (e.g., $C_1$-$C_8$ alkyl, $C_1$-$C_6$ alkyl, or $C_1$-$C_4$ alkyl). In embodiments, $R^3$ is $R^6$-substituted or unsubstituted $C_1$-$C_6$ alkyl. In embodiments, $R^3$ is $R^6$-substituted or unsubstituted $C_1$-$C_4$ alkyl.

In embodiments, $R^3$ is $R^6$-substituted or unsubstituted heteroalkyl (e.g., 2 to 8 membered heteroalkyl, 2 to 6 membered heteroalkyl, or 2 to 4 membered heteroalkyl). In embodiments, $R^3$ is $R^6$-substituted heteroalkyl (e.g., 2 to 8 membered heteroalkyl, 2 to 6 membered heteroalkyl, or 2 to 4 membered heteroalkyl). In embodiments, $R^3$ is an unsubstituted heteroalkyl (e.g., 2 to 8 membered heteroalkyl, 2 to 6 membered heteroalkyl, or 2 to 4 membered heteroalkyl).

In embodiments, $R^3$ is $R^6$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^6$-substituted cycloalkyl (e.g., $C_3$-$C_8$ cycloalkyl, $C_3$-$C_6$ cycloalkyl, or $C_5$-$C_6$ cycloalkyl). In embodiments, $R^3$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^6$-substituted $C_3$-$C_6$ cycloalkyl. In embodiments, $R^3$ is an unsubstituted $C_3$-$C_6$ cycloalkyl. In embodiments, $R^3$ is $R^6$-substituted $C_3$-$C_6$ cycloalkyl. In embodiments, $R^3$ is an unsubstituted $C_3$ cycloalkyl. In embodiments, $R^3$ is $R^6$-substituted $C_4$ cycloalkyl. In embodiments, $R^3$ is an unsubstituted $C_4$ cycloalkyl.

In embodiments, $R^3$ is $R^6$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^6$-substituted heterocycloalkyl (e.g., 3 to 8 membered heterocycloalkyl, 3 to 6 membered heterocycloalkyl, or 5 to 6 membered heterocycloalkyl). In embodiments, $R^3$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^6$-substituted or unsubstituted 3 to 6 membered heterocycloalkyl. In embodiments, $R^3$ is $R^6$ substituted or unsubstituted 4 membered heterocycloalkyl. In embodiments, $R^3$ is an unsubstituted 4 membered heterocycloalkyl.

In embodiments, $R^3$ is $R^6$-substituted or unsubstituted aryl (e.g., $C_6$-$C_{10}$ aryl, $C_{10}$ aryl, or phenyl). In embodiments, $R^3$ is $R^6$-substituted aryl (e.g., $C_6$-$C_{10}$ aryl, $C_{10}$ aryl, or phenyl). In embodiments, $R^3$ is an unsubstituted aryl (e.g., $C_6$-$C_{10}$ aryl, $C_{10}$ aryl, or phenyl).

In embodiments, $R^3$ is $R^6$-substituted or unsubstituted heteroaryl (e.g., 5 to 10 membered heteroaryl, 5 to 9 membered heteroaryl, or 5 to 6 membered heteroaryl). In embodiments, $R^3$ is $R^6$-substituted heteroaryl (e.g., 5 to 10 membered heteroaryl, 5 to 9 membered heteroaryl, or 5 to 6 membered heteroaryl). In embodiments, $R^3$ is an unsubstituted heteroaryl (e.g., 5 to 10 membered heteroaryl, 5 to 9 membered heteroaryl, or 5 to 6 membered heteroaryl).

In embodiments, $R^3$ is —$CH_2CH_3$, —OH, —$CH_3$, —$CH_2CH_2OH$, —$CH_2CH_2CH_2OH$, isopropyl, propyl, butyl, tert-butyl, pentyl, oxetan-3-yl, hexyl, 4-piperidyl, —N(CH₃)₂, or —N(CH₂CH₃)₂. In embodiments, R³ is —CH₂CH₃. In embodiments, R³ is —OH. In embodiments, R³ is —CH₃. In embodiments, R³ is —CH₂CH₂OH. In embodiments, R³ is —CH₂CH₂CH₂OH. In embodiments, R³ is isopropyl. In embodiments, R³ is propyl. In embodiments, R³ is butyl. In embodiments, R³ is tert-butyl. In embodiments, R³ is pentyl. In embodiments, R³ is oxetan-3-yl. In embodiments, R³ is hexyl, 4-piperidyl. In embodiments, R³ is —N(CH₃)₂. In embodiments, R³ is —N(CH₂CH₃)₂. In embodiments, R³ is an unsubstituted C₃ cycloalkyl, unsubstituted C₄ cycloalkyl, unsubstituted 4 membered heterocycloalkyl, or unsubstituted C₂ alkyl. In embodiments, R³ is an unsubstituted C₄ cycloalkyl or an unsubstituted 4 membered heterocycloalkyl. In embodiments, R³ is an unsubstituted C₃ cycloalkyl. In embodiments, R³ is an unsubstituted C₂ alkyl. In embodiments, R³ is an unsubstituted C₃ alkyl.

In embodiments, Y is S. In embodiments, Y is O.

In embodiments, R⁴, R⁵, and R⁶ are independently oxo, halogen, —CCl₃, —CBr₃, —CF₃, —CI₃, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCl₃, —OCHCl₂, —OCHBr₂, —OCHI₂, —OCHF₂, unsubstituted alkyl (e.g., C₁-C₈ alkyl, C₁-C₆ alkyl, or C₁-C₄ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C₃-C₈ cycloalkyl, C₃-C₆ cycloalkyl, or C₅-C₆ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C₆-C₁₀ aryl, C₁₀ aryl, or phenyl), or unsubstituted heteroaryl (e.g., 5 to 10 membered heteroaryl, 5 to 9 membered heteroaryl, or 5 to 6 membered heteroaryl).

In embodiments, the compounds as described herein are capable of crossing the blood brain barrier.

In embodiments, the compound has the formula (Ia):

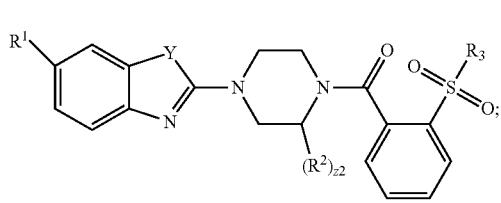

wherein R¹, R², R³, z2, and Y are as described herein.

In embodiments, the compound has the formula (Ib):

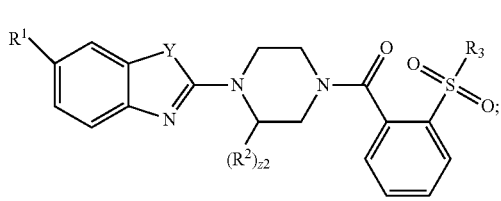

wherein R¹, R², R³, z2, and Y are as described herein.

In embodiments, the compound has the formula (Ic):

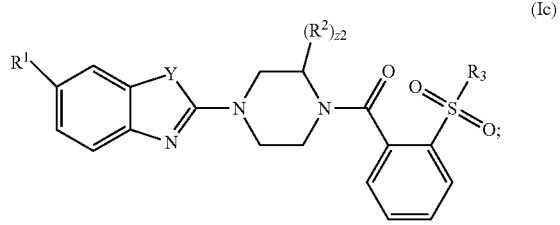

wherein R¹, R², R³, z2, and Y are as described herein.

In embodiments, the compound has the formula:

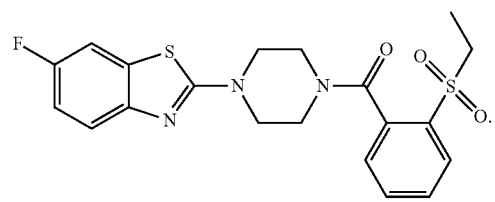 [SMILES: CCS(=O)(=O)c1ccccc1C(=O)N1CCN(c2nc3ccc(F)cc3s2)CC1]

In embodiments, the compound has the formula:

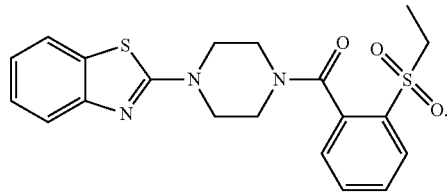 [SMILES: CCS(=O)(=O)c1ccccc1C(=O)N1CCN(c2nc3ccccc3s2)CC1]

In embodiments, the compound has the formula:

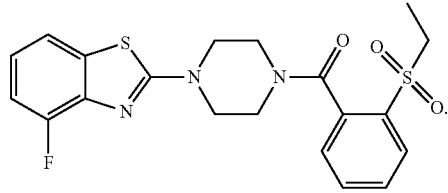 [SMILES: CCS(=O)(=O)c1ccccc1C(=O)N1CCN(c2nc3c(F)cccc3s2)CC1]

In embodiments, the compound has the formula:

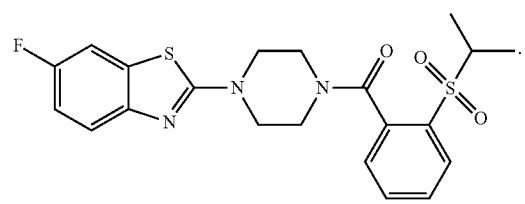 [SMILES: CC(C)S(=O)(=O)c1ccccc1C(=O)N1CCN(c2nc3ccc(F)cc3s2)CC1]

In embodiments, the compound has the formula:

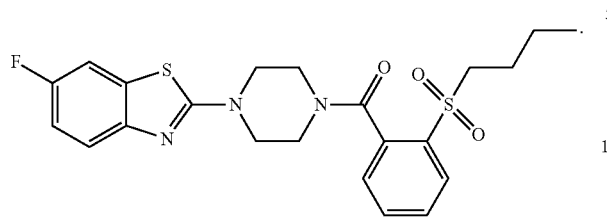

In embodiments, the compound has the formula:

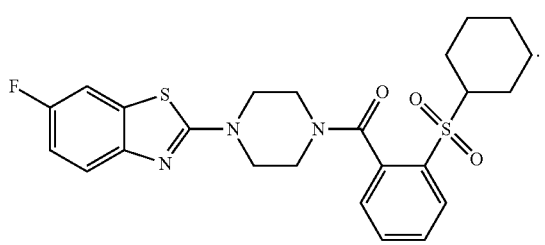 [SMILES: O=C(c1ccccc1S(=O)(=O)C1CCCCC1)N1CCN(c2nc3ccc(F)cc3s2)CC1]

In embodiments, the compound has the formula:

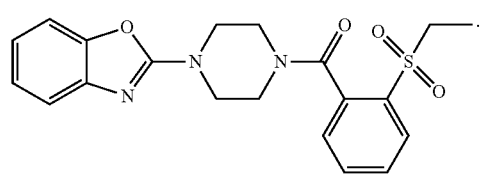 [SMILES: CCS(=O)(=O)c1ccccc1C(=O)N1CCN(c2nc3ccccc3o2)CC1]

In embodiments, the compound has the formula:

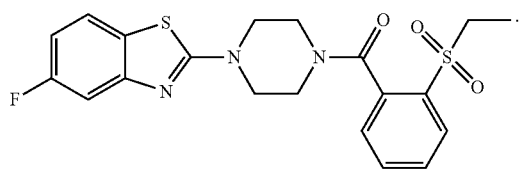 [SMILES: CCS(=O)(=O)c1ccccc1C(=O)N1CCN(c2nc3cc(F)ccc3s2)CC1]

In embodiments, the compound has the formula:

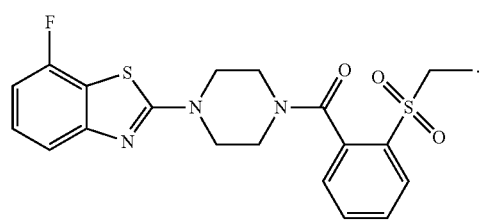 [SMILES: CCS(=O)(=O)c1ccccc1C(=O)N1CCN(c2nc3cccc(F)c3s2)CC1]

In embodiments, the compound has the formula:

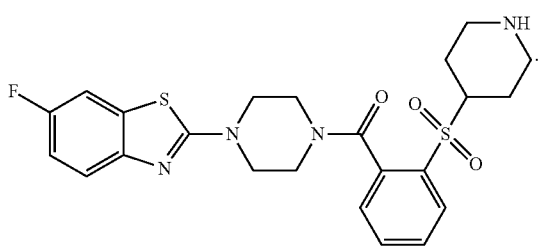 [SMILES: O=C(c1ccccc1S(=O)(=O)C1CCNCC1)N1CCN(c2nc3ccc(F)cc3s2)CC1]

In embodiments, the compound has the formula:

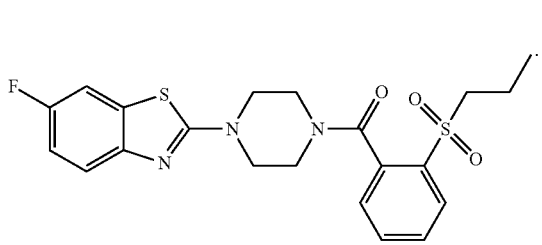 [SMILES: CCCS(=O)(=O)c1ccccc1C(=O)N1CCN(c2nc3ccc(F)cc3s2)CC1]

In embodiments, the compound has the formula:

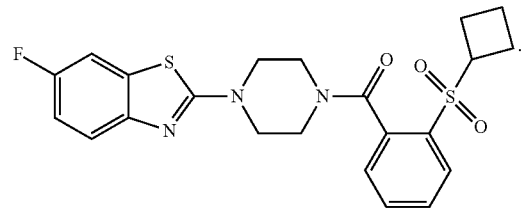 [SMILES: O=C(c1ccccc1S(=O)(=O)C1CCC1)N1CCN(c2nc3ccc(F)cc3s2)CC1]

In embodiments, the compound has the formula:

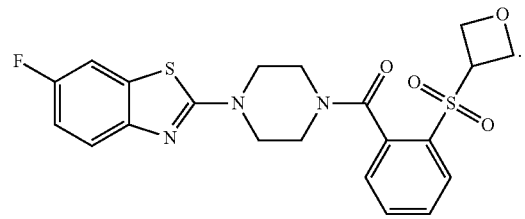 [SMILES: O=C(c1ccccc1S(=O)(=O)C1COC1)N1CCN(c2nc3ccc(F)cc3s2)CC1]

In embodiments, the compound has the formula:

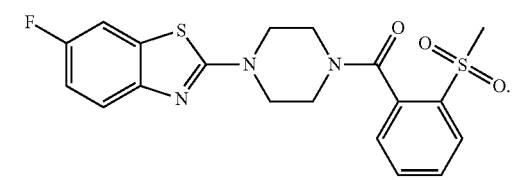 [SMILES: CS(=O)(=O)c1ccccc1C(=O)N1CCN(c2nc3ccc(F)cc3s2)CC1]

In embodiments, the compound has the formula:

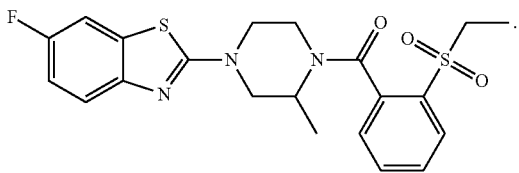 [SMILES: CCS(=O)(=O)c1ccccc1C(=O)N1CCN(c2nc3ccc(F)cc3s2)CC1C]

In embodiments, the compound has the formula:

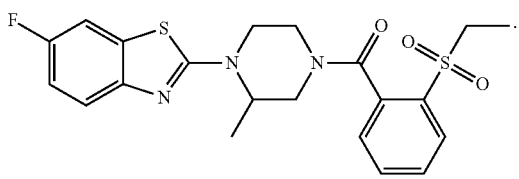

In embodiments, the compound has the formula:

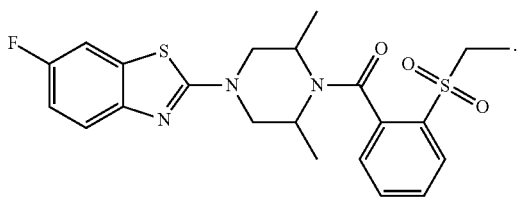 [SMILES: CCS(=O)(=O)c1ccccc1C(=O)N1C(C)CN(c2nc3ccc(F)cc3s2)CC1C]

In embodiments, the compound has the formula:

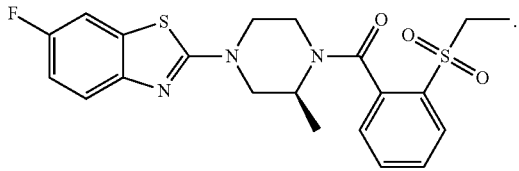

In embodiments, the compound has the formula:

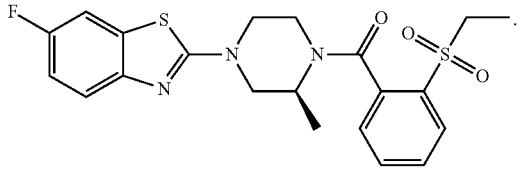

In embodiments, the compound has the formula:

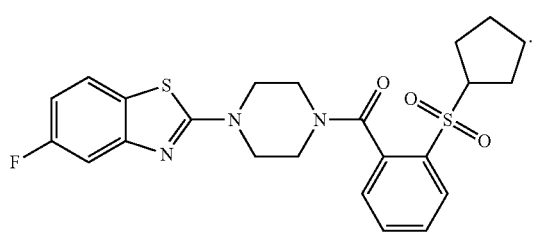 [SMILES: O=C(c1ccccc1S(=O)(=O)C1CCCC1)N1CCN(c2nc3cc(F)ccc3s2)CC1]

In embodiments, the compound has the formula:

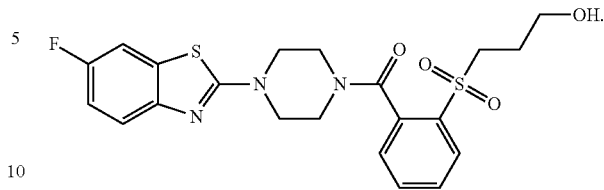

In embodiments, the compound has the formula:

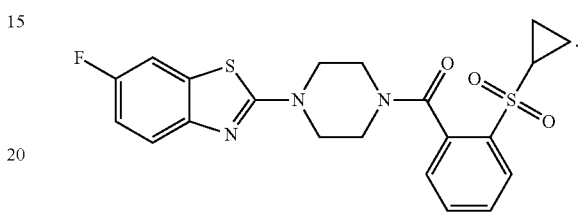

In embodiments, the compound has the formula:

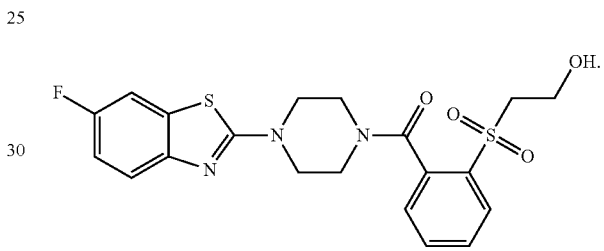

In embodiments, the compound has the formula:

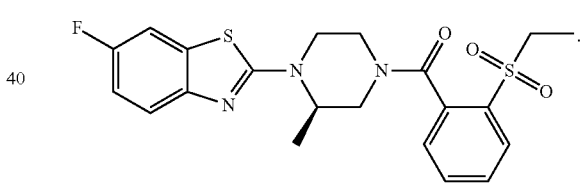

In embodiments, the compound has the formula:

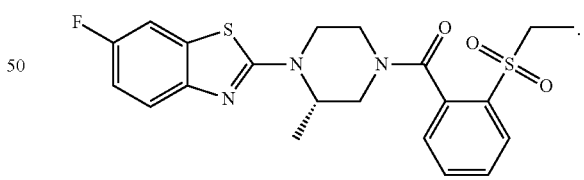

In embodiments, the compound has the formula:

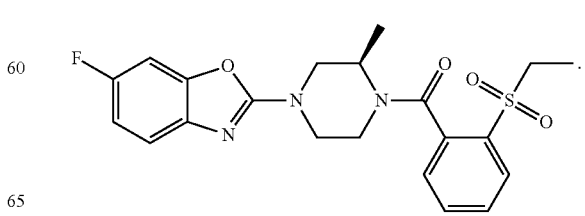

In embodiments, the compound has the formula:
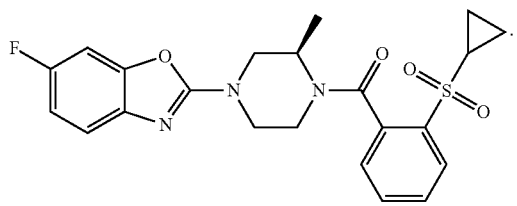 [SMILES: C[C@@H]1CN(c2nc3ccc(F)cc3o2)CCN1C(=O)c1ccccc1S(=O)(=O)C1CC1]
In embodiments, the compound has the formula:
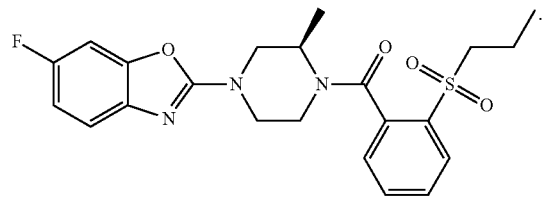 [SMILES: CCCS(=O)(=O)c1ccccc1C(=O)N1CCN(c2nc3ccc(F)cc3o2)C[C@H]1C]
In embodiments, the compound has the formula:
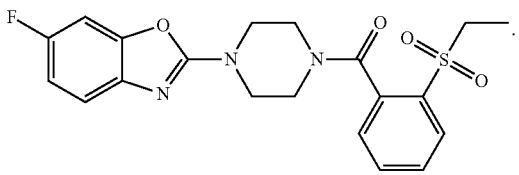 [SMILES: CCS(=O)(=O)c1ccccc1C(=O)N1CCN(c2nc3ccc(F)cc3o2)CC1]
In embodiments, the compound has the formula:
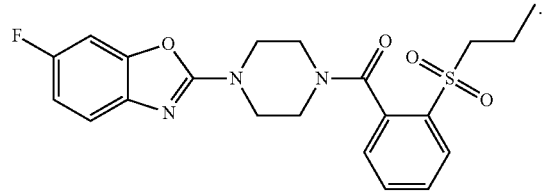 [SMILES: CCCS(=O)(=O)c1ccccc1C(=O)N1CCN(c2nc3ccc(F)cc3o2)CC1]
In embodiments, the compound has the formula:
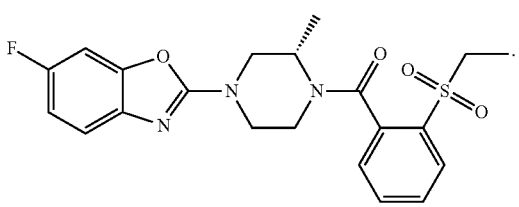 [SMILES: CCS(=O)(=O)c1ccccc1C(=O)N1CCN(c2nc3ccc(F)cc3o2)C[C@@H]1C]
In embodiments, the compound has the formula:
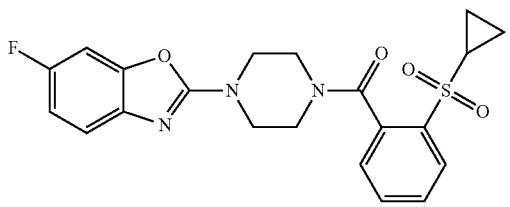
In embodiments, the compound has the formula:
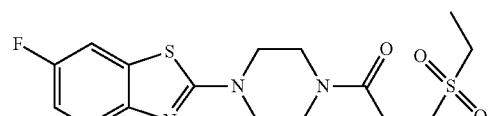
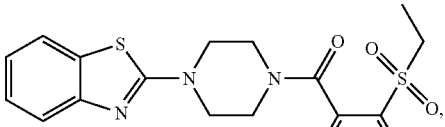
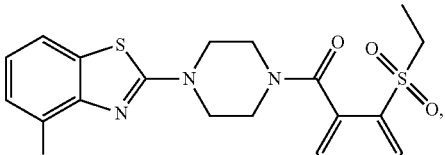
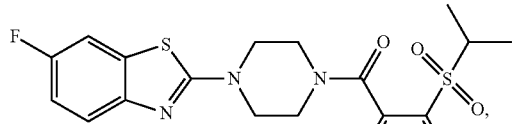
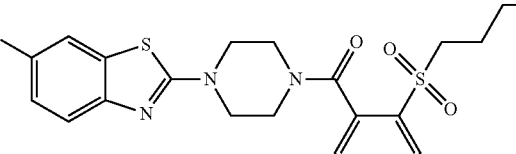
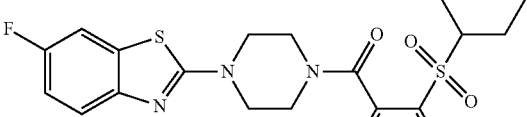
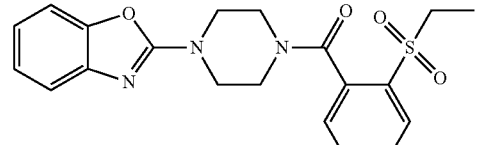

-continued
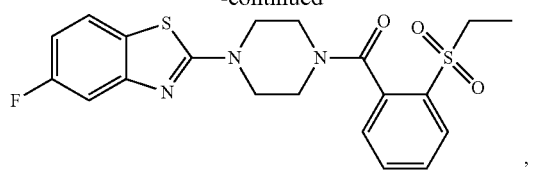,
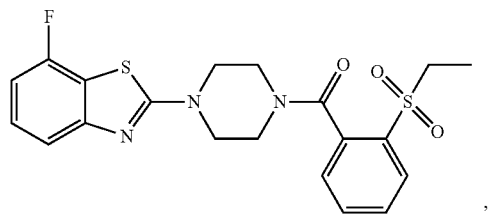,
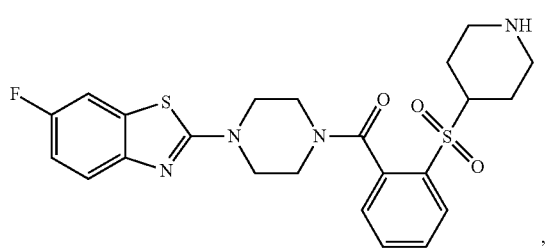,
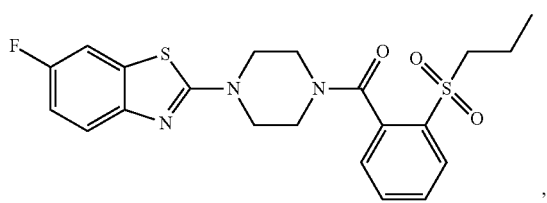,
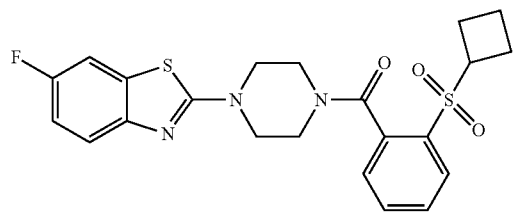,
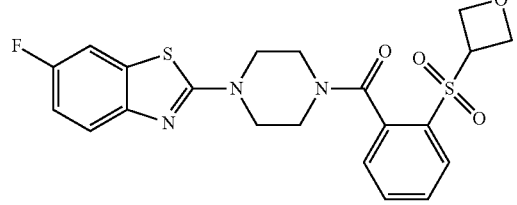,
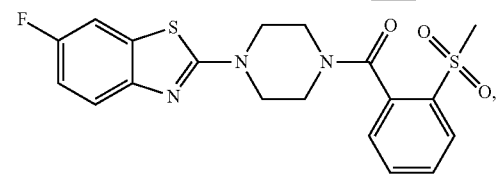,
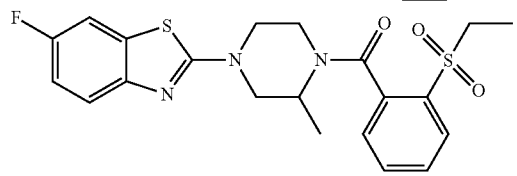,
-continued
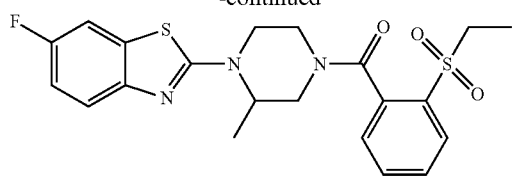,
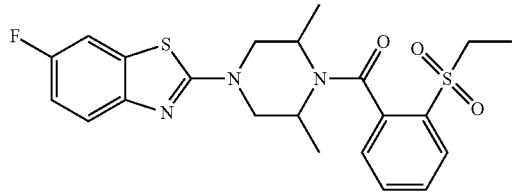,
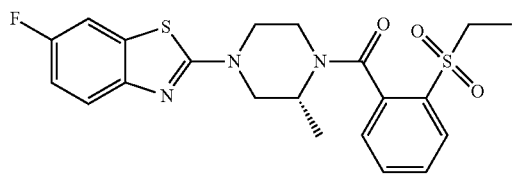,
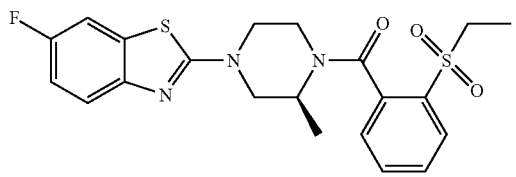,
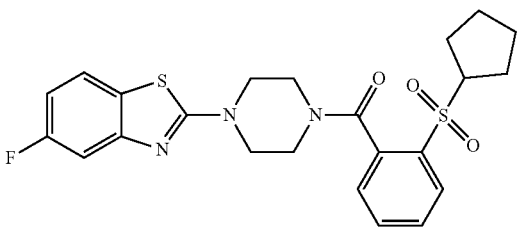,
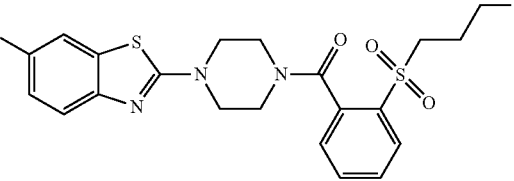,
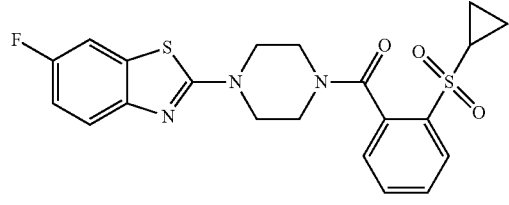,
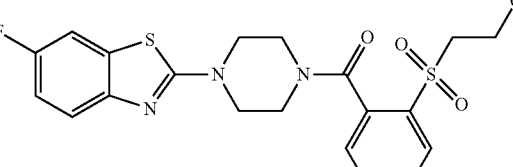,
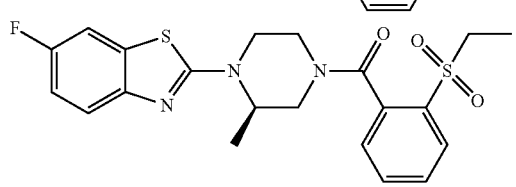, -continued
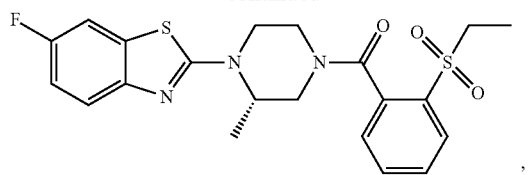
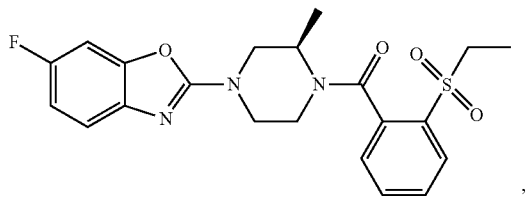
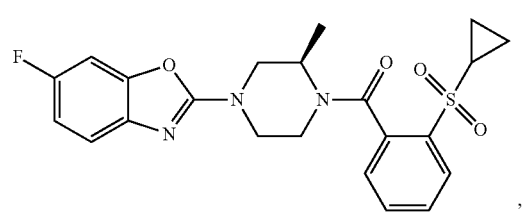
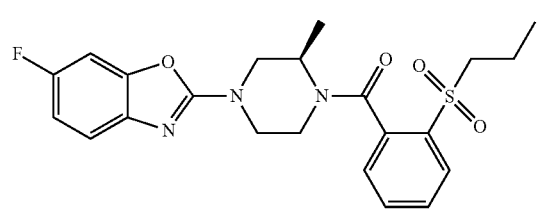
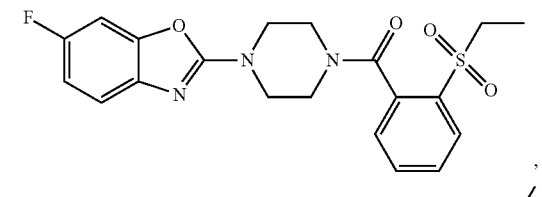
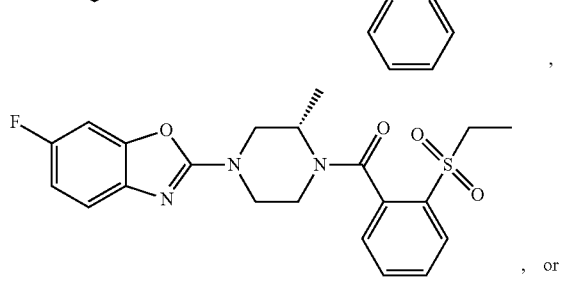
, or
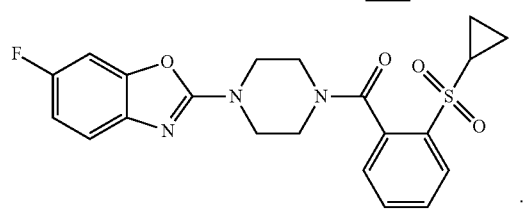
.
In embodiments, the compound has the formula:
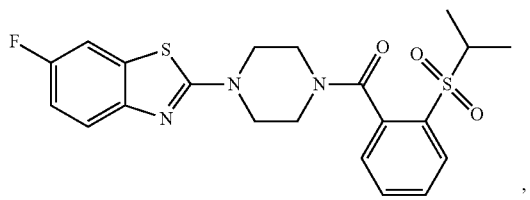
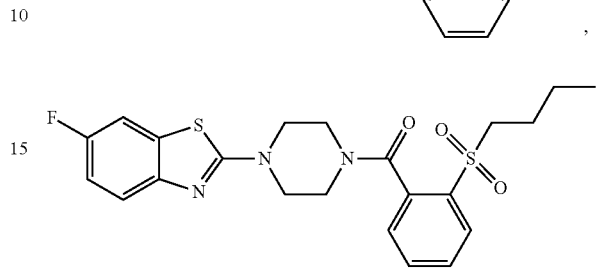
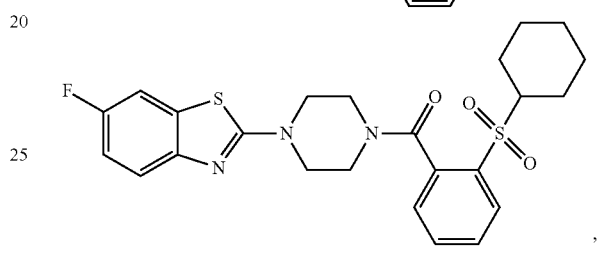
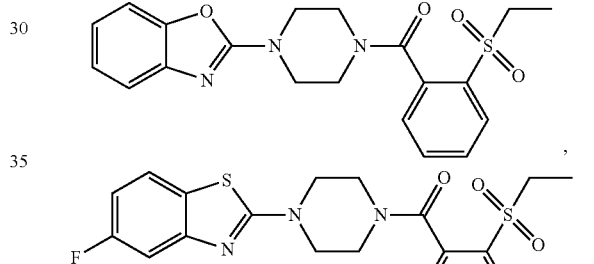
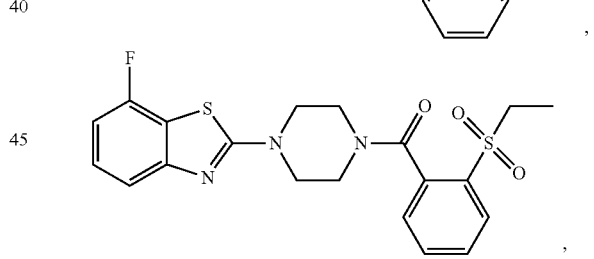
,

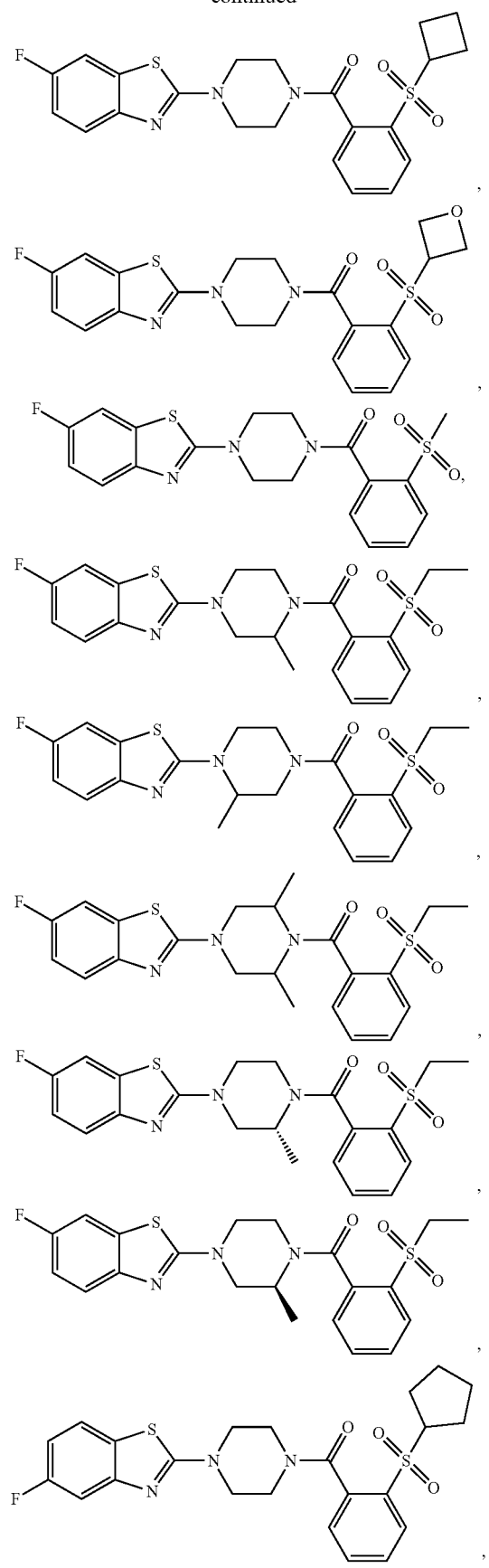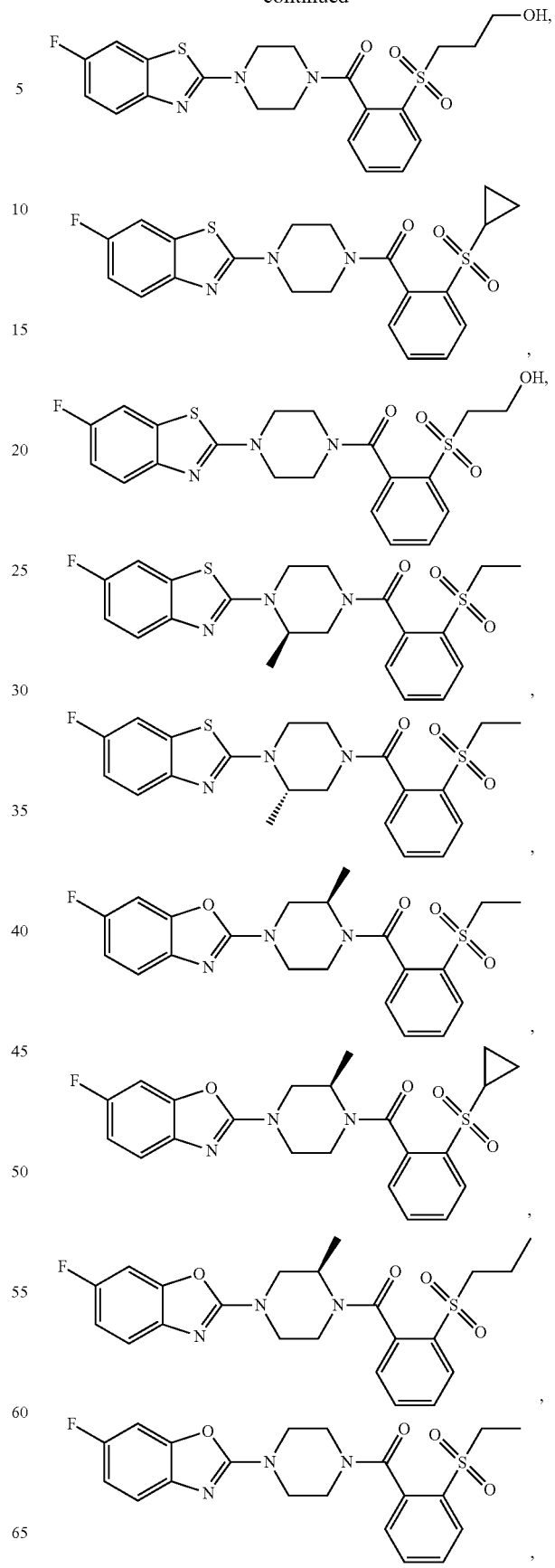

-continued

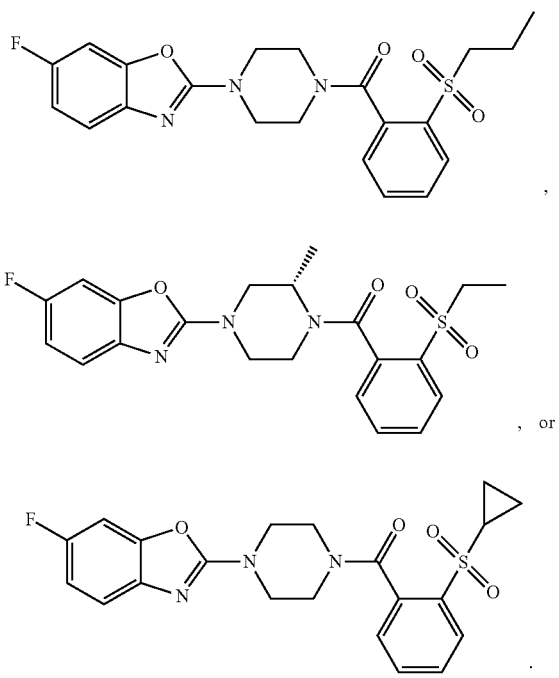
, or

In embodiments, z2 is from 0 to 2. In embodiments, z2 is from 0 to 4. In embodiments, z2 is from 1 to 2. In embodiments, z1 is 0. In embodiments, z1 is 1. In embodiments, z1 is 2. In embodiments, z1 is 3. In embodiments, z1 is 4. In embodiments, z2 is 0. In embodiments, z2 is 1. In embodiments, z2 is 2. In embodiments, z2 is 3. In embodiments, z2 is 4. In embodiments, z2 is 5. In embodiments, z2 is 6. In embodiments, z2 is 7. In embodiments, z2 is 8.

In embodiments, the compound does not have the formula:

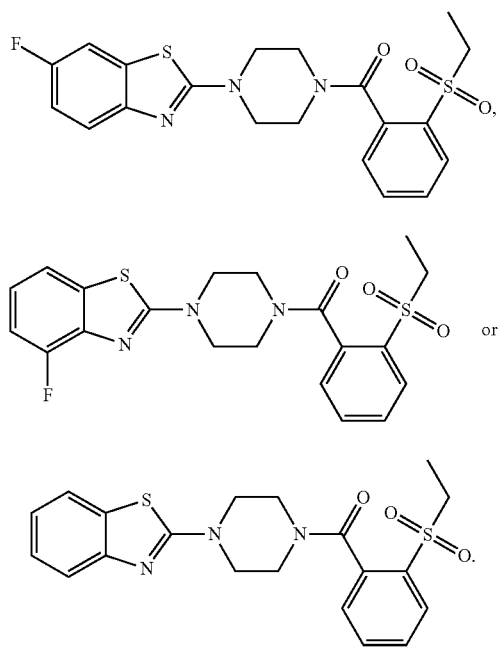

In embodiments, the compound does not have the formula:

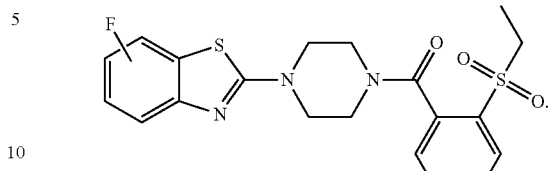

III. Pharmaceutical Compositions

In another aspect is provided a pharmaceutical composition including a pharmaceutically acceptable excipient and a compound, or pharmaceutically acceptable salt thereof, as described herein, including embodiments (e.g. in an aspect, embodiment, example, figure, table, or claim). In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments, the pharmaceutical composition includes PEA.

IV. Methods of Use

In an aspect is provided a method of inhibiting N-acylethanolamine acid amidase, the method including contacting the N-acylethanolamine acid amidase with a compound, or pharmaceutically acceptable salt thereof, as described herein, including embodiments (e.g. in an aspect, embodiment, example, figure, table, or claim). In embodiments, the compound is reversibly (e.g., noncovalently) contacting the N-acylethanolamine acid amidase.

In another aspect is provided a method of treating a pathological state, including but not limited to pain, an inflammatory condition, or a neurodegenerative disorder, the method including administering to a subject in need thereof an effective amount of a compound, or pharmaceutically acceptable salt thereof, as described herein, including embodiments (e.g. in an aspect, embodiment, example, figure, table, or claim).

In embodiments, the pathological state is a corneal neovascularization, diabetic retinopathy, dry macular degeneration, migraine, neuropathic pain, neuropathy, glossopharyngeal neuralgia, occipital neuralgia, postherpetic neuralgia, retinopathy of prematurity, sinus headache, trigeminal neuralgia, or wet macular degeneration.

In embodiments, the pathological state is pain, including but not limited to, neuropathic pain, nociceptive pain, chronic pain, neuropathy, glossopharyngeal neuralgia, occipital neuralgia, postherpetic neuralgia, trigeminal neuralgia, post herpetic neuralgia, causalgia, diabetic neuropathy, complex regional pain syndrome (CRPS), neurogenic pain, peripheral pain, polyneuropathic pain, toxic neuropathy, chronic neuropathy or pruritus. In embodiments, the method exhibits antinociceptive effects. In embodiments, administration of a compound, or pharmaceutically acceptable salt thereof, as described herein, including embodiments (e.g. in an aspect, embodiment, example, figure, table, or claim) alleviates pain behaviors elicited by chemical irritants, nerve damage, or inflammation.

In embodiments, the pathological state is an inflammatory condition, including but not limited to acute inflammation, acute respiratory distress syndrome, adult respiratory disease, arthritis, asthma, atherosclerosis, carpal tunnel syndrome, chronic bronchitis, chronic inflammation, chronic obstructive pulmonary disease (COPD), colitis, crystal induced arthritis, cystic fibrosis, dermatitis, dyslipidemia, emphysema, fibromyalgia, gall bladder disease, gingivitis, hyperoxia-induced inflammation, irritable bowel syndrome, inflammatory bowel disease, lupus, myofasciitis, nephritis, ocular inflammation, osteoarthritis, periodontitis, polymyositis, sarcoidosis, restenosis, rheumatoid arthritis, ulcerative colitis, or vasculitis.

In embodiments, the pathological state is a neurodegenerative disorder including but not limited to multiple sclerosis, dementia, Alzheimer's dementia, Parkinson's disease, Huntington's disease, or Amytrophic lateral Sclerosis. In embodiments, the neurodegenerative disorder is multiple sclerosis. In embodiments, the neurodegenerative disorder is Alzheimer's dementia. In embodiments, the neurodegenerative disorder is Parkinson's disease. In embodiments, the neurodegenerative disorder is Huntington's disease. In embodiments, the neurodegenerative disorder is Amytrophic lateral Sclerosis. In embodiments, the neurodegenerative disorder is dementia. In embodiments, the neurodegenerative disorder is myalgic encephalomyelitis or chronic fatigue syndrome.

In embodiments, certain methods herein treat a neurodegenerative disorder by treating symptoms (e.g., decreasing the production of Lewy bodies, decreasing the accumulation of alpha-synuclein, decreasing cell death, decreasing loss of dopamine-generating cells, decreasing loss of cells in the substantia nigra, decreasing loss of dopamine production, decreasing a symptom of Parkinson's disease, decreasing loss of motor function, decreasing shaking or slowing an increase in shaking (tremor), decreasing rigidity or an increase in rigidity, decreasing slowness (bradykinesia) of movement or a slowing of movement, decreasing sensory symptoms, decreasing insomnia, decreasing sleepiness, increasing mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival).

In embodiments, the method includes orally administering to a subject in need thereof an effective amount of a compound or pharmaceutical composition as described herein. In embodiments, the compound or pharmaceutical composition as described herein is a tablet, powder, capsule, pill, cachet, or lozenge.

In another aspect is provided a method of treating a pathological state, including but not limited to pain, an inflammatory condition, or a neurodegenerative disorder, the method including administering to a subject in need thereof an effective amount of a NAAA inhibitor and an additional agent. In embodiments the NAAA inhibitor is a compound, or pharmaceutically acceptable salt thereof, as described herein, including embodiments (e.g. in an aspect, embodiment, example, figure, table, or claim). In embodiments the NAAA inhibitor is as described in publication WO/2013/078430 or publication WO/2009/049238. In embodiments, the additional agent includes a corticosteroid, glucocorticoid, steroid, palmitoylethanolamide (PEA), or an anti-inflammatory agent (e.g., nonsteroidial anti-inflammatory agent). In embodiments, the additional agent is PEA.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Examples

Example 1. Second-Generation Non-Covalent NAAA Inhibitors and their Use in Multiple Sclerosis NAAA is lysosomal cysteine hydrolase that catalyses the biodegradation of PEA and OEA (FIG. 1),[1] two endogenous lipid amides that suppress inflammation by activating the ligand-operated transcription factor, peroxisome proliferator-activated receptor-α (PPAR-α). [2] Resident macrophages and other host-defense cells constitutively generate PEA and OEA in amounts that are sufficient to fully engage PPAR-α.[3] This process is halted during inflammation, however, leading to a decrease in PPAR-α-mediated signaling and an acceleration of the inflammatory response. [3] Accordingly, small-molecule NAAA inhibitors restore normal PEA and OEA levels in inflamed tissues and exert profound anti-inflammatory effects in animal models, pointing to NAAA as a potential target for therapy. [4]

Figure 2:
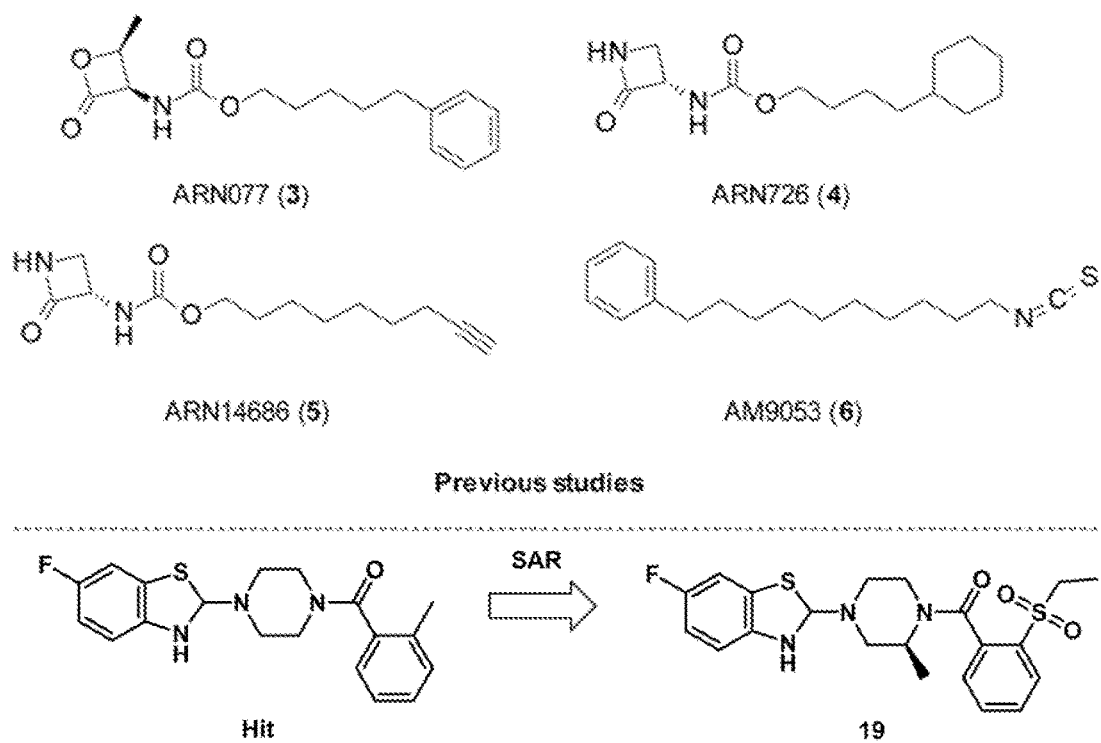
FIG. 2. Representative examples of NAAA inhibitors and result of SAR study of compound 7.

FIG. 2 illustrates representative examples of NAAA inhibitors. Each class is defined by the presence of a chemical warhead—β-lactone, pβ-lactam or isothiocyanate—that can react covalently with NAAA's catalytic cysteine (C126 in humans, and C131 in rodents) to form a hydrolysable thioester bond.[5] While potent and, in some cases, systemically active, these molecules share two features that limit their use as oral drugs: first, the presence of a reactive warhead lowers their metabolic stability (e.g., for pβ-lactone 3)[6] or increases the risk of allergic reactions (e.g., for pβ-lactam 4 and isothiocyanate 6); [7] and, second, the flexible hydrophobic fragment that ensures target recognition by these agents negatively impacts their drug-likeness.

Described herein are a series of novel piperazine benzothiazole derivatives (FIG. 2) that, in embodiments, non-covalently inhibit NAAA. In vitro and in vivo experiments indicate that compound 8, a representative member of this class as depicted as compound 19 in Table 9, is potent, selective for NAAA, and orally available. Moreover, compound 8 crosses the blood-brain barrier, elevates PEA and OEA levels in the CNS, and produces marked protective effects in a mouse model of MS.

A screening campaign aimed at discovering new chemical scaffolds for NAAA inhibition yielded the hit compound 7 (Table 1). To improve potency, focused structure-activity relationship (SAR) studies starting with modifications in the benzamide fragment were conducted. Removal of the o-methyl group (9) or replacement of such group with a halogen (10, 11) reduced activity. By contrast, substitutions with a methoxy (12), methylsulfonyl (13) or ethylsulfonyl (14) group yielded compounds of greater potency. Since moving the ethylsulfonyl substituent to the meta orpara position of the phenyl ring had a strong negative impact on activity (15, 16), we focused our exploration on o-sulfonyl derivatives containing linear, branched or cyclic alkyl groups (Table 2). The results showed that inhibitory potency was highly sensitive to length and size of the alkyl group, with bulkier substituents producing weaker inhibition (e.g., compounds 18, 23).

TABLE 1

Inhibitory potencies (IC$_{50}$ in μM) of compounds 7 and 9-16 (scaffold shown below) on the activity of recombinant hNAAA expressed in HEK-293 cells. The symbols o, m, and p, refer to ortho, meta, and para substituents as identified on the scaffold below.

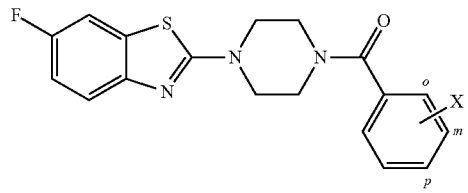

| Compound | X | NAAA IC$_{50}$ (μM)[a] |
|---|---|---|
| 7 | o-CH$_3$ | 88.9 |
| 9 | H | NA[b] |
| 10 | o-Cl | NA |
| 11 | o-F | NA |
| 12 | o-OCH$_3$ | 20.5 |
| 13 | o-SO$_2$CH$_3$ | 5.69 +/− 2.54 |
| 14 | o-SO$_2$CH$_2$CH$_3$ | 0.45 +/− 0.11 |
| 15 | m-SO$_2$CH$_2$CH$_3$ | NA |
| 16 | p-SO$_2$CH$_2$CH$_3$ | NA |

[a]Values are the mean ± SEM of three or more determinations, or the mean of triplicate determinations in a single experiment.
[b]<30% inhibition at 100 μM.

Synthesis of Benothiazole Derivatives (Table 3).

Removal of the 6-F phenyl substituent did not affect potency (24), whereas insertion of electron-withdrawing (25, 26) or -donating (27, 28) groups was detrimental. Introducing a halogen at various positions of the ring caused either minor effects or decrease in potency (29-32).

TABLE 2

Potencies of compounds 17-23 on hNAAA.

| Compound | R | hNAAA IC$_{50}$ (μM) |
|---|---|---|
| 17 | (CH$_2$)$_2$CH$_3$ | 0.39 +/− 0.06 |
| 18 | (CH$_2$)$_3$CH$_3$ | 8.80 +/− 2.40 |
| 19 | i-propyl | 0.50 +/− 0.09 |
| 20 | c-propyl | 0.19 +/− 0.03 |
| 21 | c-butyl | 0.32 +/− 0.00 |
| 22 | c-pentyl | 1.10 +/− 0.09 |
| 23 | c-hexyl | 38.11 +/− 5.49 |

Following further derivatization, as seen in Table 4, the compounds obtained displayed a range of activity levels. To examine the effect of conformational changes in the piperazine ring, we introduced one or two methyl groups at various positions of this structure (36-39). These attempts confirm the important role of a mono-substituted piperazine in this position, as shown by the drop in activity caused by 2,2-dimethyl substitution (38). Further supporting such role, we noted that inhibitory potency was highly sensitive to the absolute configuration of the methyl group, with 40, the (R)-enantiomer of racemic 36, being 15 times less potent than the (S)-enantiomer 8.

TABLE 3

Potencies of compounds 24-32 on hNAAA.

| Compound | Y | hNAAA IC$_{50}$ (μM) |
|---|---|---|
| 24 | H | 0.43 +/− 0.03 |
| 25 | 6-Cl | 1.55 +/− 0.29 |
| 26 | 6-CF$_3$ | 7.2 |
| 27 | 6-CH$_3$ | 6.87 |
| 28 | 6-OCH$_3$ | 5.73 |
| 29 | 4-F | 0.55 +/− 0.20 |
| 30 | 5-F | 2.95 +/− 0.84 |
| 31 | 7-F | 0.30 +/− 0.02 |
| 32 | 7-Cl | 0.71 +/− 0.21 |

TABLE 4

Potencies of compounds 8 and 33-42 on hNAAA.

| Compound | Structure | hNAAA IC$_{50}$ (μM) |
| --- | --- | --- |
| 36 | 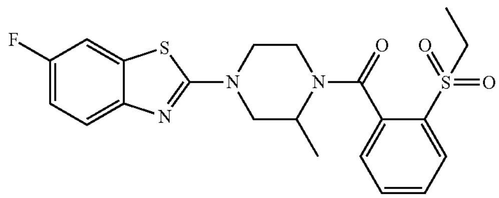 [SMILES: CCS(=O)(=O)c1ccccc1C(=O)N1CCN(c2nc3ccc(F)cc3s2)CC1C] | 0.50 +/− 0.075 |
| 37 | 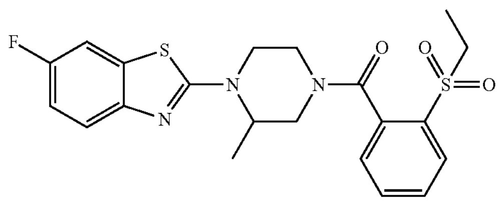 [SMILES: CCS(=O)(=O)c1ccccc1C(=O)N1CCN(c2nc3ccc(F)cc3s2)C(C)C1] | 0.72 +/− 0.12 |
| 38 | 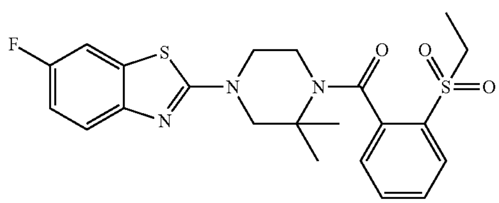 [SMILES: CCS(=O)(=O)c1ccccc1C(=O)N1CCN(c2nc3ccc(F)cc3s2)CC1(C)C] | NA |
| 39 | 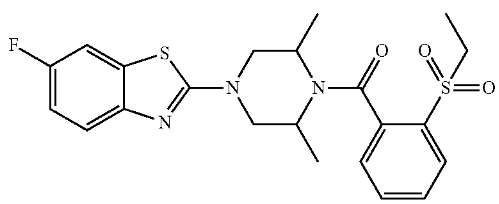 [SMILES: CCS(=O)(=O)c1ccccc1C(=O)N1C(C)CN(c2nc3ccc(F)cc3s2)CC1C] | 1.44 +/− 0.14 |
| 40 | 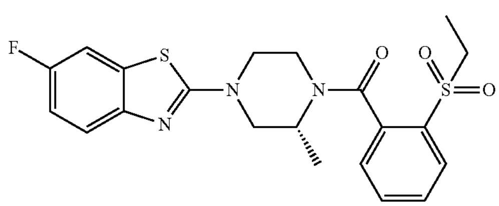 [SMILES: CCS(=O)(=O)c1ccccc1C(=O)N1CCN(c2nc3ccc(F)cc3s2)C[C@H]1C] | 3.43 +/− 0.50 |
| 8 | 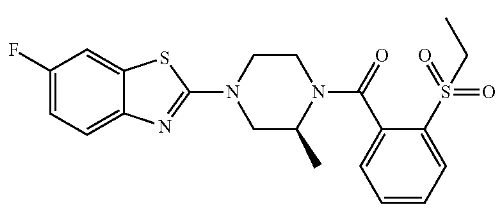 [SMILES: CCS(=O)(=O)c1ccccc1C(=O)N1CCN(c2nc3ccc(F)cc3s2)C[C@@H]1C] | 0.23 +/− 0.04 |
| 41 | 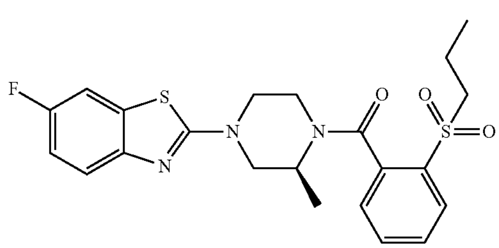 [SMILES: CCCS(=O)(=O)c1ccccc1C(=O)N1CCN(c2nc3ccc(F)cc3s2)C[C@@H]1C] | 0.20 +/− 0.05 |

TABLE 4-continued

Potencies of compounds 8 and 33-42 on hNAAA.

| Compound | Structure | hNAAA IC$_{50}$ (μM) |
|---|---|---|
| 42 | 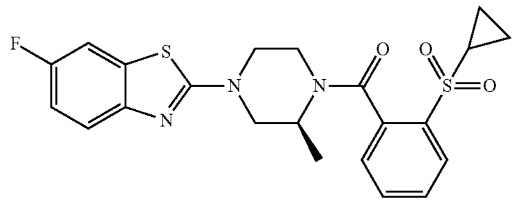 [SMILES: C[C@H]1CN(c2nc3ccc(F)cc3s2)CCN1C(=O)c1ccccc1S(=O)(=O)C1CC1] | 0.18 +/− 0.04 |

Subsequent mechanistic work on 8 and compounds with greater solubility in aqueous buffers, compared to other similarly potent compounds (Table 5; Table 7), was conducted.

TABLE 7

Solubility data in PBS, phosphate-buffered saline.

| Compound | Solubility in PBS (μM) |
|---|---|
| 8 | 139 ± 1 |
| 41 | 76 ± 1 |
| 42 | 115 ± 7 |

Figure 3A:
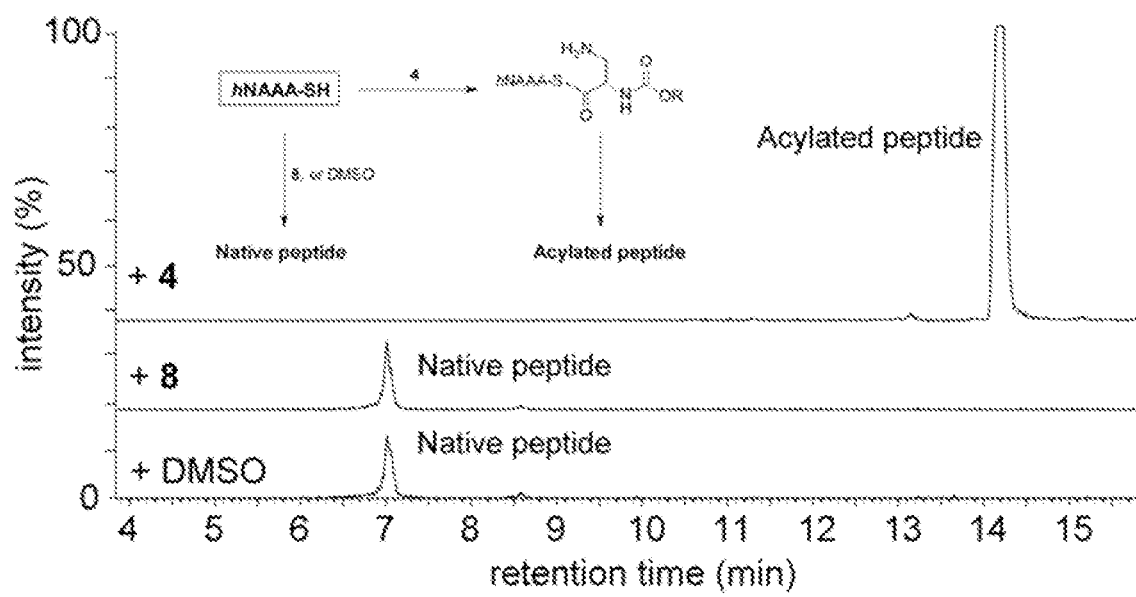
FIGS. 3A-3B. Compound 8 inhibits NAAA via a non-covalent mechanism.
Figure 3B:
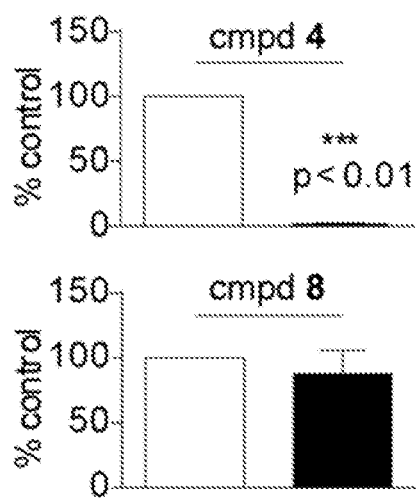
Figure 6:
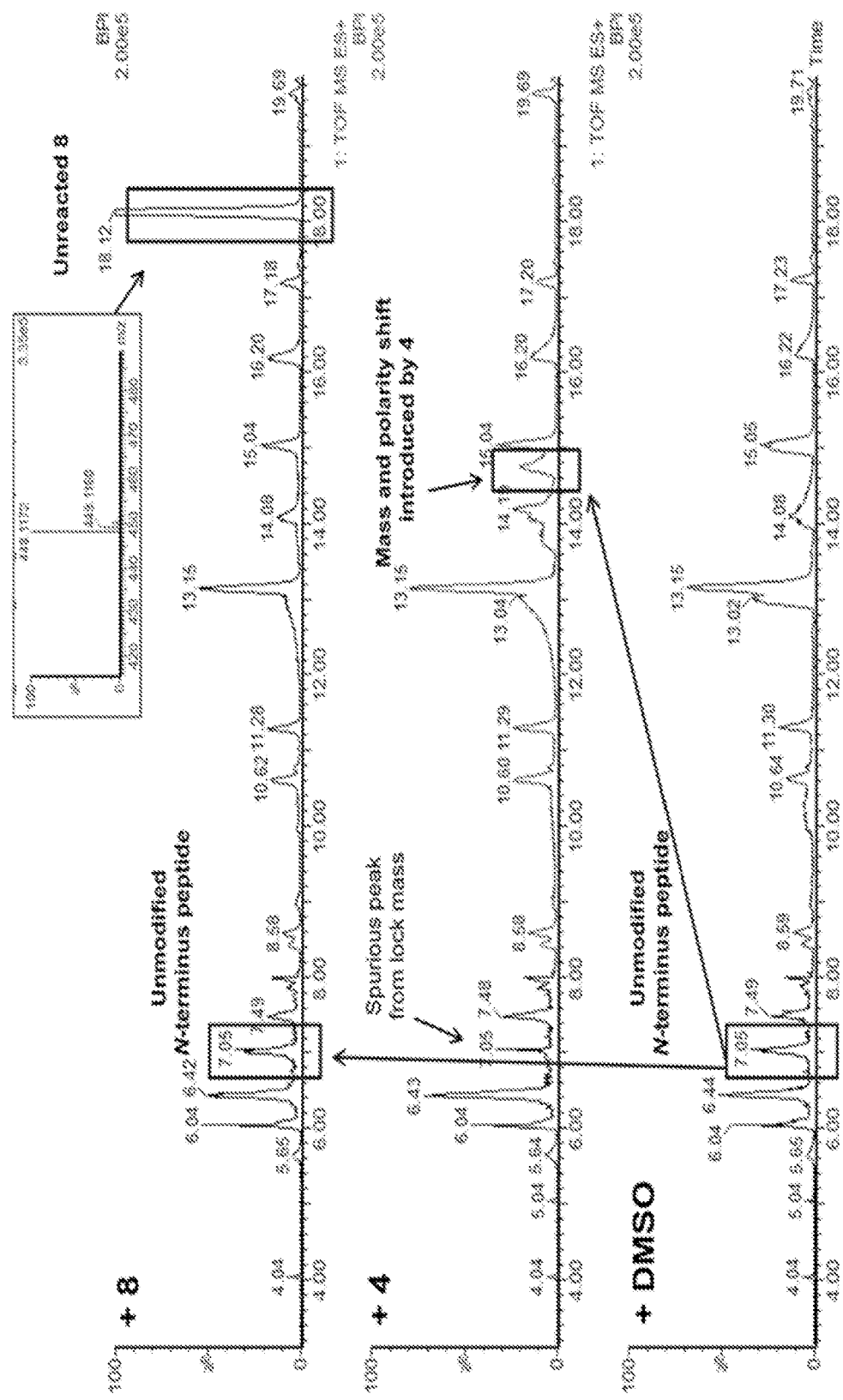
FIG. 6. Extracted-ion chromatograms of total hNAAA digest from a control incubation with DMSO (bottom chromatogram), with covalent NAAA inhibitor compound 4 (middle chromatogram) and with compound 8 (top chromatogram).
Figure 7:
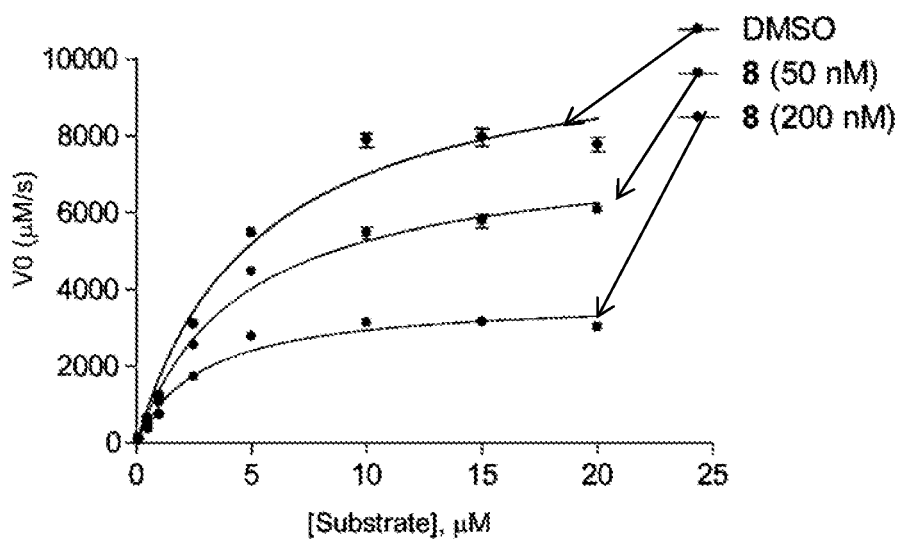
FIG. 7. Graph and corresponding table illustrating kinetic analyses revealing compound 8 inhibits NAAA via an uncompetitive (e.g., noncovalent) mechanism.
Figure 8A:
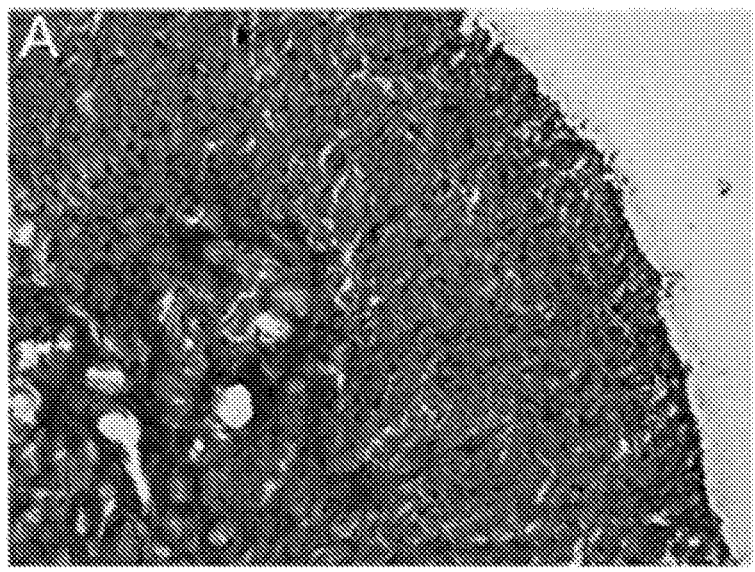
FIGS. 8A-8C, FIG. 8D (including FIG. D' inset), FIG. 8E (including FIG. E' inset) AND FIG. 8F (including FIG. F' inset). Micrographs of spinal cord cross-sections of naïve (FIGS. A, D and D') vehicle treated EAE mice (FIGS. B, E and E') and compound 8 treated EAE mice sacrificed 15 days post immunization. Sections were stained with H&E (FIGS. A-C). Regions of extensive inflammatory infiltrates on the meningeal surfaces, perivascular areas and interstitial areas were observed in vehicle treated mice (FIG. B). Mononuclear cells infiltrates were dramatically reduced by compound 8 subchronic administration (FIG. C). Analysis of the spinal cord sections immunostained with Iba1 (FIGS. D-F) revealed that inflamed areas were highly populated by activated microglia cells (FIGS. E and E') while Iba1 signal was markedly reduced in sections of 8 treated mice (FIGS. F and F').
Figure 8B:
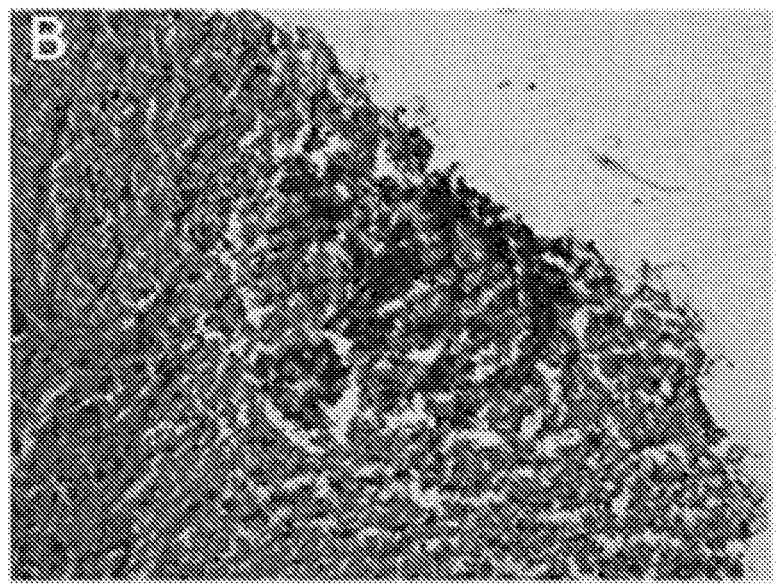
Figure 8C:
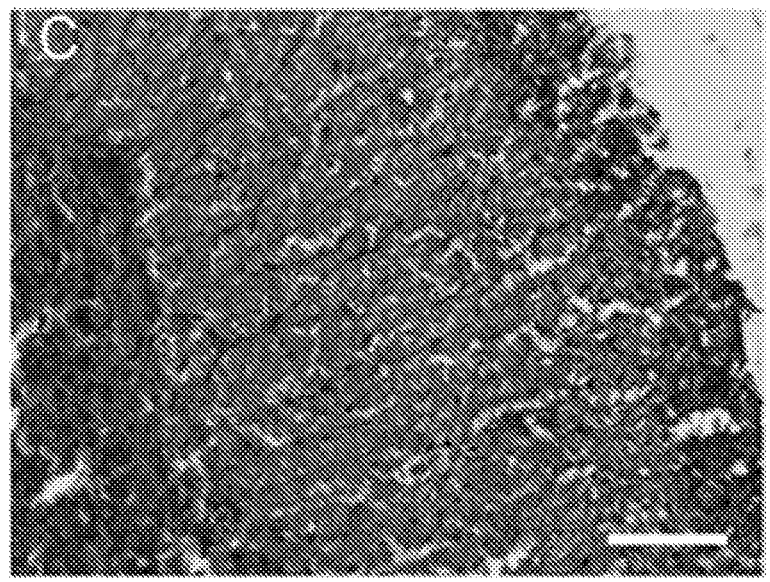
Figure 8D:
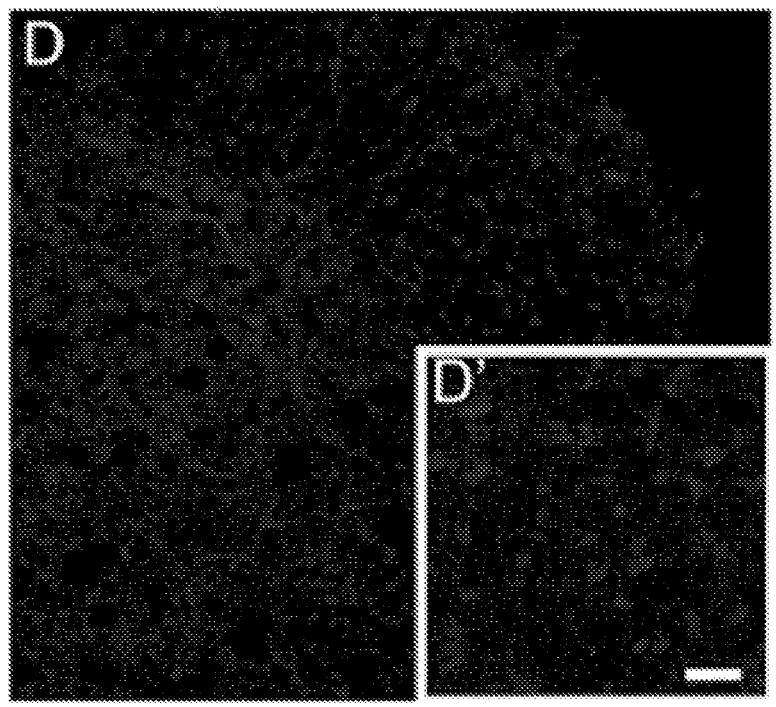
Figure 8E:
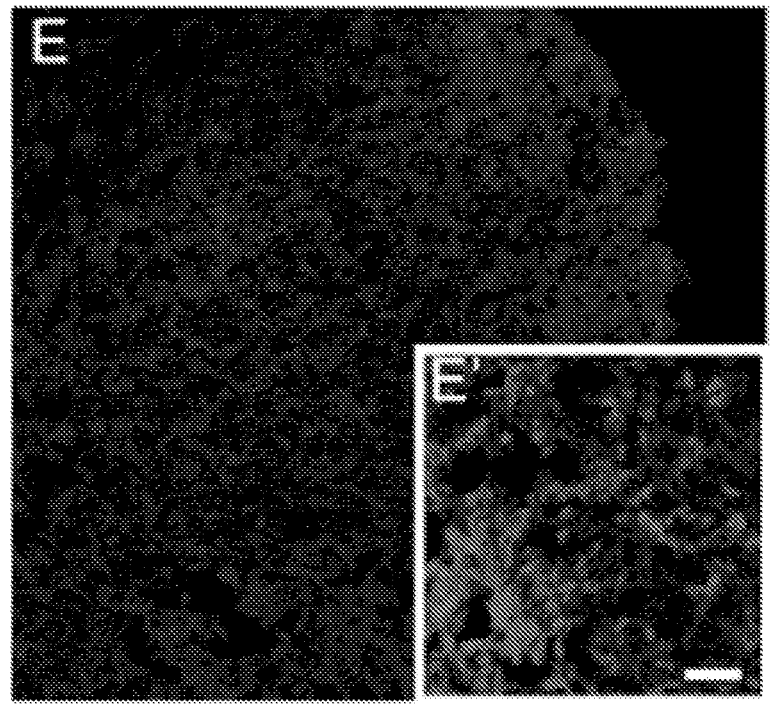
Figure 8F:
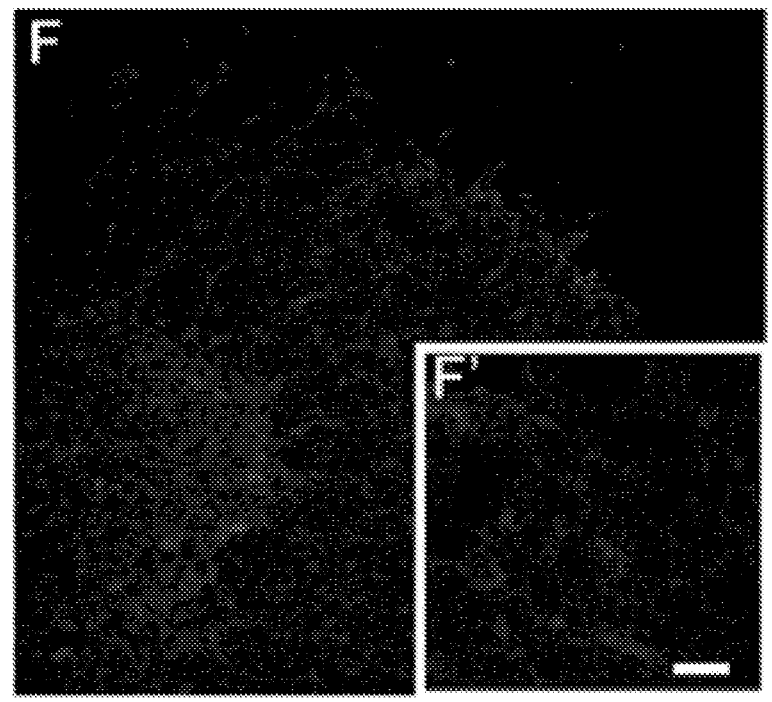
Figure 9A:
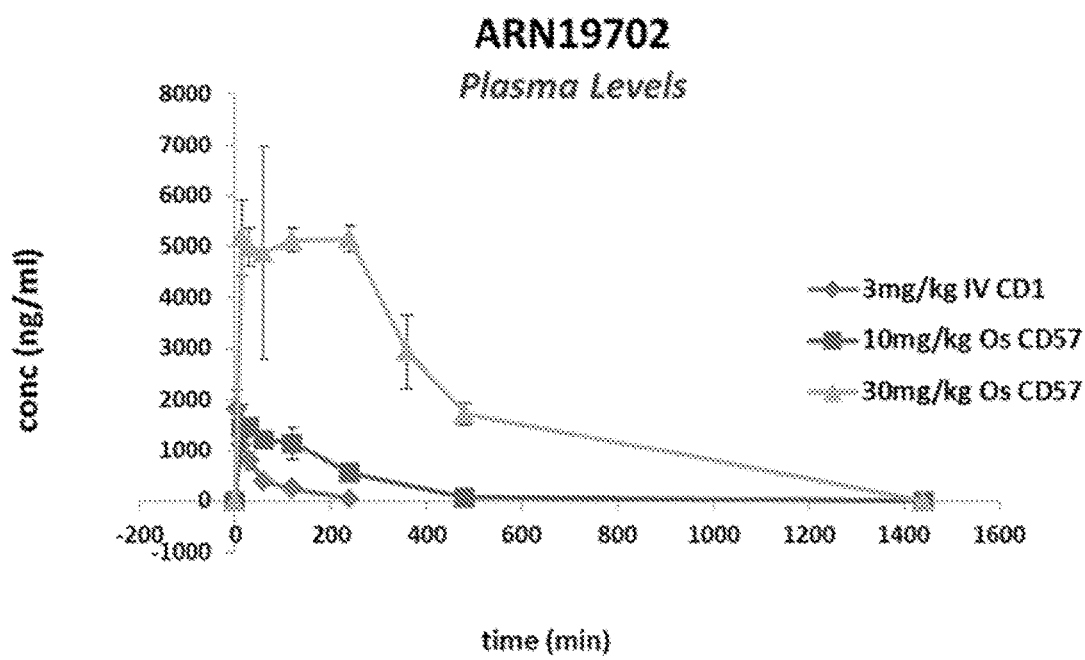
FIGS. 9A-9B. Graphs illustrating pharmacokinetic data for compound 19702 in plasma (FIG. 9A) and brain (FIG. 9B) at different concentrations.
Figure 9B:
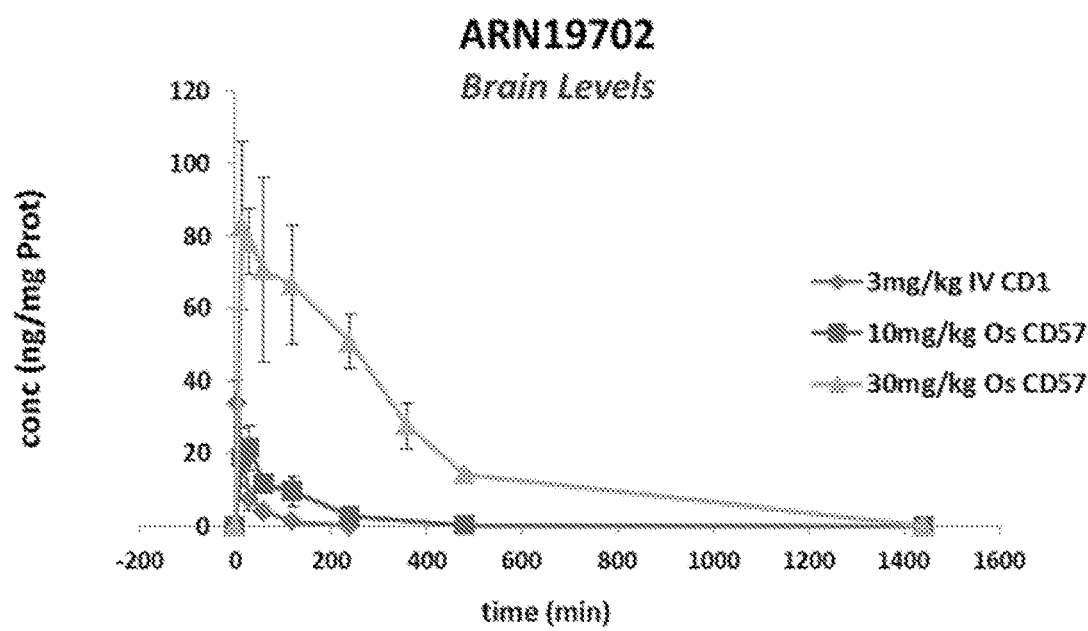
Figure 10A:
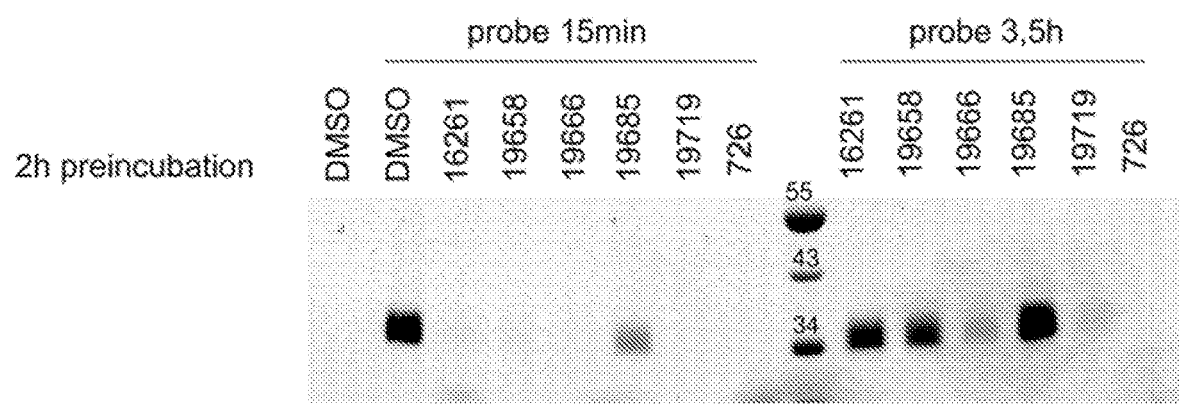
FIGS. 10A-10D. Photographs of chromatography gels illustrating competitive assay results.
Figure 10B:
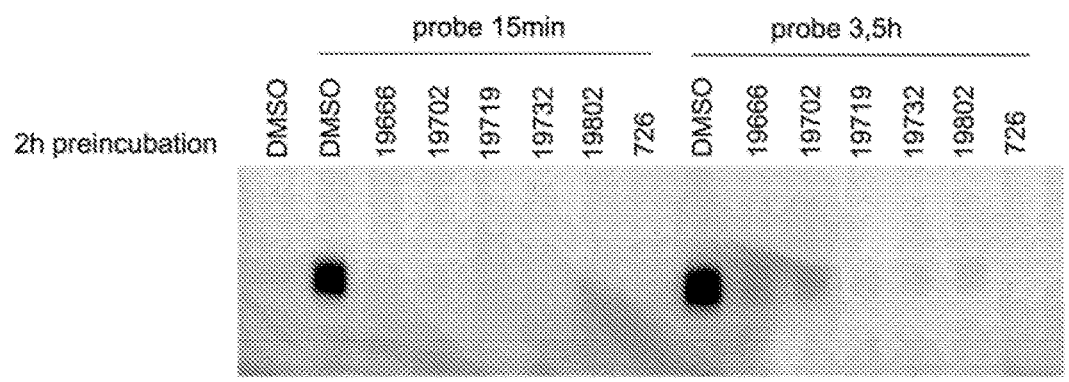
Figure 10C:
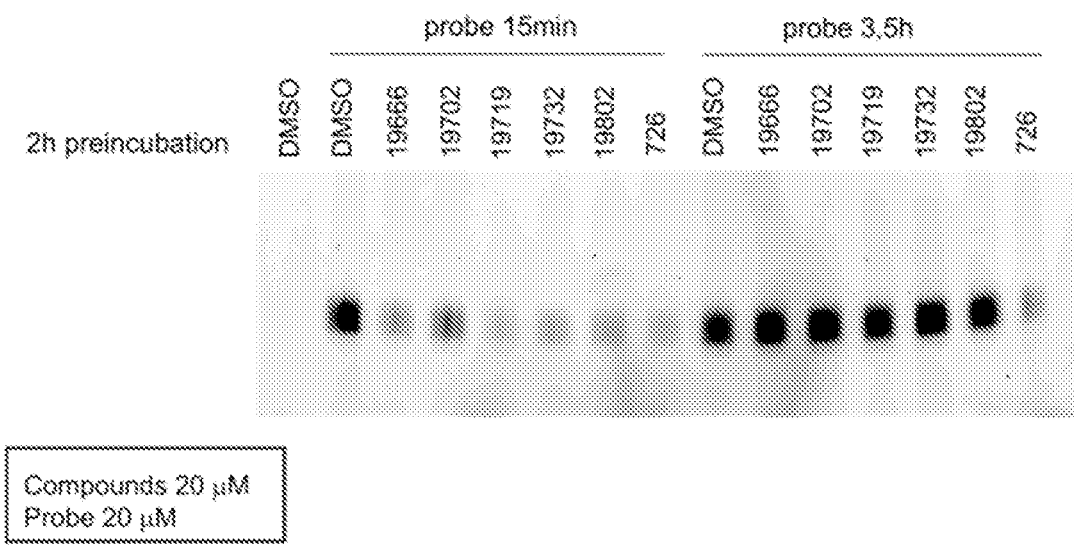
Figure 10D:
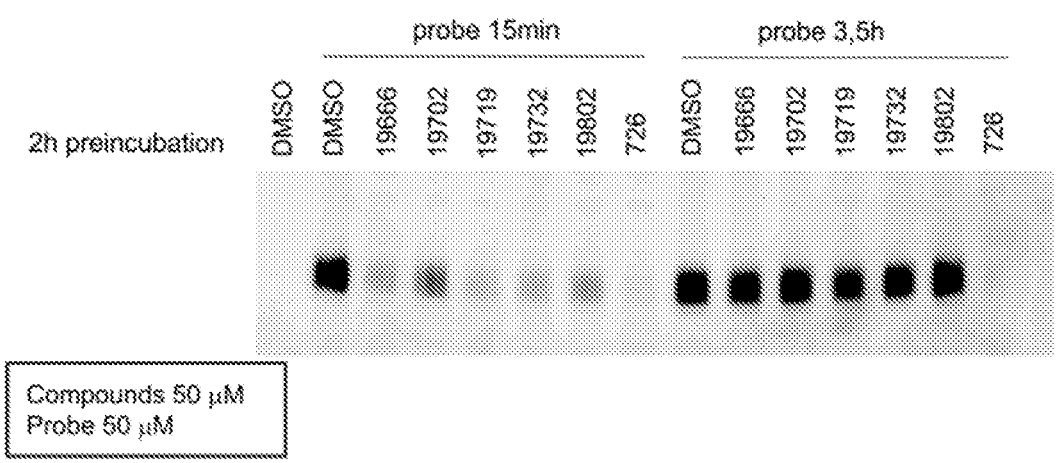
Figure 11A:
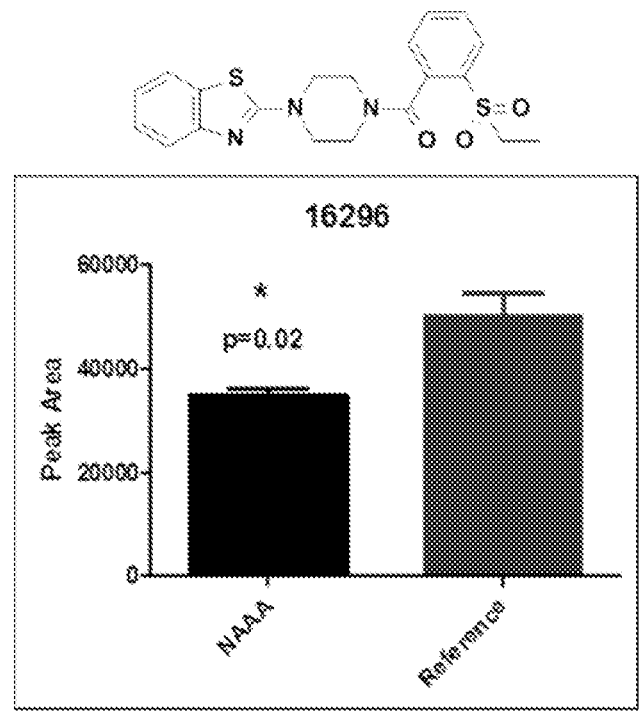
FIG. 11A-11H. LC/MS analysis for ligand-based assays utilizing purified hNAAA at 4.0 µM, and compound concentration at 1.0 µM for selected benzothiazoles and selected benzoxazoles. Compound 16296 (FIG. 11A) refers to compound 2 in Table 9, compound 19702 (FIG. 11B) refers to compound 19 in Table 9, compound 19881 (FIG. 11C) refers to compound $X^{40}$ in Table 9, compound 20022 (FIG. 11D) refers to compound 41 in Table 9, 17636 (FIG. 11E) refers to compound 6 in Table 9, compound 19802 (FIG. 11F) refers to compound 43 in Table 9, compound 19877 (FIG. 11G) refers to compound 28 in Table 9, and compound 19862 (FIG. 11H) refers to compound 27 in Table 9.
Figure 11B:
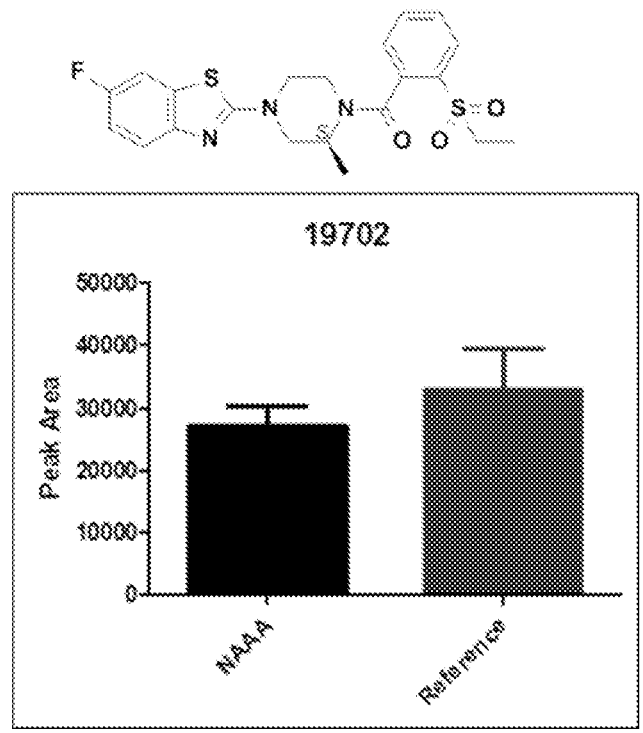
Figure 11C:
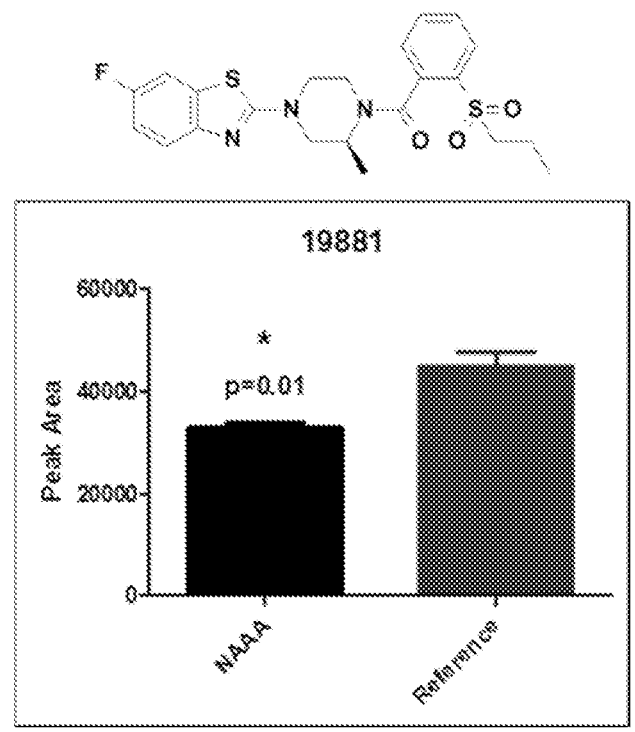
Figure 11D:
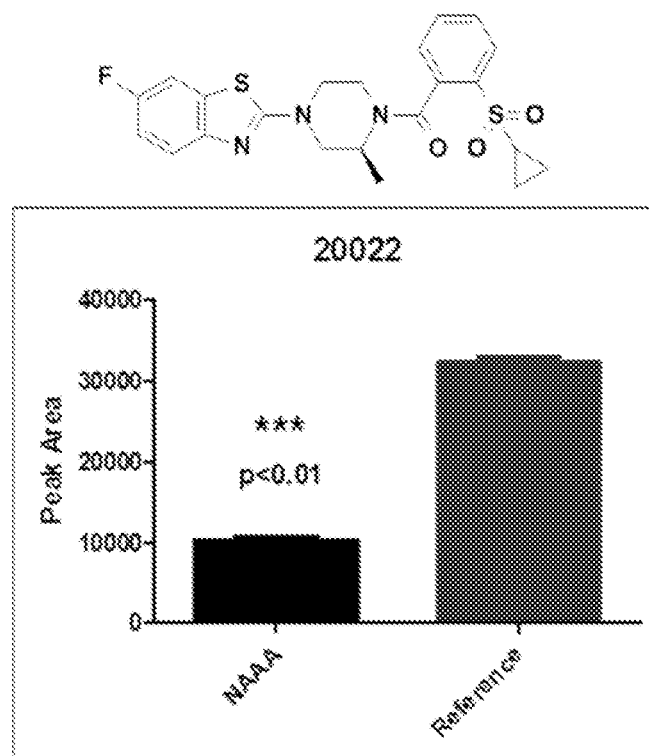
Figure 11E:
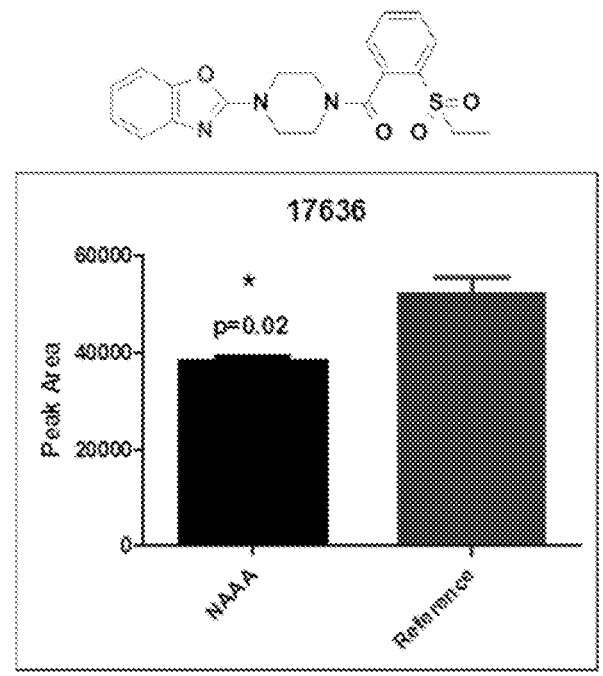
Figure 11F:
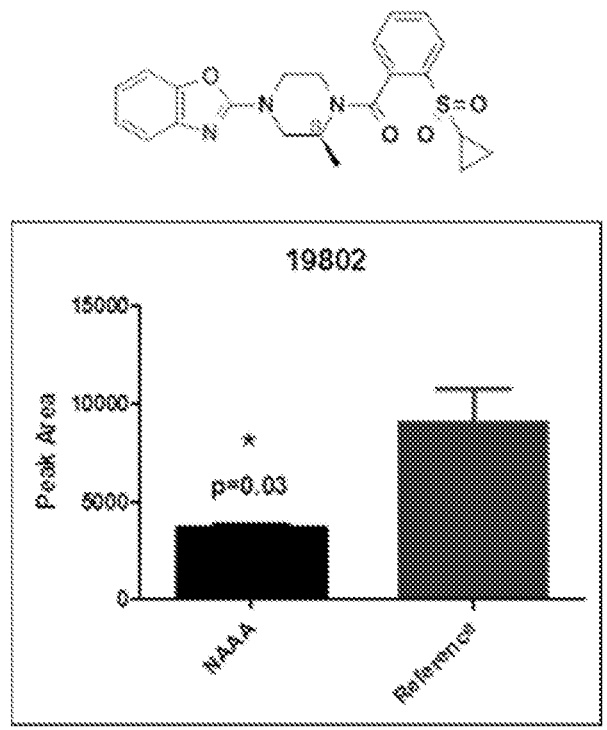
Figure 11G:
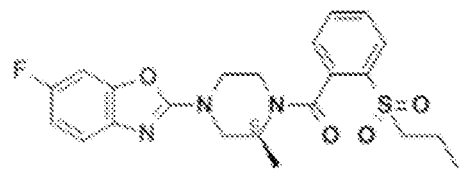
Figure 11G:
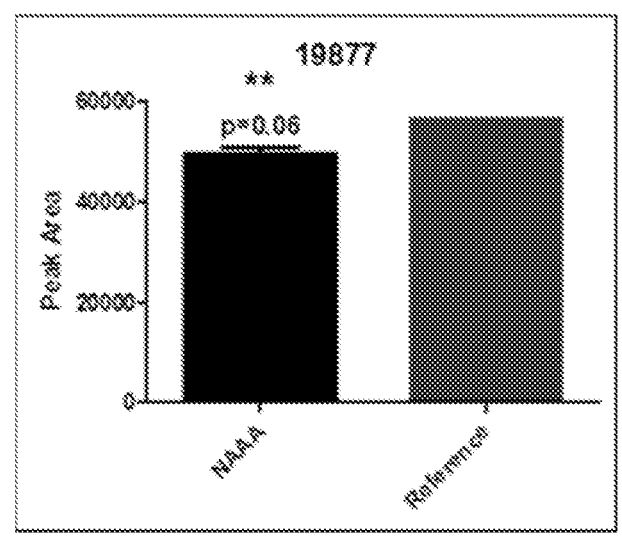
Figure 11H:
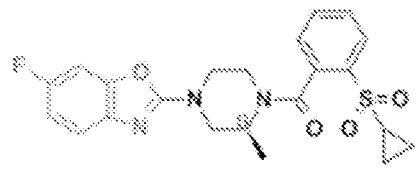
Figure 11H:
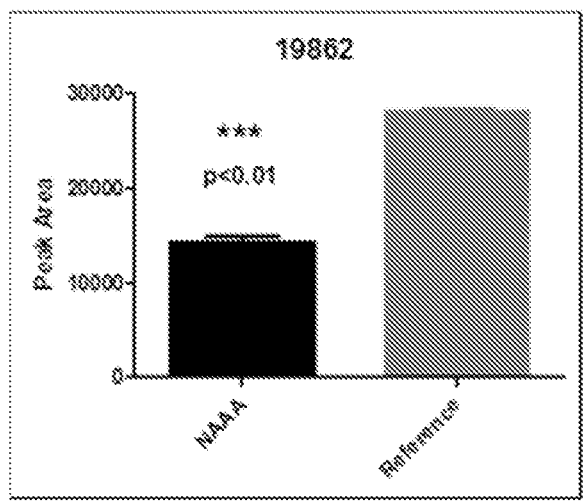
Figure 12A:
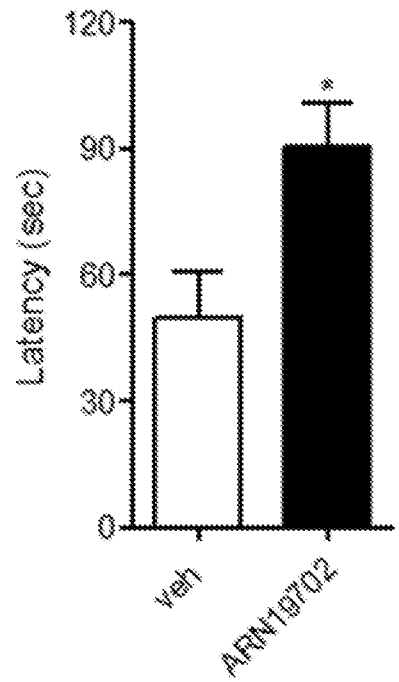
FIGS. 12A-12B. Histograms illustrating the effects of compound 19702 in the 6-hydroxydopamine (6-OHDA) model of Parkinson's disease. Mice received 30 mg/kg of ARN19702 twice per day for 21 days. Spontaneous motor tests (rotarod, FIG. 12A) was performed on day 22 post lesion, and apomorphine-induced (FIG. 12B) rotational behavior was evaluated on day 23 post lesion. All mice were pre-trained on the rotarod apparatus: the training consisted of three sessions, each lasting 180 s, performed on the day preceding the test. The final test (three sessions, each lasting 210 s) was performed at accelerating rate from 15 rpm to 40 rpm. Between trials, mice were given at least 2 min of rest in order to reduce stress and fatigue. Apomorphine-induced contralateral rotation were measured for 1 hour after the administration of apomorphine 1 mg/kg i.p. * t-Test $p<0.05$. Compound 19702 refers to compound 19 in Table 9.
Figure 12B:
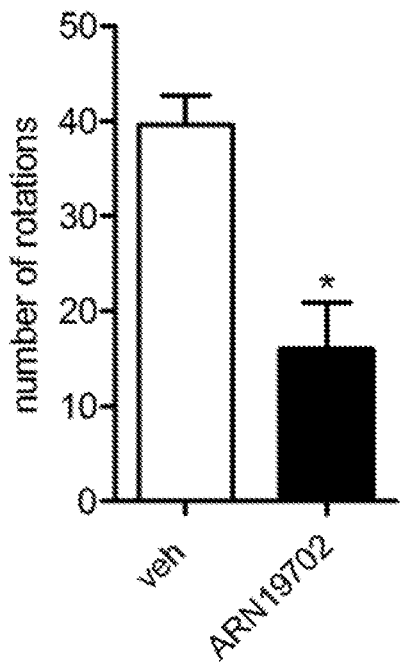
Figure 13:
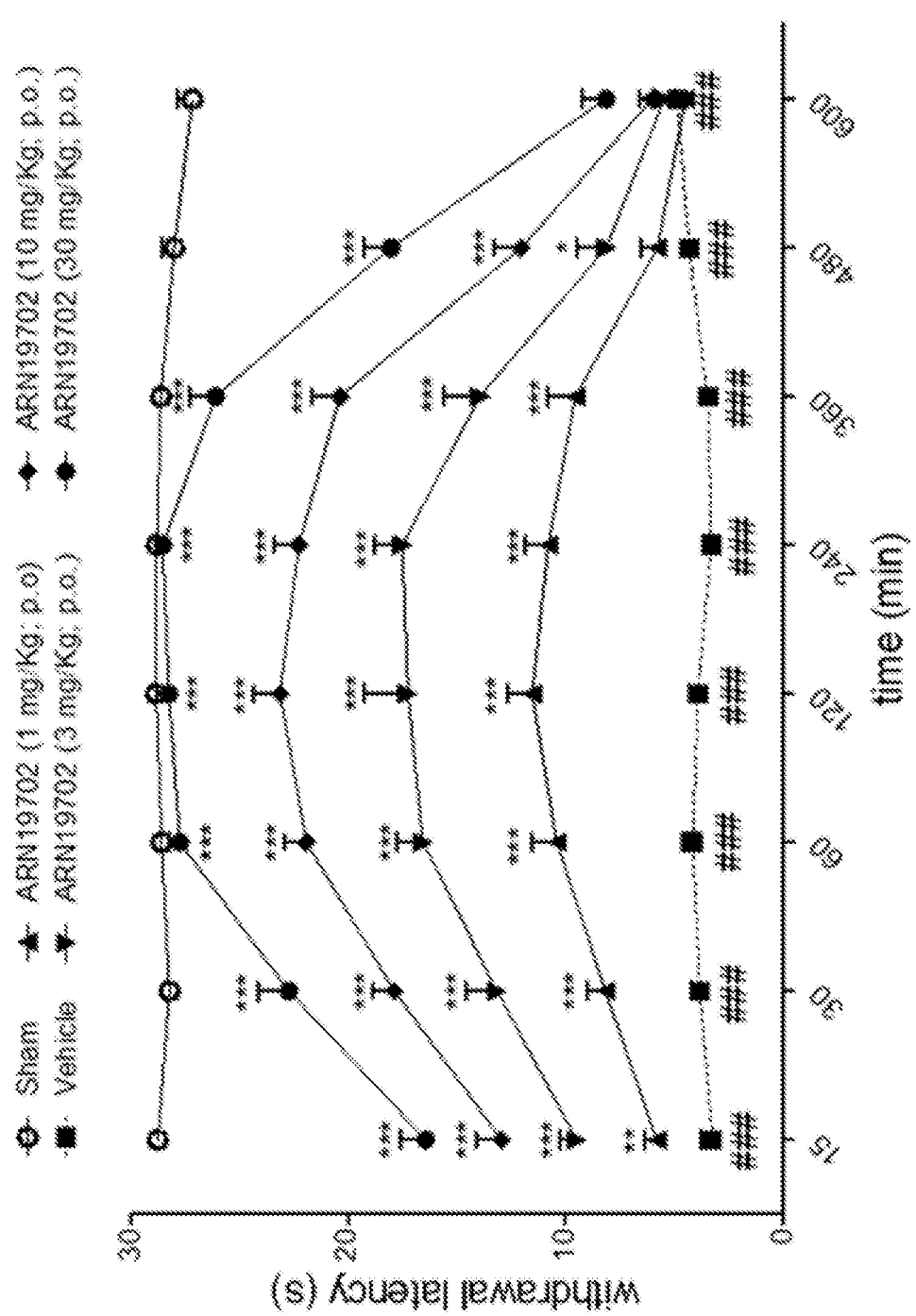
FIG. 13. Graph illustrating time-course of the effects of compound 19702 (single oral administration, 3-30 mg per kg) or vehicle on thermal hyperalgesia. Chronic neurogenic pain was induced in male Swiss mice (20 g) by ligation of the sciatic nerve, and pain-related behaviors were monitored following oral administration of compound 19702 (dose expressed in mg per kg) or its vehicle. * P<0.05; P<0.01; * or ### P<0.001.
Figure 14A:
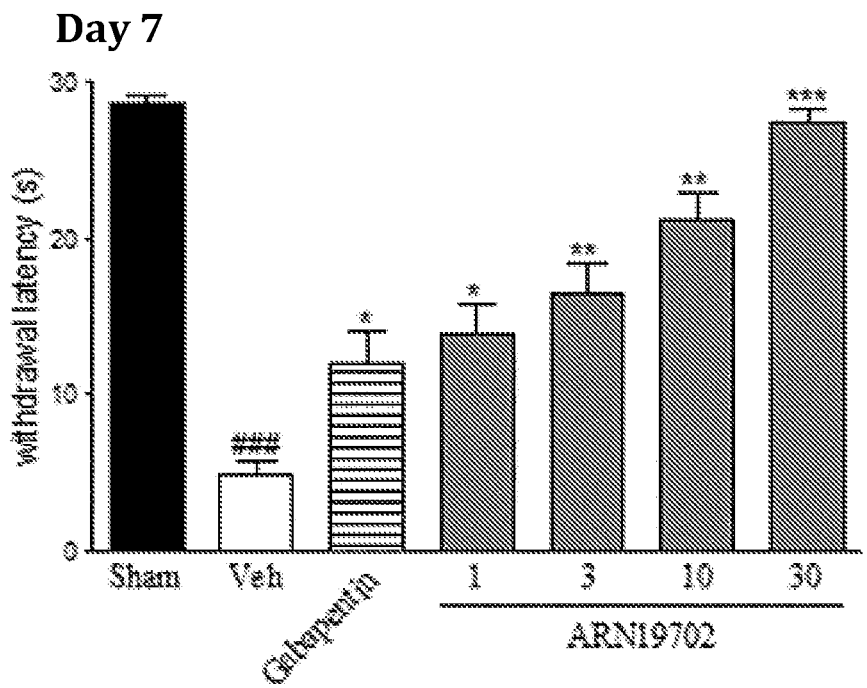
FIGS. 14A-14F. Histograms illustrating effects of repeated administration of compound 19702 and gabapentin (50 mg/kg) where chronic neurogenic pain was induced in male Swiss mice (20 g) by ligation of the sciatic nerve, and pain-related behaviors were monitored following oral administration of ARN19702 (dose expressed in mg per kg) or its vehicle.
Figure 14B:
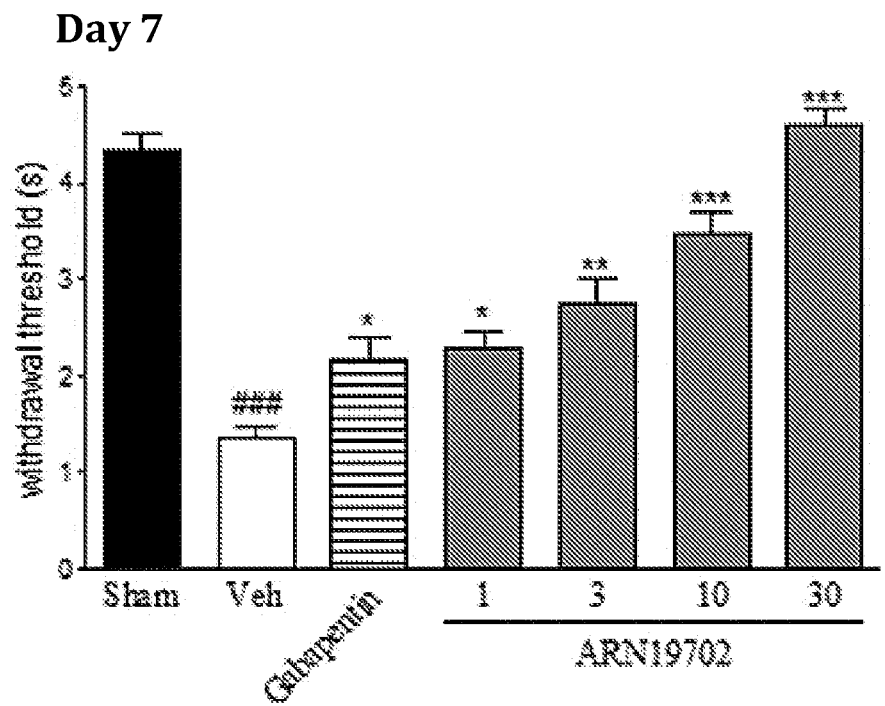
Figure 14C:
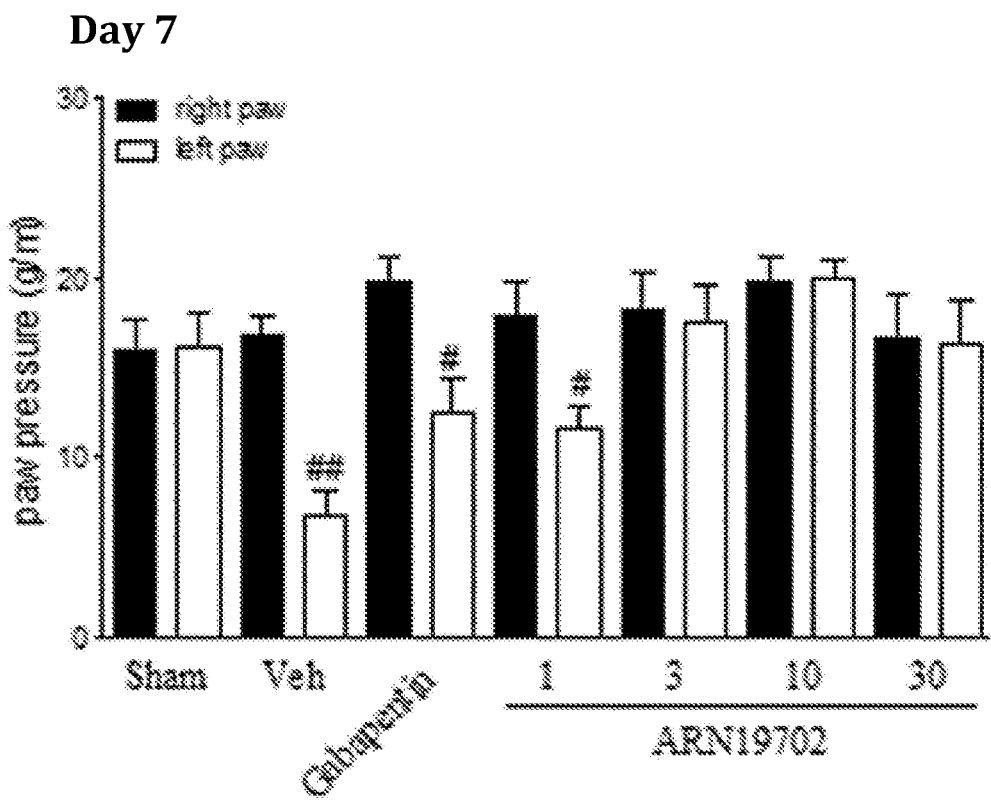
Figure 14D:
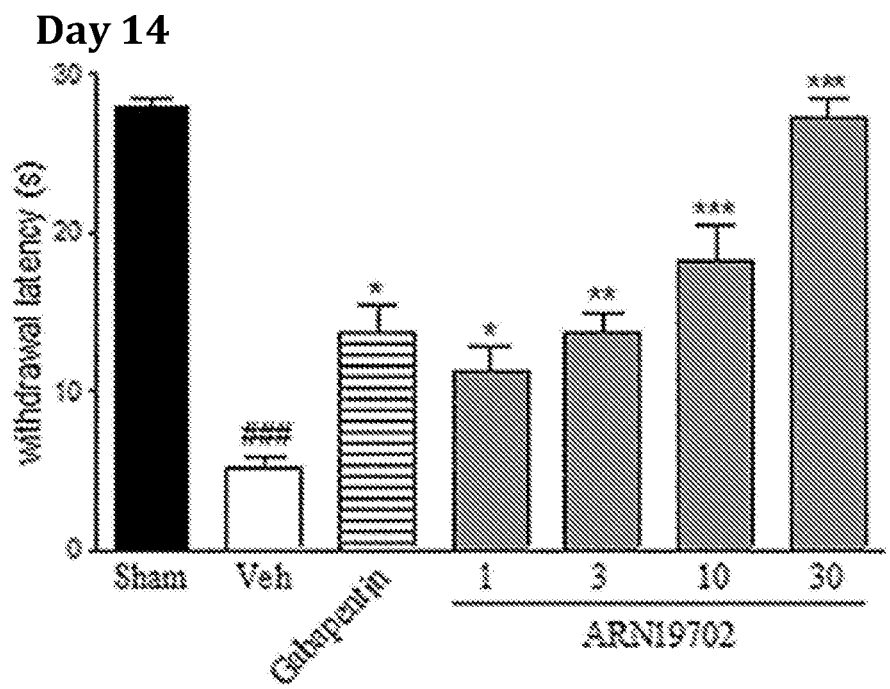
Figure 14E:
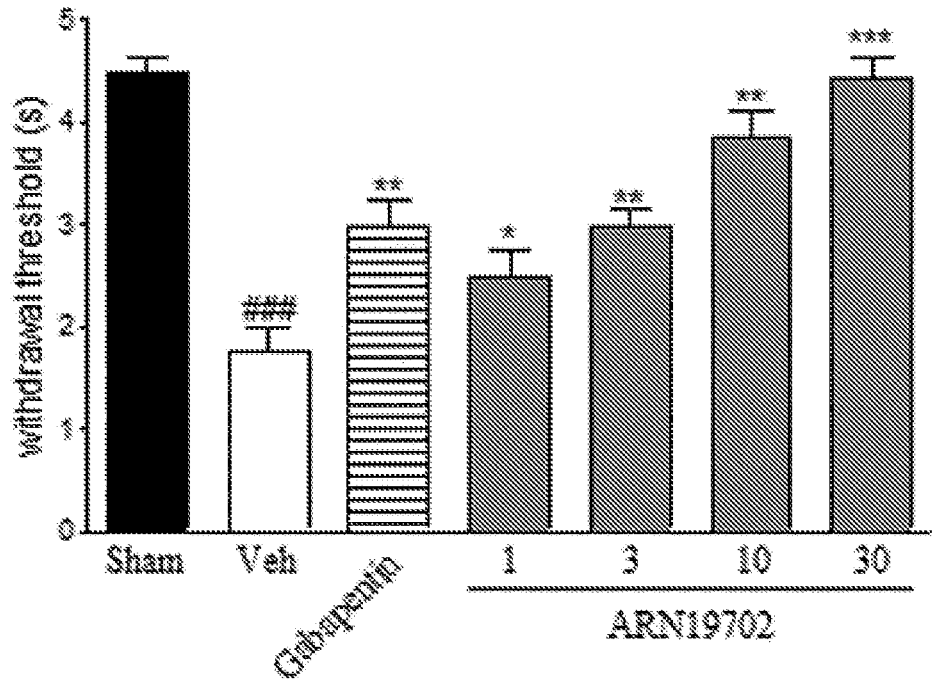
Figure 14F:
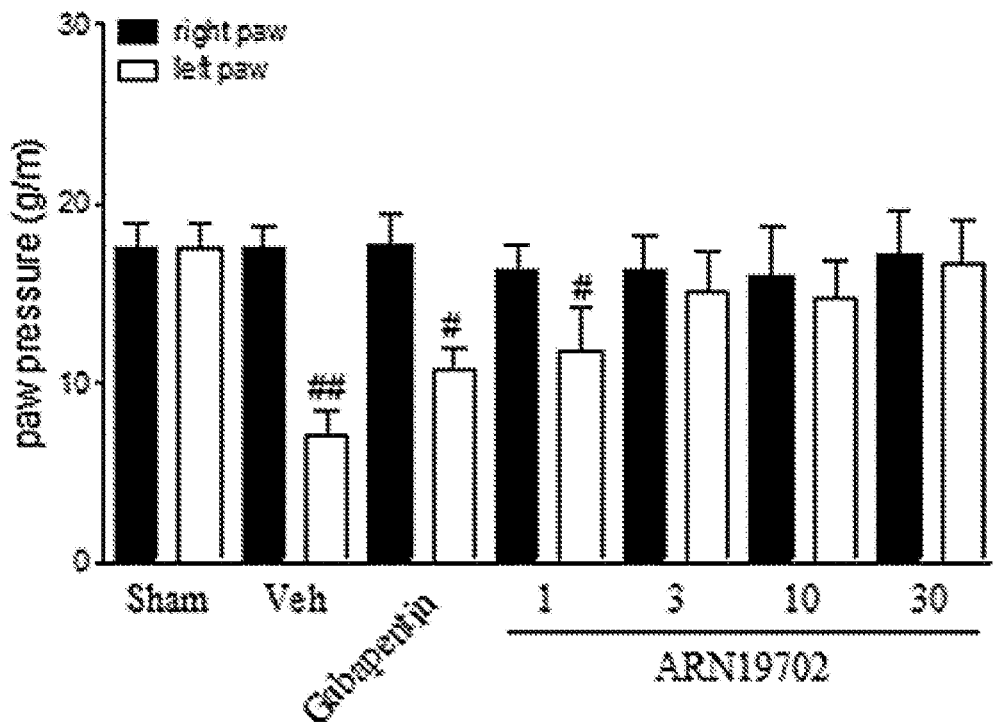
Figure 15:
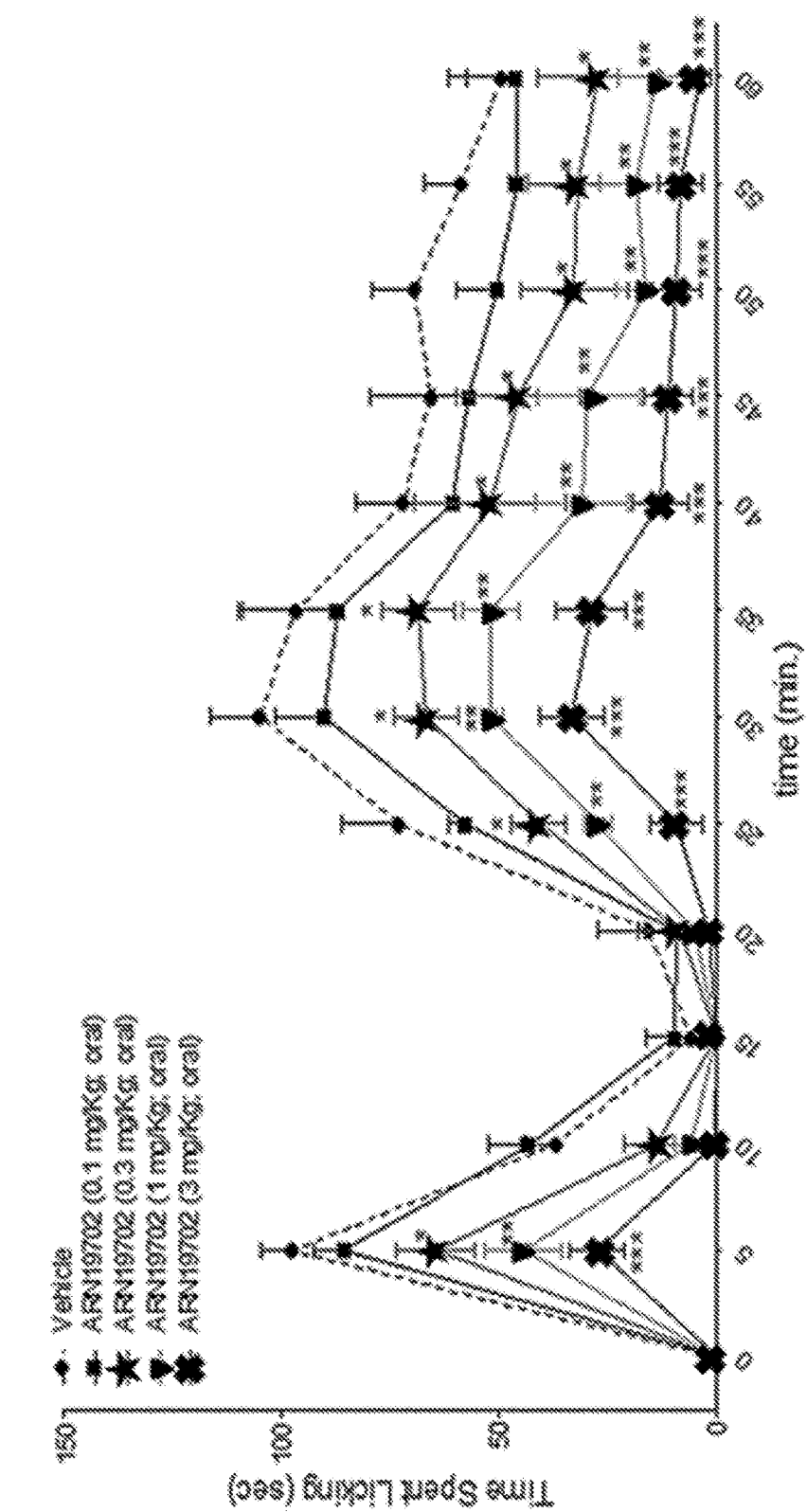
FIG. 15. Graph illustrating time-course of the effects of compound 19702 (single oral administration, 0.1-3 mg per kg) or vehicle on paw volume where acute pain was induced in male Swiss mice (20 g) by intraplantar injection of a dilute formalin solution. Pain-related behaviors were monitored following oral administration of compound 19702 (dose expressed in mg per kg) or its vehicle. * P<0.05;  P<0.01; * P<0.001.
Figure 16:
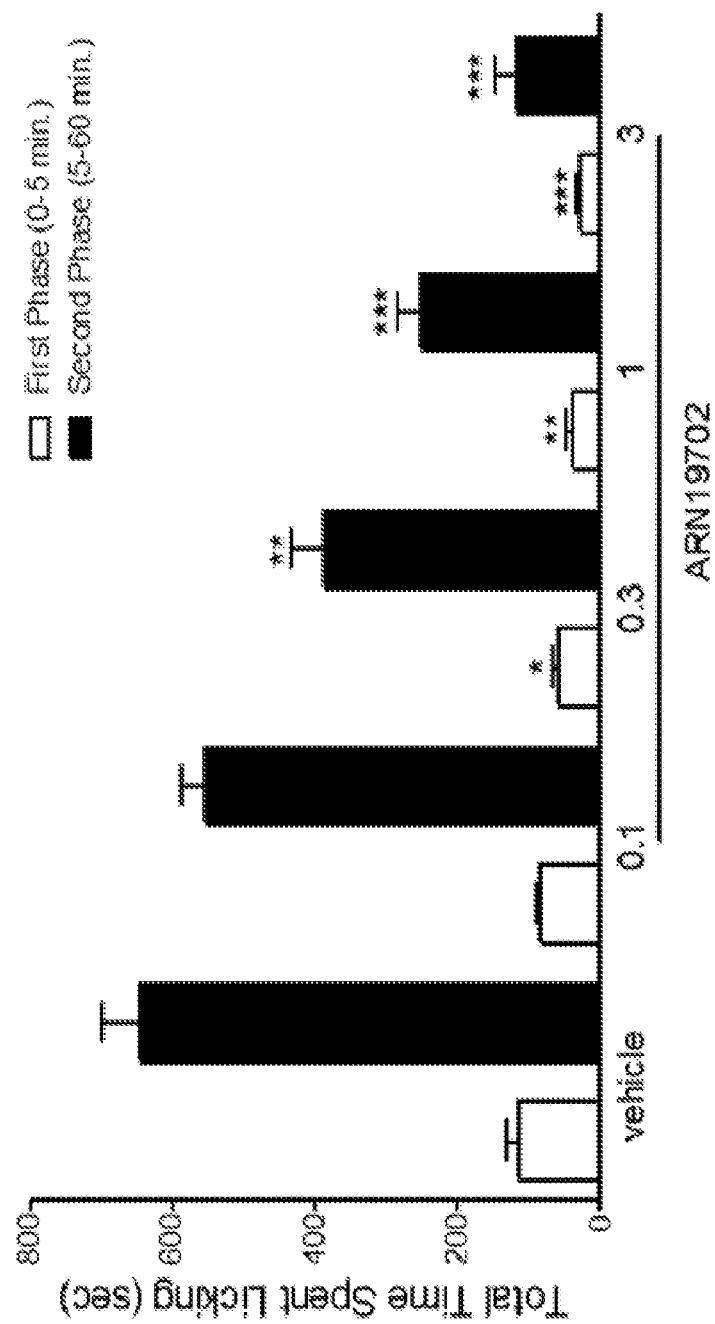
FIG. 16. Histogram illustrating time-course of the effects of compound 19702 (single oral administration, 0.1-3 mg per kg) or vehicle on paw volume where acute pain was induced in male Swiss mice (20 g) by intraplantar injection of a dilute formalin solution. Pain-related behaviors were monitored following oral administration of compound 19702 (dose expressed in mg per kg) or its vehicle. * P<0.05;  P<0.01; * P<0.001.
Figure 17:
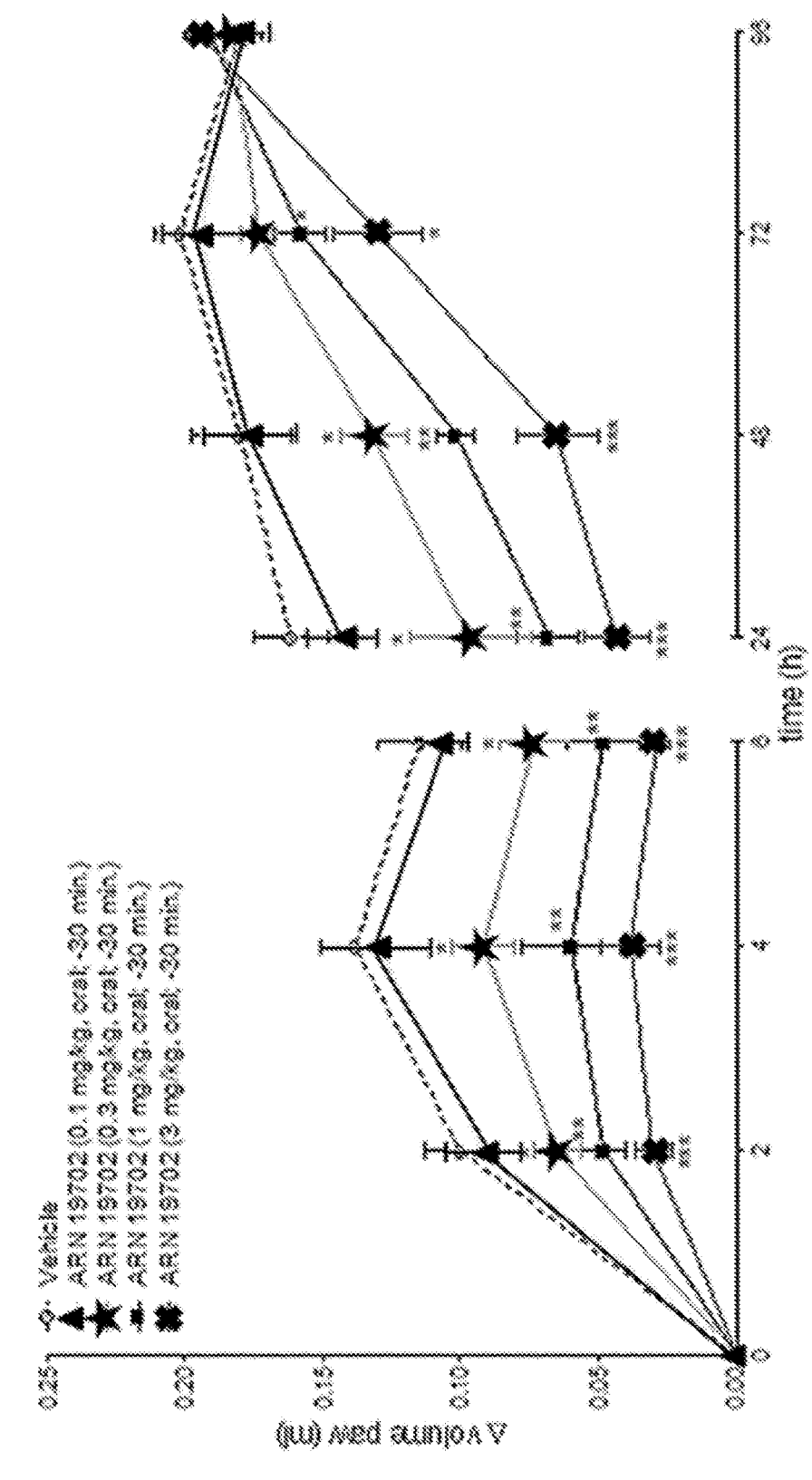
FIG. 17. Graph illustrating time-course of the effects of compound 19702 (single oral administration, 0.1-3 mg per kg, given 30 min before carrageenan) or vehicle on paw edema. Inflammatory edema and pain was induced in male Swiss mice (20 g) by intraplantar injection of carrageenan, and edema and pain-related behaviors were monitored following oral administration of compound 19702 (dose expressed in mg per kg) or its vehicle. * P<0.05;  P<0.01; * P<0.001.
Figure 18A:
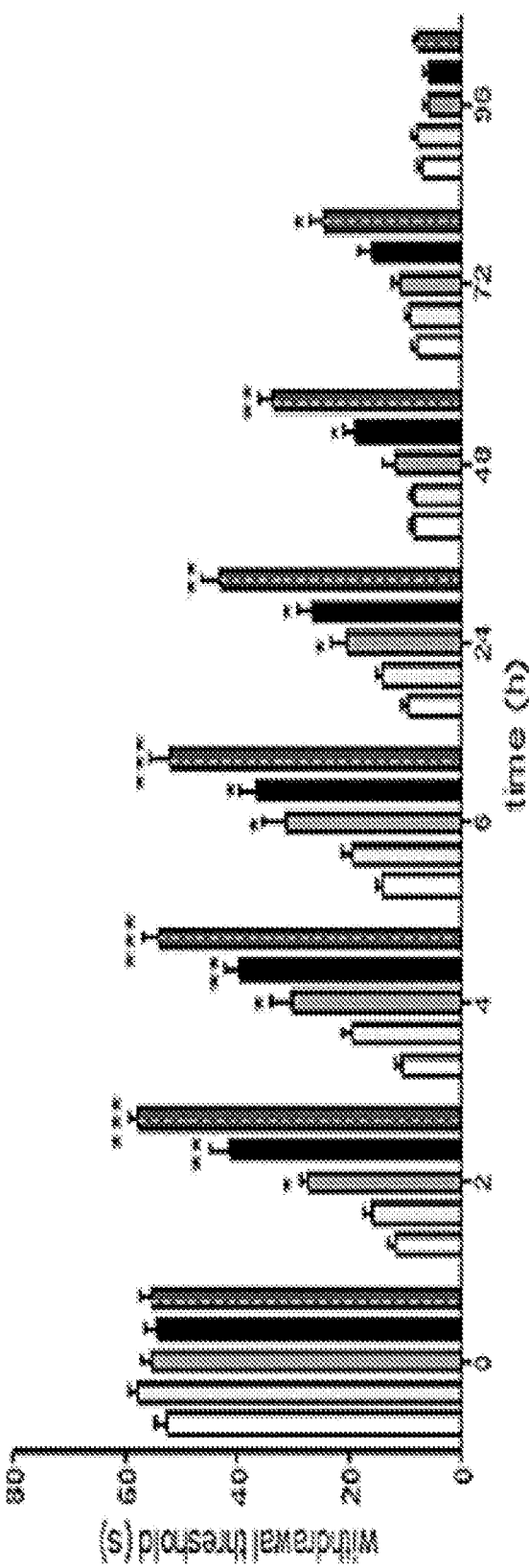
FIGS. 18A-18B. Histograms illustrating time-course of the effects of oral administration of compound 19702 or its vehicle (single oral administration of 0.1 mg/kg, 0.3 mg/kg, 1 mg/kg and –3 mg/kg, given 30 min before carrageenan) on mechanical allodynia (FIG. 18A) and thermal hyperalgesia (FIG. 18B). Inflammatory edema and pain was induced in male Swiss mice (20 g) by intraplantar injection of carrageenan, and edema and pain-related behaviors were monitored following oral administration of compound 19702 (dose expressed in mg per kg) or its vehicle. Respective histogram bins shown from left to right at time (h) 0, 2, 4, 6, 24, 48, 72 and 96 represent vehicle, 0.1 mg/kg compound 19702, 0.3 mg/kg compound 19702, 1 mg/kg compound 19702, and 3 mg/kg compound 19702, respectively. * P<0.05;  P<0.01; * P<0.001.
Figure 18B:
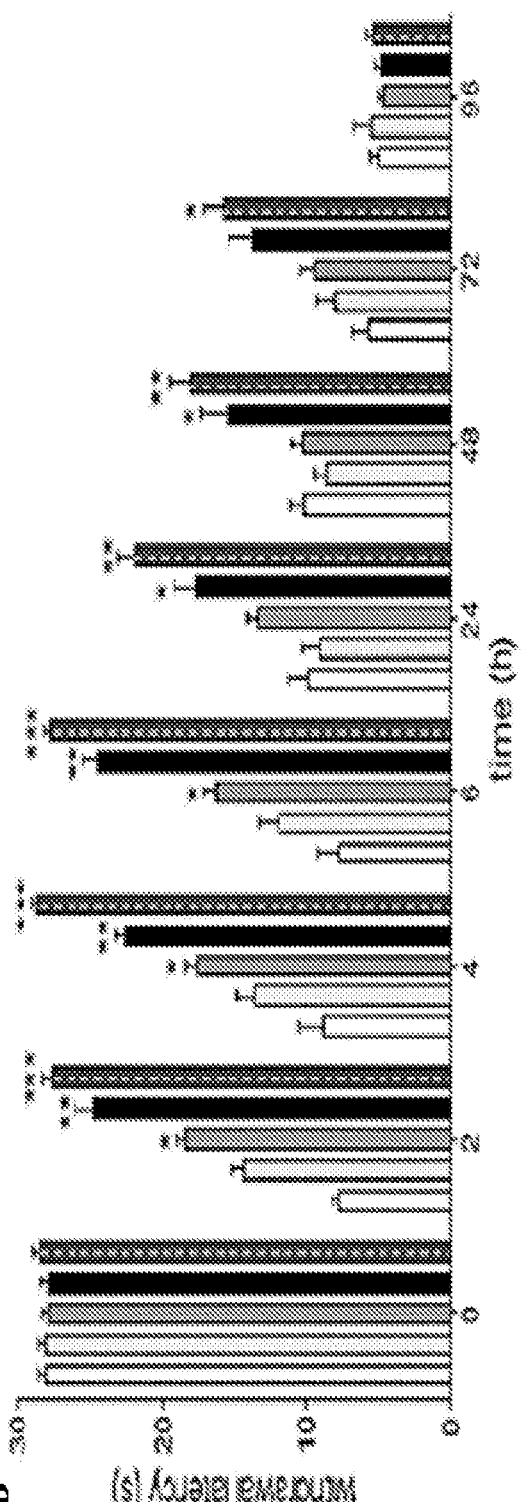
Figure 19:
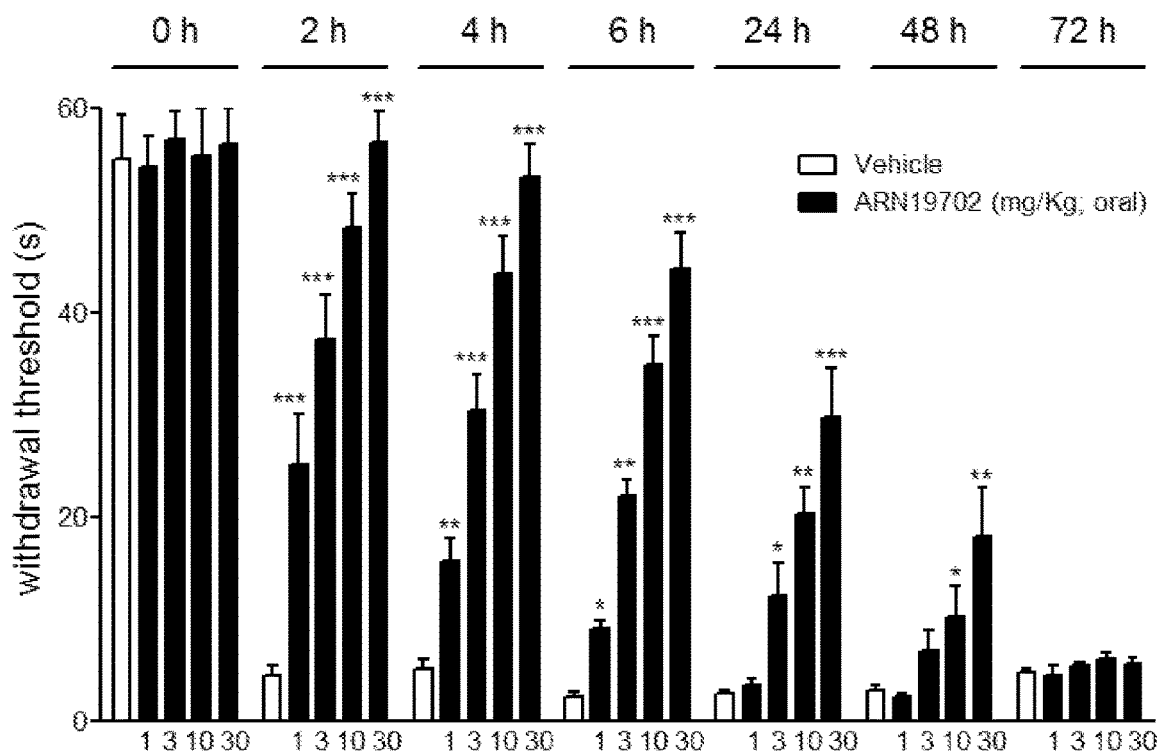
FIGS. 19-21. Histograms illustrating time-course of the effects of compound 19702 (single oral administration, 1-30 mg per kg) or vehicle on acute pain induced by performing a surgical cut on the right hind paw of male Swiss mice (20 g). Pain-related behaviors were monitored following oral administration of compound 19702 (dose expressed in mg per kg) or its vehicle on mechanical hyperalgesia (FIG. 19), thermal (heat) hyperalgesia (FIG. 20) and mechanical allodynia (FIG. 20). * P<0.05;  P<0.01; * P<0.001.
Figure 20:
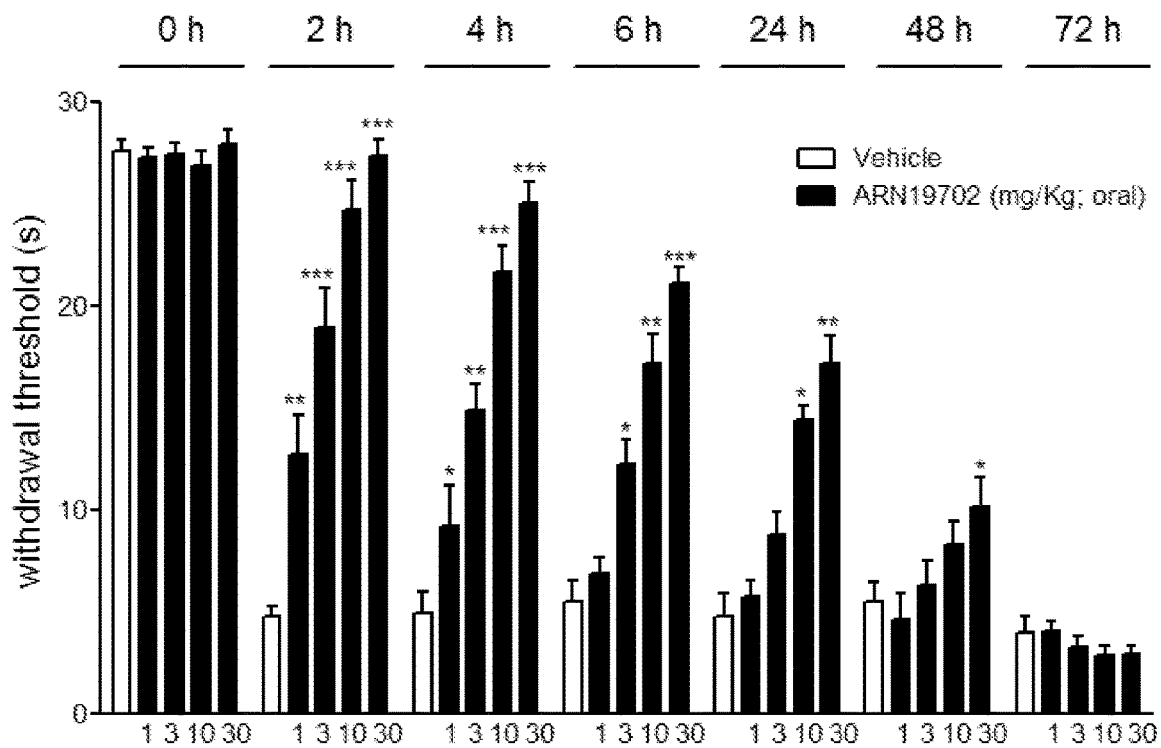
Figure 21:
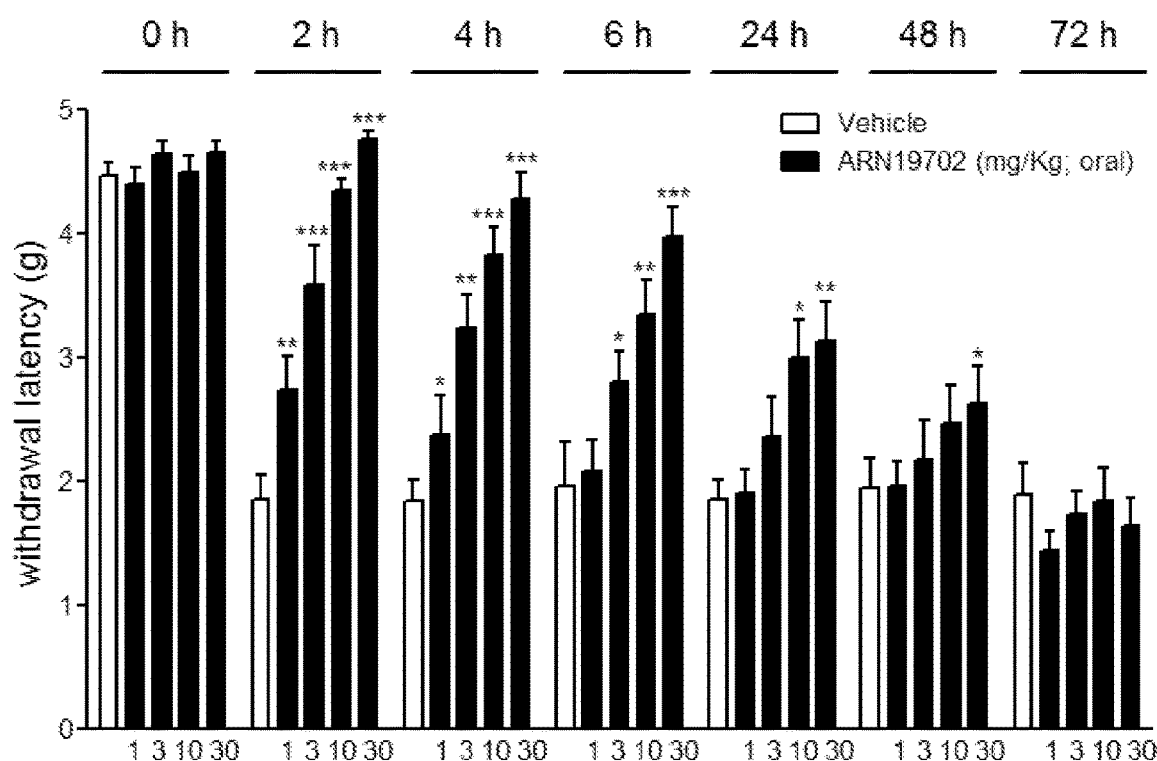

To support this work, a convergent and easily scalable synthesis was developed, as described in Scheme 1.

human (h) NAAA (2 μM) was incubated with 8 (50 μM), the samples were digested with trypsin, and then searched for covalent adducts using liquid chromatography mass spectrometry (LC-MS). The β-lactam 4 (20 μM) was included as a positive control, whose covalent interaction with NAAA is documented. [8] Incubating hNAAA with 4 yielded the expected acylated peptide, whereas no such adduct was found when the enzyme was exposed to either 8 or its vehicle (FIG. 3A). Similarly, no covalent adducts were retrieved by a search through the entire peptide map of NAAA (FIG. 6). Second, purified hNAAA (4.0 μM) was incubated with 4 or 8 (1.0 μM), precipitated the protein, and then measured the compounds in the supernatant by LC-MS. Whereas 4 was quantitatively precipitated with the enzyme, as expected from its covalent binding to NAAA, 8 was entirely recovered in the supernatant (FIG. 3B). Third, we

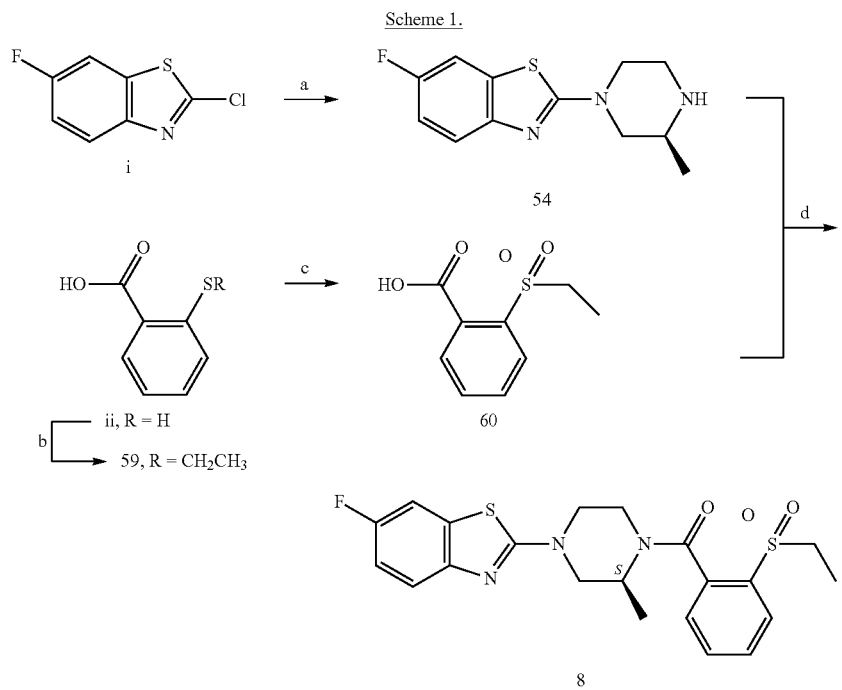

a) (2S)-2-methylpiperazine, NaHCO$_3$, EtOH/H$_2$O, reflux, 15 h, quant.;
b) EtI, 2M NaOH, EtOH, rt, 15 h, quant.;
c) Oxane, H$_2$O, 40° C., 15 h, 96%;
d) HATU, Et$_3$N, CH$_3$CN, rt, 15 h, 43%.

Figure 3C:
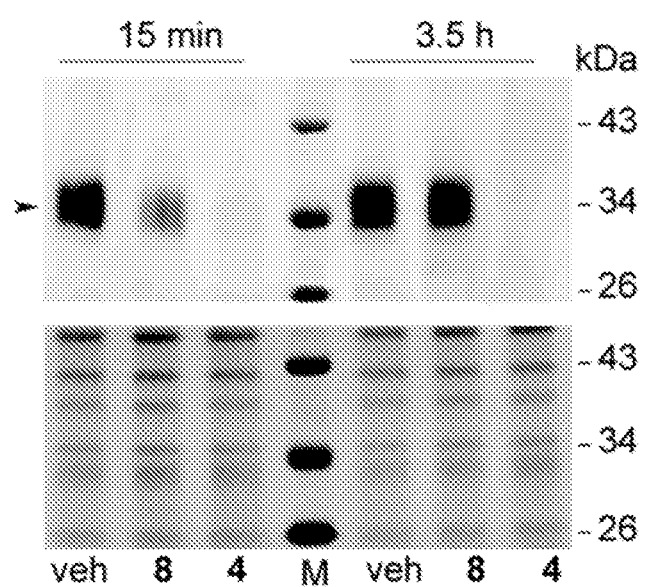
FIG. 3C. Photographs of chromatography gels [top: fluorescence data; bottom, Coomassie blue staining (loading control)] illustrating lysosomal extracts of hNAAA-overexpressing HEK293 cells that were incubated with vehicle (2% DMSO), 4 or 8 for 2 h before addition of probe 5. A rhodamine fluorophore was inserted by click chemistry. The arrowhead indicates NAAA band.
Figure 4A:
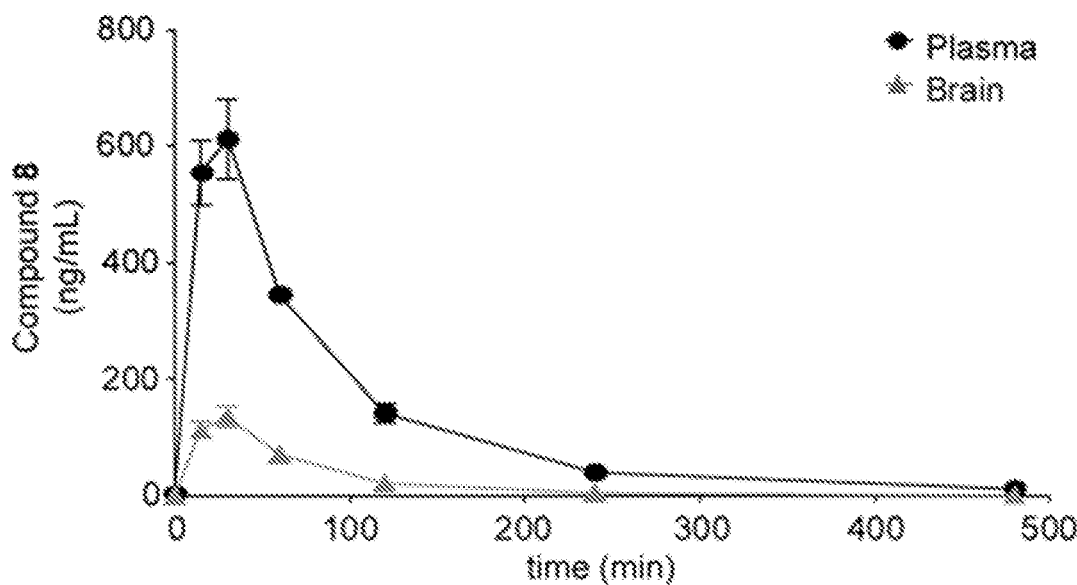
FIGS. 4A-4B. Pharmacokinetic and pharmacodynamic profiles of compound 8 in mice.
Figure 4B:
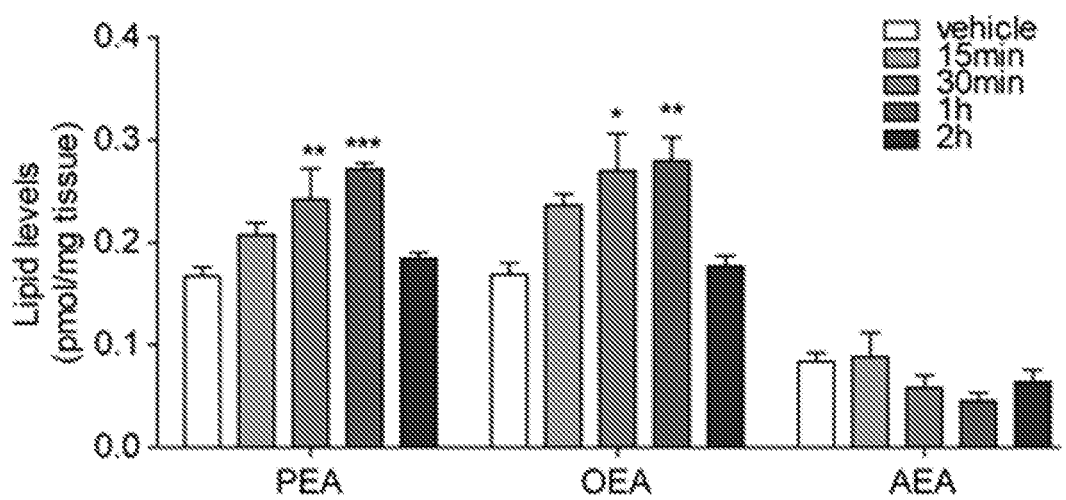

Current NAAA inhibitors react covalently with the enzyme's catalytic cysteine. To probe the interaction of 8 with NAAA, four approaches were utilized. First, purified assessed whether 8 prevents the binding of the covalent activity-based probe 5 to NAAA [9]5 strongly labeled hNAAA in cell extracts, and this effect was blocked by preincubation with 4 (FIG. 3C). By contrast, preincubation with compound 8 antagonized NAAA labeling by 5 only partially and at short incubation times (FIG. 3C), which is again consistent with a reversible interaction. Lastly, kinetic analyses revealed that 8 inhibits NAAA via an uncompetitive mechanism (FIG. 8). Together, these results identified compound 8 as a non-covalent NAAA inhibitor.

The unprecedented mechanism of action of 8 led to unexpected and surprising usefulness of the compound as an oral agent. In vitro studies demonstrated that 8 is soluble in aqueous buffer (pH 7.4) and is stable in mouse plasma (Table 5). Similarly, 8 is stable in mouse liver microsomes (MLM) supplemented with appropriate cofactors.

TABLE 5

Water solubility and in vitro metabolic stability of 8. The abbreviation NADPH represents reduced nicotinamide adenine dinucleotide phosphate; PBS represents phosphate-buffered saline; $t_{1/2}$ represents terminal half-life in minutes; UDPG represents uridine diphosphate glucose.

| | |
|---|---|
| Solubility in PBS | 165 μM |
| Plasma | $t_{1/2}$ > 120 min |
| MLM (NADPH) | $t_{1/2}$ > 60 min |
| MLM (UDPG) | $t_{1/2}$ > 60 min |

Figure 5A:
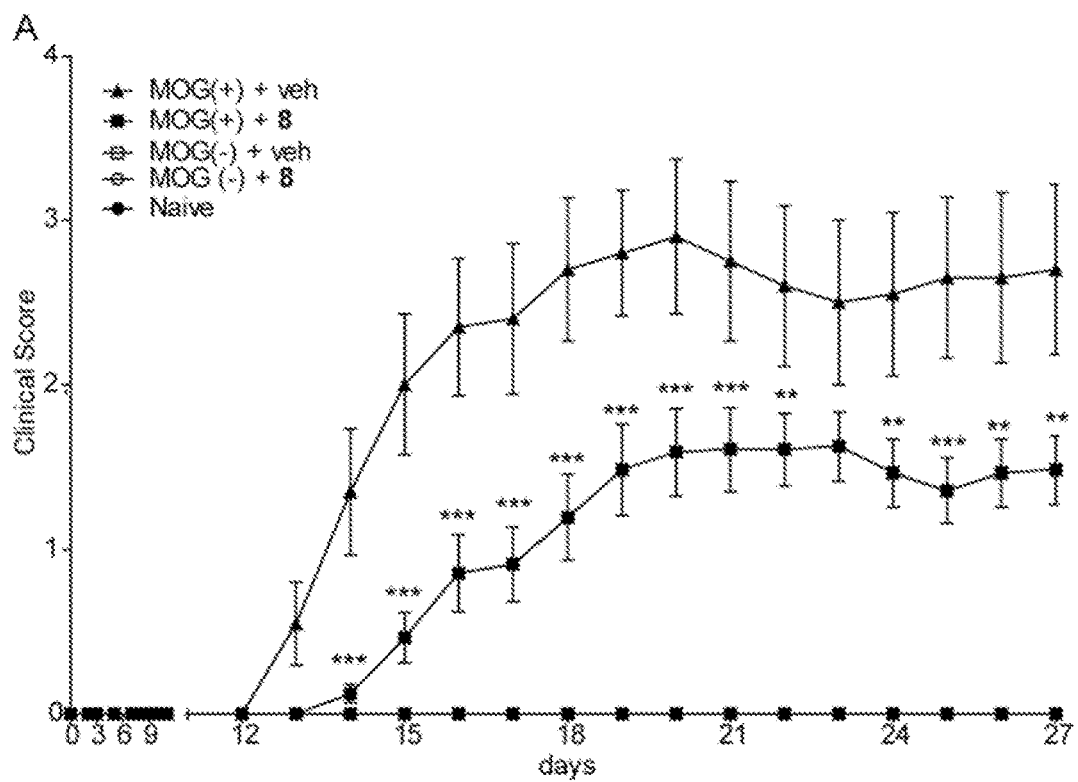
FIGS. 5A-5B. Graphs illustrating time-course of the effects of compound 8 or vehicle on clinical score (FIG. 5A) and body weight (FIG. 5B) in experimental allergic encephalomyelitis (EAE) mice and sham-immunized controls. Results are expressed as mean±SEM, n=30. * $P<0.05$; $P<0.01$; *$P<0.001$, two-way way ANOVA followed by Bonferroni post hoc test.

Experiments in mice showed that 8 is rapidly and extensively absorbed following oral administration (FIG. 5A). The pharmacokinetic parameters listed in Table 6 indicate excellent oral bioavailability and adequate terminal half-life. Terminal half-life is considerate to be adequate because it is sufficient to transiently elevate PEA and OEA levels in the brain.

TABLE 6

Pharmacokinetics of orally administered 8 (3 mg/kg) in mice. The abbreviation AUC refers to area under the curve; $C_{max}$ refers to maximal plasma concentration; F % refers to fractional absorption, calculated by comparison with intravenous 8 (3 mg/kg); $T_{max}$ refers to time (min) at which $C_{max}$ is reached.

| | |
|---|---|
| $C_{max}$ (ng/mL) | 613 |
| $T_{max}$ (min) | 30 |
| $t_{1/2}$ (min) | 104 |
| $AUC_{plasma}$ (h × ng/mL) | 988 |
| $AUC_{brain}$ (h × ng/mL) | 181 |
| F % | 72 |

Figure 5B:
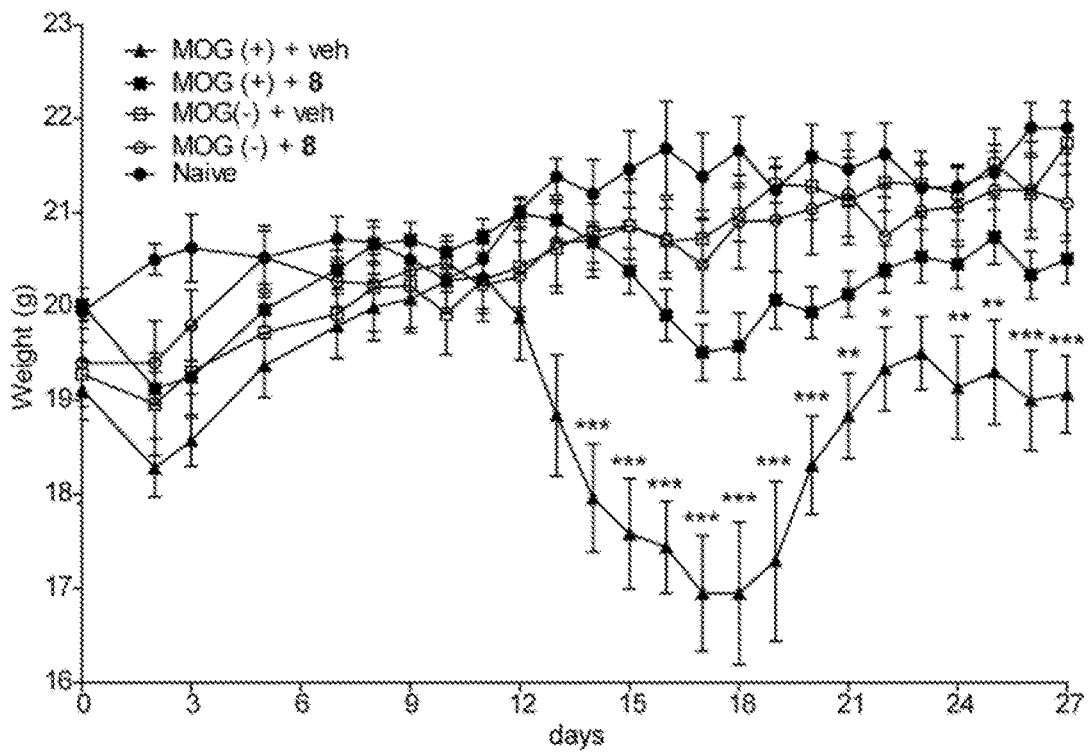

Importantly, compound 8 crossed the blood-brain barrier, reaching a brain-to-plasma ratio of 0.25 and causing a substantial, reversible accumulation of PEA and OEA in brain tissue (FIGS. 5A-5B). No changes were seen instead in the levels of anandamide, an endocannabinoid lipid amide that is degraded by fatty acid amide hydrolase (FAAH) rather than by NAAA.[3]

An initial target selectivity screen showed that 8 (10 μM) had little or no effect on a panel of >50 common receptors, ion channels and neurotransmitter transporters (Table 8). Moreover, as expected from the target engagement studies reported in FIG. 5B, 8 had a weak inhibitory effect on FAAH ($IC_{50} \approx 10$ μM),[10] and no effect on either acid ceramidase, a cysteine amidase that has 33-34% sequence identity with NAAA[1] or monoacylglycerol lipase, a serine esterase that degrades the endocannabinoid ester, 2-arachidonoyl-sn-glycerol.[11]

TABLE 8

Assays were performed at Eurofins (Paris, France). $AT_1$, angiotensin receptor 1; $A_1$, $A_{2a}$, $A_3$, adenosine receptor 1, 2a and 3; BZD, benzodiazepine; $B_2$, bradykinin receptor 2; $CB_1$, cannabinoid receptor 1; $CCK_1$, cholecystokinin A; C; CXCR2, interleukin $8_\beta$; $D_1$, $D_{2s}$, dopamine receptor 1, 2s; $EP_4$, prostaglandin $E_2$ receptor 4; $ET_A$, endothelin receptor A; GABA, γ-aminobutyric acid; $GAL_2$, galactose transporter; $H_1$, $H_2$, histamine receptor 1, 2; 5-HT, serotonin receptor; $K_V$, potassium channel V; $M_1$, $M_2$, $M_3$, muscarinic receptor 1, 2 and 3; $MC_4$, melanocortin-4 receptor; $MT_1$, melatonin receptor 1; $NK_2$, $NK_3$, neurokinin receptor 2 and 3; NOP, nociception receptor; $NTS_1$, neurotensin receptor 1; $OX_1$, $OX_2$, orexin receptor 1 and 2, $SK_{Ca}$, small conductance calcium-activated potassium channels; sst, somatostatin receptor; TP, tromboxane receptor; TRH1, thyrotropin-releasing hormone receptor; TRPV1, vanilloid receptor; $V_{1a}$, vasopressin receptor $1_a$; $VPAC_1$, vasoactive intestinal peptide (VIP) receptor 1; $Y_1$, $Y_2$, neuropeptide Y receptor 1 and 2; $\alpha_1$, $\alpha_2$, $\beta_1$, $\beta_2$, adrenergic receptor $\alpha_1$, $\alpha_2$, $\beta_1$ and $\beta_2$; $\delta_2$, δ-opioid receptor 2. κ, κ-opioid receptor; μ, μ-opioid receptor.

| Target | Reference | 1st | 2nd | Mean |
|---|---|---|---|---|
| $A_1$ (h) (antagonist radioligand) | DPCPX | −7.5 | 6.4 | −0.5 |
| $A_{2A}$ (h) (agonist radioligand) | NECA | 9.9 | 6.1 | 8 |
| $A_3$ (h) (agonist radioligand) | IB-MECA | 34.7 | 36.1 | 35.4 |
| $\alpha_1$ (non-selective) (antagonist radioligand) | prazosin | −2.2 | 6 | 1.9 |
| $\alpha_2$ (non-selective) (antagonist radioligand) | yohimbine | 5.6 | 11.3 | 8.5 |
| $\beta_1$ (h) (agonist radioligand) | atenolol | −4.4 | 4.9 | 0.2 |
| $\beta_2$ (h) (agonist radioligand) | ICI 118551 | 11.3 | 15.6 | 13.4 |
| $AT_1$ (h) (antagonist radioligand) | saralasin | 13 | 9.5 | 11.2 |
| BZD (central) (agonist radioligand) | diazepam | −0.8 | −2.6 | −1.7 |
| $B_2$ (h) (agonist radioligand) | NPC 567 | −10.1 | 2.4 | −3.8 |
| $CB_1$ (h) (agonist radioligand) | CP 55940 | 13.3 | 13.9 | 13.6 |
| $CCK_1$ (CCKA) (h) (agonist radioligand) | CCK-8s | 20.6 | 16.6 | 18.6 |
| $D_1$ (h) (antagonist radioligand) | SCH 23390 | −18.1 | 1.7 | −8.2 |
| $D_{2S}$ (h) (antagonist radioligand) | (+)butaclamol | −1.8 | 6.8 | 2.5 |
| $ET_A$ (h) (agonist radioligand) | endothelin-1 | −17.1 | −15.6 | −16.4 |
| GABA (non-selective) (agonist radioligand) | GABA | 3.5 | 1.5 | 2.5 |
| $GAL_2$ (h) (agonist radioligand) | galanin | 3.7 | −8.2 | −2.2 |
| CXCR2 (IL-8B) (h) (agonist radioligand) | IL-8 | 6.1 | 3.5 | 4.8 |

TABLE 8-continued

Assays were performed at Eurofins (Paris, France). $AT_1$, angiotensin receptor 1; $A_1$, $A_{2a}$, $A_3$, adenosine receptor 1, 2a and 3; BZD, benzodiazepine; $B_2$, bradykinin receptor 2; $CB_1$, cannabinoid receptor 1; $CCK_1$, cholecystokinin A; C; CXCR2, interleukin $8_\beta$; $D_1$, $D_{2s}$, dopamine receptor 1, 2s; $EP_4$, prostaglandin $E_2$ receptor 4; $ET_A$, endothelin receptor A; GABA, γ-aminobutyric acid; $GAL_2$, galactose transporter; $H_1$, $H_2$, histamine receptor 1, 2; 5-HT, serotonin receptor; $K_V$, potassium channel V; $M_1$, $M_2$, $M_3$, muscarinic receptor 1, 2 and 3; $MC_4$, melanocortin-4 receptor; $MT_1$, melatonin receptor 1; $NK_2$, $NK_3$, neurokinin receptor 2 and 3; NOP, nociception receptor; $NTS_1$, neurotensin receptor 1; $OX_1$, $OX_2$, orexin receptor 1 and 2, $SK_{Ca}$, small conductance calcium-activated potassium channels; sst, somatostatin receptor; TP, tromboxane receptor; TRH1, thyrotropin-releasing hormone receptor; TRPV1, vanilloid receptor; $V_{1a}$, vasopressin receptor $1_a$; $VPAC_1$, vasoactive intestinal peptide (VIP) receptor 1; $Y_1$, $Y_2$, neuropeptide Y receptor 1 and 2; $α_1$, $α_2$, $β_1$, $β_2$, adrenergic receptor $α_1$, $α_2$, $β_1$ and $β_2$; $δ_2$, δ-opioid receptor 2. κ, κ-opioid receptor; μ, μ-opioid receptor.

| Target | Reference | 1st | 2nd | Mean |
|---|---|---|---|---|
| $H_1$ (h) (antagonist radioligand) | pyrilamine | 5.4 | 5.7 | 5.6 |
| $H_2$ (h) (antagonist radioligand) | cimetidine | 17.4 | 25.9 | 21.6 |
| $MC_4$ (h) (agonist radioligand) | NDP-α-MSH | 8.3 | 13 | 10.7 |
| $MT_1$ ($ML_{1A}$) (h) (agonist radioligand) | melatonin | 52.6 | 43.8 | 48.2 |
| $M_1$ (h) (antagonist radioligand) | pirenzepine | −6.3 | 0.4 | −2.9 |
| $M_2$ (h) (antagonist radioligand) | methoctramine | −5.6 | 5.6 | 0 |
| $M_3$ (h) (antagonist radioligand) | 4-DAMP | 1.8 | 5.6 | 3.7 |
| $NK_2$ (h) (agonist radioligand) | [Nleu$^{10}$]-NKA (4-10) | 22.6 | 27.5 | 25.1 |
| $NK_3$ (h) (antagonist radioligand) | SB 222200 | −3.7 | 29.1 | 12.7 |
| $Y_1$ (h) (agonist radioligand) | NPY | 6.2 | −7.7 | −0.7 |
| $Y_2$ (h) (agonist radioligand) | NPY | 11.1 | 9.9 | 10.5 |
| $NTS_1$ ($NT_1$) (h) (agonist radioligand) | neurotensin | 5.3 | −0.8 | 2.3 |
| $δ_2$ (DOP) (h) (agonist radioligand) | DPDPE | 0 | 1.6 | 0.8 |
| κ (KOP) (agonist radioligand) | U 50488 | 71.2 | 68.4 | 69.8 |
| μ (MOP) (h) (agonist radioligand) | DAMGO | 78.9 | 75 | 76.9 |
| NOP (ORL1) (h) (agonist radioligand) | nociceptin | 5.4 | 4 | 4.7 |
| $EP_4$ (h) (agonist radioligand) | $PGE_2$ | 9.2 | 14.8 | 12 |
| $5-HT_{1A}$ (h) (agonist radioligand) | 8-OH-DPAT | −5 | 4.5 | −0.3 |
| $5-HT_{1B}$ (antagonist radioligand) | serotonin | 6.4 | 3 | 4.7 |
| $5-HT_{2A}$ (h) (antagonist radioligand) | ketanserin | 33 | 30.8 | 31.9 |
| $5-HT_{2B}$ (h) (agonist radioligand) | (±)DOI | 95.1 | 85.6 | 90.4 |
| $5-HT_{3}$ (h) (antagonist radioligand) | MDL 72222 | −4.8 | 29.9 | 12.6 |
| $5-HT_{5a}$ (h) (agonist radioligand) | serotonin | 17.7 | 19 | 18.3 |
| $5-HT_6$ (h) (agonist radioligand) | serotonin | −27 | −17.7 | −22.4 |
| $5-HT_7$ (h) (agonist radioligand) | serotonin | −5.5 | 3.5 | −1 |
| sst (non-selective) (agonist radioligand) | somatostatin-14 | −2 | 4.1 | 1.1 |
| $VPAC_1$ (VIP1) (h) (agonist radioligand) | VIP | −3.7 | −14.9 | −9.3 |
| V1 a (h) (agonist radioligand) | [d(CH$_2$)$_5$ $^1$, Tyr(Me)$_2$]-AVP | −6.4 | 13.1 | 3.3 |
| Ca$^{2+}$ channel (L, verapamil site) (phenylalkylamine) (antagonist radioligand) | D 600 | 2.2 | 12.1 | 7.2 |
| $K_V$ channel (antagonist radioligand) | α-dendrotoxin | −1.3 | 7 | 2.8 |
| $SK_{Ca}$ channel (antagonist radioligand) | apamin | 6.1 | −7.8 | −0.9 |
| Na+ channel (site 2) (antagonist radioligand) | veratridine | 16.4 | 25.1 | 20.7 |
| Cl- channel (GABA-gated) (antagonist radioligand) | picrotoxinin | 38.1 | 33 | 35.5 |
| norepinephrine transporter (h) (antagonist radioligand) | protriptyline | 13.4 | 7.1 | 10.3 |
| dopamine transporter (h) (antagonist radioligand) | BTCP | −8.1 | 5.1 | −1.5 |
| 5-HT transporter (h) (antagonist radioligand) | imipramine | 57.3 | 56.2 | 56.8 |
| $OX_1$ (h) (antagonist effect) | SB 334867 | 11.4 | 10.0 | 10.0 |
| $OX_2$ (h) (antagonist effect) | JNJ 10397049 | 47.9 | 55.2 | 51.5 |

MS is a chronic neuroinflammatory disorder accompanied by alterations in cerebrospinal and plasma levels of PEA and OEA.[8,12] Because PEA administration attenuates spasticity in the experimental allergic encephalomyelitis (EAE) model of MS,[13] we tested whether accrual of intrinsic PEA/OEA signaling by treatment with compound 8 is beneficial in this model. EAE mice and sham-immunized controls were treated with 8 (30 mg/kg, twice daily) or its vehicle for 28 days while recording clinical scores and body weight gain. Treatment with compound 8 had no effect on sham-immunized mice, whereas it delayed the onset of disease symptoms, attenuated their intensity, and normalized body weight gain in EAE animals. Moreover, 8 reduced mononuclear cells infiltration and microglia activation in spinal cord of EAE mice (FIG. 8), two key neuroanatomical correlates of disease.

In embodiments, the present example describes a novel class of benzothiazole piperazine derivatives that inhibit NAAA activity. In embodiments, the compounds inhibit NAAA activity through a non-covalent and uncompetitive mechanism. A representative member of this class, 8, shows excellent oral PK properties, good brain penetration (e.g., ability to cross the blood brain barrier) and strong protective activity in a validated mouse model of MS. This agent exemplifies a new generation of non-covalent NAAA inhibitors that may find therapeutic applications in the treatment of neuroinflammatory disorders such as MS.

Example 2. General Experimental Details

Solvents and reagents were obtained from commercial suppliers and were used without further purification. For simplicity, solvents and reagents were indicated as follows: acetonitrile ($CH_3CN$), ammonium chloride ($NH_4Cl$), 1-[bis-(dimethylamino)methylene]-1H-1,2,3-triazolo[4,5-b]pyridinium 3-oxide hexafluorophosphate (HATU), butyl lithium (nBuLi), cesium carbonate ($Cs_2CO_3$), cyclohexane (Cy), dichloromethane (DCM), diethyl ether ($Et_2O$), dimethylsulfoxide (DMSO), ethanol (EtOH), ethyl acetate (EtOAc), hydrochloric acid (HCl), lithium aluminium hydride (LiAlH$_4$), methanesulfonyl chloride (MsCl), methanol (MeOH), N,N-dimethylformamide (DMF), N-methylpyrrolidone (NMP), potassium carbonate ($K_2CO_3$), potassium peroxymonosulfate (Oxone™), potassium tert butoxide (tBuOK), room temperature (rt), sodium bicarbonate ($NaHCO_3$), sodium carbonate ($Na_2CO_3$), sodium hydroxide (NaOH), tetrahydrofuran (THF), toluene (Tol), triethylamine ($Et_3N$), water ($H_2O$).

Automated column chromatography purifications were done using a Teledyne ISCO apparatus (CombiFlash® Rf) with pre-packed silica gel columns of different sizes (from 4 g until 120 g). Mixtures of increasing polarity of Cy and EtOAc or DCM and MeOH were used as eluents. TLC analyses were performed using Supelco silica gel on TLC Al foils 0.2 mm with fluorescence indicator 254 nm.

NMR experiments were run on a Bruker Avance III 400 system (400.13 MHz for $^1$H, and 100.62 MHz for $^{13}$C), equipped with a BBI probe and Z-gradients. Spectra were acquired at 300 K, using deuterated dimethylsulfoxide (DMSO-d$_6$) as solvent. Chemical shifts for $^1$H and $^{13}$C spectra were recorded in parts per million using the residual non-deuterated solvent as the internal standard (for DMSO-d$_6$: 2.50 ppm, $^1$H; 39.52 ppm, $^{13}$C). Data are reported as follows: chemical shift (ppm), multiplicity (indicated as: bs, broad signal; s, singlet; d, doublet; t, triplet; q, quartet; p, quintet, sx, sextet; m, multiplet and combinations thereof), coupling constants (J) in Hertz (Hz) and integrated intensity.

Accurate mass measurements were performed on a Synapt G2 Quadrupole-ToF Instrument (Waters, USA), equipped with an ESI ion source; compounds were diluted to 50 µM in $H_2O$/$CH_3CN$ and analyzed. Leucine Enkephalin (2 ng/mL) was used as lock mass reference compound for spectra calibration.

UPLC/MS analyses were run on a Waters ACQUITY UPLC/MS system consisting of a SQD (Single Quadropole Detector) Mass Spectrometer equipped with an Electrospray Ionization interface and a Photodiode Array Detector. PDA range was 210-400 nm. Analyses were performed on an ACQUITY UPLC BEH C18 column (50×2.1 mmID, particle size 1.7 m) with a VanGuard BEH C18 pre-column (5×2.1 mmID, particle size 1.7 µm). Mobile phase was either 10 mM NH$_4$OAc in $H_2O$ at pH 5 adjusted with AcOH. Electrospray ionization in positive and negative mode was applied. Analyses were performed with a gradient: 5 to 95% B over 3 min. Flow rate 0.5 mL/min. Temperature 40° C.

Optical rotations were measured on a Rudolf Research Analytical Autopol II Automatic polarimeter using a sodium lamp (589 nm) as the light source; concentrations expressed in g/100 mL using CHCl$_3$ as a solvent and a 1 dm cell. All final compounds displayed ≥95% purity as determined by NMR and UPLC/MS analysis.

General Procedure A.

To a solution of the appropriate piperazine (1.0 eq.) in EtOH (5 mL) was added NaHCO$_3$ (3.0 eq.) in H$_2$O (3 mL) followed by the addition of appropriate 2-chlorobenzothiazole (1.0 eq.). The reaction mixture was stirred at reflux for 15 h and, then, the solvent was evaporated under reduced pressure. The residue was then partitioned between EtOAc and H$_2$O and the organic phase was washed with brine and dried over Na$_2$SO$_4$. After evaporation of the solvent, the crude was purified by column chromatography, eluting with Cy/EtOAc or DCM/MeOH as indicated in each case.

General Procedure B.

To a solution of the corresponding benzoic acid (1.0 eq.), Et$_3$N (1.1 eq.) and HATU (1.0 eq.) in CH$_3$CN (5 mL) the appropriate piperazine (0.5 eq.) was added after 5 min. The reaction was stirred at rt for 15 h, and, then, the solvent was evaporated under reduced pressure. The residue was then partitioned between EtOAc and H$_2$O, and the organic phase was washed with NaHCO$_3$, H$_2$O, brine, and dried over Na$_2$SO$_4$. After evaporation of the solvent, the crude was purified by column chromatography, eluting with Cy/EtOAc as indicated in each case.

General Procedure C.

To a solution of 2-sulfanylbenzoic acid (1.0 eq.) in EtOH (5 mL) the corresponding alkyl bromide or alkyl iodide (2.0 eq.) and 2M NaOH (2.0 eq.) were added. The mixture was stirred at rt for 15 h and, then, the solvent was evaporated under reduced pressure. The residue was then triturated in 2M HCl, filtered and dried under reduced pressure to obtain the corresponding 2-alkylsulfanylbenzoic acid.

General Procedure D.

To a suspension of appropriate 2-alkylsulfanylbenzoic acid (1.0 eq.) in H$_2$O (5 mL) Oxone (2.5 eq.) was added. The mixture was stirred at 40° C. for 15 h, then, cooled to rt and extracted with EtOAc. The combined organic layers were dried over Na$_2$SO$_4$. After evaporation of the solvent, the crude was used in the next step without further purification.

[4-(6-fluoro-1,3-benzothiazol-2-yl)piperazin-1-yl]-(o-tolyl)methanone (Herein Referred to as 7 or Compound 7)

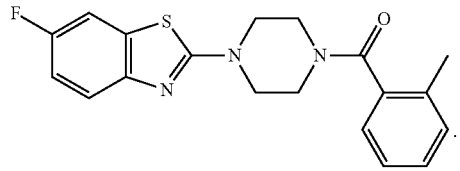

Compound 7 was prepared according to general procedure B using 43 and 2-methylbenzoic acid (34 mg, 0.25 mmol). The crude was purified by column chromatography (Cy: EtOAc, 50:50) to afford 7 as a white solid (60 mg, 68%). $^1$H NMR (400 MHz, DMSO-d$_6$) δ 7.74 (dd, J=8.7, 2.7, 1H), 7.46 (dd, J=8.8, 4.8, 1H), 7.33 (ddd, J=7.6, 6.7, 1.8, 1H), 7.29 (dd, J=7.6, 1.8, 1H), 7.25 (dd, J=6.7, 1.6, 1H), 7.23 (dd, J=7.5, 1.8, 1H), 7.13 (td, J=9.1, 2.7, 1H), 3.82 (bs, 2H), 3.74-3.60 (m, 2H), 3.60-3.47 (m, 2H), 3.32-3.27 (m, 2H), 2.24 (s, 3H). $^{13}$C NMR (101 MHz, DMSO-d$_6$) δ 168.7, 168.0, 157.3 (d, J=237.4), 148.9, 136.0, 133.8, 131.4 (d, J=11.2), 130.2, 128.8, 125.8, 125.8, 119.3 (d, J=8.8), 113.5 (d, J=23.7), 108.1 (d, J=27.5), 48.1, 47.7, 45.5, 40.2, 18.6.

UPLC-MS: 2.58 min, 356 [M+H]$^+$. HRMS C$_{19}$H$_{19}$FN$_3$OS [M+H]$^+$: calculated 356.1233 measured: 356.1241 Δppm 2.2.

(2-ethylsulfonylphenyl)-[(2S)-4-(6-fluoro-1,3-benzo-thiazol-2-yl)-2-methyl-piperazin-1-yl]methanone (Herein Referred to as 8 or Compound 8)

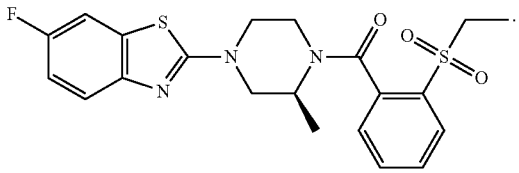 [SMILES: CCS(=O)(=O)c1ccccc1C(=O)N1CCN(c2nc3ccc(F)cc3s2)C[C@@H]1C]

Compound 8 was prepared according to general procedure B using 54 and 60 (56 mg, 0.26 mmol). The crude was purified by column chromatography (DCM:MeOH, 99:1) to afford 8 as a white solid (43 mg, 43%). $^1$H NMR (400 MHz, DMSO-d$_6$) δ 8.03-7.90 (m, 1H), 7.90-7.79 (m, 1H), 7.78-7.65 (m, 2H), 7.63-7.46 (m, 1H), 7.46-7.39 (m, 1H), 7.16-7.07 (m, 1H), 5.03-3.07 (m, 9H), 1.33-1.07 (m, 6H). $^{13}$C NMR (101 MHz, DMSO) (168.5, 167.5, 166.7, 158.4, 156.0, 149.0, 136.6, 136.4, 135.1, 134.4, 134.3, 131.3, 131.2, 130.6, 130.5, 130.2, 129.7, 129.6, 127.65, 127.0, 125.4, 123.1, 119.1, 119.0, 118.7, 115.3, 114.7, 113.6, 113.4, 111.8, 110.2, 108.2, 108.1, 107.7, 52.1, 51.8, 51.6, 51.1, 50.5, 50.4, 47.0, 46.9, 44.6, 44.2, 41.6, 41.5, 16.5, 15.7, 15.4, 14.6, 13.7, 6.8, 6.7. UPLC-MS: 2.26 min, 448 [M+H]$^+$. HRMS C$_{21}$H$_{23}$FN$_3$O$_3$S$_2$ [M+H]$^+$: calculated 448.1165 measured: 448.1177 Δppm 2.7. [α]$^{20}_D$=+390 (c 1.0, CHCl$_3$).

[4-(6-fluoro-1,3-benzothiazol-2-yl)piperazin-1-yl]-phenyl-methanone (Herein Referred to as 9 or Compound 9)

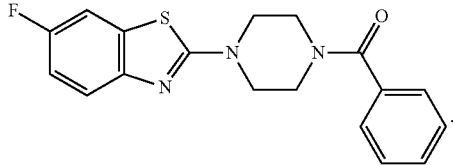 [SMILES: O=C(c1ccccc1)N1CCN(c2nc3ccc(F)cc3s2)CC1]

Compound 9 was prepared according to general procedure B using 43 and benzoic acid (26 mg, 0.21 mmol). The crude was purified by column chromatography (Cy:EtOAc, 50:50) to afford 9 as a white solid (64 mg, 88%). $^1$H NMR (400 MHz, DMSO-d$_6$) δ 7.74 (dd, J=8.7, 2.7, 1H), 7.52-7.42 (m, 6H), 7.14 (td, J=9.1, 2.8, 1H), 3.90-3.42 (m, 8H). $^{13}$C NMR (101 MHz, DMSO-d$_6$) δ 169.79, 168.53, 157.76 (d, J=237.3), 149.37, 135.98, 131.82 (d, J=11.5), 130.23, 128.97, 127.50, 119.80 (d, J=9.5), 114.06 (d, J=23.1), 108.62 (d, J=27.7), 48.89-47.81 (m), 47.42-46.48 (m), 41.75-41.15 (m). UPLC-MS: 2.38 min, 342 [M+H]$^+$. HRMS C$_{18}$H$_{17}$FN$_3$OS [M+H]$^+$: calculated 342.1076 measured: 342.1076 Δppm 0.

(2-chlorophenyl)-[4-(6-fluoro-1,3-benzothiazol-2-yl) piperazin-1-yl]methanone (Herein Referred to as 10 or Compound 10)

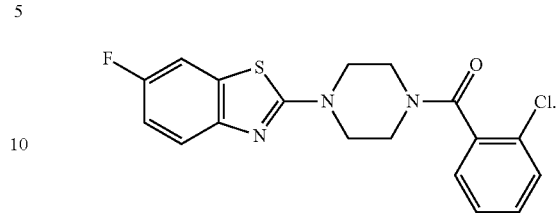

Compound 10 was prepared according to general procedure B using 43 and 2-chlorobenzoic acid (78 mg, 0.5 mmol). The crude was purified by column chromatography (Cy: EtOAc, 70:30) to afford 10 as a white solid (150 mg, 68%). $^1$H NMR (400 MHz, DMSO-d$_6$) δ 7.73 (dd, J=8.7, 2.7, 1H), 7.56 (dd, J=6.8, 1.7, 1H), 7.51-7.40 (m, 4H), 7.13 (td, J=9.1, 2.7, 1H), 3.82 (dq, J=13.1, 7.8, 6.6, 2H), 3.67 (t, J=5.2, 2H), 3.61-3.52 (m, 2H), 3.33-3.26 (m, 2H). $^{13}$C NMR (101 MHz, DMSO-d$_6$) δ 168.0, 165.8, 157.4 (d, J=237.7), 148.9, 135.4, 131.4 (d, J=11.3), 130.7, 129.5, 129.2, 128.1, 127.7, 119.4 (d, J=8.9), 113.6 (d, J=23.9), 108.2 (d, J=27.4), 48.0, 47.6, 45.5, 40.5. UPLC-MS: 2.34 min, 376 378 [M+H]$^+$. HRMS C$_{18}$H$_{16}$ClFN$_3$OS [M+H]$^+$: calculated 376.0687 measured: 376.0692 Δppm 1.3.

[4-(6-fluoro-1,3-benzothiazol-2-yl)piperazin-1-yl]-(2-fluorophenyl)methanone (Herein Referred to as 11 or Compound 11)

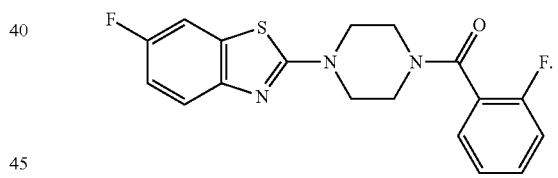

Compound 11 was prepared according to general procedure B using 43 and 2-fluorobenzoic acid (35 mg, 0.25 mmol). The crude was purified by column chromatography (Cy: EtOAc, 50:50) to afford 11 as a white solid (69 mg, 76%). $^1$H NMR (400 MHz, DMSO-d$_6$) δ 7.74 (dd, J=8.7, 2.7, 1H), 7.54 (dddd, J=8.5, 7.3, 5.5, 1.8, 1H), 7.50-7.43 (m, 2H), 7.37-7.28 (m, 2H), 7.13 (td, J=9.1, 2.7, 1H), 3.82 (t, J=5.2, 2H), 3.67 (t, J=5.3, 2H), 3.55 (dd, J=6.5, 4.0, 2H), 3.40 (t, J=5.2, 2H). 13C NMR (101 MHz, DMSO-d$_6$) δ 168.0, 164.2, 157.6 (d, J=246.1), 157.3 (d, J=237.7), 148.9, 131.7 (d, J=8.1), 131.4 (d, J=11.1), 128.9 (d, J=3.6), 125.0 (d, J=3.2), 123.7 (d, J=18.0), 119.3 (d, J=8.8), 115.9 (d, J=21.3), 113.6 (d, J=23.7), 108.2 (d, J=27.4), 48.1, 47.6, 45.8, 40.7. UPLC-MS: 2.52 min, 360 [M+H]$^+$. HRMS C$_{18}$H$_{16}$F$_2$N$_3$OS [M+H]$^+$: calculated 360.0982 measured: 360.0982 Δppm 0.

[4-(6-fluoro-1,3-benzothiazol-2-yl)piperazin-1-yl]-(2-methoxyphenyl)methanone (Herein Referred to as 12 or Compound 12)

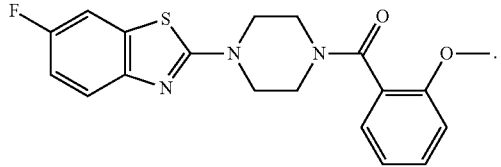 [SMILES: COc1ccccc1C(=O)N1CCN(c2nc3ccc(F)cc3s2)CC1]

Compound 12 was prepared according to general procedure B using 43 and 2-methoxybenzoic acid (32 mg, 0.21 mmol). The crude was purified by column chromatography (Cy:EtOAc, 30:70) to afford 12 as an off-white solid (60 mg, 78%). $^1$H NMR (400 MHz, DMSO-$d_6$) δ 7.73 (dd, J=8.7, 2.7, 1H), 7.46 (dd, J=8.8, 4.8, 1H), 7.42 (ddd, J=8.3, 7.4, 1.8, 1H), 7.24 (dd, J=7.4, 1.7, 1H), 7.13 (td, J=9.2, 2.8, 1H), 7.11 (dd, J=8.5, 0.8, 1H), 7.02 (td, J=7.4, 0.9, 1H), 3.81 (s, 3H), 3.80-3.72 (m, 2H), 3.68-3.60 (m, 2H), 3.53 (t, J=5.2, 1H), 3.29 (t, J=5.8, 1H). 13C NMR (101 MHz, DMSO-d6) δ 168.5, 167.2, 157.8 (d, J=237.5), 155.3, 149.3, 131.8 (d, J=9.6), 131.1, 128.3, 125.6, 121.2, 119.8 (d, J=9.6), 114.0 (d, J=24.2), 111.8, 108.6 (d, J=26.4), 55.9, 48.6, 48.2, 46.1, 40.9. UPLC-MS: 2.48 min, 372 [M+H]$^+$. HRMS $C_{19}H_{19}FN_3O_2S$ [M+H]$^+$: calculated 372.1182 measured: 372.118 Δppm −0.5.

[4-(6-fluoro-1,3-benzothiazol-2-yl)piperazin-1-yl]-(2-methylsulfonylphenyl)methanone (Herein Referred to as 13 or Compound 13)

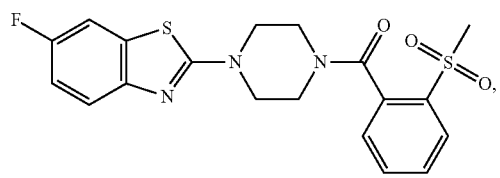 [SMILES: CS(=O)(=O)c1ccccc1C(=O)N1CCN(c2nc3ccc(F)cc3s2)CC1]

Compound 13 was prepared according to general procedure B using 43 and 2-methylsulfonylbenzoic acid (66 mg, 0.33 mmol). The crude was purified by column chromatography (DCM:MeOH, 90:10) to afford 13 as an off-white solid (80 mg, 60%). $^1$H NMR (400 MHz, DMSO-$d_6$) δ 8.02 (dd, J=7.9, 1.2, 1H), 7.84 (td, J=7.5, 1.3, 1H), 7.74 (td, J=7.7, 1.3, 1H), 7.74 (dd, J=8.8, 2.7, 1H), 7.58 (dd, J=7.5, 1.3, 1H), 7.47 (dd, J=8.8, 4.8, 1H), 7.14 (td, J=9.1, 2.7, 1H), 3.89 (ddd, J=12.8, 6.8, 3.5, 1H), 3.74 (td, J=12.1, 5.3, 2H), 3.67-3.48 (m, 3H), 3.43-3.19 (m, 2H), 3.30 (s, 3H). $^{13}$C NMR (101 MHz, DMSO-$d_6$) δ 167.5, 167.2, 157.5 (d, J=237.9), 149.0, 137.5, 135.9, 134.4, 131.5 (d, J=11.4), 130.1, 129.5, 127.7, 119.5 (d, J=8.9), 113.8 (d, J=23.7), 108.3 (d, J=27.7), 47.4, 46.3, 45.1, 40.8. UPLC-MS: 2.06 min, 420 [M+H]$^+$. HRMS $C_{19}H_{19}N_3O_3FS_2$ [M+H]$^+$: calculated 420.0852 measured: 420.085 Δppm −0.5.

(2-ethylsulfonylphenyl)-[4-(6-fluoro-1,3-benzothiazol-2-yl)piperazin-1-yl]methanone (Herein Referred to as 14 or Compound 14)

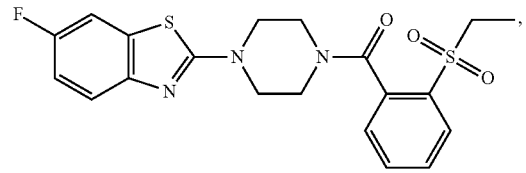 [SMILES: CCS(=O)(=O)c1ccccc1C(=O)N1CCN(c2nc3ccc(F)cc3s2)CC1]

Compound 14 was prepared according to general procedure B using 43 and 60 (45 mg, 0.21 mmol). The crude was purified by column chromatography (DCM:MeOH, 95:5) to afford 14 as an off-white solid (52 mg, 57%). $^1$H NMR (400 MHz, DMSO-$d_6$) δ 7.96 (dd, J=7.9, 1.2, 1H), 7.84 (td, J=7.5, 1.3, 1H), 7.76-7.71 (m, 2H), 7.58 (dd, J=7.5, 1.3, 1H), 7.47 (dd, J=8.8, 4.8, 1H), 7.13 (td, J=9.1, 2.8, 1H), 3.92-3.81 (m, 1H), 3.78-3.68 (m, 2H), 3.66-3.58 (m, 1H), 3.60-3.52 (m, 2H), 3.49-3.38 (m, 2H), 3.38-3.33 (m, 1H), 3.23 (dt, J=13.4, 4.9, 1H), 1.12 (t, J=7.4, 3H). $^{13}$C NMR (101 MHz, DMSO-$d_6$) δ 167.9, 167.2, 157.3 (d, J=237.6), 148.9, 136.2, 135.2, 134.3, 131.4 (d, J=11.7), 130.4, 129.7, 127.7, 119.4 (d, J=8.7), 113.5 (d, J=23.7), 108.1 (d, J=27.6), 50.4, 47.2, 46.1, 40.7, 6.8. UPLC-MS: 2.32 min, 434 [M+H]$^+$. HRMS $C_{20}H_{21}FN_3O_3S_2$ [M+H]$^+$: calculated 434.1008 measured: 434.1015 Δppm 1.6

(3-ethyl sulfonylphenyl)-[4-(6-fluoro-1,3-benzothiazol-2-yl)piperazin-1-yl]methanone (Herein Referred to as 15 or Compound 15)

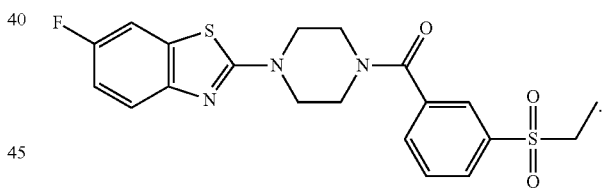

Compound 15 was prepared according to general procedure B using 43 and 3-ethylsulfonylbenzoic acid (54 mg, 0.12 mmol). The crude was purified by column chromatography (DCM:MeOH, 90:10) to afford 15 as a white solid (79 mg, 73%). $^1$H NMR (400 MHz, DMSO-$d_6$) δ 8.00 (dt, J=7.7, 1.5, 1H), 7.95 (t, J=1.7, 1H), 7.84 (dt, J=7.6, 1.4, 1H), 7.77 (t, J=7.7, 1H), 7.74 (dd, J=8.7, 2.6, 1H), 7.47 (dd, J=8.8, 4.8, 1H), 7.14 (td, J=9.1, 2.8, 1H), 3.81 (bs, 2H), 3.69 (bs, 2H), 3.61 (bs, 2H), 3.49 (bs, 2H), 3.36 (q, J=7.4, 2H), 1.13 (t, J=7.4, 3H). 13C NMR (101 MHz, DMSO-$d_6$) δ 168.5, 168.0, 157.8 (d, J=237.5), 149.4, 139.4, 137.2, 132.6, 131.9 (d, J=11.1), 130.4, 129.3, 126.8, 119.8 (d, J=8.9), 114.0 (d, J=23.8), 108.7 (d, J=27.5), 49.5, 48.3 (bs), 46.2, 41.5, 7.6. UPLC-MS: 2.29 min, 434 [M+H]$^+$. HRMS $C_{20}H_{21}FN_3O_3S_2$ [M+H]$^+$: calculated 434.1008 measured: 434.101 Δppm 0.5.

(4-ethylsulfonylphenyl)-[4-(6-fluoro-1,3-benzothiazol-2-yl)piperazin-1-yl]methanone (herein referred to as 16 or Compound 16):

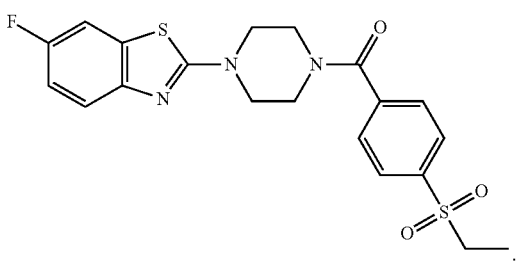 [SMILES: CCS(=O)(=O)c1ccc(C(=O)N2CCN(c3nc4ccc(F)cc4s3)CC2)cc1]

Compound 16 was prepared according to general procedure B using 43 and 4-ethylsulfonylbenzoic acid (54 mg, 0.12 mmol). The crude was purified by column chromatography (DCM:MeOH, 90:10) to afford 16 as a white solid (79 mg, 73%). $^1$H NMR (400 MHz, DMSO-$d_6$) δ 8.00-7.96 (m, 2H), 7.77-7.70 (m, 3H), 7.47 (dd, J=8.9, 4.8, 1H), 7.14 (td, J=9.1, 2.7, 1H), 3.81 (bs, 1H), 3.70 (bs, 1H), 3.59 (bs, 1H), 3.45 (bs, 1H), 3.36 (q, J=7.4, 1H), 1.13 (t, J=7.3, 2H). $^{13}$C NMR (101 MHz, DMSO-$d_6$) δ 168.0, 167.8, 157.3 (d, J=237.3), 148.9, 140.6, 139.3, 131.4 (d, J=11.4), 128.2, 127.9, 119.4 (d, J=8.8), 113.6 (d, J=23.6), 108.2 (d, J=27.3), 49.0, 47.7 (bs), 46.0 (bs), 40.7 (bs), 7.1. UPLC-MS: 2.3 min, 434 [M+H]$^+$. HRMS $C_{20}H_{21}FN_3O_3S_2$ [M+H]$^+$: calculated 434.1008 measured: 434.1017 Δppm 2.1.

[4-(6-fluoro-1,3-benzothiazol-2-yl)piperazin-1-yl]-(2-propylsulfonylphenyl)methanone (Herein Referred to as 17 or Compound 17)

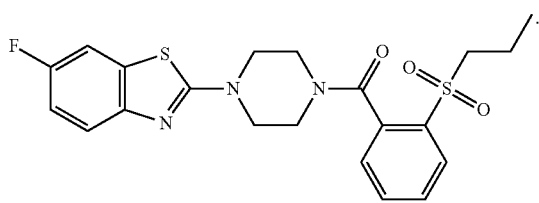 [SMILES: CCCS(=O)(=O)c1ccccc1C(=O)N1CCN(c2nc3ccc(F)cc3s2)CC1]

Compound 17 was prepared according to general procedure B using 43 and 2-propylsulfonylbenzoic acid (47 mg, 0.21 mmol). The crude was purified by column chromatography (DCM:MeOH, 85:15) to afford 17 as an off-white solid (50 mg, 54%). $^1$H NMR (400 MHz, DMSO-$d_6$) δ 7.97 (dd, J=7.9, 1.2, 1H), 7.84 (td, J=7.5, 1.3, 1H), 7.77-7.70 (m, 2H), 7.57 (dd, J=7.5, 1.3, 1H), 7.46 (dd, J=8.9, 4.8, 1H), 7.13 (td, J=9.1, 2.8, 1H), 3.91-3.82 (m, 1H), 3.79-3.68 (m, 2H), 3.65-3.58 (m, 1H), 3.56 (t, J=5.6, 2H), 3.46-3.35 (m, 2H), 3.31 (s, 1H), 3.23 (dt, J=13.5, 5.0, 1H), 1.75-1.59 (m, 1H), 1.58-1.41 (m, 1H), 0.92 (t, J=7.4, 3H). $^{13}$C NMR (101 MHz, DMSO-$d_6$) δ 168.1, 167.3, 157.4 (d, J=237.2), 149.0, 136.2, 135.9, 134.4, 131.5 (d, J=11.0), 130.2, 129.8, 127.8, 119.4 (d, J=8.6), 113.6 (d, J=24.3), 108.2 (d, J=27.2), 57.5, 47.3, 46.2, 40.7, 15.9, 12.7. UPLC-MS: 2.54 min, 448 [M+H]$^+$. HRMS $C_{21}H_{23}FN_3O_3S_2$ [M+H]$^+$: calculated 448.1165 measured: 448.1185 Δppm 4.5.

(2-butylsulfanylphenyl)-[4-(6-fluoro-1,3-benzothiazol-2-yl)piperazin-1-yl]methanone (Herein Referred to as 18 or Compound 18)

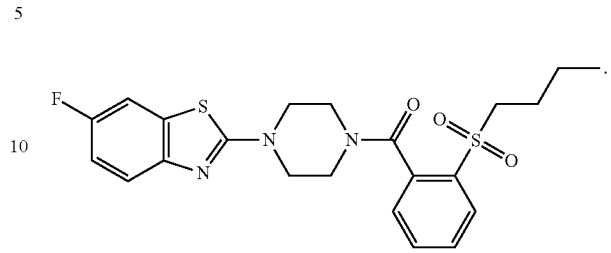

Compound 18 was prepared according to general procedure B using 43 and 2-butylsulfonylbenzoic acid (64 mg, 0.26 mmol). The crude was purified by column chromatography (Cy:EtOAc, 30:70) to afford 18 as an off-white solid (65 mg, 56%). $^1$H NMR (400 MHz, DMSO-$d_6$) δ 7.97 (dd, J=7.9, 1.2, 1H), 7.84 (td, J=7.5, 1.3, 1H), 7.78-7.68 (m, 2H), 7.57 (dd, J=7.5, 1.2, 1H), 7.46 (dd, J=8.8, 4.8, 1H), 7.13 (td, J=9.1, 2.7, 1H), 3.87 (ddd, J=12.7, 6.9, 3.6, 1H), 3.80-3.68 (m, 2H), 3.66-3.58 (m, 1H), 3.56 (t, J=5.2, 1H), 3.49-3.38 (m, 2H), 3.38-3.29 (m, 1H), 3.23 (dt, J=13.5, 4.9, 1H), 1.73-1.58 (m, 1H), 1.50-1.38 (m, 1H), 1.38-1.27 (m, 2H), 0.83 (t, J=7.2, 3H). $^{13}$C NMR (101 MHz, DMSO-$d_6$) δ 168.2, 167.5, 157.5 (d, J=237.5), 149.0, 136.2, 135.9, 134.5, 131.5 (d, J=10.1), 130.3, 130.0, 127.9, 119.6 (d, J=8.8), 113.8 (d, J=23.7), 108.3 (d, J=27.5), 55.7, 47.4, 46.3, 40.9, 24.1, 21.0, 13.5. UPLC-MS: 2.73 min, 462 [M+H]$^+$. HRMS $C_{22}H_{25}FN_3O_3S_2$ [M+H]$^+$: calculated 462.1321 measured: 462.1325 Δppm 0.9.

[4-(6-fluoro-1,3-benzothiazol-2-yl)piperazin-1-yl]-(2 isopropylsulfonylphenyl)methanone (Herein Referred to as 19 or Compound 19)

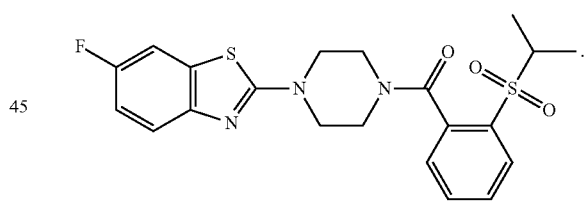

Compound 19 was prepared according to general procedure B using 43 and 2-isopropylsulfonylbenzoic acid (64 mg, 0.28 mmol). The crude was purified by column chromatography (DCM:MeOH, 90:10) to afford 19 as an off-white solid (84 mg, 67%). $^1$H NMR (400 MHz, DMSO-$d_6$) δ 7.94 (dd, J=7.9, 1.2, 1H), 7.84 (td, J=7.5, 1.3, 1H), 7.79-7.68 (m, 2H), 7.58 (dd, J=7.5, 1.2, 1H), 7.47 (dd, J=8.8, 4.8, 1H), 7.13 (td, J=9.1, 2.8, 1H), 3.91-3.80 (m, 1H), 3.77-3.71 (m, 2H), 3.71-3.65 (m, 1H), 3.65-3.58 (m, 1H), 3.58-3.53 (m, 2H), 3.39-3.28 (m, 2H), 3.22 (dt, J=13.6, 5.0, 1H), 1.29 (d, J=6.9, 3H), 1.04 (d, J=6.8, 3H). $^{13}$C NMR (101 MHz, DMSO-$d_6$) δ 168.3, 167.5, 157.5 (d, J=237.8), 149.0, 136.6, 134.5, 134.3, 131.5 (d, J=11.7), 131.1, 129.8, 128.0, 119.5 (d, J=8.8), 113.8 (d, J=22.6), 108.3 (d, J=28.4), 55.1, 47.4, 46.3, 40.9, 16.5, 13.1. UPLC-MS: 2.53 min, 448 [M+H]$^+$. HRMS $C_{21}H_{23}FN_3O_3S_2$ [M+H]$^+$: calculated 448.1165 measured: 448.1177 Δppm 2.7.

(2-cyclopropylsulfonylphenyl)-[4-(6-fluoro-1,3-benzothiazol-2-yl)piperazin-1-yl]methanone (Herein Referred to as 20 or Compound 20)

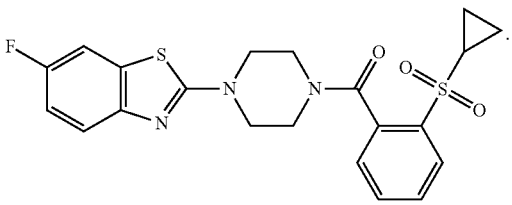 [SMILES: O=C(c1ccccc1S(=O)(=O)C1CC1)N1CCN(c2nc3ccc(F)cc3s2)CC1]

To a solution of 54 (108 mg, 0.20 mmol) in THF (4 mL) was added tBuOK (34 mg, 0.30 mmol) and the mixture was stirred at rt for 2 h. The reaction was quenched with a solution of NH$_4$Cl (5 mL) and the compound was extracted with EtOAc, dried over Na$_2$SO$_4$ and evaporated to give a residue which was purified by column chromatography (DCM:MeOH 99:1) to afford 20 as a white solid (60 mg, 67%). $^1$H NMR (400 MHz, DMSO-d$_6$) δ 7.91 (dd, J=7.9, 0.9, 1H), 7.82 (td, J=7.5, 1.2, 1H), 7.74 (dd, J=8.7, 2.7, 1H), 7.71 (td, J=7.8, 1.3, 1H), 7.57 (dd, J=7.5, 1.0, 1H), 7.47 (dd, J=8.8, 4.8, 1H), 7.13 (td, J=9.1, 2.7, 1H), 3.87 (ddd, J=13.6, 6.5, 3.6, 1H), 3.79-3.69 (m, 2H), 3.63 (ddd, J=12.4, 7.5, 3.7, 1H), 3.56 (t, J=5.3, 2H), 3.35 (dt, J=13.4, 5.3, 1H), 3.24 (dt, J=13.7, 5.0, 1H), 3.02 (tt, J=8.0, 4.8, 1H), 1.37-1.25 (m, 1H), 1.17-1.06 (m, 1H), 1.05-0.97 (m, 1H), 0.97-0.88 (m, 1H). $^{13}$C NMR (101 MHz, DMSO-d$_6$) δ 167.9, 167.3, 157.3 (d, J=237.4), 148.9, 137.1, 135.9, 134.0, 131.4 (d, J=11.3), 129.9, 129.3, 127.6, 119.3 (d, J=8.9), 113.5 (d, J=23.9), 108.1 (d, J=27.5), 47.3, 46.1, 40.6, 32.9, 6.2, 5.0. UPLC-MS: 2.2 min, 446 [M+H]$^+$. HRMS C$_{21}$H$_{21}$FN$_3$O$_3$S$_2$ [M+H]$^+$: calculated 446.1008 measured: 446.1022 Δppm 3.1.

(2-cyclobutylsulfonylphenyl)-[4-(6-fluoro-1,3-benzothiazol-2-yl)piperazin-1-yl]methanone (Herein Referred to as 21 or Compound 21)

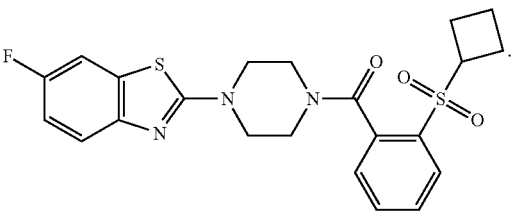 [SMILES: O=C(c1ccccc1S(=O)(=O)C1CCC1)N1CCN(c2nc3ccc(F)cc3s2)CC1]

Compound 21 was prepared according to general procedure B using 43 and 2-cyclobutylsulfonylbenzoic acid (130 mg, 0.54 mmol). The crude was purified by column chromatography (DCM:MeOH, 90:10) to afford 21 as an off-white solid (149 mg, 60%). $^1$H NMR (400 MHz, DMSO-d$_6$) δ 7.96 (dd, J=7.9, 1.2, 1H), 7.82 (td, J=7.5, 1.3, 1H), 7.76-7.67 (m, 2H), 7.56 (td, J=7.5, 7.0, 1.3, 1H), 7.46 (dd, J=8.8, 4.8, 1H), 7.13 (td, J=9.1, 2.7, 1H), 4.28 (p, J=8.0, 1H), 3.89-3.79 (m, 1H), 3.78-3.66 (m, 2H), 3.65-3.58 (m, 1H), 3.55 (t, J=5.3, 2H), 3.31 (dt, J=13.5, 5.8, 5.2, 1H), 3.21 (dt, J=13.5, 5.1, 1H), 2.54-2.43 (m, 1H), 2.29-2.14 (m, 2H), 2.04-1.83 (m, 3H). $^{13}$C NMR (101 MHz, DMSO-d$_6$) δ 168.0, 167.2, 157.3 (d, J=237.3), 148.9, 136.4, 134.4, 134.4, 131.4 (d, J=11.2), 130.5, 129.8, 127.8, 119.4 (d, J=8.9), 113.6 (d, J=23.6), 108.2 (d, J=26.6), 56.3, 47.3, 46.2, 40.7, 23.0, 20.6, 16.3. UPLC-MS: 2.31 min, 460 [M+H]$^+$. HRMS C$_{22}$H$_{23}$FN$_3$O$_3$S$_2$ [M+H]$^+$: calculated 460.1165 measured: 460.1174 Δppm 2.

(2-cyclopentylsulfonylphenyl)-[4-(6-fluoro-1,3-benzothiazol-2-yl)piperazin-1-yl]methanone (Herein Referred to as 22 or Compound 22)

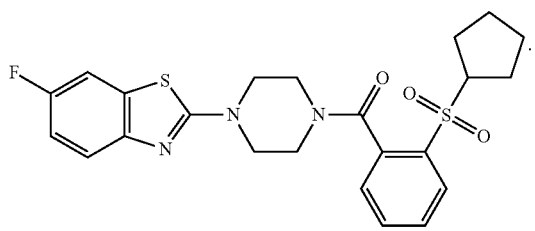 [SMILES: O=C(c1ccccc1S(=O)(=O)C1CCCC1)N1CCN(c2nc3ccc(F)cc3s2)CC1]

Compound 22 was prepared according to general procedure B using 43 and 2-cyclopentylsulfonylbenzoic acid (127 mg, 0.5 mmol). The crude was purified by column chromatography (Cy:EtOAc, 50:50) to afford 22 as a white solid (183 mg, 77%). $^1$H NMR (400 MHz, DMSO-d$_6$) δ 7.98 (dd, J=7.9, 0.9, 1H), 7.83 (td, J=7.5, 1.2, 1H), 7.76-7.69 (m, 2H), 7.56 (dd, J=7.5, 1.0, 1H), 7.46 (dd, J=8.8, 4.8, 1H), 7.13 (td, J=9.1, 2.7, 1H), 4.01-3.93 (m, 1H), 3.84 (ddd, J=13.4, 6.6, 3.7, 1H), 3.73 (ddd, J=18.0, 8.0, 3.4, 2H), 3.62 (ddt, J=11.0, 7.2, 3.8, 1H), 3.55 (t, J=5.4, 2H), 3.37-3.27 (m, 1H), 3.20 (dt, J=13.4, 4.8, 1H), 2.16-2.02 (m, 1H), 1.96-1.83 (m, 1H), 1.78-1.46 (m, 6H). $^{13}$C NMR (101 MHz, DMSO-d$_6$) δ 168.0, 167.3, 157.3 (d, J=237.4), 148.9, 136.2, 135.5, 134.2, 131.4 (d, J=11.7), 130.5, 129.7, 127.8, 119.3 (d, J=8.8), 113.5 (d, J=24.0), 108.1 (d, J=27.3), 63.5, 47.2, 46.1, 40.7, 28.0, 25.6, 25.4, 24.9. UPLC-MS: 2.42 min, 474 [M+H]$^+$. HRMS C$_{23}$H$_{25}$FN$_3$O$_3$S$_2$ [M+H]$^+$: calculated 474.1321 measured: 474.133 Δppm 1.9.

(2-cyclohexylsulfonylphenyl)-[4-(6-fluoro-1,3-benzothiazol-2-yl)piperazin-1-yl]methanone (Herein Referred to as 23 or Compound 23)

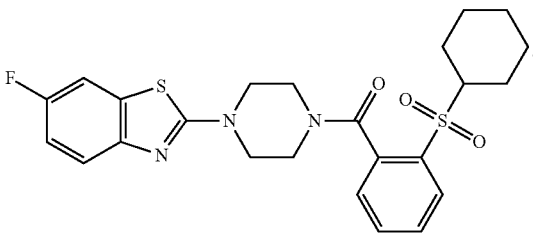 [SMILES: O=C(c1ccccc1S(=O)(=O)C1CCCCC1)N1CCN(c2nc3ccc(F)cc3s2)CC1]

Compound 23 was prepared according to general procedure B using 43 and 2-cyclohexylsulfonylbenzoic acid (56 mg, 0.21 mmol). The crude was purified by column chromatography (DCM:MeOH, 30:70) to afford 23 as a white solid (75 mg, 73%). $^1$H NMR (400 MHz, DMSO-d$_6$) δ 7.91 (dd, J=7.9, 1.2, 1H), 7.84 (td, J=7.5, 1.2, 1H), 7.77-7.69 (m, 2H), 7.57 (dd, J=7.6, 1.2, 1H), 7.46 (dd, J=8.8, 4.8, 1H), 7.13 (td, J=9.1, 2.8, 1H), 3.92-3.82 (m, 1H), 3.80-3.67 (m, 2H), 3.66-3.58 (m, 1H), 3.56 (t, J=5.4, 2H), 3.44 (tt, J=12.4, 3.5, 1H), 3.32 (dt, J=13.5, 5.0, 1H), 3.22 (dt, J=13.5, 5.0, 1H), 2.09 (d, J=12.7, 1H), 1.85 (d, J=12.4, 1H), 1.71 (d, J=10.9, 1H), 1.61 (d, J=9.6, 1H), 1.57-1.42 (m, 2H), 1.41-1.29 (m, 1H), 1.29-1.00 (m, 3H). ¹³C NMR (151 MHz, DMSO-d₆) δ 168.2, 167.5, 157.5 (d, J=237.1), 149.0, 136.6, 134.5, 134.3, 131.5 (d, J=10.9), 131.2, 129.7, 128.0, 119.6 (d, J=8.5), 113.8 (d, J=24.0), 108.3 (d, J=28.4), 62.6, 47.4, 47.4, 46.3, 40.9, 26.3, 24.9, 24.6, 24.5, 22.9. UPLC-MS: 2.83 min, 488 [M+H]⁺. HRMS C₂₄H₂₇FN₃O₃S₂ [M+H]⁺: calculated 488.1478 measured: 488.1487 Δppm 1.8.

[4-(1,3-benzothiazol-2-yl)piperazin-1-yl]-(2-ethyl-sulfonylphenyl)methanone (Herein Referred to as 24 or Compound 24)

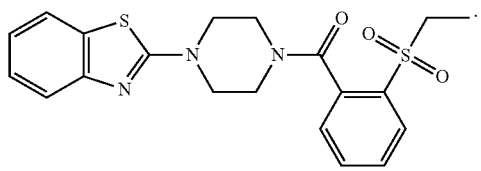

Compound 24 was prepared according to general procedure A using 44 and 2-chloro-1,3-benzothiazole (58 mg, 0.34 mmol). The crude was purified by column chromatography (Cy: EtOAc, 90:10) to afford 24 as a white solid (60 mg, 54%). ¹H NMR (400 MHz, DMSO-d₆) δ 7.96 (dd, J=7.9, 1.2, 1H), 7.85 (td, J=7.5, 1.3, 1H), 7.78 (dd, J=8.0, 1.2, 1H), 7.73 (td, J=7.7, 1.3, 1H), 7.58 (dd, J=7.5, 1.3, 1H), 7.48 (dd, J=8.2, 1.1, 7H), 7.29 (ddd, J=8.2, 7.3, 1.3, 1H), 7.09 (td, J=7.6, 1.2, 1H), 3.92-3.81 (m, 1H), 3.82-3.68 (m, 2H), 3.68-3.60 (m, 1H), 3.58 (t, J=5.2, 2H), 3.49-3.36 (m, 2H), 3.36-3.32 (m, 1H), 3.23 (dt, J=13.5, 5.0, 1H), 1.12 (t, J=7.4, 3H). ¹³C NMR (101 MHz, DMSO-d₆) δ 152.2, 136.3, 135.3, 134.3, 130.4, 130.4, 129.7, 127.8, 126.0, 121.5, 121.3, 118.7, 50.4, 47.3, 46.2, 40.7, 6.8. UPLC-MS: 2.33 min, 415 [M+H]⁺. HRMS C₂₀H₂₂N₃O₃S₂[M+H]⁺: calculated 416.1103 measured: 416.1103 Δppm 0.

[4-(6-chloro-1,3-benzothiazol-2-yl)piperazin-1-yl]-(2-ethylsulfonylphenyl)methanone (Herein Referred to as 25 or Compound 25)

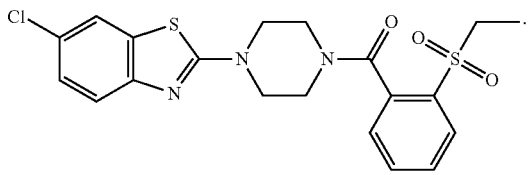 [SMILES: CCS(=O)(=O)c1ccccc1C(=O)N1CCN(c2nc3ccc(Cl)cc3s2)CC1]

Compound 25 was prepared according to general procedure A using 44 and 2,6-dichloro-1,3-benzothiazole (61 mg, 0.3 mmol). The crude was purified by column chromatography (Cy:EtOAc, 70:30) to afford 25 as a white solid (83 mg, 65%). ¹H NMR (400 MHz, DMSO-d₆) δ 7.96 (dd, J=7.9, 1.1, 1H), 7.94 (d, J=2.3, 1H), 7.85 (td, J=7.5, 1.2, 1H), 7.73 (td, J=7.7, 1.2, 1H), 7.58 (dd, J=7.5, 1.2, 1H), 7.45 (d, J=8.6, 1H), 7.30 (dd, J=8.6, 2.3, 1H), 3.87 (ddd, J=11.9, 6.7, 2.8, 1H), 3.81-3.68 (m, 2H), 3.67-3.60 (m, 1H), 3.58 (t, J=6.3, 2H), 3.48-3.34 (m, 2H), 3.34-3.27 (m, 2H), 3.24 (dt, J=13.3, 4.9, 1H), 1.12 (t, J=7.4, 2H). ¹³C NMR (101 MHz, DMSO-d₆) δ 169.1, 167.8, 151.5, 136.6, 135.6, 134.8, 132.4, 130.8, 130.3, 128.2, 126.7, 125.7, 121.4, 120.1, 50.9, 47.7, 46.6, 41.2, 7.2. UPLC-MS: 2.65 min, 450 [M+H]⁺. HRMS C₂₀H₂₁ClN₃O₃S₂ [M+H]⁺: calculated 450.0713 measured: 450.072 Δppm 1.6.

(2-ethylsulfonylphenyl)-[4-[6-(trifluoromethyl)-1,3-benzothiazol-2-yl]piperazin-1-yl]methanone (Herein Referred to as 26 or Compound 26)

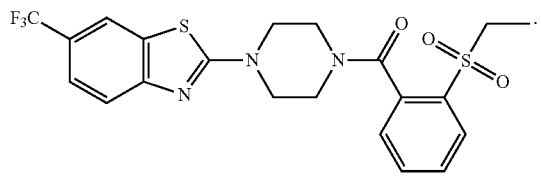 [SMILES: CCS(=O)(=O)c1ccccc1C(=O)N1CCN(c2nc3ccc(C(F)(F)F)cc3s2)CC1]

Compound 26 was prepared according to general procedure A using 44 and 2-chloro-6-(trifluoromethyl)-1,3-benzothiazole (140 mg, 0.59 mmol). The crude was purified by column chromatography (DCM:EtOAc, 80:20) to afford 26 as a white solid (120 mg, 51%). ¹H NMR (400 MHz, DMSO-d₆) δ 8.28 (s, 1H), 7.97 (dd, J=7.9, 1.2, 1H), 7.85 (td, J=7.5, 1.3, 1H), 7.74 (td, J=7.7, 1.3, 1H), 7.63-7.56 (m, 3H), 3.94-3.84 (m, 1H), 3.84-3.78 (m, 1H), 3.79-3.73 (m, 1H), 3.73-3.67 (m, 1H), 3.67-3.58 (m, 2H), 3.49-3.37 (m, 2H), 3.37-3.32 (m, 1H), 3.29-3.21 (m, 1H), 1.13 (t, J=7.4, 3H). ¹³C NMR (101 MHz, DMSO-d₆) δ 170.3, 167.2, 155.2, 136.2, 135.2, 134.3, 130.9, 130.4, 129.7, 127.7, 123.1, 121.6 (q, J=30.5), 120.7 (q, J=245.0), 119.1, 118.5, 50.4, 47.3, 46.1, 40.7, 6.8. UPLC-MS: 2.38 min, 483 [M+H]⁺. HRMS C₂₁H₂₁FN₃O₃₃S₂[M+H]⁺: calculated 484.0976 measured: 484.098 Δppm 0.8.

(2-ethylsulfonylphenyl)-[4-(6-methyl-1,3-benzothiazol-2-yl)piperazin-1-yl]methanone (Herein Referred to as 27 or Compound 27)

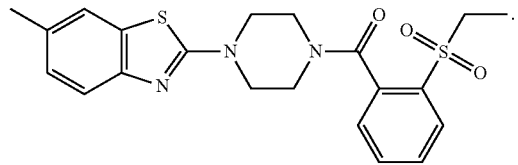 [SMILES: CCS(=O)(=O)c1ccccc1C(=O)N1CCN(c2nc3ccc(C)cc3s2)CC1]

Compound 27 was prepared according to general procedure A using 44 and 2-chloro-6-methyl-1,3-benzothiazole (56 mg, 0.31 mmol). The crude was purified by column chromatography (Cy:EtOAc, 50:50) to afford 27 as a white solid (71 mg, 57%). ¹H NMR (400 MHz, DMSO-d₆) δ 7.96 (dd, J=7.9, 1.2, 1H), 7.84 (td, J=7.5, 1.2, 1H), 7.73 (td, J=7.7, 1.3, 1H), 7.63-7.54 (m, 2H), 7.37 (d, J=8.2, 1H), 7.10 (dd, J=8.2, 1.7, 1H), 3.85 (dt, J=11.8, 4.6, 1H), 3.78-3.67 (m, 2H), 3.66-3.57 (m, 1H), 3.54 (t, J=5.3, 2H), 3.49-3.36 (m, 2H), 3.36-3.27 (m, 1H), 3.23 (dt, J=13.5, 5.0, 1H), 2.34 (s, 3H), 1.12 (t, J=7.4, 3H). ¹³C NMR (101 MHz, DMSO-d₆) δ 167.5, 167.3, 150.1, 136.3, 135.3, 134.4, 130.8, 130.6, 130.4, 129.8, 127.8, 127.2, 121.2, 118.5, 50.5, 47.3, 46.2, 40.8, 20.8, 6.9. UPLC-MS: 2.52 min, 429 [M+H]⁺. HRMS C₂₁H₂₄N₃O₃S₂[M+H]⁺: calculated 430.1259 measured: 430.1267 Δppm 1.9.

(2-ethylsulfonylphenyl)-[4-(6-methoxy-1,3-benzothiazol-2-yl)piperazin-1-yl]methanone (Herein Referred to as 28 or Compound 28)

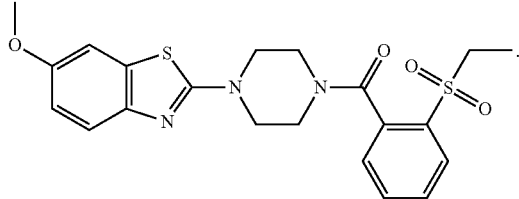 [SMILES: CCS(=O)(=O)c1ccccc1C(=O)N1CCN(c2nc3ccc(OC)cc3s2)CC1]

Compound 28 was prepared according to general procedure A using 44 and 2-chloro-6-methoxy-1,3-benzothiazole (61 mg, 0.31 mmol). The crude was purified by column chromatography (Cy:EtOAc, 30:70) to afford 28 as a white solid (49 mg, 35%). $^1$H NMR (400 MHz, DMSO-$d_6$) δ 7.96 (dd, J=7.8, 1.2, 1H), 7.84 (td, J=7.4, 1.2, 1H), 7.73 (td, J=7.7, 1.4, 2H), 7.58 (dd, J=7.5, 1.2, 1H), 7.43 (d, J=2.6, 1H), 7.39 (d, J=8.8, 1H), 6.89 (dd, J=8.8, 2.7, 1H), 3.85 (ddd, J=13.5, 6.8, 3.7, 1H), 3.75 (s, 3H), 3.69 (m, 2H), 3.57 (ddd, J=12.0, 7.6, 3.8, 1H), 3.52 (t, J=5.3, 2H), 3.47-3.36 (m, 2H), 3.36-3.27 (m, 1H), 3.22 (dt, J=13.4, 4.9, 1H), 1.12 (t, J=7.4, 3H). $^{13}$C NMR (101 MHz, DMSO-$d_6$) δ 167.6, 167.0, 154.9, 146.4, 136.4, 135.4, 134.6, 131.7, 130.6, 130.0, 128.0, 119.5, 114.1, 105.7, 55.8, 50.7, 47.5, 47.5, 46.4, 41.0, 7.0. UPLC-MS: 2.3 min, 445 [M+H]$^+$. HRMS $C_{21}H_{24}N_3O_4S_2$ [M+H]$^+$: calculated 446.1208 measured: 446.1214 Δppm 1.3.

(2-ethylsulfonylphenyl)-[4-(4-fluoro-1,3-benzothiazol-2-yl)piperazin-1-yl]methanone (Herein Referred to as 29 or Compound 29)

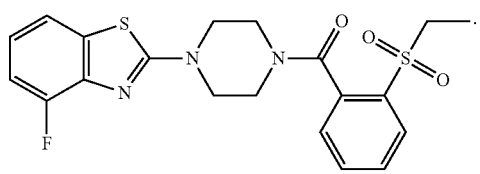 [SMILES: CCS(=O)(=O)c1ccccc1C(=O)N1CCN(c2nc3c(F)cccc3s2)CC1]

Compound 29 was prepared according to general procedure A using 44 and 2-chloro-4-fluoro-1,3-benzothiazole (67 mg, 0.36 mmol). The crude was purified by column chromatography (Cy:EtOAc, 50:50) to afford 29 as a white solid (74 mg, 59%). $^1$H NMR (400 MHz, DMSO-$d_6$) δ 7.96 (dd, J=8.0, 1.2, 1H), 7.85 (td, J=7.6, 1.3, 1H), 7.74 (td, J=7.7, 1.3, 1H), 7.62 (dd, J=7.8, 1.2, 1H), 7.59 (dd, J=7.5, 1.3, 1H), 7.15 (ddd, J=11.2, 8.1, 1.2, 1H), 7.08 (td, J=8.0, 4.8, 1H), 3.92-3.83 (m, 1H), 3.83-3.70 (m, 2H), 3.69-3.63 (m, 1H), 3.60 (t, J=5.6, 2H), 3.49-3.38 (m, 2H), 3.38-3.28 (m, 1H), 3.24 (dt, J=13.8, 5.0, 1H), 1.13 (t, J=7.4, 3H). $^{13}$C NMR (101 MHz, DMSO-$d_6$) δ 168.3, 167.3, 152.5 (d, J=248.6), 140.3 (d, J=13.3), 136.2, 135.3, 134.4, 133.1 (d, J=4.4), 130.4, 129.8, 127.8, 122.0 (d, J=6.8), 117.4 (d, J=3.7), 112.2 (d, J=17.9), 50.5, 47.4, 47.3, 46.1, 40.7, 6.8. UPLC-MS: 2.39 min, 433 [M+H]$^+$. HRMS $C_{20}H_{21}FN_3O_3S_2$ [M+H]$^+$: calculated 434.1008 measured: 434.1013 Δppm 1.2.

(2-ethylsulfonylphenyl)-[4-(5-fluoro-1,3-benzothiazol-2-yl)piperazin-1-yl]methanone (Herein Referred to as 30 or Compound 30)

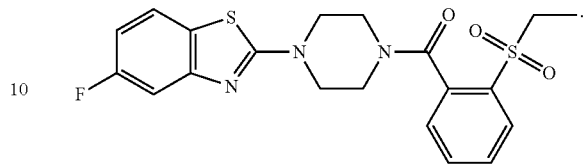

Compound 30 was prepared according to general procedure A using 44 and 2-chloro-5-fluoro-1,3-benzothiazole (49 mg, 0.26 mmol). The crude was purified by column chromatography (Cy:EtOAc, 50:50) to afford 30 as a white solid (40 mg, 35%). $^1$H NMR (400 MHz, DMSO-$d_6$) δ 7.96 (dd, J=7.9, 1.1, 2H), 7.85 (td, J=7.5, 1.2, 1H), 7.80 (dd, J=8.7, 5.5, 1H), 7.73 (td, J=7.7, 1.3, 1H), 7.58 (dd, J=7.5, 1.2, 2H), 7.29 (dd, J=10.4, 2.5, 1H), 6.95 (td, J=9.0, 2.6, 1H), 3.92-3.82 (m, 1H), 3.82-3.68 (m, 2H), 3.70-3.60 (m, 1H), 3.61-3.55 (m, 2H), 3.49-3.36 (m, 2H), 3.36-3.27 (m, 1H), 3.24 (dt, J=13.5, 4.9, 1H), 1.12 (t, J=7.4, 3H). $^{13}$C NMR (101 MHz, DMSO-$d_6$) δ 170.2, 167.4, 161.6 (d, J=238.9), 153.6 (d, J=12.4), 136.3, 135.3, 134.5, 130.5, 129.9, 127.9, 126.1, 122.4 (d, J=10.1), 109.0 (d, J=24.2), 105.3 (d, J=24.1), 50.6, 47.3, 46.2, 40.8, 6.9. UPLC-MS: 2.37 min, 433 [M+H]$^-$. HRMS $C_{20}H_{21}FN_3O_3S_2$ [M+H]$^+$: calculated 434.1008 measured: 434.1012 Δppm 0.9.

(2-ethylsulfonylphenyl)-[4-(7-fluoro-1,3-benzothiazol-2-yl)piperazin-1-yl]methanone (Herein Referred to as 31 or Compound 31)

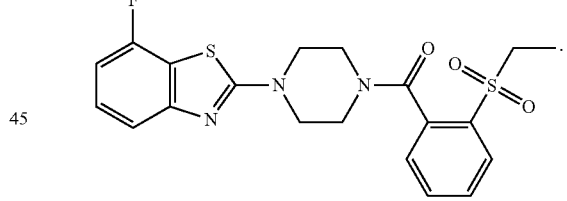

Compound 31 was prepared according to general procedure A using 44 and 2-chloro-7-fluoro-1,3-benzothiazole (50 mg, 0.27 mmol). The crude was purified by column chromatography (Cy:EtOAc, 50:50) to afford 31 as white solid (66 mg, 56%). $^1$H NMR (400 MHz, DMSO-$d_6$) δ 7.97 (dd, J=7.7, 1.0, 1H), 7.86 (td, J=7.5, 0.8, 1H), 7.75 (t, J=7.6, 1H), 7.60 (dd, J=7.8, 1.0, 2H), 7.39-7.29 (m, 2H), 7.00 (ddd, J=9.5, 6.3, 2.7, 1H), 3.88 (dd, J=8.5, 3.9, OH), 3.85-3.71 (m, 1H), 3.71-3.65 (m, OH), 3.65-3.58 (m, 2H), 3.48-3.37 (m, 2H), 3.37-3.29 (m, 1H), 3.26 (dt, J=8.3, 4.6, OH), 1.13 (t, J=7.4, 3H). $^{13}$C NMR (101 MHz, DMSO-$d_6$) δ 168.5, 167.5, 156.2 (d, J=244.7), 155.3 (d, J=2.5), 136.3, 135.3, 134.5, 130.5, 130.0, 127.9, 127.6 (d, J=7.7), 116.4 (d, J=16.1), 115.2 (d, J=2.2), 107.6 (d, J=18.4), 50.6, 47.6, 46.2, 40.9, 6.9. UPLC-MS: 2.49 min, 433 [M+H]$^+$. HRMS $C_{20}H_{21}FN_3O_3S_2$ [M+H]$^+$: calculated 434.1008 measured: 434.1011 Δppm 0.7.

[4-(7-chloro-1,3-benzothiazol-2-yl)piperazin-1-yl]-(2-ethylsulfonylphenyl)methanone (Herein Referred to as 32 or Compound 32)

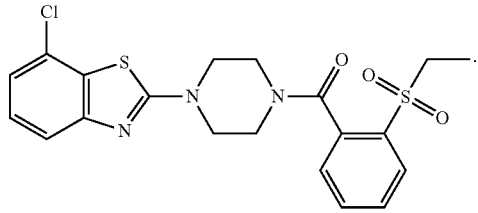 [SMILES: CCS(=O)(=O)c1ccccc1C(=O)N1CCN(c2nc3cccc(F)c3s2)CC1]

Compound 32 was prepared according to general procedure A using 44 and 2,6-dichloro-1,3-benzothiazole (101 mg, 0.5 mmol). The crude was purified by column chromatography (Cy:EtOAc, 50:50) to afford 32 as a white solid (103 mg, 46%). $^1$H NMR (400 MHz, DMSO-$d_6$) δ 7.98 (d, J=7.8 Hz, 1H), 7.86 (t, J=7.4 Hz, 1H), 7.75 (t, J=7.6 Hz, 1H), 7.60 (d, J=7.4 Hz, 1H), 7.45 (d, J=7.9 Hz, 1H), 7.34 (t, J=8.0 Hz, 1H), 7.19 (d, J=7.8 Hz, 1H), 3.96-3.55 (m, 6H), 3.50-3.17 (m, 4H), 1.14 (t, J=7.4 Hz, 3H). $^{13}$C NMR (101 MHz, DMSO-$d_6$) δ 167.5, 167.3, 153.2, 136.2, 135.3, 134.4, 130.4, 130.0, 129.8, 127.8, 127.6, 124.8, 121.0, 117.4, 50.4, 47.3 (2×C), 46.1, 40.7, 6.8. UPLC-MS: 2.65 min, 450 [M+H]$^+$. HRMS $C_{20}H_{21}ClN_3O_3S_2$ [M+H]$^+$: calculated 450.0713 measured: 450.0713 Δppm 0.9.

(2-ethylsulfonylphenyl)-[4-(6-fluoro-1,3-benzothiazol-2-yl)-2-methyl-piperazin-1-yl]methanone (Herein Referred to as 36 or Compound 36)

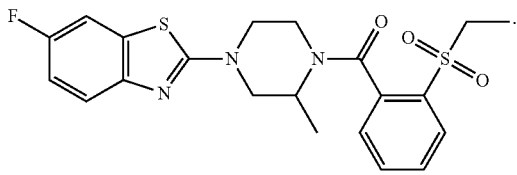

Compound 36 was prepared according to general procedure B using 46 and 60 (125 mg, 0.58 mmol). The crude was purified by column chromatography (DCM:MeOH, 50:50) to afford 36 as a white solid (120 mg, 42%). $^1$H NMR (400 MHz, DMSO-$d_6$) δ 8.00-7.91 (m, 1H), 7.89-7.79 (m, 1H), 7.77-7.68 (m, 2H), 7.63-7.46 (m, 1H), 7.46-7.41 (m, 1H), 7.16-7.08 (m, 1H), 5.03-3.05 (m, 9H), 1.36-1.05 (m, 6H). $^{13}$C NMR (101 MHz, DMSO) δ 168.5, 167.5, 166.7, 158.4, 156.0, 149.0, 136.6, 136.4, 135.1, 134.4, 134.3, 131.3, 131.2, 130.6, 130.5, 130.2, 129.7, 129.6, 127.65, 127.0, 125.4, 123.1, 119.1, 119.0, 118.7, 115.3, 114.7, 113.6, 113.4, 111.8, 110.2, 108.2, 108.1, 107.7, 52.1, 51.8, 51.6, 51.1, 50.5, 50.4, 47.0, 46.9, 44.6, 44.2, 41.6, 41.5, 16.5, 15.7, 15.4, 14.6, 13.7, 6.8, 6.7. UPLC-MS: 2.22 min, 448 [M+H]$^+$. HRMS $C_{21}H_{23}FN_3O_3S_2$ [M+H]$^+$: calculated 448.1165 measured: 448.1172 Δppm 1.6.

(2-ethylsulfonylphenyl)-[4-(6-fluoro-1,3-benzothiazol-2-yl)-3-methyl-piperazin-1-yl]methanone (Herein Referred to as 37 or Compound 37)

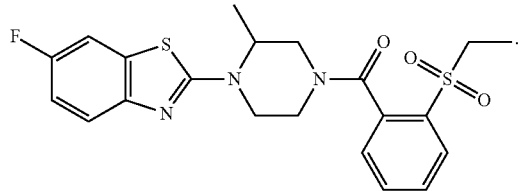 [SMILES: CCS(=O)(=O)c1ccccc1C(=O)N1CCN(c2nc3ccc(F)cc3s2)C(C)C1]

Compound 37 was prepared according to general procedure B using 50 and 60 (39 mg, 0.18 mmol). The crude was purified by column chromatography (Cy:EtOAc, 30:70) to afford 37 as a white solid (30 mg, 43%). $^1$H NMR (400 MHz, DMSO-$d_6$) δ 8.02-7.92 (m, 1H), 7.90-7.78 (m, 1H), 7.78-7.50 (m, 3H), 7.45 (dt, J=8.8, 4.4, 1H), 7.17-7.06 (m, 1H), 4.54-2.82 (m, 9H), 1.42-1.05 (m, 6H). $^{13}$C NMR (101 MHz, DMSO-$d_6$) δ 168.6, 168.4, 167.4, 158.4, 156.1, 156.0, 149.0, 148.9, 136.5, 136.3, 136.2, 135.5, 135.0, 134.9, 134.4, 134.3, 134.2, 131.2, 131.1, 130.3, 130.2, 130.1, 129.7, 128.0, 127.9, 119.3, 119.2, 119.1, 113.6, 113.4, 108.2, 108.0, 51.9, 51.3, 51.1, 50.8, 50.5, 50.4, 46.3, 45.3, 44.9, 42.6, 42.3, 41.0, 26.3, 13.9, 6.8. UPLC-MS: 2.28 min, 448 [M+H]$^+$. HRMS $C_{21}H_{23}FN_3O_3S_2$ [M+H]$^+$: calculated 448.1165 measured: 448.1165 Δppm 0.

(2-ethylsulfonylphenyl)-[4-(6-fluoro-1,3-benzothiazol-2-yl)-2,2-dimethyl-piperazin-1-yl]methanone (Herein Referred to as 38 or Compound 38)

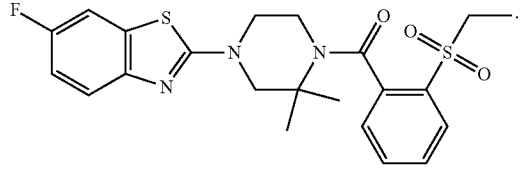 [SMILES: CCS(=O)(=O)c1ccccc1C(=O)N1CCN(c2nc3ccc(F)cc3s2)CC1(C)C]

Compound 38 was prepared according to general procedure B using 51 and 60 (50 mg, 0.23 mmol). The crude was purified by column chromatography (DCM:MeOH, 99:1) to afford 38 as white solid (30 mg, 34%). $^1$H NMR (400 MHz, DMSO-$d_6$) δ 7.93 (d, J=7.8, 1H), 7.82 (t, J=7.4, 1H), 7.72 (dd, J=8.6, 2.5, 1H), 7.69 (t, J=7.8, 1H), 7.52 (d, J=7.4, 1H), 7.44 (dd, J=8.7, 4.8, 1H), 7.12 (td, J=9.3, 1.6, 1H), 3.80 (s, 2H), 3.63-3.50 (m, 2H), 3.49-3.16 (m, 4H), 1.61 (s, 3H), 1.54 (s, 3H), 1.11 (t, J=7.3, 3H). $^{13}$C NMR (101 MHz, DMSO-$d_6$) δ 168.0, 167.2, 157.0 (d, J=236.5), 149.3, 138.0, 134.4, 134.3, 131.0 (d, J=11.3), 130.1, 129.3, 127.2, 118.9 (d, J=8.8), 113.4 (d, J=23.7), 108.1 (d, J=27.3), 58.2, 55.1, 50.5, 46.7, 43.1, 23.3, 21.9, 6.8. UPLC-MS: 2.38 min, 462 [M+H]$^+$. HRMS $C_{22}H_{25}FN_3O_3S_2$ [M+H]$^+$: calculated 462.1321 measured: 462.1322 Δppm 0.2.

71

(2-ethylsulfonylphenyl)-[4-(6-fluoro-1,3-benzothiazol-2-yl)-2,6-dimethyl-piperazin-1-yl]methanone (Herein Referred to as 39 or Compound 39)

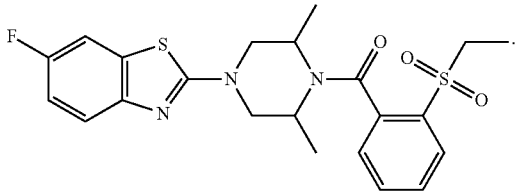 [SMILES: CCS(=O)(=O)c1ccccc1C(=O)N1C(C)CN(c2nc3ccc(F)cc3s2)CC1C]

Compound 39 was prepared according to general procedure B using 52 and 60 (45 mg, 0.21 mmol). The crude was purified by column chromatography (DCM:MeOH, 99:1) to afford 39 as white solid (11 mg, 12%). $^1$H NMR (400 MHz, DMSO-$d_6$) δ 7.97 (td, J=7.9, 1.0, 1H), 7.84 (tt, J=7.5, 1.3, 1H), 7.77-7.57 (m, 3H), 7.43 (ddd, J=8.8, 4.8, 1.9, 1H), 7.12 (tt, J=9.2, 2.2, 1H), 5.11-3.07 (m, 8H), 1.40-1.20 (m, 6H), 1.16-1.07 (m, 3H). $^{13}$C NMR (101 MHz, DMSO-$d_6$) δ 168.6, 167.4, 157.2 (d, J=233.9), 149.1, 136.9, 135.9 (d, J=26.8), 134.3, 134.3, 134.0, 130.9, 130.2, 129.6, 129.5, 128.3, 127.1, 119.0 (d, J=8.5), 113.5 (d, J=23.3), 108.1 (d, J=27.3), 51.9, 51.6, 51.3, 51.0, 50.7, 50.2, 50.0, 50.0, 44.6, 43.9, 20.1, 19.8, 19.0, 18.9, 6.8, 6.8. UPLC-MS: 2.37 min, 448 [M+H]$^+$. HRMS $C_{22}H_{25}FN_3O_3S_2$ [M+H]$^+$: calculated 462.1321 measured: 462.1319 Δppm −0.2.

(2-ethylsulfonylphenyl)-[(2R)-4-(6-fluoro-1,3-benzothiazol-2-yl)-2-methyl-piperazin-1-yl]methanone (Herein Referred to as 40 or Compound 40)

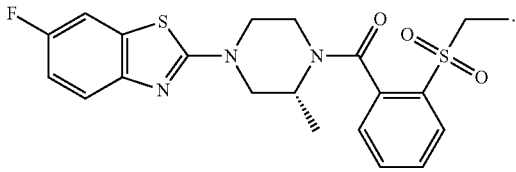 [SMILES: CCS(=O)(=O)c1ccccc1C(=O)N1CCN(c2nc3ccc(F)cc3s2)C[C@H]1C]

Compound 40 was prepared according to general procedure B using 53 and 60 (64 mg, 0.3 mmol). The crude was purified by column chromatography (DCM:MeOH, 99:1) to afford 40 as a white solid (81 mg, 70%). $^1$H NMR (400 MHz, DMSO-$d_6$) δ 8.03-7.90 (m, 1H), 7.90-7.79 (m, 1H), 7.78-7.65 (m, 2H), 7.63-7.46 (m, 1H), 7.46-7.39 (m, 1H), 7.16-7.07 (m, 1H), 5.03-3.07 (m, 9H), 1.33-1.07 (m, 6H). $^{13}$C NMR (101 MHz, DMSO) δ 168.5, 167.5, 166.7, 158.4, 156.0, 149.0, 136.6, 136.4, 135.1, 134.4, 134.3, 131.3, 131.2, 130.6, 130.5, 130.2, 129.7, 129.6, 127.65, 127.0, 125.4, 123.1, 119.1, 119.0, 118.7, 115.3, 114.7, 113.6, 113.4, 111.8, 110.2, 108.2, 108.1, 107.7, 52.1, 51.8, 51.6, 51.1, 50.5, 50.4, 47.0, 46.9, 44.6, 44.2, 41.6, 41.5, 16.5, 15.7, 15.4, 14.6, 13.7, 6.8, 6.7. UPLC-MS (2.26 min, 448 [M+H]$^+$). HRMS $C_{21}H_{23}FN_3O_3S_2$ [M+H]$^+$: calculated 448.1165 measured: 448.117 Δppm 1.1. [α]$^{20}_D$=−36° (c 1.0, CHCl$_3$).

72

[(2S)-4-(6-fluoro-1,3-benzothiazol-2-yl)-2-methyl-piperazin-1-yl]-(2-propylsulfonylphenyl)methanone (Herein Referred to as 41 or Compound 41)

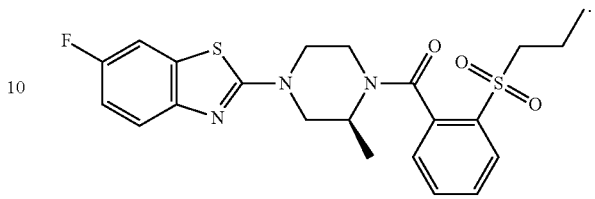

Compound 41 was prepared according to general procedure B using 54 and 4-propylsulfonylbenzoic acid (170 mg, 0.7 mmol). The crude was purified by column chromatography (Cy:EtOAc, 50:50) to afford 41 as a white solid (250 mg, 74%). $^1$H NMR (400 MHz, DMSO-$d_6$) δ 8.00-7.96 (m, 2H), 7.77-7.70 (m, 3H), 7.47 (dd, J=8.9, 4.8, 1H), 7.14 (td, J=9.1, 2.7, 1H), 3.81 (bs, 1H), 3.70 (bs, 1H), 3.59 (bs, 1H), 3.45 (bs, 1H), 3.36 (q, J=7.4, 1H), 1.13 (t, J=7.3, 2H). 13C NMR (101 MHz, DMSO-$d_6$) δ 168.0, 167.8, 157.3 (d, J=237.3), 148.9, 140.6, 139.3, 131.4 (d, J=11.4), 128.2, 127.9, 119.4 (d, J=8.8), 113.6 (d, J=23.6), 108.2 (d, J=27.3), 49.0, 47.7 (bs), 46.0 (bs), 40.7 (bs), 7.1. UPLC-MS: 2.3 min, 434 [M+H]$^+$. HRMS $C_{22}H_{25}FN_3O_3S_2$ [M+H]$^+$: calculated 462.1321 measured: 462.1328 Δppm 1.5. [α]$^{20}_D$=+350 (c 1.0, CHCl$_3$).

(2-cyclopropylsulfonylphenyl)-[(2S)-4-(6-fluoro-1,3-benzothiazol-2-yl)-2-methyl-piperazin-1-yl]methanone (Herein Referred to as 42 or Compound 42)

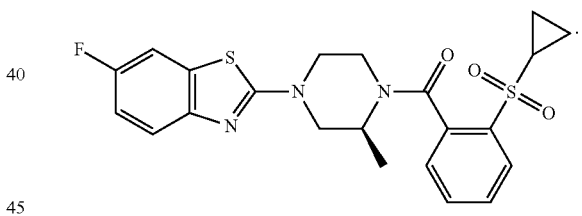

To a solution of 58 (185 mg, 0.33 mmol) in THF (7 mL) was added tBuOK (56 mg, 0.50 mmol) and the mixture was stirred at rt for 2 h. The reaction was quenched with a solution of NH$_4$Cl (5 mL) and the compound was extracted with EtOAc, dried over Na$_2$SO$_4$ and evaporated to give a residue which was purified by column chromatography (Cy:EtOAc 30:70) to afford 42 as a white solid (135 mg, 88%). $^1$H NMR (400 MHz, DMSO-$d_6$) δ 7.96-7.86 (m, 1H), 7.87-7.76 (m, 1H), 7.77-7.66 (m, 2H), 7.65-7.46 (m, 1H), 7.46-7.40 (m, 1H), 7.19-7.04 (m, 1H), 5.10-2.83 (m, 8H), 1.38-0.86 (m, 7H). $^{13}$C NMR (101 MHz, DMSO-$d_6$) δ 168.6, 168.5, 168.4, 168.3, 167.6, 167.0, 166.9, 166.8, 158.4, 156.1, 149.0, 137.4, 137.0, 136.2, 136.1, 135.8, 134.1, 134.0, 133.8, 131.3, 131.2, 129.9, 129.8, 129.6, 129.4, 129.2, 128.0, 127.6, 127.5, 126.9, 119.2, 119.1, 113.6, 113.4, 108.2, 108.0, 52.2, 51.8, 51.6, 51.1, 50.4, 50.1, 47.4, 47.1, 46.9, 44.6, 44.2, 41.6, 41.5, 40.1, 35.5, 35.4, 33.0, 32.9, 15.7, 15.4, 14.5, 13.7, 6.3, 6.2, 5.1, 5.0, 4.9. UPLC-MS: 2.28 min, 460 [M+H]$^+$. HRMS $C_{22}H_{23}FN_3O_3S_2$ [M+H]$^+$: calculated 460.1165 measured: 460.1173 Δppm 1.7. [α]$^{20}_D$=+49° (c 1.0, CHCl$_3$).

6-fluoro-2-piperazin-1-yl-1,3-benzothiazole (herein referred to as 43 or Compound 43). Compound 43 was prepared according to general procedure A using 2-chloro-6-fluoro-1,3-benzothiazole (374 mg, 2.0 mmol) and piperazine. The crude was purified by column chromatography (Cy:EtOAc, 1:1) to afford 43 as a white solid (384 mg, 81%). $^1$H NMR (400 MHz, DMSO-$d_6$) δ 7.7 (dd, J=8.8, 2.7, 1H), 7.4 (dd, J=8.8, 4.8, 1H), 7.1 (td, J=9.1, 2.8, 1H), 3.5-3.4 (m, 4H), 2.8-2.8 (m, 4H). UPLC-MS: 1.51 min, 237 [M+H]$^+$.

(2-ethylsulfonylphenyl)-piperazin-1-yl-methanone (herein referred to as 44 or Compound 44). Compound 44 was prepared according to general procedure B using 60 (1.07 g, 5.00 mmol) and piperazine. The crude was purified by column chromatography (DCM:MeOH, 99:1) to afford 44 as a white solid (1.28 g, 91%). $^1$H NMR (400 MHz, DMSO-$d_6$) δ 7.9 (d, J=7.9, 1H), 7.8 (td, J=7.5, 1.2, 1H), 7.7 (td, J=7.7, 1.2, 1H), 7.5 (d, J=7.4, 1H), 3.6 (ddd, J=12.9, 6.2, 3.7, 1H), 3.5 (ddd, J=9.2, 6.9, 3.5, 1H), 3.4-3.3 (m, 2H), 3.0 (ddd, J=13.1, 6.4, 3.5, 1H), 3.0 (ddd, J=13.0, 7.0, 3.3, 1H), 2.8-2.6 (m, 3H), 2.6 (ddt, J=10.6, 7.0, 3.5, 1H), 1.1 (t, J=7.4, 3H). UPLC-MS: 1.08 min, 283 [M+H]$^+$.

6-fluoro-2-(4-piperidyl)-1,3-benzothiazole (Herein Referred to as 45 or Compound 45)

Step 1:

To a solution of 1-tert-butoxycarbonylpiperidine-4-carboxylic acid (2.29 g, 10 mmol) in DCM (xx mL) was added at 0° C. oxalyl chloride (1.03 mL, 12 mmol and the solution was stirred at rt for 30 min. 2,4-difluoroaniline (1.02 mL, 10 mmol was then added followed by the dropwise addition of pyridine (0.81 mL, 10 mmol). The mixture was stirred at rt for 1 h and then evaporated under reduced pressure. The residue was purified by column chromatography (Cy:EtOAc 70:30) to obtain the tert-butyl 4-[(2,4-difluorophenyl)carbamoyl]piperidine-1-carboxylate as a white solid (2.43 g, 71%). $^1$H NMR (400 MHz, DMSO-$d_6$) δ 9.68 (s, 1H), 7.76 (td, J=9.0, 6.4, 1H), 7.28 (ddd, J=11.4, 9.1, 2.8, 1H), 7.09-6.99 (m, 1H), 3.97 (d, J=12.7, 2H), 2.76 (s, 2H), 2.63 (tt, J=11.3, 3.5, 1H), 1.77 (d, J=11.1, 2H), 1.46 (qd, J=12.3, 4.0, 2H), 1.40 (s, 9H). UPLC-MS: 2.47 min, 283 [M-$C_4H_9$]$^+$, 339 [M-H]$^-$.

Step 2:

To a solution of compound from step 1 (2.43 g, 7.14 mmol) in Tol (14 mL) was added the Lawesson reagent (2.89 g, 7.14 mmol) and the mixture was stirred at reflux for 6 h. The solvent was removed under reduced pressure and the residue was washed with $Et_2O$ to give a white solid which was used in the next step without any further purification. The solid was dissolved in NMP (28 mL) and $K_2CO_3$ (0.99 g, 7.14 mmol) and the mixture was stirred at 100° C. for 2 h. The suspension was poured in $H_2O$ and extracted with EtOAc, dried over $Na_2SO_4$ and evaporated to give 45 as a yellow solid (0.51 g, 39%). $^1$H NMR (400 MHz, DMSO-$d_6$) δ 7.96 (dd, J=8.9, 2.6, 1H), 7.95 (dd, J=8.8, 5.1, 1H), 7.34 (td, J=9.1, 2.7, 1H), 3.18 (tt, J=11.5, 3.7, 1H), 3.03 (dt, J=12.4, 3.2, 2H), 2.63 (td, J=12.1, 2.0, 2H), 2.01 (dq, J=13.1, 3.4, 2H), 1.66 (qd, J=12.1, 3.9, 2H). UPLC-MS: 1.51 min, 237 [M+H]$^+$.

(2-ethylsulfonylphenyl)-(4-piperidyl)methanone (Herein Referred to as 46 or Compound 46)

Step 1:

To a solution of 2-bromothiophenol (0.50 g, 0.31 mL, 2.64 mmol) in DMF (9 mL) was added $Cs_2CO_3$ (0.86 g, 2.64 mmol), followed by iodoethane (0.53 mL, 6.61 mmol). The reaction was stirred at rt for 15 h. The mixture was diluted with EtOAc and $H_2O$ was added. The two layers were separated and the aqueous phase was extracted with EtOAc (3 times). The combined organic phase was dried over $Na_2SO_4$, filtered and evaporated under reduce pressure to obtain 1-bromo-2-ethylsulfonyl-benzene as a brown oil (0.53 g, 93%). $^1$H NMR (400 MHz, DMSO-$d_6$) δ 7.60 (dd, J=7.9, 1.1, 0H), 7.38 (td, J=7.5, 7.0, 1.2, 1H), 7.34 (dd, J=7.9, 1.8, 0H), 7.09 (ddd, J=8.0, 7.1, 1.8, 0H), 3.01 (q, J=7.3, 2H), 1.28 (t, J=7.3, 3H). UPLC-MS: 2.85 min.

Step 2:

In an oven-dried flask, compound from step 1 (188 mg, 0.75 mmol) was dissolved in dry THF (4 mL) and the solution cooled to −78° C. nBuLi (0.48 mL, 1.21 mmol) was added and the mixture was stirred under nitrogen at −78° C. for 30 min. Then, a solution of tert-butyl 4-formylpiperidine-1-carboxylate (107 mg, 0.50 mmol) in dry THF (2 mL) was added and the reaction was stirred for 4 h. The solvent was removed under reduced pressure and the residue was purified by column chromatography (Cy:EtOAc 80:20) to give tert-butyl 4-[(2-ethylsulfonylphenyl)-hydroxy-methyl]piperidine-1-carboxylate (48 mg, 27%). $^1$H NMR (400 MHz, DMSO-$d_6$) δ 7.42 (dd, J=7.1, 2.2, 1H), 7.32 (dd, J=7.5, 1.7, 1H), 7.25-7.16 (m, 2H), 5.21 (d, J=4.5, 1H), 4.78 (t, J=5.0, 1H), 3.92 (bs, 2H), 2.96 (q, J=7.3, 2H), 2.55 (bs, 2H), 1.62 (s, 2H), 1.58-1.49 (m, 1H), 1.38 (s, 9H), 1.34-1.26 (m, 2H), 1.17 (t, J=7.1, 3H). UPLC-MS: 2.90 min, 352 [M+H]$^+$.

Step 3:

Compound from step 2 (38 mg, 0.10 mmol) was dissolved in dry DCM (2 mL) and Dess-Martin periodinane (61 mg, 0.14 mmol) was added and the reaction was stirred at rt for 12 h. The mixture was diluted with DCM and $H_2O$ was added. The two phases were separated and aqueous layer was extracted with DCM (3 times). The combined organic phase was dried over $Na_2SO_4$ and evaporated to obtain tert-butyl 4-(2-ethylsulfonylbenzoyl)piperidine-1-carboxylate (38 mg, quant.). $^1$H NMR (400 MHz, DMSO-$d_6$) δ 7.98 (dd, J=7.8, 1.3, 1H), 7.85 (td, J=7.5, 1.3, 1H), 7.77 (dd, J=7.7, 1.4, 1H), 7.75 (td, J=7.5, 1.3, 1H), 3.97 (d, J=13.3, 2H), 3.38 (q, J=7.5, 2H), 3.20 (tt, J=11.5, 3.8, 1H), 2.76 (bs, 2H), 1.80 (d, J=12.8, 2H), 1.43 (qd, J=12.9, 3.9, 2H), 1.40 (s, 9H), 1.14 (t, J=7.4, 3H). UPLC-MS: 2.54 min, 381 [M+H]$^+$, 380 [M-H]$^-$.

Step 4:

Compound from step 3 (68 mg, 0.18 mmol) was dissolved in a 4M HCl in dioxane (1 mL) and the mixture was stirred at rt for 12 h. The solvent was evaporated under reduced pressure to obtain 46 as a white solid (57 mg, quant.). UPLC-MS: 1.29 min, 282 [M+H]$^+$.

2-ethylsulfonylbenzaldehyde (Herein Referred to as 47 or Compound 47)

Step 1:

To a solution of 60 (50 mg, 0.24 mmol) in THF (3 mL) was added 2M $LiAlH_4$ (0.24 mL, 0.48 mmol) and the resulting mixture was stirred at rt for 3 h. The reaction was quenched with $H_2O$ (2 mL) and stirred for 30 min. The solid formed was filtered through a Celite pad and the filtrate was diluted with EtOAc, washed with $H_2O$, dried over $Na_2SO_4$ and evaporated to obtain (2-ethylsulfonylphenyl)methanol (46 mg, quant.). $^1$H NMR (400 MHz, DMSO-$d_6$) δ 8.00 (dd, J=7.9, 1.3, 1H), 7.67 (td, J=7.5, 1.3, 1H), 7.60 (dd, J=7.6, 1.5, 1H), 7.53 (td, J=7.6, 1.4, 1H), 4.93 (s, 2H), 3.26 (q, J=7.4, 2H), 1.31 (t, J=7.5, 3H). UPLC-MS: 1.39 min, 201 [M+H]$^+$, 218 [M+$NH_4$]$^+$.

Step 2:

To a solution of compound from step 1 (46 mg, 0.24 mmol) in Et$_2$O (5 mL) was added manganese dioxide (83 mg, 0.96 mmol). The suspension was stirred at rt for 15 h, then filtered through a celite pad and washed with DCM. The filtrate was evaporated to give 47 as a yellow oil (45 mg, quant.). $^1$H NMR (400 MHz, DMSO-d$_6$) δ 10.84 (s, 1H), 8.17-8.09 (m, 2H), 7.90-7.78 (m, 2H), 3.33 (q, J=7.5, 2H), 1.36 (t, J=7.4, 3H). UPLC-MS: 1.62 min, 199 [M+H]$^+$, 216 [M+NH$_4$]$^+$.

6-fluoro-2-(3-methylpiperazin-1-yl)-1,3-benzothiazole (herein referred to as 48 or Compound 48). Compound 48 was prepared according to general procedure A using 2-chloro-6-fluoro-1,3-benzothiazole (187 mg, 1.00 mmol) and 2-methylpiperazine to afford 48 as a yellow solid (251 mg, quant.). $^1$H NMR (400 MHz, DMSO-d$_6$) δ 7.68 (dd, J=8.7, 2.7, 1H), 7.41 (dd, J=8.8, 4.8, 1H), 7.10 (td, J=9.1, 2.7, 1H), 3.83 (d, J=10.5, 1H), 3.78 (d, J=12.3, 1H), 3.05 (td, J=12.0, 3.3, 1H), 2.95 (d, J=12.2, 1H), 2.79-2.63 (m, 3H), 1.02 (d, J=5.8, 3H). UPLC-MS: 1.40 min, 252 [M+H]$^+$.

tert-butyl 4-(6-fluoro-1,3-benzothiazol-2-yl)-3-methylpiperazine-1-carboxylate (herein referred to as 49 or Compound 49). Compound 49 was prepared according to general procedure A using 2-chloro-4-fluoro-1,3-benzothiazole (88 mg, 0.5 mmol). and tert-butyl 3-methylpiperazine-1-carboxylate. The crude was purified by column chromatography (Cy: EtOAc, 95:5) to afford 49 as a white solid (58 mg, 35%). UPLC-MS: 2.69 min, 352 [M+H]$^+$.

6-fluoro-2-(2-methylpiperazin-1-yl)-1,3-benzothiazole (herein referred to as 50 or Compound 50). To a solution of 49 (58 mg, 0.16 mmol) was dissolved in DCM, trifluoroacetic acid (0.1 mL, 1.31 mmol) was added at 0° C. and the mixture was stirred at rt for 3 h. The solvent was evaporated and the residue was dissolved in EtOAc and washed with a solution of saturated Na$_2$CO$_3$, dried over Na$_2$SO$_4$ and evaporated to afford 50 as brown oil (40 mg, quant.). $^1$H NMR (400 MHz, DMSO-d$_6$) δ 7.69 (dd, J=8.7, 2.8, 1H), 7.44-7.37 (m, 1H), 7.10 (td, J=9.1, 2.8, 1H), 4.13-4.02 (m, 1H), 3.72-3.60 (m, 1H), 3.25 (qd, J=12.8, 3.8, 1H), 3.02-2.93 (m, 1H), 2.87 (dd, J=12.4, 3.9, 1H), 2.80 (d, J=12.4, 1H), 2.66 (td, J=12.3, 3.7, 1H), 1.28 (d, J=6.7, 3H). UPLC-MS: 1.49 min, 352 [M+H]$^+$.

2-(3,3-dimethylpiperazin-1-yl)-6-fluoro-1,3-benzothiazole (herein referred to as 51 or Compound 51). Compound 51 was prepared according to general procedure A using 2-chloro-6-fluoro-1,3-benzothiazole (187 mg, 1.00 mmol) and 2,2-dimethylpiperazine to afford 51 as a yellow solid (265 mg, quant.). $^1$H NMR (400 MHz, DMSO-d$_6$) δ 7.66 (dd, J=8.7, 2.7, 1H), 7.38 (dd, J=8.8, 4.8, 1H), 7.09 (td, J=9.1, 2.7, 1H), 3.47-3.42 (m, 2H), 3.26 (s, 2H), 2.86-2.81 (m, 2H), 1.07 (s, 6H). UPLC-MS: 1.51 min, 266 [M+H]$^+$.

2-(3,5-dimethylpiperazin-1-yl)-6-fluoro-1,3-benzothiazole (herein referred to as 52 or Compound 52). Compound 52 was prepared according to general procedure A using 2-chloro-6-fluoro-1,3-benzothiazole (187 mg, 1.00 mmol) and 2,6-dimethylpiperazine to afford 52 as a yellow solid (265 mg, quant.). $^1$H NMR (400 MHz, DMSO-d$_6$) δ 7.67 (dd, J=8.7, 2.7, 1H), 7.41 (dd, J=8.8, 4.9, 1H), 7.10 (td, J=9.2, 2.8, 1H), 3.81 (dd, J=12.2, 2.3, 2H), 2.87-2.72 (m, 2H), 2.62 (dd, J=12.0, 10.9, 2H), 1.03 (d, J=6.3, 6H). UPLC-MS: 1.54 min, 266 [M+H]$^+$.

6-fluoro-2-[(3R)-3-methylpiperazin-1-yl]-1,3-benzothiazole (herein referred to as 53 or Compound 53). Compound 53 was prepared according to general procedure A using 2-chloro-6-fluoro-1,3-benzothiazole (187 mg, 1.00 mmol) and (2R)-2-methylpiperazine to afford 53 as a yellow solid (251 mg, quant.). $^1$H NMR (400 MHz, DMSO-d$_6$) δ 7.68 (dd, J=8.7, 2.7, 1H), 7.41 (dd, J=8.8, 4.8, 1H), 7.10 (td, J=9.1, 2.7, 1H), 3.83 (d, J=10.5, 1H), 3.78 (d, J=12.3, 1H), 3.05 (td, J=12.0, 3.3, 1H), 2.95 (d, J=12.2, 1H), 2.79-2.63 (m, 3H), 1.02 (d, J=5.8, 3H). UPLC-MS: 1.40 min, 252 [M+H]$^+$. [α]$^{20}_D$=+66° (c 1.0, CHCl$_3$).

6-fluoro-2-[(3 S)-3-methylpiperazin-1-yl]-1,3-benzothiazole (herein referred to as 54 or Compound 54). Compound 54 was prepared according to general procedure A using 2-chloro-6-fluoro-1,3-benzothiazole (187 mg, 1.00 mmol) and (2S)-2-methylpiperazine to afford 54 as a yellow solid (251 mg, quant.). $^1$H NMR (400 MHz, DMSO-d$_6$) δ 7.68 (dd, J=8.7, 2.7, 1H), 7.41 (dd, J=8.8, 4.8, 1H), 7.10 (td, J=9.1, 2.7, 1H), 3.83 (d, J=10.5, 1H), 3.78 (d, J=12.3, 1H), 3.05 (td, J=12.0, 3.3, 1H), 2.95 (d, J=12.2, 1H), 2.79-2.63 (m, 3H), 1.02 (d, J=5.8, 3H). UPLC-MS: 1.40 min, 252 [M+H]$^+$. [α]$^{20}_D$=−64° (c 1.0, CHCl$_3$).

[4-(6-fluoro-1,3-benzothiazol-2-yl)piperazin-1-yl]-[2-(3-hydroxypropylsulfonyl) phenyl]methanone (herein referred to as 55 or Compound 55). Compound 55 was prepared according to general procedure B using 43 and 2-(3-hydroxypropylsulfonyl)benzoic acid (244 mg, 1.0 mmol). The crude was purified by column chromatography (EtOAc) to afford 55 as a white solid (383 mg, 83%). $^1$H NMR (400 MHz, DMSO-d$_6$) δ 7.97 (dd, J=7.9, 0.9, 1H), 7.84 (td, J=7.5, 1.1, 1H), 7.78-7.70 (m, 2H), 7.58 (dd, J=7.5, 0.9, 1H), 7.47 (dd, J=8.8, 4.8, 1H), 7.13 (td, J=9.1, 2.7, 1H), 4.63 (t, J=5.4, 1H), 3.92-3.81 (m, 1H), 3.79-3.68 (m, 2H), 3.67-3.58 (m, 1H), 3.56 (t, J=5.3, 2H), 3.50-3.38 (m, 4H), 3.35 (dd, J=14.5, 6.0, 1H), 3.23 (dt, J=13.4, 4.8, 1H), 1.87-1.73 (m, 1H), 1.67-1.54 (m, 1H). UPLC-MS: 1.95 min, 464 [M+H]$^+$, 522 [M+AcO]$^-$.

3-[2-[4-(6-fluoro-1,3-benzothiazol-2-yl)piperazine-1-carbonyl]phenyl]sulfonylpropyl methanesulfonate (herein referred to as 56 or Compound 56). To a solution of 55 (232 mg, 0.5 mmol) in DCM (6 mL) MsCl (46 μL, 0.6 mmol, 1.2 eq.) and Et$_3$N (84 μL, 0.60 mmol, 1.2 eq.) were added and the mixture was stirred at rt for 3 h. The solution was diluted with DCM and washed with 2M HCl and H$_2$O, dried over Na$_2$SO$_4$ and evaporated under reduced pressure to obtain 56 as a white solid (255 mg, 94%). $^1$H NMR (400 MHz, DMSO-d$_6$) δ 8.00 (dd, J=7.9, 1.0, 1H), 7.87 (td, J=7.5, 1.2, 1H), 7.75 (td, J=7.7, 1.3, 1H), 7.74 (dd, J=8.6, 2.8, 1H), 7.60 (dd, J=7.5, 1.0, 1H), 7.47 (dd, J=8.8, 4.8, 1H), 7.13 (td, J=9.1, 2.7, 1H), 4.25 (t, J=6.2, 2H), 3.88 (ddd, J=12.4, 6.6, 3.4, 1H), 3.80-3.68 (m, 2H), 3.65-3.48 (m, 5H), 3.40-3.35 (m, 1H), 3.24 (ddd, J=13.5, 5.9, 4.1, 1H), 3.16 (s, 3H), 2.14-2.01 (m, 1H), 1.98-1.86 (m, 1H). UPLC-MS: 2.16 min, 542 [M+H]$^+$, 600 [M+AcO]$^-$.

[(2S)-4-(6-fluoro-1,3-benzothiazol-2-yl)-2-methyl-piperazin-1-yl]-[2-(3-hydroxypropylsulfonyl)phenyl]methanone (herein referred to as 57 or Compound 57). Compound 57 was prepared according to general procedure B using 54 and 2-(3-hydroxypropylsulfonyl)benzoic acid (244 mg, 1.0 mmol). The crude was purified by column chromatography (EtOAc) to afford 57 as a white solid (215 mg, 45%). $^1$H NMR (400 MHz, DMSO-d$_6$) δ 8.03-7.92 (m, 1H), 7.91-7.80 (m, 1H), 7.80-7.68 (m, 2H), 7.67-7.47 (m, 1H), 7.45 (ddd, J=7.6, 4.8, 2.6, 1H), 7.24-7.07 (m, 1H), 5.12-3.00 (m, 12H), 1.34-1.18 (m, 3H), 1.18-1.06 (m, 2H). UPLC-MS: 2.03 min, 478 [M+H]$^+$, 536 [M+AcO]$^-$.

3-[2-[4-(6-fluoro-1,3-benzothiazol-2-yl)piperazine-1-carbonyl]phenyl]sulfonylpropyl methanesulfonate (herein referred to as 58 or Compound 58). To a solution of 58 (215 mg, 0.4 mmol) in DCM (7 mL) MsCl (70 μL, 0.9 mmol, 2.0 eq.) and Et$_3$N (125 μL, 0.90 mmol, 2 eq.) were added and the mixture was stirred at rt for 3 h. The solution was diluted with DCM and washed with 2M HCl and H$_2$O, dried over Na$_2$SO$_4$ and evaporated under reduced pressure to obtain a residue which was purified by column chromatography (EtOAC) to afford 58 as a white solid (201 mg, 80%). $^1$H NMR (400 MHz, DMSO-d$_6$) δ 8.06-7.94 (m, 1H), 7.91-7.80 (m, 1H), 7.80-7.67 (m, 2H), 7.67-7.46 (m, 1H), 7.48-7.38 (m, 1H), 7.21-7.06 (m, 1H), 5.06-3.02 (m, 14H), 2.16-1.83 (m, 2H), 1.34-1.16 (m, 3H). UPLC-MS: 2.24 min, 556 [M+H]$^+$, 614 [M+AcO]$^-$.

2-ethylsulfanylbenzoic acid (herein referred to as 59 or Compound 59). Compound 59 was prepared according to general procedure C using 2-sulfanylbenzoic acid (1.0 g, 6.4 mmol) and ethyl iodide to afford 59 as a white solid (1.09 g, quant.). $^1$H NMR (400 MHz, DMSO-d$_6$) δ 12.95 (s, 1H), 7.86 (dd, J=7.8, 1.5, 1H), 7.51 (ddd, J=7.9, 7.3, 1.6, 1H), 7.39 (dd, J=8.1, 1.1, 1H), 7.19 (td, J=7.5, 1.3, 1H), 2.93 (q, J=7.3, 2H), 1.27 (t, J=7.3, 3H). UPLC-MS: 1.37 min, 183 [M+H]$^+$, 181 [M−H]$^-$.

2-ethylsulfonylbenzoic acid (herein referred to as 60 or Compound 60). Compound 60 was prepared according to general procedure D using 59 (300 mg, 1.6 mmol) to afford 60 as a white solid (340 mg, 96%.). $^1$H NMR (400 MHz, DMSO-d$_6$) δ=13.72 (s, 1H), 7.95 (dd, J=7.6, 1.3, 1H), 7.82 (td, J=7.6, 1.4, 1H), 7.75 (td, J=7.7, 1.6, 1H), 7.73 (dd, J=7.3, 1.3, 1H), 3.52 (q, J=7.4, 2H), 1.16 (t, J=7.4, 3H). UPLC-MS: 0.78 min, 197 [M-OH]$^+$, 215 [M+H]$^+$, 232 [M+NH$_4$]$^+$, 169 [M-COOH]$^-$, 231 [M−H]$^-$.

2-propylsulfanylbenzoic acid (herein referred to as 61 or Compound 61). Compound 61 was prepared according to general procedure C using 2-sulfanylbenzoic acid (1.54 g, 10.0 mmol) and propyl iodide to afford 61 as a white solid (1.89 g, 96%). $^1$H NMR (400 MHz, DMSO-d$_6$) δ 12.95 (s, 1H), 7.85 (dd, J=7.8, 1.6, 1H), 7.51 (ddd, J=8.6, 7.3, 1.6, 1H), 7.40 (dd, J=8.2, 1.1, 1H), 7.20 (td, J=7.5, 1.1, 1H), 2.90 (t, J=7.3, 2H), 1.64 (h, J=7.3, 2H), 1.02 (t, J=7.3, 3H). UPLC-MS: 1.58 min, 179 [M-OH]$^+$, 197 [M+H]$^+$, 151 [M-COOH]$^-$, 195 [M−H]$^-$.

2-propylsulfonylbenzoic acid (herein referred to as 62 or Compound 62). Compound 62 was prepared according to general procedure D using 61 (1.89 g, 9.2 mmol) to afford 62 as a yellow oil (1.90 g, 91%). $^1$H NMR (400 MHz, DMSO-d$_6$) δ=13.71 (s, 1H), 7.96 (dd, J=7.7, 1.3, 1H), 7.81 (td, J=7.5, 1.4, 1H), 7.75 (td, J=7.6, 1.6, OH), 7.73 (dd, J=7.3, 1.2, 2H), 3.55-3.46 (m, 2H), 1.68-1.58 (m, 2H), 0.94 (t, J=7.4, 3H). UPLC-MS: 0.95 min, 211 [M-OH]$^+$, 229 [M+H]$^+$, 246 [M+NH$_4$]$^+$, 183 [M-COOH]$^-$, 227 [M−H]$^-$.

2-butylsulfanylbenzoic acid (herein referred to as 63 or Compound 63). Compound 63 was prepared according to general procedure C using 2-sulfanylbenzoic acid (300 mg, 2.2 mmol) and butyl iodide to afford 63 as a white solid (426 mg, 93%). $^1$H NMR (400 MHz, DMSO-d$_6$) δ 12.94 (s, 1H), 7.85 (dd, J=7.8, 1.6, 1H), 7.50 (ddd, J=8.8, 7.3, 1.6, 1H), 7.39 (dd, J=8.2, 1.1, 1H), 7.19 (td, J=7.5, 1.1, 1H), 2.93-2.87 (m, 2H), 1.66-1.52 (m, 2H), 1.51-1.36 (m, 2H), 0.91 (t, J=7.3, 3H). UPLC-MS: 1.86 min, 193 [M-OH]$^+$, 211 [M+H]$^+$, 165 [M-COOH]$^-$, 209 [M−H]$^-$.

2-butylsulfonylbenzoic acid (herein referred to as 64 or Compound 64). Compound 64 was prepared according to general procedure D using 63 (1.89 g, 9.2 mmol) to afford 64 as a white solid (370 mg, 70%). $^1$H NMR (400 MHz, DMSO-d$_6$) δ 13.71 (s, 1H), 7.99 (dd, J=7.6, 1.5, 1H), 7.85 (td, J=7.6, 1.6, 1H), 7.81-7.78 (m, 1H), 7.77-7.73 (m, 2H), 3.50-3.44 (m, 2H), 1.69-1.52 (m, 4H), 1.47-1.28 (m, 4H), 0.85 (t, J=7.3, 4H). UPLC-MS: 0.95 min, 225 [M-OH]$^+$, 243 [M+H]$^+$, 260 [M+NH$_4$]$^+$, 197 [M-COOH]$^-$, 241 [M−H].

2-isopropylsulfanylbenzoic acid (herein referred to as 65 or Compound 65). Compound 65 was prepared according to general procedure C using 2-sulfanylbenzoic acid (334 mg, 2.2 mmol) and isopropyl iodide to afford 65 as a white solid (410 mg, 96%). $^1$H NMR (400 MHz, DMSO-d$_6$) δ=12.95 (s, 1H), 7.79 (dd, J=7.7, 1.5, 1H), 7.50 (ddd, J=8.4, 6.8, 1.5, 1H), 7.46 (dd, J=8.2, 1.5, 1H), 7.21 (ddd, J=8.1, 6.9, 1.5, 1H), 3.58 (hept, J=6.6, 1H), 1.27 (d, J=6.6, 6H). UPLC-MS: 1.49 min, 179 [M-OH]$^+$, 197 [M+H]$^+$, 151 [M-COOH]$^-$, 195 [M−H]$^-$.

2-isopropylsulfonylbenzoic acid (herein referred to as 66 or Compound 66). Compound 66 was prepared according to general procedure D using 65 (410 mg, 2.1 mmol) to afford 66 as a yellow solid (350 mg, 70%). $^1$H NMR (400 MHz, DMSO-d$_6$) δ 13.72 (s, 1H), 7.93 (dd, J=8.1, 1.3, 1H), 7.84-7.79 (m, 1H), 7.77-7.71 (m, 2H), 3.89 (hept, J=6.9, 1H), 1.20 (d, J=6.9, 6H). UPLC-MS: 0.94 min, 211 [M-OH]$^+$, 229 [M+H]$^+$, 246 [M+NH$_4$]$^+$, 183 [M-COOH]$^-$, 227 [M−H]$^-$.

2-(3-hydroxypropylsulfanyl)benzoic acid (herein referred to as 67 or Compound 67). Compound 67 was prepared according to general procedure C using 2-sulfanylbenzoic acid (1.54 g, 10.0 mmol) and 3-hydroxypropyl bromide to afford 67 as a white solid (2.0 g, 95%). $^1$H NMR (400 MHz, DMSO-d$_6$) δ 7.85 (dd, J=7.8, 1.5, 1H), 7.50 (ddd, J=8.2, 7.2, 1.6, 1H), 7.40 (dd, J=8.2, 1.0, 1H), 7.19 (td, J=7.4, 1.0, 1H), 4.61 (bs, 1H), 3.52 (t, J=6.2, 2H), 2.94 (t, J=7.4, 2H), 1.75 (p, J=6.4, 2H). UPLC-MS: 0.98 min, 195 [M-OH]$^+$, 213 [M+H]$^+$, 211 [M−H]$^-$.

2-(3-hydroxypropylsulfonyl)benzoic acid (herein referred to as 68 or Compound 68). Compound 68 was prepared according to general procedure D using 67 (2.12 g, 10.0 mmol) to afford 68 as a white solid (2.05 mg, 84%). $^1$H NMR (400 MHz, DMSO-d$_6$) δ=13.70 (bs, 1H), 7.96 (dd, J=7.6, 1.0, 1H), 7.81 (td, J=7.5, 1.4, 1H), 7.75 (td, J=7.6, 1.6, 1H), 7.73 (dd, J=7.3, 1.2, 1H), 4.64 (bs, 1H), 3.58-3.51 (m, 2H), 3.44 (t, J=6.2, 2H), 1.78-1.68 (m, 2H). UPLC-MS: 0.50 min, 227 [M-OH]$^+$, 245 [M+H]$^+$, 262 [M+NH$_4$]$^+$, 199 [M-COOH]$^-$, 243 [M−H]$^-$.

2-cyclobutylsulfanylbenzoic acid (herein referred to as 69 or Compound 69). Compound 69 was prepared according to general procedure C using 2-sulfanylbenzoic acid (250 mg, 1.6 mmol) and cyclobutyl bromide to afford 69 as a brown oil (134 mg, 40%). $^1$H NMR (400 MHz, DMSO-d$_6$) δ=13.49 (s, 1H), 8.02 (dd, J=7.7, 1.5, 1H), 7.62 (dd, J=8.2, 1.2, 1H), 7.56 (ddd, J=8.3, 7.1, 1.5, 1H), 7.34 (td, J=7.4, 1.3, 1H), 3.95 (p, J=7.8, 1H), 2.59-2.51 (m, 2H), 2.10-1.87 (m, 4H). UPLC-MS: 1.71 min, 191 [M-OH]$^+$, 209 [M+H]$^+$, 207 [M−H]$^-$.

2-cyclobutylsulfonylbenzoic acid (herein referred to as 70 or Compound 70). Compound 70 was prepared according to general procedure D using 69 (134 g, 0.6 mmol) to afford 70 as an off-white solid (147 mg, 94%). $^1$H NMR (400 MHz, DMSO-d$_6$) δ 13.64 (s, 1H), 7.95 (dd, J=7.8, 1.3, 1H), 7.79 (td, J=7.5, 1.4, 1H), 7.76-7.67 (m, 2H), 4.47 (p, J=8.2, 1H), 2.45-2.33 (m, 2H), 2.20-2.08 (m, 2H), 2.04-1.85 (m, 2H). UPLC-MS: 1.03 min, 223 [M-OH]$^+$, 241 [M+H]$^+$, 258 [M+NH$_4$]$^+$, 195 [M-COOH]$^-$, 239 [M−H]$^-$.

2-cyclopentylsulfanylbenzoic acid (herein referred to as 71 or Compound 71). Compound 71 was prepared according to general procedure C using 2-sulfanylbenzoic acid (1.54 g, 10.0 mmol) and cyclopentyl bromide to afford 71 as a yellow oil (2.22 g, quant.). $^1$H NMR (400 MHz, DMSO-d$_6$) δ 12.93 (s, 1H), 7.83 (dd, J=7.8, 1.4, 1H), 7.50 (ddd, J=8.3, 6.9, 1.5, 1H), 7.45 (dd, J=8.2, 1.5, 1H), 7.19 (ddd, J=8.0, 6.9, 1.5, 1H), 3.69 (tt, J=7.5, 5.9, 1H), 2.14 (dq, J=12.7, 6.7, 2H), 1.77-1.54 (m, 4H), 1.50 (dq, J=13.0, 6.3, 2H). UPLC-MS: 1.70 min, 205 [M-OH]$^+$, 223 [M+H]$^+$, 177 [M-COOH]$^-$, 221 [M−H]$^-$.

2-cyclopentylsulfonylbenzoic acid (herein referred to as 72 or Compound 72). Compound 72 was prepared according to general procedure D using 71 (2.12 g, 10.0 mmol) to afford 72 as a white solid (2.41 g, 95%). $^1$H NMR (400 MHz, DMSO-$d_6$) δ 13.67 (s, 1H), 7.96 (dd, J=7.7, 1.3, 1H), 7.79 (dd, J=7.4, 1.3, 1H), 7.76-7.69 (m, 2H), 4.19 (tt, J=8.8, 6.6, 1H), 1.94 (dq, J=12.9, 6.5, 2H), 1.87-1.65 (m, 4H), 1.65-1.52 (m, 2H). UPLC-MS: 0.50 min, 239 [M-OH]$^+$, 255 [M+H]$^+$, 272 [M+NH$_4$]$^+$, 209 [M-COOH]$^-$, 237 [M-OH]$^-$, 253 [M-H]$^-$.

2-cyclohexylsulfanylbenzoic acid (72). Compound 72 was prepared according to general procedure C using 2-sulfanylbenzoic acid (250 mg, 1.8 mmol) and cyclohexyl iodide to afford 72 as a brown oil (125 mg, 29%). $^1$H NMR (400 MHz, DMSO-$d_6$) δ 13.50 (s, 1H), 8.02 (dd, J=7.7, 1.5, 1H), 7.62 (dd, J=8.2, 1.2, 1H), 7.56 (ddd, J=8.3, 7.1, 1.5, 1H), 7.34 (td, J=7.5, 1.3, 1H), 3.34 (tt, J=6.5, 3.3, 1H), 2.02-1.90 (m, 2H), 1.78-1.67 (m, 2H), 1.66-1.54 (m, 1H), 1.47-1.16 (m, 5H). UPLC-MS: 2.01 min, 219 [M-OH]$^+$, 237 [M+H]$^+$, 191 [M-COOH]$^-$, 235 [M-H]$^-$.

2-cyclohexylsulfonylbenzoic acid (herein referred to as 74 or Compound 74). Compound 74 was prepared according to general procedure D using 73 (125 mg, 0.5 mmol) to afford 74 as an off-white solid (120 mg, 85%). $^1$H NMR (400 MHz, DMSO-$d_6$) δ 13.21 (s, 1H), 7.90 (dd, J=7.7, 1.6, 1H), 7.85-7.76 (m, 1H), 7.76-7.70 (m, 2H), 3.63 (tt, J=12.1, 3.3, 1H), 1.90-1.75 (m, 4H), 1.68-1.58 (m, 1H), 1.43 (qd, J=12.8, 11.5, 3.5, 2H), 1.26-1.08 (m, 3H). UPLC-MS: 1.27 min, 251 [M-OH]$^+$, 269 [M+H]$^+$, 286 [M+NH$_4$]$^+$, 223 [M-COOH]$^-$, 267 [M-H]$^-$.

3-ethylsulfanylbenzoic acid (herein referred to as 75 or Compound 75). Compound 75 was prepared according to general procedure C using 3-sulfanylbenzoic acid (250 mg, 1.6 mmol) and ethyl iodide to afford 75 as a white solid (285 mg, 96%). $^1$H NMR (400 MHz, DMSO-$d_6$) δ 7.82 (t, J=1.8, 1H), 7.73 (dt, J=7.6, 1.4, 1H), 7.49 (ddd, J=7.8, 2.0, 1.2, 1H), 7.40 (t, J=7.7, 1H), 3.01 (q, J=7.3, 2H), 1.25 (t, J=7.3, 3H). UPLC-MS: 1.59 min, 181 [M-H]$^-$.

3-ethylsulfonylbenzoic acid (herein referred to as 76 or Compound 76). Compound 76 was prepared according to general procedure D using 75 (280 mg, 1.5 mmol) to afford 76 as an yellow solid (300 mg, 96%). $^1$H NMR (400 MHz, DMSO-$d_6$) δ 13.53 (s, 1H), 8.35 (t, J=1.8, 1H), 8.28 (dt, J=7.8, 1.4, 1H), 8.13 (ddd, J=7.8, 2.0, 1.2, 1H), 7.81 (t, J=7.8, 1H), 3.36 (q, J=7.3, 2H), 1.10 (t, J=7.3, 3H). UPLC-MS: 0.90 min, 232 [M+NH$_4$]$^+$, 213 [M-H].

4-ethylsulfanylbenzoic acid (herein referred to as 77 or Compound 77). Compound 77 was prepared according to general procedure C using 4-sulfanylbenzoic acid (250 mg, 1.6 mmol) and ethyl iodide to afford 77 as a yellow solid (250 mg, 86%). $^1$H NMR (400 MHz, DMSO-$d_6$) δ 12.83 (s, 1H), 7.84 (d, J=8.5, 1H), 7.36 (d, J=8.5, 1H), 3.06 (q, J=7.3, 1H), 1.28 (t, J=7.3, 2H). UPLC-MS: 1.68 min, 183 [M+H]$^+$, 200 [M+NH$_4$]$^+$, 181 [M-H]$^-$.

4-ethylsulfonylbenzoic acid (herein referred to as 79 or Compound 79). Compound 79 was prepared according to general procedure D using 77 (280 mg, 1.5 mmol) to afford 79 as an yellow solid (300 mg, 96%). $^1$H NMR (400 MHz, DMSO-$d_6$) δ=13.53 (s, 1H), 8.17 (d, J=8.5, 2H), 8.01 (d, J=8.5, 2H), 3.36 (q, J=7.3, 3H), 1.10 (t, J=7.3, 3H). UPLC-MS: 0.79 min, 232 [M+NH$_4$]$^+$, 213 [M-H]$^-$.

NAAA Assay. Preparation of Enzyme-Enriched Lysate.

Cells were suspended in 20 mM Tris HCl (pH 7.4) with 0.32 M sucrose, sonicated and centrifuged at 800×g for 15 min at 4° C. Supernatants were then ultracentrifuged at 12.000×g for 30 min at 4° C. Pellets were re-suspended in PBS buffer (pH 7.4) and subjected to three freeze-thaw cycles at −80° C. The suspension was finally ultracentrifuged at 105.000×g for 1 h at 4° C., supernatants were collected, protein concentration was measured and samples aliquoted and stored at −80° C. until use.

Fluorogenic h-NAAA Assay.

HEK293 cells stably transfected with the human NAAA coding sequence cloned from a human spleen cDNA library (catalog no. 639124, Clontech, Mountain View, Calif., USA) were used as enzyme source. The assay was run in 96-well microplates (Black OptiPlate™-96 F; PerkinElmer, Massachusetts, USA), in a total reaction volume of 200 μL. hNAAA protein preparation (4.0 μg) was pre-incubated for 10 minutes with various concentrations of test compounds or vehicle control (5% DMSO) in 100 mM citrate/phosphate buffer (pH 4.5) containing 3.0 mM DTT, 0.1% NP40 0.1%, 0.05% BSA, 150 mM NaCl. N-(4-methyl-2-oxo-chromen-7-yl)-hexadecanamide (PAMCA) was used as a substrate (5.0 μM) and the reaction carried for 50 min at 37° C. Fluorescence was measured with EnVision 2014 Multilabel Reader (PerkinElmer, Massachusetts, USA) using an excitation wavelength of 340 nm and emission 450 nm. IC$_{50}$ values were calculated by non-linear regression analysis of log[concentration]/inhibition curves using GraphPad Prism 5 (GraphPad Software Inc., CA, USA) applying a standard slope curve fitting.

In vitro metabolic stability. Microsomes stability experiments. In vitro incubation with mouse microsomes (NADPH and UDPG system). Compounds were preincubated with microsomes in 100 mM TRIS buffer pH 7.4 for 15 min. At time zero, cofactors were added. The final incubation conditions for each sample were: 1.25 mg/mL liver microsomes, 5 mM compound (final DMSO 0.1%) and 1 mM NADP, 20 mM G6P, 2 mM MgCl$_2$, G6P dehydrogenase 2 Units (NADPH system) or 5 mM UDP glucaric acid, 5 mM saccharic acid 1.4 lactone and 2 mM MgCl$_2$ cofactors (UDPG system). The mixture was kept at 37° C. under shaking. Aliquots (50 mL) were taken at various time points and crashed with 0.15 mL of CH$_3$CN spiked with 500 nM warfarin (internal standard). Reference incubation, with microsomes but without cofactors, was kept at 37° C. and sampled at the end of the time course. After vortexing and centrifugation, 3 mL of supernatant were analyzed by LCMS/MS and detected by multiple reaction monitoring (MRM).

Plasma Stability Experiments.

Compounds were added to blank rat plasma pre-incubated at 37° C. The final molecule concentration was 2 mM. Final DMSO concentration was 2.5%. The mixture was kept at 37° C. under shaking. Aliquots (50 mL) were taken at various time points and crashed with 150 mL of CH$_3$CN spiked with 500 nM warfarin (internal standard). After vortexing and centrifugation, 3 mL of supernatant are analyzed by LCMS/MS by multiple reaction monitoring (MRM).

Aqueous Kinetic Solubility.

The aqueous kinetic solubility was determined from a 10 mM DMSO stock solution of test compound in phosphate-buffered Saline (PBS) at pH 7.4. The study was performed by incubation of an aliquot of 10 mM DMSO stock solution in PBS (pH 7.4) at a target concentration of 250 μM resulting in a final concentration of 2.5% DMSO. The incubation was carried out under shaking at 25° C. for 24 h followed by centrifugation and quantification of dissolved compound in the supernatant by UPLC/MS. The final aqueous kinetic solubility was determined by UV quantification at a specific wavelength (215 nm) and it was calculated by dividing the peak area of the supernatant by the peak area of the test compound reference and further multiplied by the concentration of the test compound reference and dilution factor. UPLC/MS analyses were performed on a Waters ACQUITY UPLC/MS system consisting of a SQD (Single Quadrupole Detector) Mass Spectrometer equipped with an Electrospray Ionization interface and a Photodiode Array Detector. The PDA range was 210-400 nm. The analyses were run on an ACQUITY UPLC BEH $C_{18}$ column (50×2.1 mmID, particle size 1.7 m) with a VanGuard BEH $C_{18}$ pre-column (5×2.1 mmID, particle size 1.7 µm). The mobile phase was 10 mM $NH_4OAc$ in $H_2O$ at pH 5 adjusted with AcOH (A) and 10 mM $NH_4OAc$ in MeCN—$H_2O$ (95:5) at pH 5 (B).

Electrospray ionization in positive mode was applied in the mass scan range 100-500 Da using the following generic MS tune parameters: capillary 3.0 kV; cone voltage 25V; ion source temperature 125° C.; cone gas 100 L/h; desolvation gas 800 L/h; desolvation temperature 400° C.

Animal Models.

Animal handling. Male C57BL/6 mice (20-35 g, Charles River) were group-housed in ventilated cages and had free access to food and water. They were maintained under a 12 h light/dark cycle (lights on at 8:00 am) at controlled temperature (21±1° C.) and relative humidity (55%±10%). All efforts were made to minimize animal suffering and to use the minimal number of animals required to produce reliable results. All procedures were performed in accordance with the Ethical Guidelines of European Communities Council (Directive 2010/63/EU of 22 Sep. 2010) and accepted by the Italian Ministry of Health.

EAE Induction and Evaluation of Clinical Disease.

Experimental allergic encephalomyelitis was actively induced in 10 weeks old female C57BL/6 mice (Charles River) with myelin oligodendrocyte glycoprotein 35-55 (MOG35-55) (Hooke laboratories Inc. Lawrence, Mass.) according to the methods described by Stromnes I. M. & Goverman J. M., 2006. Each mouse received 200 µg of MOG35-55 emulsified in incomplete Freund's adjuvant containing 8 mg/mL *Mycobacterium tuberculosis* (strain H37Ra; Difco). Pertussis toxin (200 ng, Sigma) was injected on the day of the immunization and two days later. Control mice (sham-immunized) received the same treatment with the exception of MOG35-55. MOG35-55 immunized and control mice were treated with 8 (30 mg/kg dissolved in 15% PEG, 15% TWEEN 80 saline solution) or vehicle twice at day starting from day 1 post immunization. Body weight and clinical scores (0=No clinical signs; 0.5=partially limp tail 1=paralyzed tail; 2=Loss in coordinated movement, hind limb paresis; 2.5=one hind limb paralyzed; 3=both hind limbs paralyzed; 3.5=hind limbs paralyzed and weakness in forelimbs; 4=forelimbs paralyzed; 5=moribund) were monitored every day.

Histopathology and Immunofluorescence.

Mice were euthanized 15 days post immunization and transcardially perfused with ice-cold 4% paraformaldehyde in PBS (pH 7.4). Spinal cords were removed, post-fixed in the same fixative overnight at 4° C. and frozen, 20 µm serial sagittal sections were collected. The assessment of immune cell infiltration was performed on haematoxylin and eosin (H&E) stained sections; Iba1 immunofluorescence stained sections were analyzed for microglia/macrophage activation state (Iba-1, Wako, Richmond, Va., USA). Immunostaing for Iba1 was visualized with 546 Alexa Fluor secondary antibody (Thermo Fischer Scientific, Waltham, Mass.).

Pharmacokinetics Study.

Compounds were administered orally or intravenously to C57B6/J mice at 3 mg/kg and 3 mg/kg dose, respectively. Vehicle was PEG400/Tween80/saline solution at 15/15/70% in volume, respectively. Three animals per dose were used. Blood and brain samples at 0, 15, 30, 60, 120, 240, 480 min were collected after oral administration. Blood and brain samples at 0, 5, 15, 30, 60, 120 and 240 min were collected after intravenous administration. Control animals treated with vehicle were also included in the study. Animals were sacrificed at time-points and blood and brain samples were collected. Plasma was separated from blood by centrifugation for 15 min at 3.270×g a 4° C., collected in an Eppendorf tube and frozen (−80° C.). Brain samples were homogenized in RIPA buffer (150 mM NaCl, 1.0% Triton X-100, 0.5% sodium deoxycholate, 0.1% sodium dodecyl sulfate, 50 mM Tris, pH 8.0) and were then split in two aliquots kept at −80° C. until analysis. An aliquot was used for compound brain level evaluations, following the same procedure described below for plasma samples. The second aliquot was kept for protein content evaluation by bicinchoninic acid (BCA) assay. Samples (plasma and brain homogenate) were thawed in an ice bath, then centrifuged for 20 min and an aliquot of each (50 µL) was transferred into a 96-deepwell plate and added with 150 µl of the extraction solution, consisting of cold acetonitrile spiked with 200 nM of a structural analog of the analyte (14), closely eluting with the analyte itself, as internal standard. After agitation (3 min) the plate was centrifuged at 3000×g for 20 min at 4° C. 80 µl of supernatant was then transferred in a 96-well plate and added with 80 µL of $H_2O$. Standard compound was spiked in net solvent (PBS pH 7.4 added with 20% $CH_3CN$) to prepare a calibration curve over the 1 nM-10 µM range. 3 quality controls samples were also prepared spiking the compound in blank mouse plasma to final 20, 200 and 2000 nM concentrations. Calibrators and QCs were crashed with the same extraction solution used for the plasma samples. Dosing solutions, previously diluted 100000 fold in the net solvent, were also included in the samples and tested. Plasma and brain levels were monitored on a Waters ACQUITY UPLC/MS TQD system consisting of a TQD (Triple Quadrupole Detector) mass spectrometer equipped with an electrospray ionization interface; 3 uL of each sample were injected on a reversed phase column (Acquity UPLC BEH C18 2.1×50 mm, 1.7 µm particle size) and separated with a linear $CH_3CN$ gradient. Column and UPLC-MS system were purchased from Waters Inc. Milford, USA. Flow rate was set 0.5 mL/min. Eluents were A=$H_2O$ and B=$CH_3CN$, both added with 0.1% formic acid. After 0.5 min at 10% B, a linear gradient of B was applied from 10% to 100% in 2 min then hold at 100% for 10 s. After the gradient, the system was reconditioned at 10% B for 1 min. Compounds were quantified monitoring their MRM peak areas: (Parent: m/z=448→169 at 40 eV of collision energy and m/z=448→197 at 25 eV of collision energy; Internal Standard: m/z=434→169 at 40 eV of collision energy and m/z=434→197 at 40 eV of collision energy). and the response factors, calculated on the basis of the internal standard peak area, were then plotted over the calibration curve. MS parameters were: positive ion mode; capillary 2.5 KV; cone 35V; source temperature 130° C.; cone gas 100 L/h; desolvation gas 800 L/h; desolvation temperature 400° C. The time/concentration profiles measured with the above mentioned system were then analyzed using PK Solutions Excel application (Summit Research Service, USA) to derive the pharmacokinetic data (Maximum observed concentration ($C_{max}$); maximum time ($T_{max}$); cumulative area under curve (AUC) for experimental time points; distribution volume ($V_d$); systemic clearance (Cl)).

Mechanism of Inhibition. hNAAA Purification and Activation.

hNAAA was produced and purified from hNAAA overexpressing HEK293 cell line as described (A. Armirotti, et al., *ACS Med Chem Lett* 2012, 3, 422-426) The purified enzyme was incubated in activation buffer [100 mM Sodium Phosphate/Sodium Citrate Buffer, 3 mM DL-dithiothreitol (DTT), 0.1% Triton $X^{100}$, pH 4.5] for 3 h at 37° C. and the enzyme activation was checked by SDS-PAGE and Coomassie blue staining.

Analysis of Covalent Adducts by LC-MS/MS.

The presence of possible inhibitor covalent adducts on hNAAA was investigated by high-resolution nano LC-MS/MS analysis. A solution of purified hNAAA (2 µM) was incubated with 8 (50 µM in 2% DMSO, final concentration) for 1.5 h at 37° C. 4 (20 µM) was used as positive control of C126 acylation. A no-inhibitor control (DMSO 2%) was also included. After the reaction time, samples were precipitated with 10 volumes of cold acetone and centrifuged 10 min at 12000×g. The pellets were re-suspended in 50 µl of 50 mM $NH_4HCO_3$ pH 8 and trypsin (1:50 w/w) was added for 16 h at 37° C. The pellets were resuspended in 50 µl of $NH_4HCO_3$ pH 8 and proteomic grade trypsin (1:50 w/w) was added for 16 h at 37° C. The resulting peptides were analyzed on a UPLC chromatographic system equipped with a BEH C18 reversed phase column (1×100 mm). Peptides were eluted with a linear gradient of $CH_3CN$ in water (both added with 0.1% formic acid) from 3 to 50% in 8 min. Flow rate was set to 0.09 mL/min. Eluted peptides were analyzed in positive ion mode by high-resolution tandem mass spectrometry on a Synapt G2 qTOF mass spectrometer (UPLC, column and qTOF instrument were purchased from Waters, Milford Mass., USA). A linear ramp of the collision energy from 15 to 45 eV was used to induce backbone fragmentation of the eluting peptides. 500 nM gluco-fibrino peptide infused at 500 nL/min was used as lock spray mass. MS/MS data were analyzed using the BioLynx software embedded in the MassLynx software suite. MassLynx and ProteinLynx software (Waters, USA) were used for the interpretation of LC-MS data.

Competitive Activity Based Protein Profiling (ABPP).

For competitive ABPP, 50 µl of lysosomal enrichment (0.5 mg/mL) from of hNAAA-overexpressing HEK293 cell line were incubated 2 h at 37° C. with the indicated inhibitors at a final concentration of 20 µM (DMSO 2%). At the end of this preincubation time, the activity based probe 5 (S. Romeo et. al. *ACS Chem. Biol.* 2015, 10, 2057-2064) was added at 20 µM for 15 min or for 3.5 h at 37° C. Next, click chemistry reaction was performed by adding the following reagents at the indicated final concentrations: 100 µM Azide-PEG3-Alexa Fluor 545 (CLK-AZ109, Jena Bioscience), 1 mM tris(2-carboxyethyl)phosphine (TCEP) hydrochloride, 100 µM Tris [(1-benzyl-1H-1,2,3-triazol-4-yl)methyl]amine (TBTA), 1 mM $CuSO_4.5H_2O$ (A. E. Speers, B. F. Cravatt. *Curr Protoc. Chem. Biol.* 2009, 1, 29-41). TBTA was first dissolved in DMSO at 83.5 mM and then diluted with four volumes of t-butanol. The reaction was mixed by vortexing and incubated 2 h at 25° C. Samples (10 µL) were analyzed by SDS-PAGE and gel florescence was scanned at 532 nm wavelength (Fuji Film FLA-9000 instrument).

Inhibitors Recovery Assay.

hNAAA (25 µL of a 4 µM solution) was incubated with the indicated inhibitors at the concentration of 1 µM in activation buffer, 2 h at 37° C. Samples were next precipitated with ten volumes of acetonitrile and centrifuged 10 min at 12000×g. The supernatants were recovered and analyzed by LC-MS/MS for the presence of the added inhibitors. No-protein control samples (buffer only) were used as 100% recovery reference. Inhibitors were detected and quantified using the same method described above for the pharmacokinetics study.

Example 3. Inhibition Data

TABLE 9

| Cmpd | Molecular Structure | hNAAA $IC_{50}$ (µM) | Aq. $S_{kin}$ (µM) | m-LM stab. $t_{1/2}$ (min) | m-plasma stab. $t_{1/2}$ (min) | h-AC inh (%) 30 µM | h-AC inh (%) 30 µM |
|---|---|---|---|---|---|---|---|
| 1 | 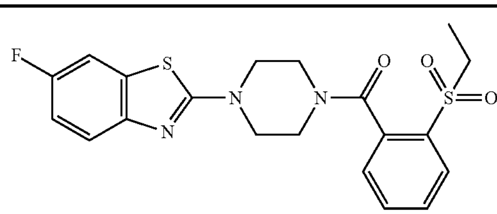 | 0.449 ± 0.107 (n = 6) | 5 | >60 | >120 | 8 | −3 |
| 2 | 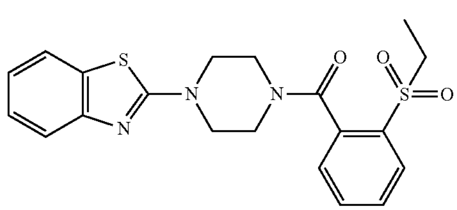 [SMILES: CCS(=O)(=O)c1ccccc1C(=O)N1CCN(c2nc3ccccc3s2)CC1] | 0.432 ± 0.033 (n = 3) | | | | | |

TABLE 9-continued

| Cmpd | Molecular Structure | hNAAA IC$_{50}$ (μM) | Aq. S$_{kin}$ (μM) | m-LM stab. t$_{1/2}$ (min) | m-plasma stab. t$_{1/2}$ (min) | h-AC inh (%) 30 μM | h-AC inh (%) 30 μM |
|---|---|---|---|---|---|---|---|
| 3 | 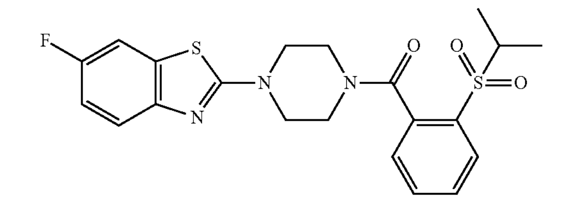 [SMILES: CC(C)S(=O)(=O)c1ccccc1C(=O)N1CCN(c2nc3ccc(F)cc3s2)CC1] | 0.496 ± 0.087 (n = 3) | | | | | |
| 4 | 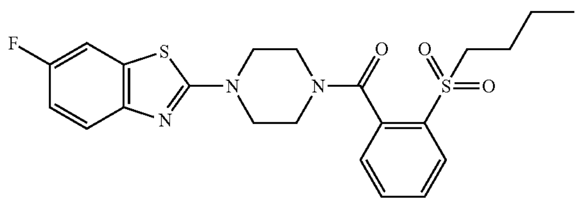 [SMILES: CCCCS(=O)(=O)c1ccccc1C(=O)N1CCN(c2nc3ccc(F)cc3s2)CC1] | 8.80 ± 2.40 (n = 3) | | | | | |
| 5 | 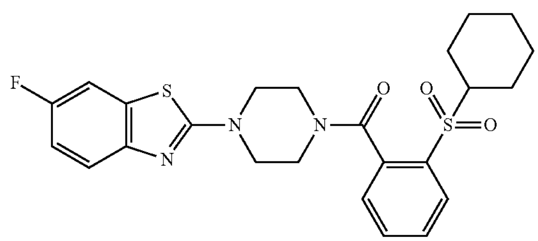 [SMILES: O=C(c1ccccc1S(=O)(=O)C1CCCCC1)N1CCN(c2nc3ccc(F)cc3s2)CC1] | 38.11 ± 5.49 (n = 2) | | | | | |
| 6 | 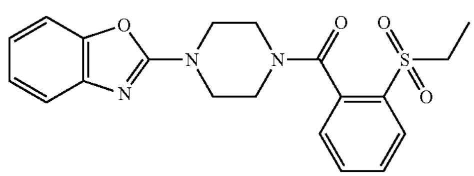 [SMILES: CCS(=O)(=O)c1ccccc1C(=O)N1CCN(c2nc3ccccc3o2)CC1] | 0.851 ± 0.056 (n = 3) | >250 | 27 | >120 | 64 | 0 |
| 7 | 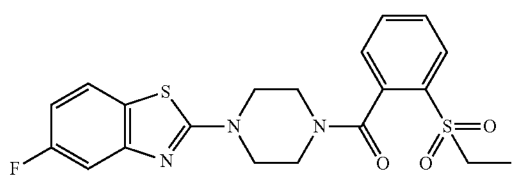 [SMILES: CCS(=O)(=O)c1ccccc1C(=O)N1CCN(c2nc3cc(F)ccc3s2)CC1] | 2.95 ± 0.84 (n = 4) | | | | | |
| 8 | 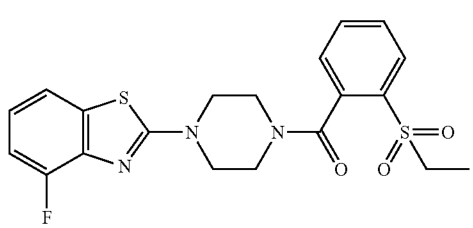 [SMILES: CCS(=O)(=O)c1ccccc1C(=O)N1CCN(c2nc3c(F)cccc3s2)CC1] | 0.554 ± 0.201 (n = 3) | 50 | 16 | >120 | 8 | −3 |
| 9 | 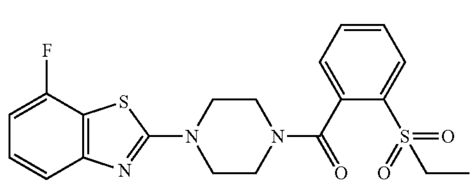 [SMILES: CCS(=O)(=O)c1ccccc1C(=O)N1CCN(c2nc3cccc(F)c3s2)CC1] | 0.298 ± 0.020 (n = 3) | 5 | 16 | >120 | 8 | −3 |

TABLE 9-continued

| Cmpd | Molecular Structure | hNAAA IC$_{50}$ (μM) | Aq. S$_{kin}$ (μM) | m-LM stab. t$_{1/2}$ (min) | m-plasma stab. t$_{1/2}$ (min) | h-AC inh (%) 30 μM | h-AC inh (%) 30 μM |
|---|---|---|---|---|---|---|---|
| 10 | 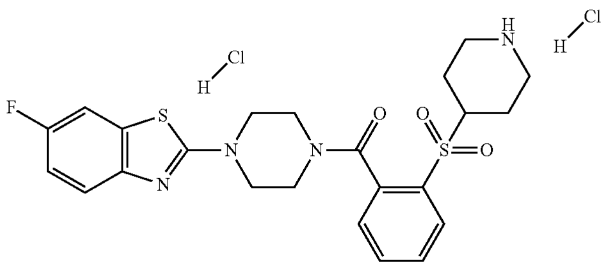 | | | | | | |
| 11 | 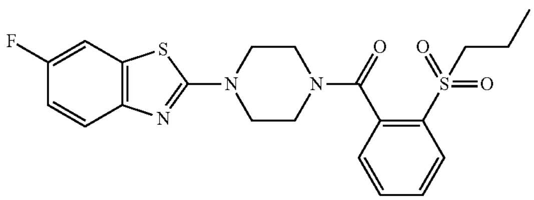 [SMILES: CCCS(=O)(=O)c1ccccc1C(=O)N1CCN(c2nc3ccc(F)cc3s2)CC1] | 0.387 ± 0.062 (n = 3) | <1 | >60 | >120 | 13 | 2 |
| 12 | 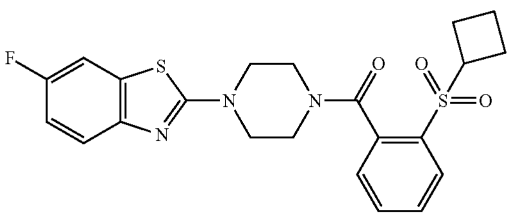 [SMILES: O=C(c1ccccc1S(=O)(=O)C1CCC1)N1CCN(c2nc3ccc(F)cc3s2)CC1] | 0.325 ± 0.003 (n = 3) | 5 | >60 | >120 | −8 | −3 |
| 13 | 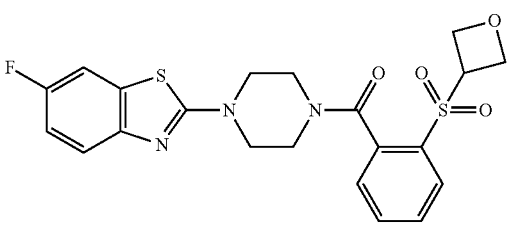 [SMILES: O=C(c1ccccc1S(=O)(=O)C1COC1)N1CCN(c2nc3ccc(F)cc3s2)CC1] | 0.558 ± 0.032 (n = 3) | 22 | >60 | >120 | | |
| 14 | 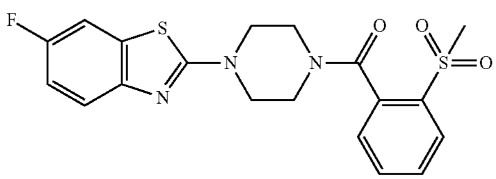 [SMILES: CS(=O)(=O)c1ccccc1C(=O)N1CCN(c2nc3ccc(F)cc3s2)CC1] | 5.69 ± 2.54 (n = 3) | | | | | |
| 15 | 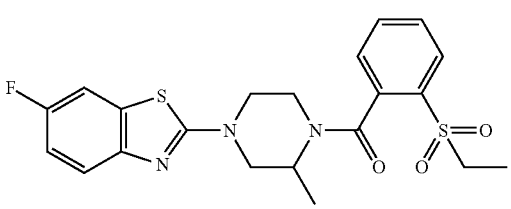 [SMILES: CCS(=O)(=O)c1ccccc1C(=O)N1CCN(c2nc3ccc(F)cc3s2)CC1C] | 0.500 ± 0.075 (n = 3) | | | | 30 | 7 |
| 16 | 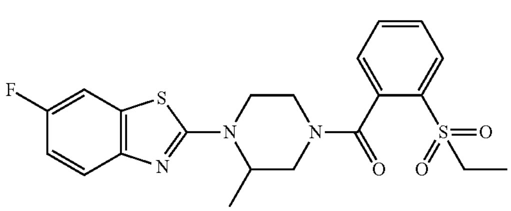 [SMILES: CCS(=O)(=O)c1ccccc1C(=O)N1CCN(c2nc3ccc(F)cc3s2)C(C)C1] | 0.725 ± 0.122 (n = 4) | | | | 52 | 25 |

TABLE 9-continued

| Cmpd | Molecular Structure | hNAAA IC$_{50}$ (μM) | Aq. S$_{kin}$ (μM) | m-LM stab. t$_{1/2}$ (min) | m-plasma stab. t$_{1/2}$ (min) | h-AC inh (%) 30 μM | h-AC inh (%) 30 μM |
|---|---|---|---|---|---|---|---|
| 17 | 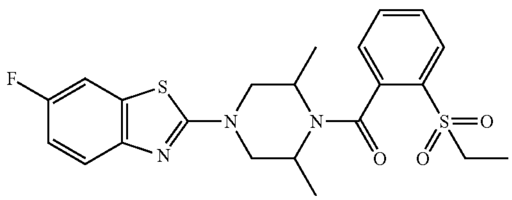 [SMILES: CCS(=O)(=O)c1ccccc1C(=O)N1C(C)CN(c2nc3ccc(F)cc3s2)CC1C] | 1.44 ± 0.140 (n = 3) | | | | | |
| 18 | 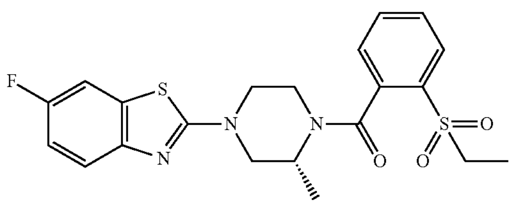 [SMILES: CCS(=O)(=O)c1ccccc1C(=O)N1CCN(c2nc3ccc(F)cc3s2)C[C@H]1C] | 3.430 ± 0.499 (n = 3) | | | | | |
| 19 | 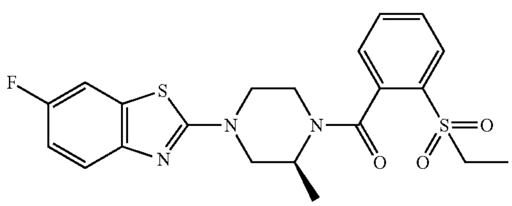 [SMILES: CCS(=O)(=O)c1ccccc1C(=O)N1CCN(c2nc3ccc(F)cc3s2)C[C@@H]1C] | 0.228 ± 0.043 (n = 4) | 165 | >60 | >120 | 7 | 2 |
| 20 | 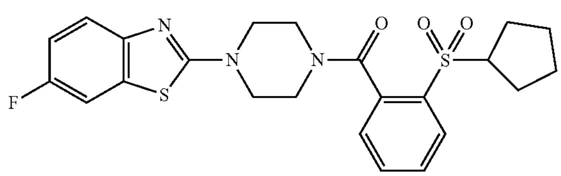 [SMILES: O=C(c1ccccc1S(=O)(=O)C1CCCC1)N1CCN(c2nc3ccc(F)cc3s2)CC1] | 1.10 ± 0.090 (n = 3) | | | | | |
| 21 | 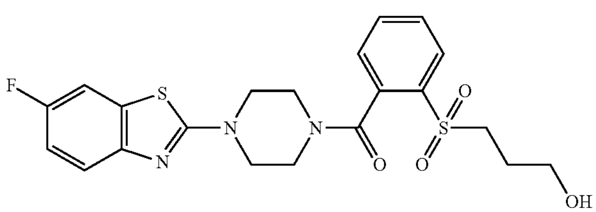 [SMILES: O=C(c1ccccc1S(=O)(=O)CCCO)N1CCN(c2nc3ccc(F)cc3s2)CC1] | 2.72 (n = 1) | | | | | |
| 22 | 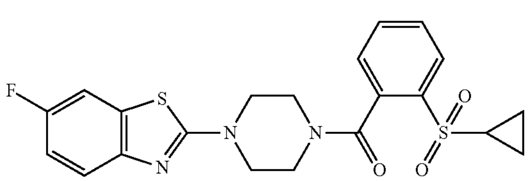 [SMILES: O=C(c1ccccc1S(=O)(=O)C1CC1)N1CCN(c2nc3ccc(F)cc3s2)CC1] | 0.189 ± 0.035 (n = 3) | 10 | >60 | >120 | 33 | −1 |
| 23 | 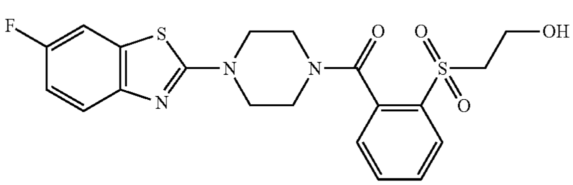 [SMILES: O=C(c1ccccc1S(=O)(=O)CCO)N1CCN(c2nc3ccc(F)cc3s2)CC1] | 5.00 (n = 1) | | | | | |

TABLE 9-continued

| Cmpd | Molecular Structure | hNAAA IC$_{50}$ (μM) | Aq. S$_{kin}$ (μM) | m-LM stab. t$_{1/2}$ (min) | m-plasma stab. t$_{1/2}$ (min) | h-AC inh (%) 30 μM | h-AC inh (%) 30 μM |
|---|---|---|---|---|---|---|---|
| 24 | 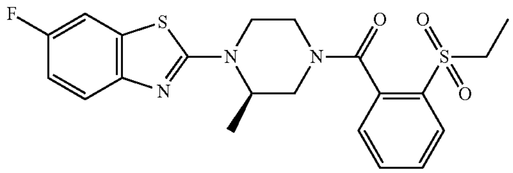 [SMILES: CCS(=O)(=O)c1ccccc1C(=O)N1CCN(c2nc3ccc(F)cc3s2)[C@H](C)C1] | 0.394 ± 0.030 (n = 3) | | | | 21 | 1 |
| 25 | 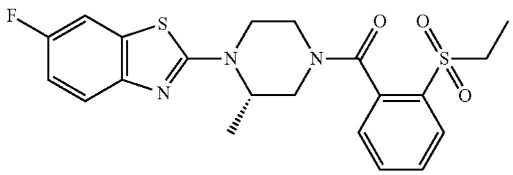 [SMILES: CCS(=O)(=O)c1ccccc1C(=O)N1CCN(c2nc3ccc(F)cc3s2)[C@@H](C)C1] | 2.263 ± 0.414 (n = 3) | | | | | |
| 26 | 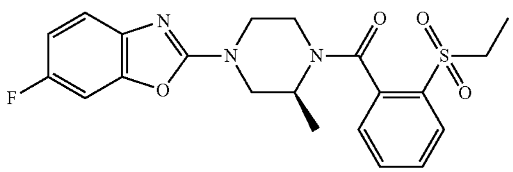 [SMILES: CCS(=O)(=O)c1ccccc1C(=O)N1CCN(c2nc3ccc(F)cc3o2)C[C@@H]1C] | 2.117 ± 0.896 (n = 5) | 6 | >60 | >120 | −3 | −12 |
| 27 | 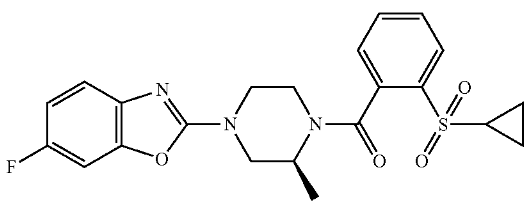 [SMILES: C[C@H]1CN(c2nc3ccc(F)cc3o2)CCN1C(=O)c1ccccc1S(=O)(=O)C1CC1] | 0.224 ± 0.038 (n = 4) | 124 | 60 | >120 | 9 | −12 |
| 28 | 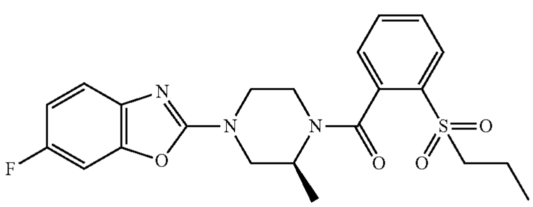 [SMILES: CCCS(=O)(=O)c1ccccc1C(=O)N1CCN(c2nc3ccc(F)cc3o2)C[C@@H]1C] | 0.760 ± 0.328 (n = 3) | 45 | 60 | >120 | 14 | −11 |
| 29 | 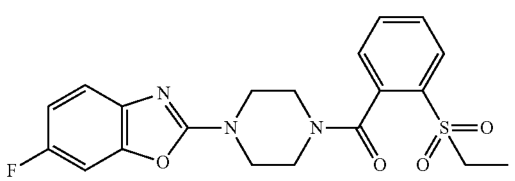 [SMILES: CCS(=O)(=O)c1ccccc1C(=O)N1CCN(c2nc3ccc(F)cc3o2)CC1] | 2.18 (n = 1) | | | | | |
| 30 | 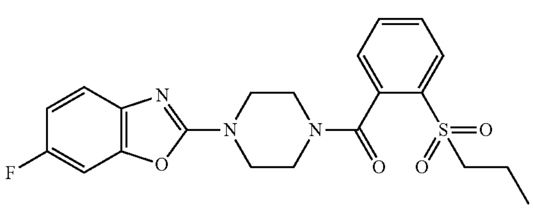 [SMILES: CCCS(=O)(=O)c1ccccc1C(=O)N1CCN(c2nc3ccc(F)cc3o2)CC1] | 0.499 (n = 1) | | | | | |
| 31 | 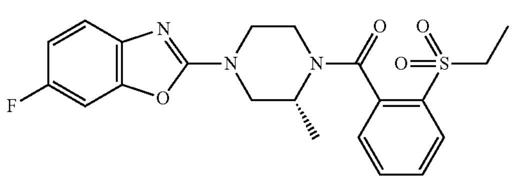 [SMILES: CCS(=O)(=O)c1ccccc1C(=O)N1CCN(c2nc3ccc(F)cc3o2)C[C@H]1C] | 15.9 (n = 1) | | | | | |

TABLE 9-continued

| Cmpd | Molecular Structure | hNAAA IC$_{50}$ (μM) | Aq. S$_{kin}$ (μM) | m-LM stab. t$_{1/2}$ (min) | m-plasma stab. t$_{1/2}$ (min) | h-AC inh (%) 30 μM | h-AC inh (%) 30 μM |
|---|---|---|---|---|---|---|---|
| 32 | 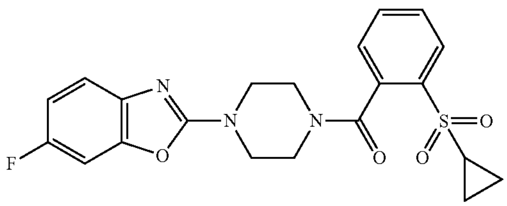 [SMILES: O=C(c1ccccc1S(=O)(=O)C1CC1)N1CCN(c2nc3ccc(F)cc3o2)CC1] | 0.311 ± 0.004 (n = 2) | | | | | |
| 33 | 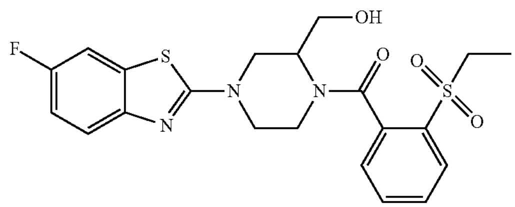 [SMILES: CCS(=O)(=O)c1ccccc1C(=O)N1CCN(c2nc3ccc(F)cc3s2)CC1CO] | 2.10 (n = 1) | | | | | |
| 34 | 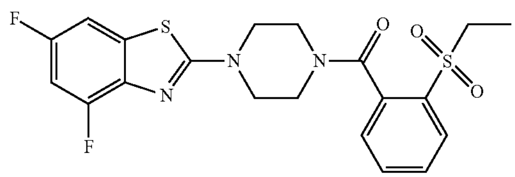 [SMILES: CCS(=O)(=O)c1ccccc1C(=O)N1CCN(c2nc3c(F)cc(F)cc3s2)CC1] | 0.718 ± 0.138 (n = 3) | | | | 17 | 4 |
| 35 | 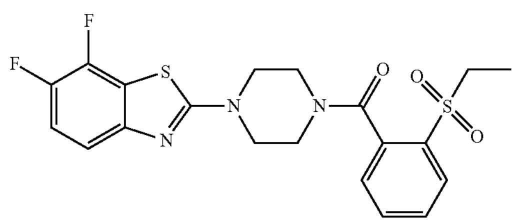 [SMILES: CCS(=O)(=O)c1ccccc1C(=O)N1CCN(c2nc3ccc(F)c(F)c3s2)CC1] | 0.246 ± 0.052 (n = 3) | 7 | >60 | >120 | 12 | 0 |
| 36 | 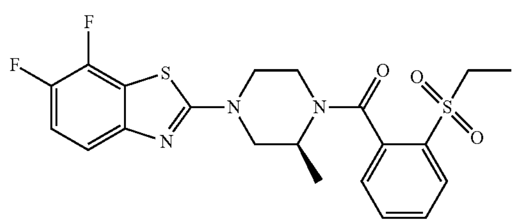 [SMILES: CCS(=O)(=O)c1ccccc1C(=O)N1CCN(c2nc3ccc(F)c(F)c3s2)C[C@@H]1C] | 0.158 ± 0.025 (n = 3) | 1 | >60 | >120 | 18 | 3 |
| 37 | 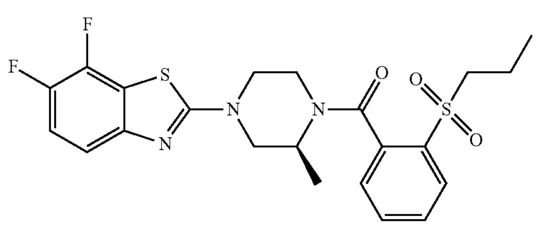 [SMILES: CCCS(=O)(=O)c1ccccc1C(=O)N1CCN(c2nc3ccc(F)c(F)c3s2)C[C@@H]1C] | 0.225 ± 0.031 (n = 3) | 8 | >60 | >120 | 35 | 9 |
| 38 | 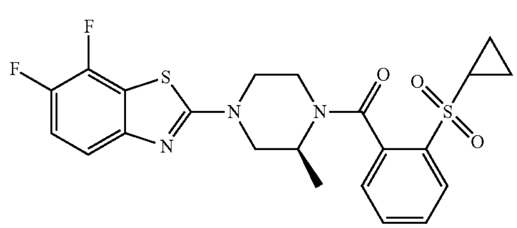 [SMILES: C[C@H]1CN(c2nc3ccc(F)c(F)c3s2)CCN1C(=O)c1ccccc1S(=O)(=O)C1CC1] | 0.181 ± 0.024 (n = 3) | 14 | =60 | >120 | 28 | −4 |

TABLE 9-continued

| Cmpd | Molecular Structure | hNAAA IC$_{50}$ (µM) | Aq. S$_{kin}$ (µM) | m-LM stab. t$_{1/2}$ (min) | m-plasma stab. t$_{1/2}$ (min) | h-AC inh (%) 30 µM | h-AC inh (%) 30 µM |
|---|---|---|---|---|---|---|---|
| 39 | 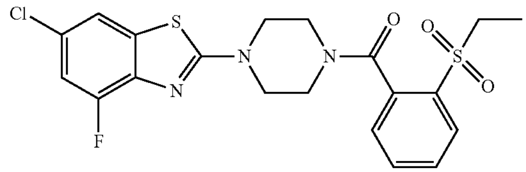 [SMILES: CCS(=O)(=O)c1ccccc1C(=O)N1CCN(c2nc3c(F)cc(Cl)cc3s2)CC1] | 5.17 ± 1.967 (n = 3) | | | | | |
| 40 | | 0.205 ± 0.048 (n = 3) | | | | 6 | −15 |
| 41 | | 0.177 ± 0.038 (n = 3) | | | | 15 | −5 |
| 42 | | 0.314 (n = 1) | | | | | |
| 43 | 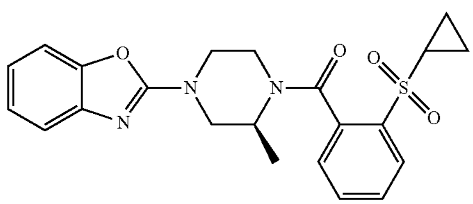 [SMILES: C[C@H]1CN(c2nc3ccccc3o2)CCN1C(=O)c1ccccc1S(=O)(=O)C1CC1] | 0.215 ± 0.046 (n = 3) | | | | | |

TABLE 10

Modification of the substituents for a structure having the formula:

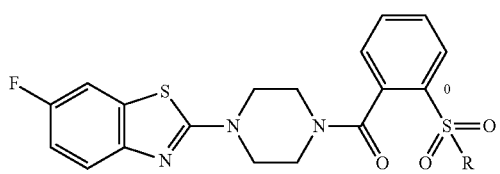

| R | h-NAAA IC$_{50}$ (µM) | Aq. Kinetic Solubility (µM) |
|---|---|---|
| CH$_2$CH$_3$ | 0.449 ± 0.107 (n = 6) | 5 |
| OH | | — |
| CH$_3$ | 5.69 ± 2.54 (n = 3) | — |
| CH$_2$CH$_2$CH$_3$ | 0.387 ± 0.062 (n = 3) | <1 |
| CH$_2$CH$_2$CH$_2$CH$_3$ | 8.80 ± 2.40 (n = 3) | <1 |
| CH$_2$CH$_2$OH | 5.00 (n = 1) | — |
| CH$_2$CH$_2$CH$_2$OH | 2.72 (n = 1) | 49 |
| i-Pr | 0.496 ± 0.087 (n = 3) | <1 |

TABLE 10-continued

Modification of the substituents for a structure having the formula:

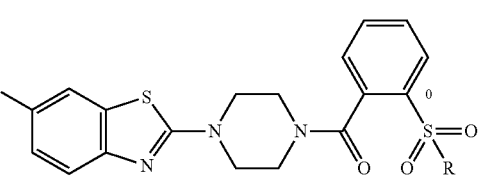

| R | h-NAAA IC$_{50}$ (µM) | Aq. Kinetic Solubility (µM) |
|---|---|---|
| c-propyl | 0.189 ± 0.035 (n = 3) | 10 |
| c-butyl | 0.325 ± 0.003 (n = 3) | 5 |
| c-pentyl | 1.10 ± 0.090 (n = 3) | <1 |
| oxetan-3-yl | 0.558 ± 0.032 (n = 3) | 22 |
| c-hexyl | 38.11 ± 5.486 (n = 2) | — |
| 4-piperidyl | | — |
| N(CH$_2$CH$_3$)$_2$ | | |

TABLE 11

Modification of the substituents for a structure having the formula:

[Structure with R group at position 6 of benzothiazole, connected via piperazine to carbonyl-phenyl-sulfonyl-ethyl]

| R | h-NAAA IC$_{50}$ (µM) | Aq. Kinetic Solubility (µM) |
|---|---|---|
| F | 0.449 ± 0.107 (n = 6) | 5 |
| H | 0.432 ± 0.033 (n = 3) | 196 |
| Cl | 1.549 ± 0.288 (n = 3) | 2 |
| Br | 12.30 ± 9.667 (n = 3) | — |
| CH$_3$ | 6.87 (n = 1) | 181 |
| CF$_3$ | 7.2 (n = 1) | — |
| CN | — | — |
| OMe | 5.73 (n = 1) | 39 |
| NO$_2$ | 6.22 (n = 1) | — |
| NH$_2$ | — | — |
| N(CH$_3$)$_2$ | — | — |
| NHCOCH$_3$ | — | — |
| phenyl | 11.2 (n = 1) | — |

TABLE 12

Modification of the substituents for a structure having the formula:

[Structure with R group at positions 4-7 of benzothiazole, connected via piperazine to carbonyl-phenyl-sulfonyl-ethyl]

| R | h-NAAA IC$_{50}$ (µM) | Aq. Kinetic Solubility (µM) |
|---|---|---|
| 6-F | 0.449 ± 0.107 (n = 6) | 5 |
| 4-F | 0.554 ± 0.201 (n = 3) | 50 |
| 5-F | 2.95 ± 0.84 (n = 4) | 8 |
| 7-F | 0.298 ± 0.020 (n = 3) | 5 |
| 7-Cl | 0.711 ± 0.212 (n = 3) | <1 |
| 7-Br | 1.259 ± 0.0195 (n = 2) | 1 |
| 7-CH$_3$ | 2.46 ± 1.37 (n = 2) | — |
| 7-CF$_3$ | 3.68 (n = 1) | — |
| 7-CN | 7.87 (n = 1) | — |

Example 4. Competitive Assays

Competitive assay results can be found in FIGS. 10A-10D. Assay conditions include HEK29-hNAAA lysosome preparation (0.5 mg/mL). The compound concentration was 50 µM. The probe concentration was 5 µM. Azide Fluor 545 addition by Click Chemistry, and fluorescence detection was at 532 nm.

TABLE 13

CD1 Mouse PK data (iv, 3 mpk). AUC calculations: Total circulating blood volume for a mouse = 1 mL (based on literature); plasma levels = blood levels; AUC (plasma) as ng*min/ml becomes ng*min/BOD, AUC (brain) as ng*min/ml becomes ng*min/BRAIN.

| Parameters (3 mkp, i.v.) | plasma | brain |
|---|---|---|
| C$_{max}$ (ng/mL) | 1809 | 1612 |
| T$_{max}$ (min) | (5.0) | (5.0) |
| t$_{1/2}$ (min) | 53.6 | 43.5 |
| Cl (mL/min/Kg) | 30.987 | — |
| V$_{ss}$ (L/Kg) | 2.40 | — |
| AUC (h × ng/mL) | 1554.7 | 866.8 |
| AUC$_{brain}$/AUC$_{plasma}$ (%) | 55.7 | |
| Total AUC | 2421.5 | |
| % distribution | 64 | 36 |

TABLE 14

C57 Mouse PK data (po, 10 mpk). AUC calculations: Total circulating blood volume for a mouse = 1 mL (based on literature); plasma levels = blood levels; AUC (plasma) as ng*min/ml becomes ng*min/BOD, AUC (brain) as ng*min/ml becomes ng*min/BRAIN.

| Parameters (10 mkp, p.o.) | plasma | brain |
|---|---|---|
| C$_{max}$ (ng/mL) | 1469 | 392 |
| T$_{max}$ (min) | 30 | 30 |
| t$_{1/2}$ (min) | 80.4 | 73.3 |
| Cl (mL/min/Kg) | 30.429 | — |
| V$_{ss}$ (L/Kg) | 3.53 | — |
| AUC (h × ng/mL) | 5341.8 | 1341.2 |
| AUC$_{brain}$/AUC$_{plasma}$ (%) | 25.1 | |
| Total AUC (AUC$_{plasma}$ + AUC$_{brain}$) | 6683 | |
| % distribution (AUC$_{organ}$/(AUC$_{plasma}$ + AUC$_{brain}$)) | 80 | 20 |

TABLE 15

C57 Mouse PK data (po, 30 mpk). AUC calculations: Total circulating blood volume for a mouse = 1 mL (based on literature); plasma levels = blood levels; AUC (plasma) as ng*min/ml becomes ng*min/BOD, AUC (brain) as ng*min/ml becomes ng*min/BRAIN.

| Parameters (30 mkp, p.o.) | plasma | brain |
|---|---|---|
| C$_{max}$ (ng/mL) | 5173.0 | 2238 |
| T$_{max}$ (min) | 15 | 15 |
| t$_{1/2}$ (min) | 84.3 | 188.5 |
| Cl (mL/min/Kg) | 10.817 | — |
| V$_{ss}$ (L/Kg) | 1.32 | — |
| AUC (h × ng/mL) | 46221.8 | 3225.9 |
| AUC$_{brain}$/AUC$_{plasma}$ (%) | 7 | |
| Total AUC | 49447.7 | |
| % distribution | 93 | 7 |

Figure 22A:
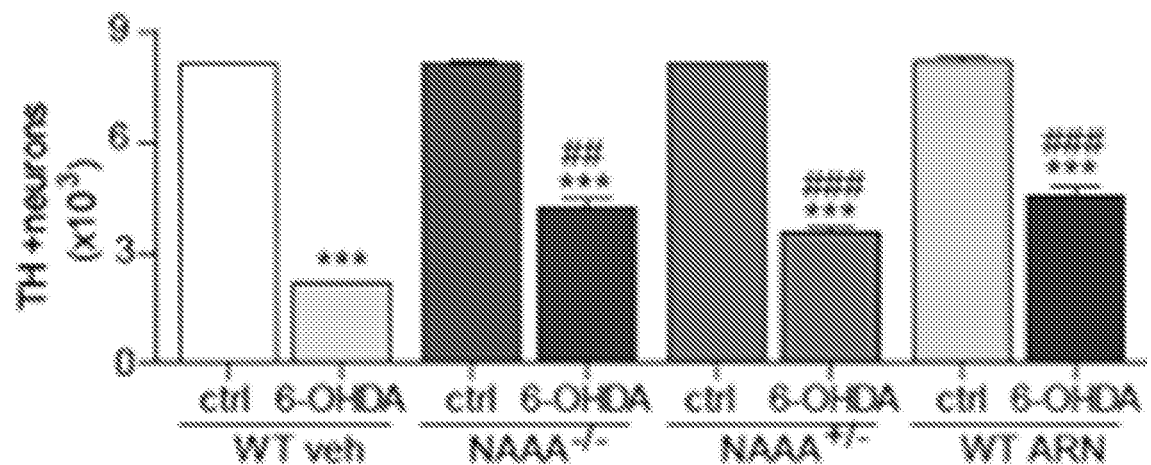
FIGS. 22A-22F. Histograms illustrating that treatment of wild-type mice exposed to 6-hydroxydopamine (6-OHDA) with compound 19702 exerted a set of neuroprotective effects that included, in the SN, enhanced survival of $TH^+$ neurons (FIG. 22A) and, in the striatum, increased dopamine and dopamine metabolite content (FIG. 22B) and greater $TH^+$ fiber density (FIG. 22C), attenuated the behavioral response to apomorphine (FIG. 22D), prolonged the latency to fall in the rotarod test (FIG. 22E), and decreased mortality (FIG. 22F). * or # P<0.05;  or ## P<0.01; * or ### P<0.001.
Figure 22B:
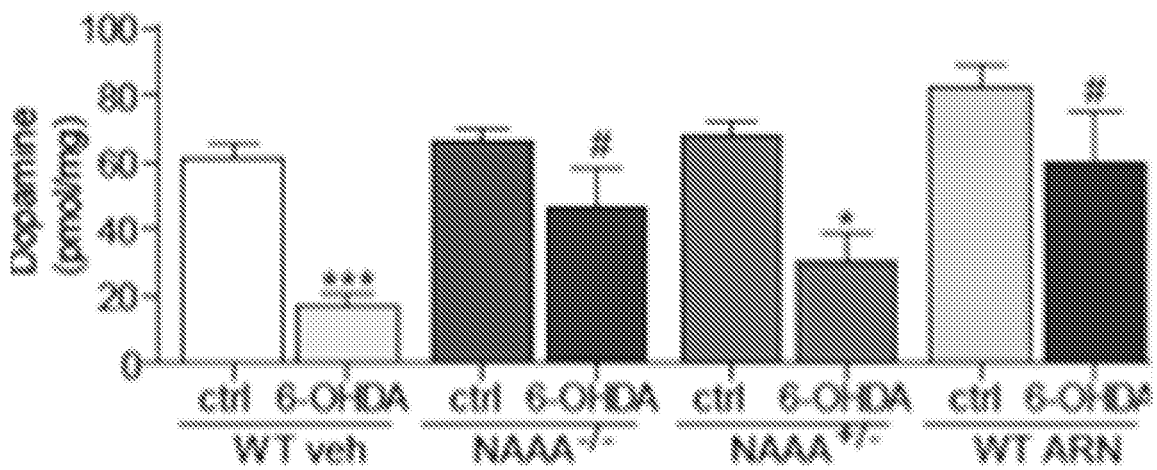
Figure 22C:
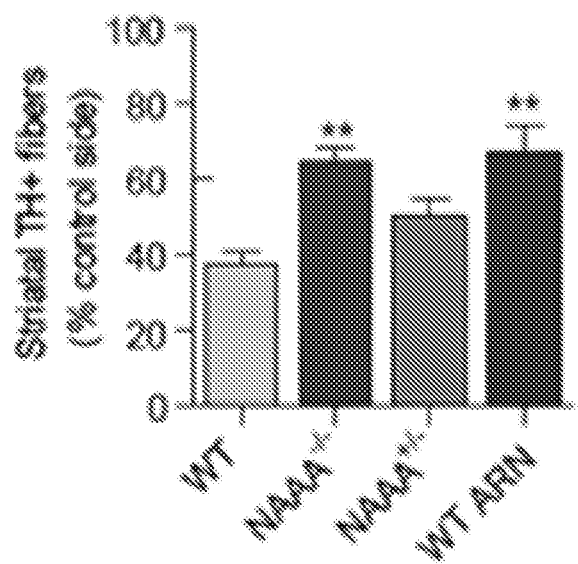
Figure 22D:
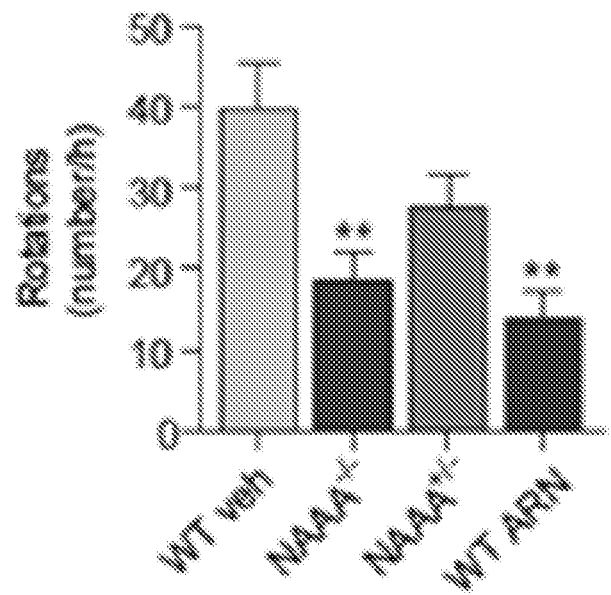
Figure 22E:
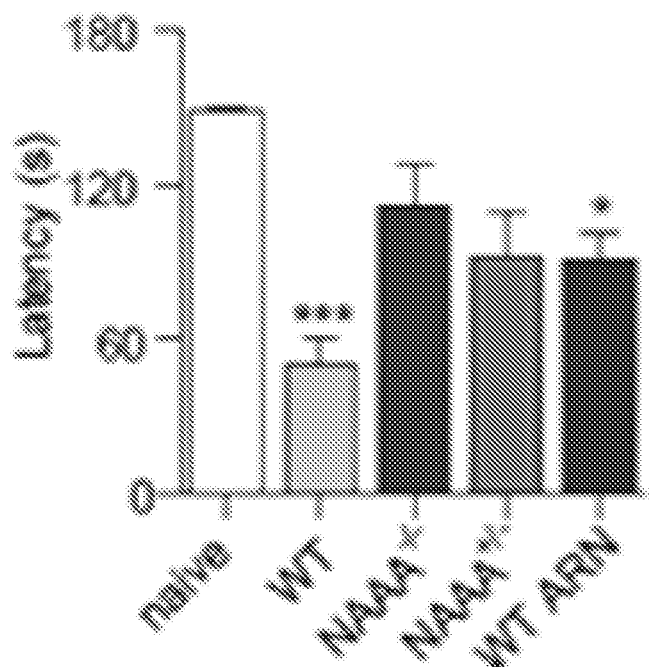
Figure 22F:
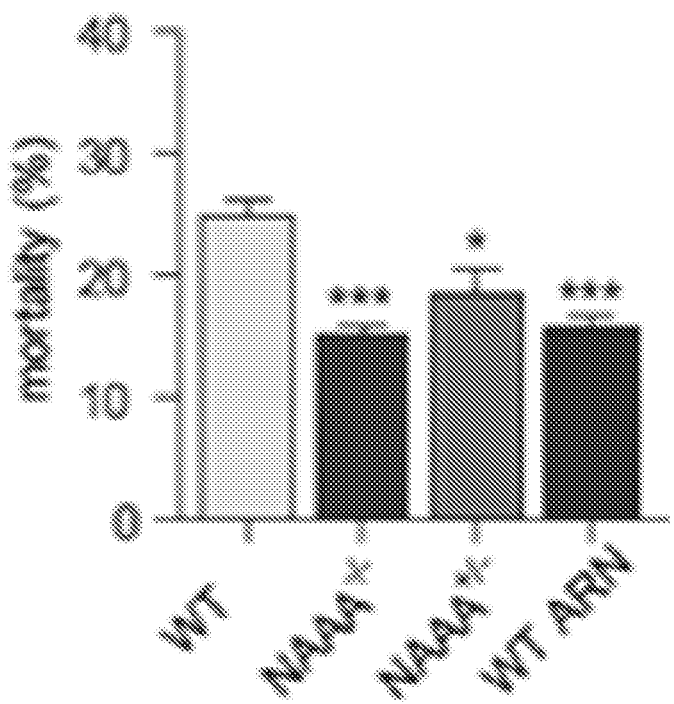

Example 5. Role of NAAA in the 6-Hydroxydopamine (6-OHDA) Model of Parkinson's Disease The role of NAAA in the 6-hydroxydopamine (6-OHDA) model of Parkinson's disease was investigated, using genetically modified mice that express the protein in a frame-shifted catalytically inactive form (NAAA$^{-/-}$ mice). NAAA$^{-/-}$ mice constitutively lack NAAA mRNA, protein and enzyme activity, and do not compensate for this absence with altered expression of isofunctional enzymes (lipid amidases such as fatty acid amide hydrolase and acid ceramidase) or PEA-producing enzymes (N-acyl-phosphatidylethanolamine phospholipase D, NAPE-PLD). Homozygous NAAA deletion protected mice against the cytological, neurochemical and behavioral consequences of 6-OHDA administration: three weeks after toxin injections, comparison with wild-type littermates showed that NAAA$^{-/-}$ mice had (i) enhanced survival of nigral TH$^+$ neurons (FIG. 22A); (ii) higher striatal levels of dopamine (FIG. 22B); and (iii) greater density of striatal TH$^+$ fibers (FIG. 22C). Moreover, relative to wild-type controls, NAAA$^{-/-}$ mice had (iv) markedly attenuated motor responses (contralateral rotations) to the dopaminergic agonist apomorphine (0.1 mg·kg$^{-1}$, subcutaneous; FIG. 22D); (v) prolonged latency to fall in the rotarod performance test (FIG. 22E); and (vi) significantly lower mortality rate (FIG. 22F). Comparable, albeit slightly weaker, resistance to 6-OHDA was observed in heterozygous NAAA$^{+/-}$ mice (FIGS. 22A-F). The striking neuroprotective phenotype that accompanies genetic NAAA deletion unmasks an important role for this enzyme in the neurotoxic reaction to 6-OHDA.

It was found that treatment with 19702 (compound 19) phenocopied genetic NAAA removal. In wild-type mice exposed to 6-OHDA, a 3-week twice-daily regimen with compound 19702 (30 mg·kg$^{-1}$, intraperitoneal) exerted a set of neuroprotective effects that included, in the SN, enhanced survival of TH$^+$ neurons (FIG. 22A) and, in the striatum, increased dopamine and dopamine metabolite content (FIG. 22B) and greater TH$^+$ fiber density (FIG. 22C). Additionally, treatment with the NAAA inhibitor attenuated the behavioral response to apomorphine (FIG. 22D), prolonged the latency to fall in the rotarod test (FIG. 22E), and decreased mortality (FIG. 22F). A similar regimen with a lower dose of 19702 (10 mg·kg$^{-1}$) also dampened lethality, but did not significantly affect the response to apomorphine (not shown). Thus, as seen with partial or complete ablation of the Naaa gene, pharmacological inhibition of intracellular NAAA activity strongly counters 6-OHDA neurotoxicity.

EMBODIMENTS

Embodiment 1

A compound having the formula of Embodiment 1,

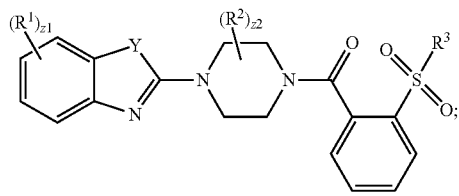

wherein
R$^1$ is independently
halogen, —CF$_3$, —CCl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is independently
halogen, —CF$_3$, —CCl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is independently
halogen, —CF$_3$, —CCl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
Y is S or O;
z1 is independently an integer from 0 to 4;
z2 is independently an integer from 0 to 8; and
wherein the compound does not have the formula:

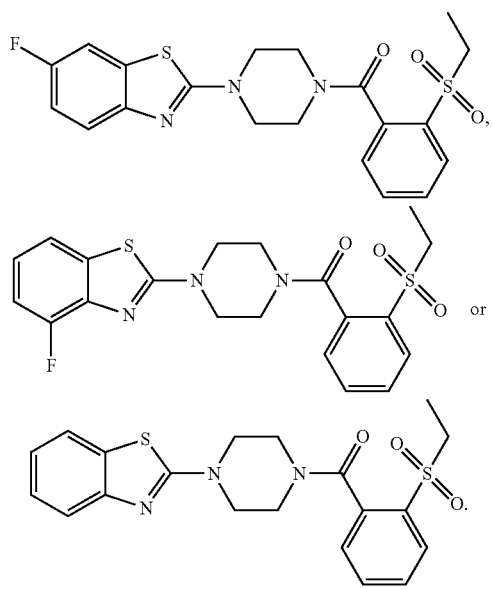

Embodiment 2

The compound of Embodiment 1, wherein $R^1$ is independently
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl;

$R^2$ is independently
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted $C_1$-$C_5$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl;

$R^3$ is independently
halogen, —$CF_3$, —$CCl_3$, —$CI_3$, —$CBr_3$, —$CHF_2$, —$CHCl_2$, —$CHI_2$, —$CHBr_2$, —$OCH_2F$, —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$, —$OCBr_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

Embodiment 3

The compound of Embodiments 1 or 2, wherein the compound has the formula:

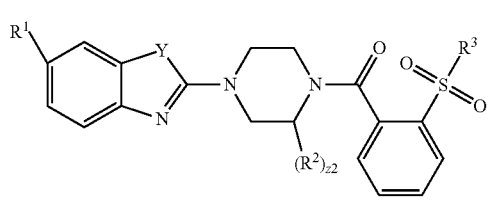

where z2 is from 0-2.

Embodiment 4

The compound of Embodiments 1 or 2, wherein the compound has the formula:

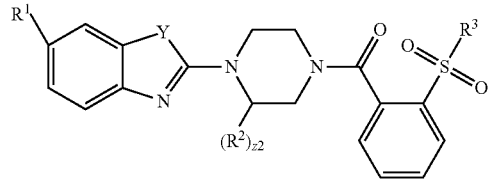

where z2 is from 0-2.

Embodiment 5

The compound of Embodiments 1 or 2, wherein the compound has the formula:

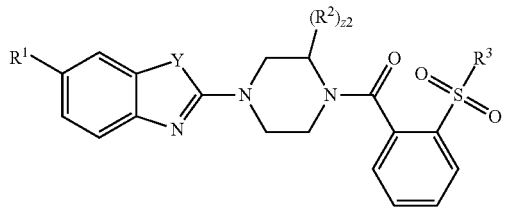

where z2 is from 0-2.

Embodiment 6

The compound of any one of Embodiments 1 or 2, wherein z1 is 1.

Embodiment 7

The compound of any one of Embodiments 1 to 6, wherein $R^1$ is a halogen.

Embodiment 8

The compound of any one of Embodiments 1 to 7, wherein $R^1$ is —F.

Embodiment 9

The compound of any one of Embodiments 1 to 8, wherein Y is S.

Embodiment 10

The compound of any one of Embodiments 1 to 8, wherein Y is O.

Embodiment 11

The compound of any one of Embodiments 1 to 5, wherein z2 is from 1 to 2.

Embodiment 12

The compound of any one of Embodiments 1 to 5, wherein z2 is 2.

Embodiment 13

The compound of any one of Embodiments 1 to 12, wherein $R^2$ is substituted or unsubstituted alkyl or substituted or unsubstituted heteroalkyl.

Embodiment 14

The compound of any one of Embodiments 1 to 12, wherein $R^2$ is substituted or unsubstituted $C_1$-$C_8$ alkyl or substituted or unsubstituted 2 to 8 membered heteroalkyl.

Embodiment 15

The compound of any one of Embodiments 1 to 12, wherein $R^2$ is substituted or unsubstituted $C_1$-$C_4$ alkyl.

Embodiment 16

The compound of any one of Embodiments 1 to 12, wherein $R^2$ is unsubstituted $C_1$-$C_4$ alkyl.

Embodiment 17

The compound of any one of Embodiments 1 to 12, wherein $R^2$ is unsubstituted methylene.

Embodiment 18

The compound of any one of Embodiments 1 to 17, wherein $R^3$ is substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

Embodiment 19

The compound of any one of Embodiments 1 to 17, wherein $R^3$ is substituted or unsubstituted $C_1$-$C_8$ alkyl.

Embodiment 20

The compound of any one of Embodiments 1 to 17, wherein $R^3$ is substituted or unsubstituted $C_1$-$C_4$ alkyl.

Embodiment 21

The compound of any one of Embodiments 1 to 17, wherein $R^3$ is substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

Embodiment 22

The compound of any one of Embodiments 1 to 17, wherein $R^3$ is substituted or unsubstituted $C_3$-$C_8$ cycloalkyl, or substituted or unsubstituted 3 to 6 membered heterocycloalkyl.

Embodiment 23

The compound of any one of Embodiments 1 to 17, wherein $R^3$ is substituted or unsubstituted $C_3$-$C_8$ cycloalkyl.

Embodiment 24

The compound of Embodiment 1, wherein the compound has the formula:

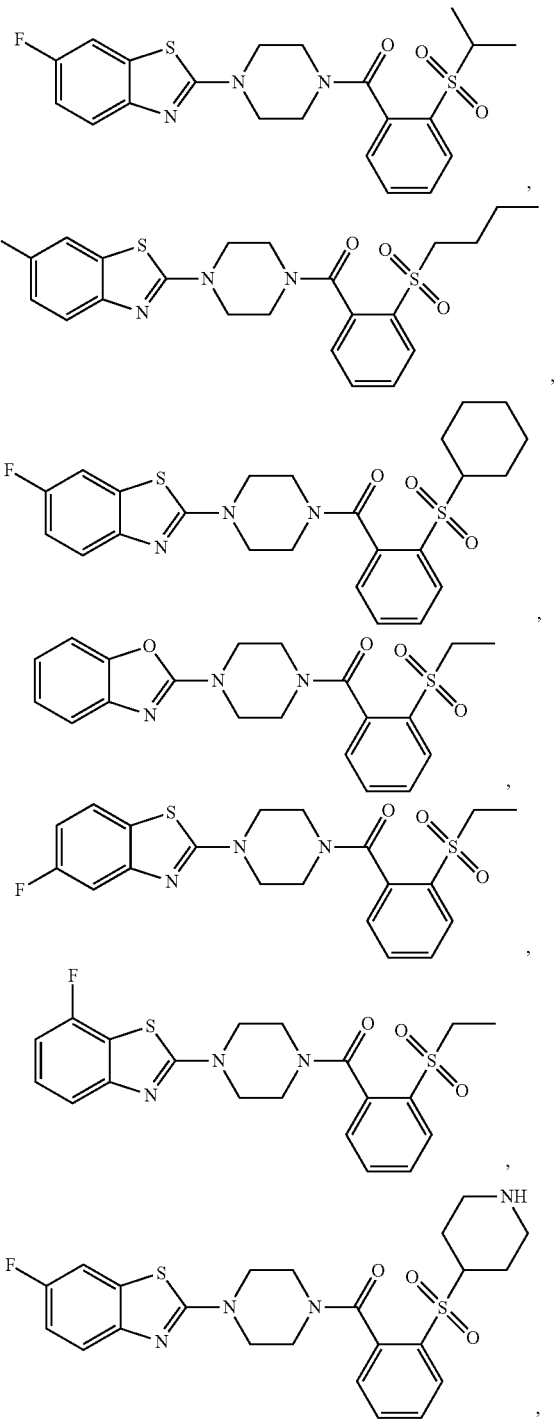

105
-continued
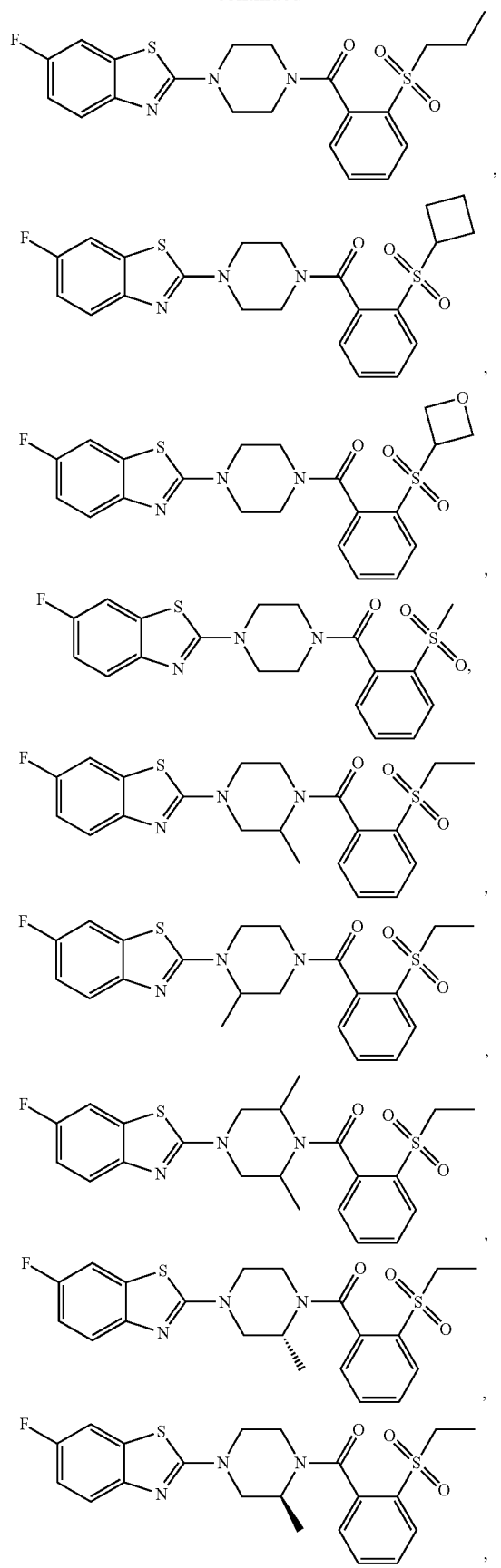
106
-continued
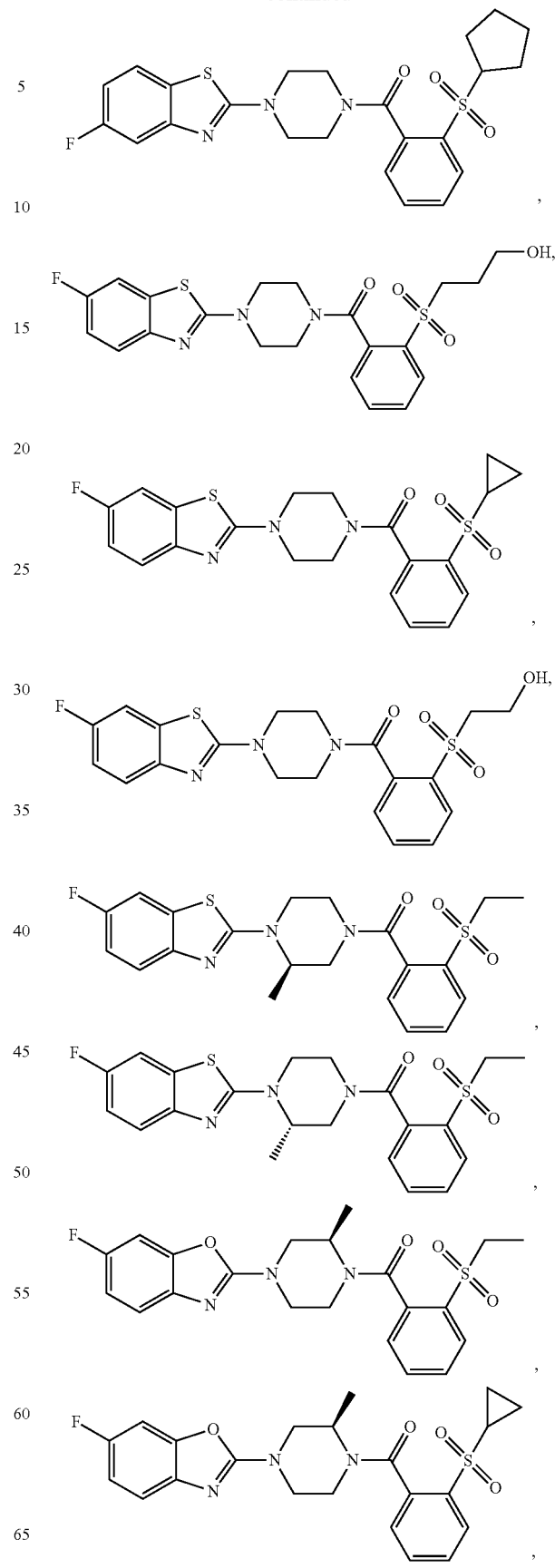

107

-continued

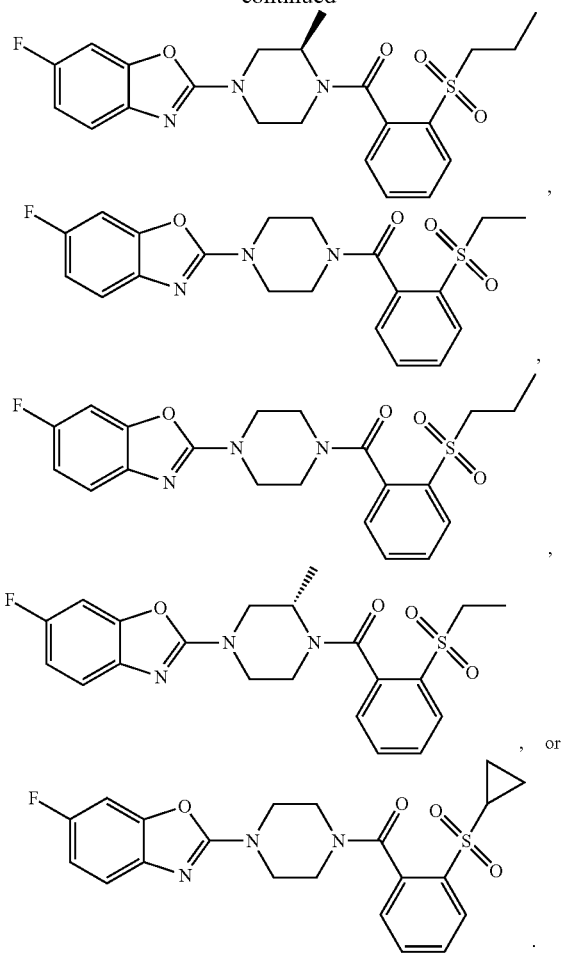

Embodiment 25

A pharmaceutical composition comprising the compound of any one of Embodiments 1 to 24 and a pharmaceutically acceptable excipient.

Embodiment 26

A method of inhibiting N-acylethanolamine acid amidase, the method comprising contacting the N-acylethanolamine acid amidase with a compound having the formula:

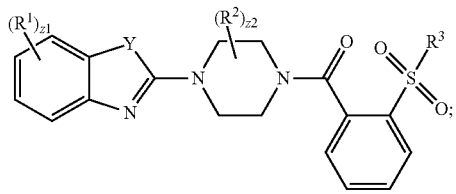

wherein
R$^1$ is independently
halogen, —CX$^{13}$, —CHX$^{12}$, —OCH$_2$X$^1$, —CN, —OH, —NH$_2$, —COOH, —CONH$_2$, —NO$_2$, —SH, —SO$_3$H, —SO$_4$H, —SO$_2$NH$_2$, —NNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{13}$, —OCHX$^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is independently
halogen, —CX$^{23}$, —CHX$^{22}$, —OCH$_2$X$^2$, —CN, —OH, —NH$_2$, —COOH, —CONH$_2$, —NO$_2$, —SH, —SO$_3$H, —SO$_4$H, —SO$_2$NH$_2$, —NNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{23}$, —OCHX$^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^3$ is independently
halogen, —CX$^3_3$, —CHX$^3_2$, —OCH$_2$X$^3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^3_3$, —OCHX$^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
Y is S or O;
X$^1$, X$^2$, and X$^3$ are independently —F, —Cl, —Br, or —I; and
z1 is independently an integer from 0 to 4;
z2 is independently an integer from 0 to 8.

Embodiment 27

A method of treating a pathological state, the method comprising administering to a subject in need thereof an effective amount of a compound having the formula:

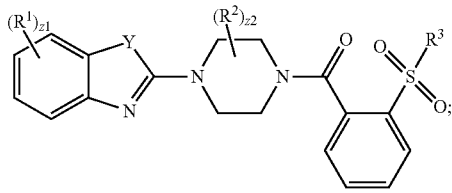

wherein
R$^1$ is independently
halogen, —CX$^{13}$, —CHX$^{12}$, —OCH$_2$X$^1$, —CN, —OH, —NH$_2$, —COOH, —CONH$_2$, —NO$_2$, —SH, —SO$_3$H, —SO$_4$H, —SO$_2$NH$_2$, —NNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{13}$, —OCHX$^{12}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is independently
halogen, —CX$^{23}$, —CHX$^{22}$, —OCH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{23}$, —OCHX$^{22}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is independently halogen, $-CX^3{}_3$, $-CHX^3{}_2$, $-OCH_2X^3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^3{}_3$, $-OCHX^3{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Y is S or O;

$X^1$, $X^2$, and $X^3$ are independently $-F$, $-Cl$, $-Br$, or $-I$; and z1 is independently an integer from 0 to 4;

z2 is independently an integer from 0 to 8.

Embodiment 28

The method of Embodiment 26 or 27, wherein $R^1$ is independently halogen, $-CF_3$, $-CCl_3$, $-CI_3$, $-CBr_3$, $-CHF_2$, $-CHCl_2$, $-CHI_2$, $-CHBr_2$, $-OCH_2F$, $-OCH_2Cl$, $-OCH_2I$, $-OCH_2Br$, $-OCHF_2$, $-CHCl_2$, $-OCHI_2$, $-OCHBr_2$, $-OCF_3$, $-OCCl_3$, $-OCI_3$, $-OCBr_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; $R^2$ is independently halogen, $-CF_3$, $-CCl_3$, $-CI_3$, $-CBr_3$, $-CHF_2$, $-CHCl_2$, $-CHI_2$, $-CHBr_2$, $-OCH_2F$, $-OCH_2Cl$, $-OCH_2I$, $-OCH_2Br$, $-OCHF_2$, $-CHCl_2$, $-OCHI_2$, $-OCHBr_2$, $-OCF_3$, $-OCCl_3$, $-OCI_3$, $-OCBr_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl; $R^3$ is independently halogen, $-CF_3$, $-CCl_3$, $-CI_3$, $-CBr_3$, $-CHF_2$, $-CHCl_2$, $-CHI_2$, $-CHBr_2$, $-OCH_2F$, $-OCH_2Cl$, $-OCH_2I$, $-OCH_2Br$, $-OCHF_2$, $-CHCl_2$, $-OCHI_2$, $-OCHBr_2$, $-OCF_3$, $-OCCl_3$, $-OCI_3$, $-OCBr_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

Embodiment 29

The method of any one of Embodiments 26 to 28, wherein the compound has the formula:

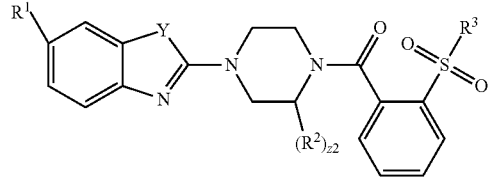

where z2 is 0-2.

Embodiment 30

The method of any one of Embodiments 26 to 28, wherein the compound has the formula:

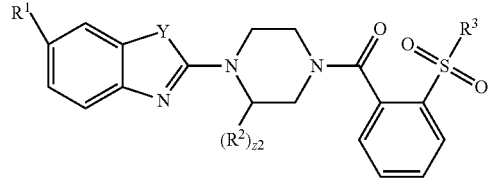

where z2 is 0-2.

Embodiment 31

The method of any one of Embodiments 26 to 28, wherein the compound has the formula:

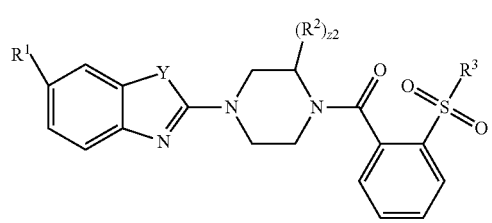

where z2 is 0-2.

Embodiment 32

The method of any one of Embodiments 26 to 28, wherein z1 is 1.

Embodiment 33

The method of any one of Embodiments 26 to 32, wherein $R^1$ is halogen.

Embodiment 34

The method of any one of Embodiments 26 to 33, wherein $R^1$ is $-F$.

Embodiment 35

The method of any one of Embodiments 26 to 34, wherein Y is S.

Embodiment 36

The method of any one of Embodiments 26 to 34, wherein Y is O.

Embodiment 37

The method of any one of Embodiments 26 to 31, wherein z2 is from 1 to 2.

Embodiment 38

The method of any one of Embodiments 26 to 371, wherein z2 is 2.

Embodiment 39

The method of any one of Embodiments 26 to 38, wherein $R^2$ is substituted or unsubstituted alkyl or substituted or unsubstituted heteroalkyl.

Embodiment 40

The method of any one of Embodiments 26 to 39, wherein $R^2$ is substituted or unsubstituted $C_1$-$C_8$ alkyl or substituted or unsubstituted 2 to 8 membered heteroalkyl.

Embodiment 41

The method of any one of Embodiments 26 to 39, wherein $R^2$ is substituted or unsubstituted $C_1$-$C_4$ alkyl.

Embodiment 42

The method of any one of Embodiments 26 to 39, wherein $R^2$ is unsubstituted $C_1$-$C_4$ alkyl.

Embodiment 43

The method of any one of Embodiments 26 to 39, wherein $R^2$ is unsubstituted methylene.

Embodiment 44

The method of any one of Embodiments 26 to 43, wherein $R^3$ is substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

Embodiment 45

The method of any one of Embodiments 26 to 43, wherein $R^3$ is substituted or unsubstituted $C_1$-$C_8$ alkyl.

Embodiment 46

The method of any one of Embodiments 26 to 43, wherein $R^3$ is substituted or unsubstituted $C_1$-$C_4$ alkyl.

Embodiment 47

The method of any one of Embodiments 26 to 43, wherein $R^3$ is substituted or unsubstituted $C_3$-$C_8$ cycloalkyl, substituted or unsubstituted 3 to 6 membered heterocycloalkyl, substituted or unsubstituted phenyl, or substituted or unsubstituted 5 to 6 membered heteroaryl.

Embodiment 48

The method of any one of Embodiments 26 to 43, wherein $R^3$ is substituted or unsubstituted $C_3$-$C_8$ cycloalkyl, or substituted or unsubstituted 3 to 6 membered heterocycloalkyl.

Embodiment 49

The method of any one of Embodiments 26 to 43, wherein $R^3$ is substituted or unsubstituted $C_3$-$C_8$ cycloalkyl.

Embodiment 50

The method of Embodiments 26 or 27, wherein the compound has the formula:

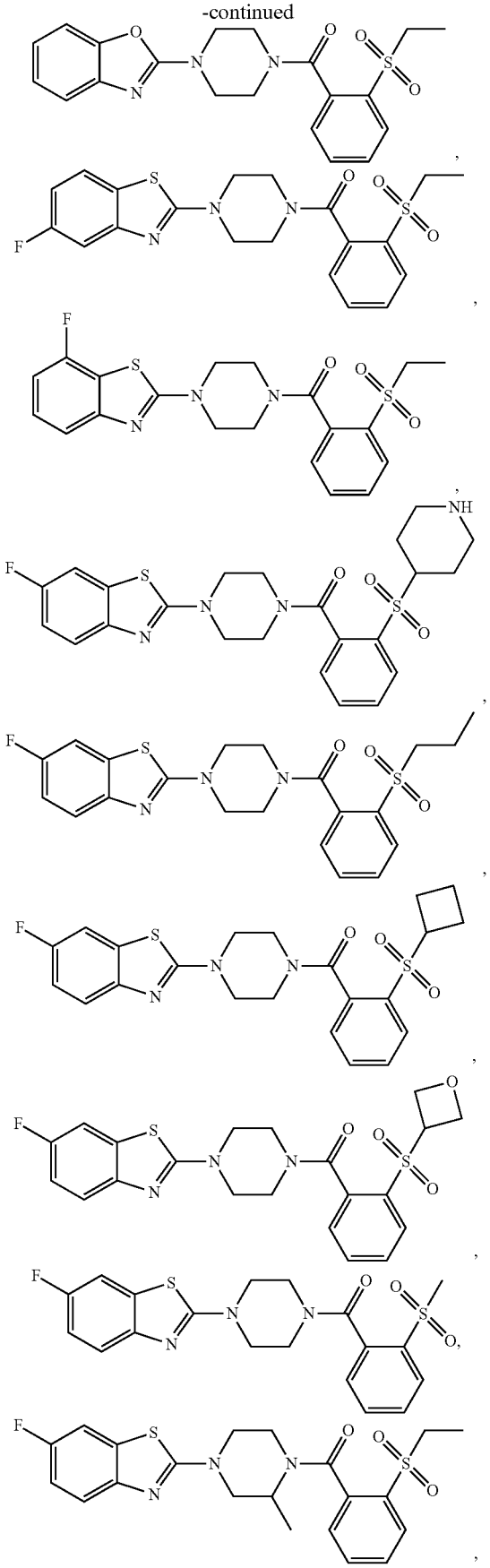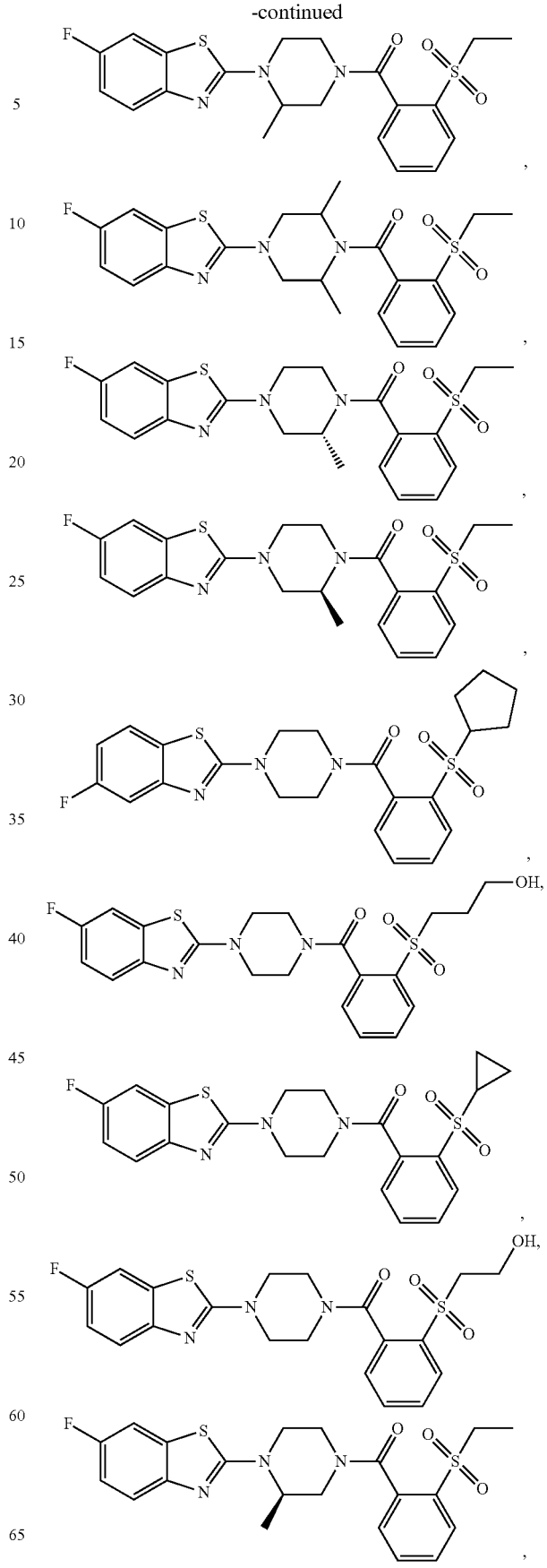

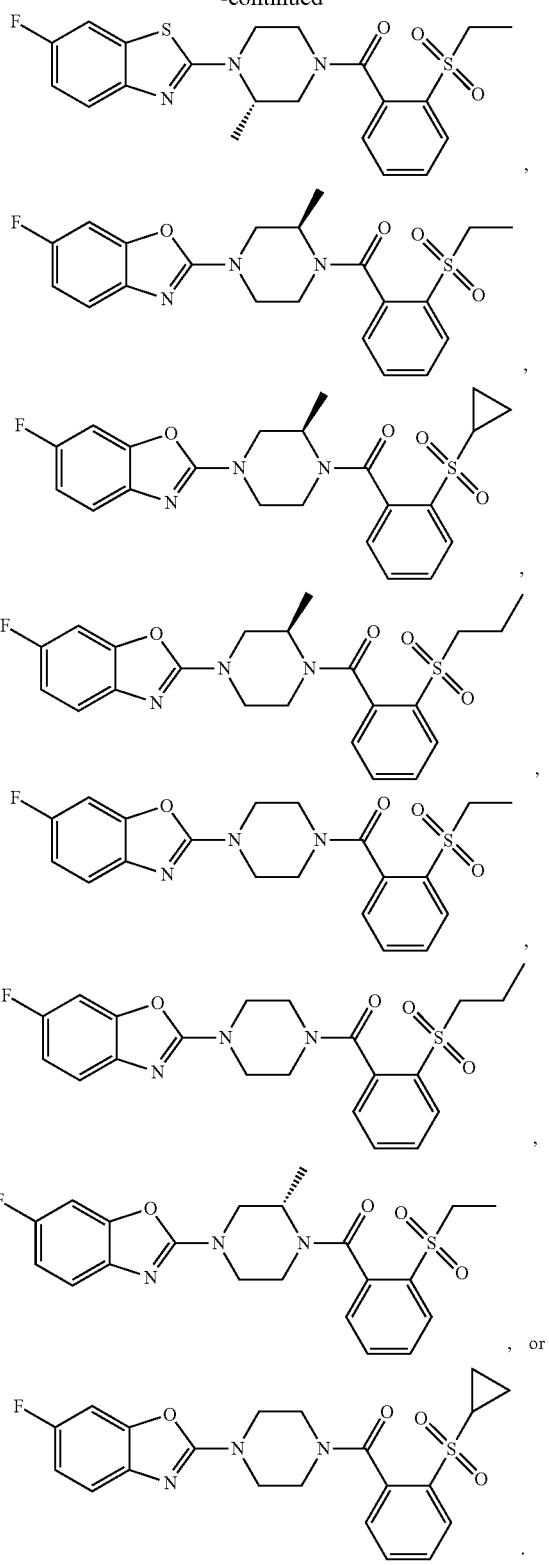

Embodiment 51

The method of Embodiment 26, wherein the compound is reversibly contacting the N-acylethanolamine acid amidase.

Embodiment 52

The method of Embodiment 27, wherein the pathological state is pain.

Embodiment 53

The method of Embodiment 27, wherein the pathological state is an inflammatory condition.

Embodiment 54

The method of Embodiment 27, wherein the pathological state is a neurodegenerative disorder.

Embodiment 55

The method of Embodiment 27, wherein the pathological state is a corneal neovascularization, diabetic retinopathy, dry macular degeneration, migraine, neuropathic pain, neuropathy, glossopharyngeal neuralgia, occipital neuralgia, pain, postherpetic neuralgia, retinopathy of prematurity, sinus headache, trigeminal neuralgia, or wet macular degeneration.

Embodiment 56

The method of Embodiment 52, wherein the pain is neuropathic pain, nociceptive pain, chronic pain, neuropathy glossopharyngeal neuralgia, occipital neuralgia, postherpetic neuralgia, trigeminal neuralgia, post herpetic neuralgia, trigeminal neuralgia, causalgia, diabetic neuropathy, complex regional pain syndrome (CRPS), neurogenic pain, peripheral pain, polyneuropathic pain, toxic neuropathy, chronic neuropathy or pruritus.

Embodiment 57

The method of Embodiment 53, wherein the inflammatory condition is acute inflammation, acute respiratory distress syndrome, adult respiratory disease, arthritis, asthma, atherosclerosis, carpal tunnel syndrome, chronic bronchitis, chronic inflammation, chronic obstructive pulmonary disease (COPD), colitis, crystal induced arthritis, cystic fibrosis, dermatitis, dyslipidemia, emphysema, fibromyalgia, gall bladder disease, gingivitis, hyperoxia-induced inflammation, irritable bowel syndrome, inflammatory bowel disease, lupus, myofasciitis, nephritis, ocular inflammation, osteoarthritis, periodontitis, polymyositis, sarcoidosis, restenosis, rheumatoid arthritis, ulcerative colitis, vasculitis.

Embodiment 58

The method of Embodiment 54, wherein the neurodegenerative disorder is multiple sclerosis, Alzheimer's dementia, Parkinson's disease, Huntington's disease, or Amytrophic lateral Sclerosis.

Embodiment 59

The method of any one of Embodiments 54 or 58, wherein the neurodegenerative disorder is multiple sclerosis.

Embodiment 60

The method of Embodiments 54 or 58, wherein the neurodegenerative disorder is Parkinson's disease.

Embodiment 61

The method of any one of Embodiments 27 to 60, the method comprising orally administering to a subject in need thereof an effective amount of a compound of any one of Embodiments 1-24.

REFERENCES

[1] a) K. Tsuboi, Y. X. Sun, Y. Okamoto, N. Araki, T. Tonai, N. Ueda, *J Biol Chem* 2005, 280, 11082-11092; b) K. Tsuboi, N. Takezaki, N. Ueda, *Chem Biodivers* 2007, 4, 1914-1925; c) N. Ueda, K. Tsuboi, T. Uyama, *Prog Lipid Res* 2010, 49, 299-315. [2] S. Pontis, A. Ribeiro, O. Sasso, D. Piomelli, *Crit Rev Biochem Mol Biol* 2016, 51, 7-14. [3] D. Piomelli, O. Sasso, *Nat Neurosci* 2014, 17, 164-174. [4] T. Bandiera, S. Ponzano, D. Piomelli, *Pharmacol Res* 2014, 86, 11-17. [5] a) A. Armirotti, E. Romeo, S. Ponzano, L. Mengatto, M. Dionisi, C. Karacsonyi, F. Bertozzi, G. Garau, G. Tarozzo, A. Reggiani, T. Bandiera, G. Tarzia, M. Mor, D. Piomelli, *ACS Med Chem Lett* 2012, 3, 422-426; b) A. Ribeiro, S. Pontis, L. Mengatto, A. Armirotti, V. Chiurchiu, V. Capurro, A. Fiasella, A. Nuzzi, E. Romeo, G. Moreno-Sanz, M. Maccarrone, A. Reggiani, G. Tarzia, M. Mor, F. Bertozzi, T. Bandiera, D. Piomelli, *ACS Chem Biol* 2015, 10, 1838-1846. [6] S. Ponzano, F. Bertozzi, L. Mengatto, M. Dionisi, A. Armirotti, E. Romeo, A. Berteotti, C. Fiorelli, G. Tarozzo, A. Reggiani, A. Duranti, G. Tarzia, M. Mor, A. Cavalli, D. Piomelli, T. Bandiera, *J Med Chem* 2013, 56, 6917-6934. [7] I. Karlsson, K. Samuelsson, D. J. Ponting, M. Tornqvist, L. L. Ilag, U. Nilsson, *Sci Rep* 2016, 6, 21203. L. Jean-Gilles, S. Feng, C. R. Tench, V. Chapman, D. A. Kendall, D. A. Barrett, C. S. Constantinescu, *J Neurol Sci* 2009, 287, 212-215. [9] E. Romeo, S. Ponzano, A. Armirotti, M. Summa, F. Bertozzi, G. Garau, T. Bandiera, D. Piomelli, *ACS Chem Biol* 2015, 10, 2057-2064. [10] K. Ahn, M. K. McKinney, B. F. Cravatt, *Chem Rev* 2008, 108, 1687-1707. [11] J. L. Blankman, G. M. Simon, B. F. Cravatt, *Chem Biol* 2007, 14, 1347-1356. [12] M. Di Filippo, L. A. Pini, G. P. Pelliccioli, P. Calabresi, P. Sarchielli, *J Neurol Neurosurg Psychiatry* 2008, 79, 1224-1229. [13] D. Baker, G. Pryce, J. L. Croxford, P. Brown, R. G. Pertwee, A. Makriyannis, A. Khanolkar, L. Layward, F. Fezza, T. Bisogno, V. Di Marzo, *FASEB J* 2001, 15, 300-302. [14] H. Lassmann, Glia 2014, 62, 1816-1830.

What is claimed is:

1. A compound having the formula:

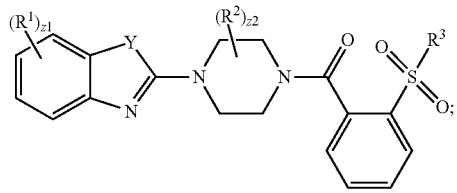

wherein

R$^1$ is independently halogen, —CF$_3$, —CCl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is independently halogen, —CF$_3$, —CCl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is independently halogen, —CF$_3$, —CCl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Y is S or O;
z1 is independently an integer from 0 to 4;
z2 is independently an integer from 0 to 8; and
wherein the compound does not have the formula:

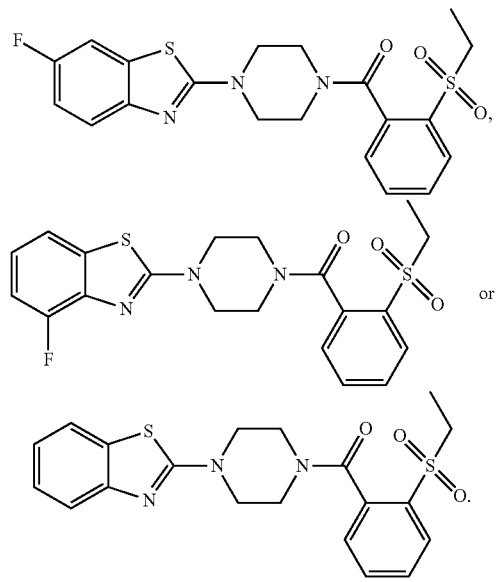

2. The compound of claim 1, wherein

R$^1$ is independently halogen, —CF$_3$, —CCl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl;

R$^2$ is independently halogen, —CF$_3$, —Cl$_3$, —CCl$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl;

R$^3$ is independently halogen, —CF$_3$, —CCl$_3$, —CI$_3$, —CBr$_3$, —CHF$_2$, —CHCl$_2$, —CHI$_2$, —CHBr$_2$, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl.

3. The compound of claim 1, wherein the compound has the formula:

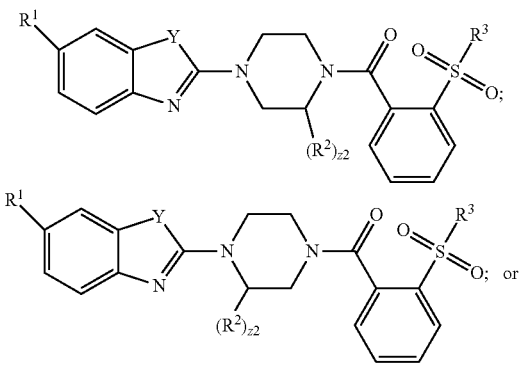

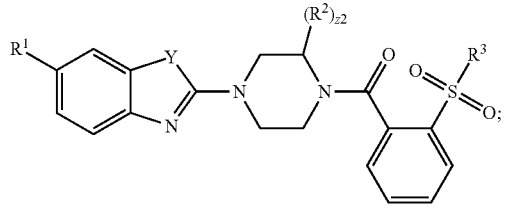

wherein z2 is 0, 1, or 2.

4. The compound of claim 1, wherein R$^1$ is a halogen.

5. The compound of claim 1, wherein R$^2$ is substituted or unsubstituted C$_1$-C$_8$ alkyl or substituted or unsubstituted 2 to 8 membered heteroalkyl.

6. The compound of claim 1, wherein R$^2$ is substituted or unsubstituted C$_1$-C$_4$ alkyl.

7. The compound of claim 1, wherein R$^2$ is unsubstituted methylene.

8. The compound of claim 1, wherein R$^3$ is substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl.

9. The compound of claim 1, wherein R$^3$ is substituted or unsubstituted C$_1$-C$_4$ alkyl.

10. The compound of claim 1, wherein R$^3$ is substituted or unsubstituted C$_3$-C$_8$ cycloalkyl, substituted or unsubstituted 3 to 6 membered heterocycloalkyl, substituted or unsubstituted phenyl, or substituted or unsubstituted 5 to 6 membered heteroaryl.

11. The compound of claim 1, wherein R$^3$ is substituted or unsubstituted C$_3$-C$_8$ cycloalkyl, or substituted or unsubstituted 3 to 6 membered heterocycloalkyl.

12. The compound of claim 1, wherein the compound has the formula:

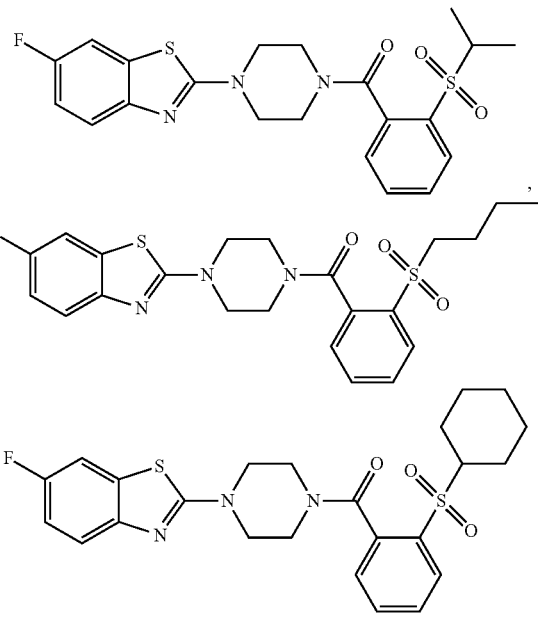

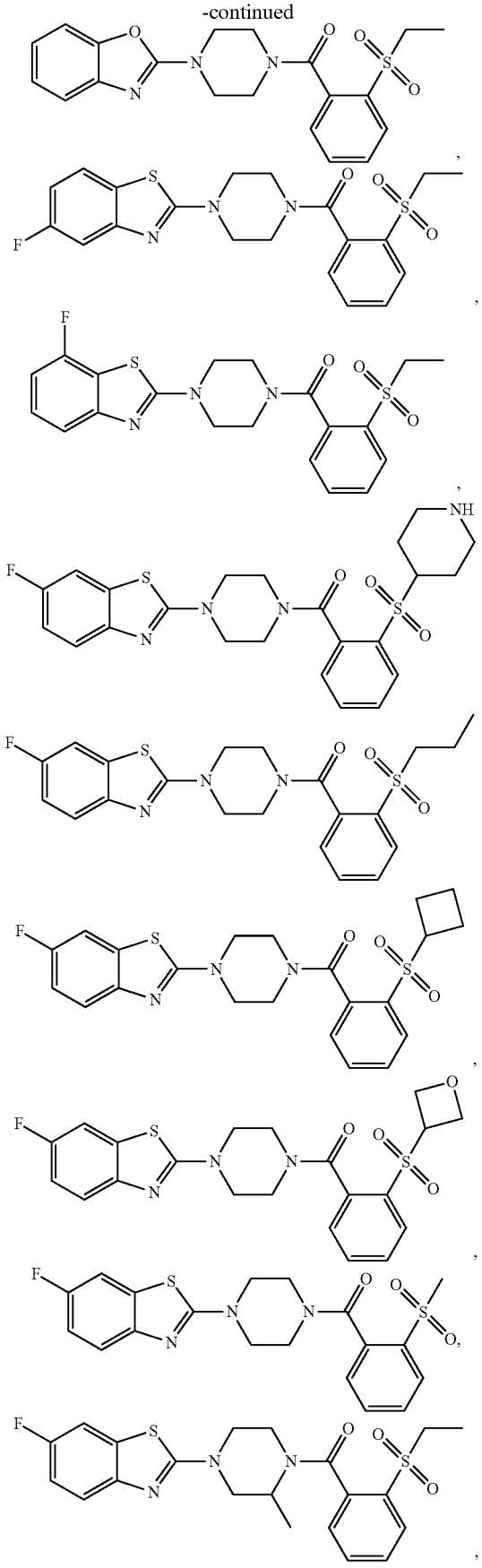
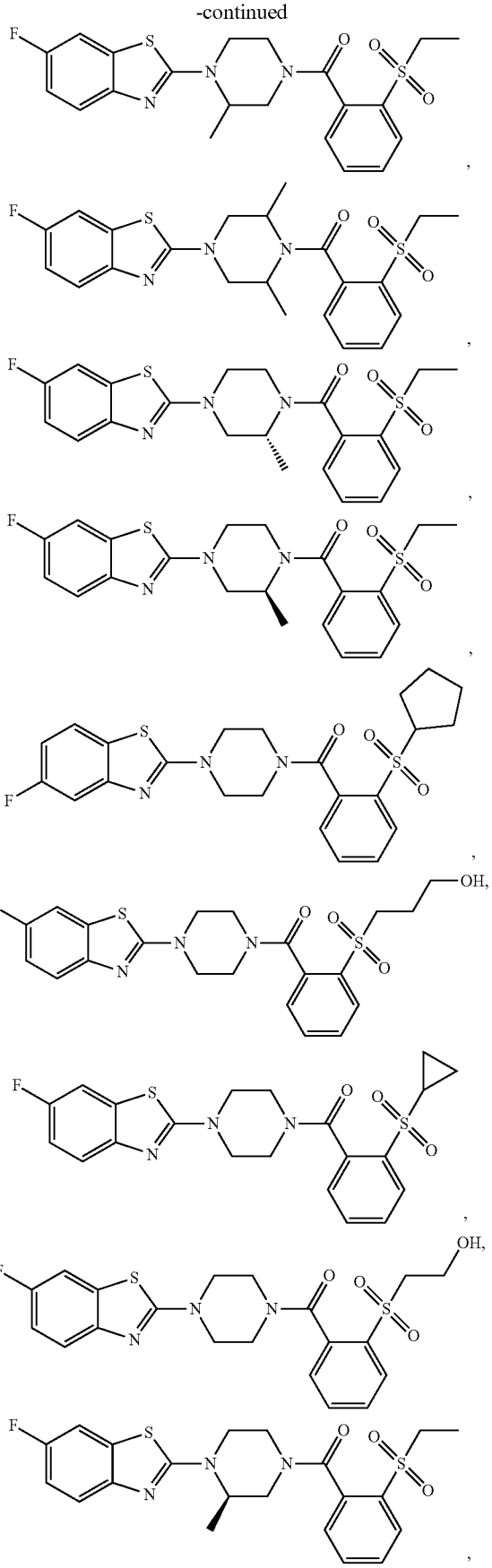

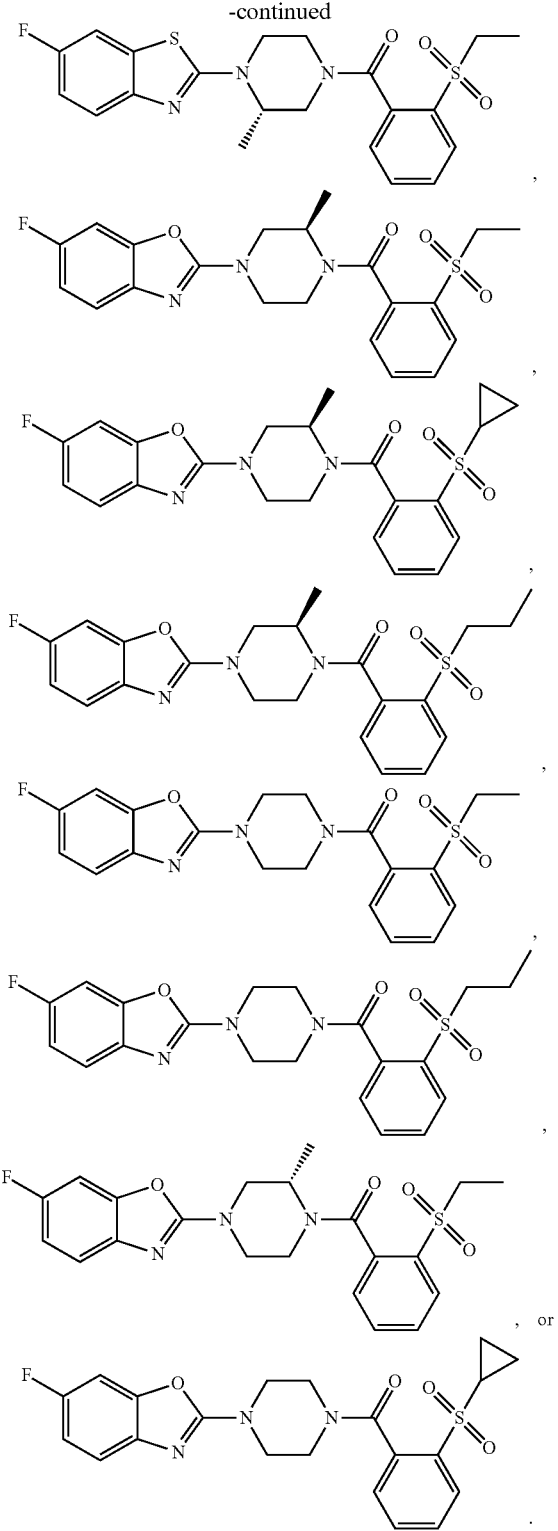

13. A pharmaceutical composition comprising the compound of claim 1 and a pharmaceutically acceptable excipient.

14. A method of inhibiting N-acylethanolamine acid amidase in a subject in need thereof, said method comprising administering to the subject an effective amount of the compound of claim 1, thereby inhibiting N-acylethanolamine acid amidase in the subject.

15. A method of treating a pathological state in a subject in need thereof, said method comprising administering to the subject an effective amount of the compound of claim 1; wherein the pathological state is corneal neovascularization, diabetic retinopathy, dry macular degeneration, migraine, pain, retinopathy of prematurity, sinus headache, or wet macular degeneration.

16. A method of treating pain in a subject in need thereof, the method comprising administering to the subject an effective amount of the compound of claim 1; wherein said pain is neuropathic pain, nociceptive pain, chronic pain, neuropathy, glossopharyngeal neuralgia, occipital neuralgia, postherpetic neuralgia, trigeminal neuralgia, post herpetic neuralgia, trigeminal neuralgia, causalgia, diabetic neuropathy, complex regional pain syndrome, neurogenic pain, peripheral pain, polyneuropathic pain, toxic neuropathy, chronic neuropathy, or pruritus.

17. A method of treating an inflammatory condition in a subject in need thereof, the method comprising administering to the subject an effective amount of the compound of claim 1; wherein the inflammatory condition is acute inflammation, acute respiratory distress syndrome, adult respiratory disease, arthritis, asthma, atherosclerosis, carpal tunnel syndrome, chronic bronchitis, chronic inflammation, chronic obstructive pulmonary disease, colitis, crystal induced arthritis, cystic fibrosis, dermatitis, dyslipidemia, emphysema, fibromyalgia, gall bladder disease, gingivitis, hyperoxia-induced inflammation, irritable bowel syndrome, inflammatory bowel disease, lupus, myofasciitis, nephritis, ocular inflammation, osteoarthritis, periodontitis, polymyositis, sarcoidosis, restenosis, rheumatoid arthritis, ulcerative colitis, or vasculitis.

18. A method of treating a neurodegenerative disorder in a subject in need thereof, the method comprising administering to the subject an effective amount of the compound of claim 1; wherein the neurodegenerative disorder is multiple sclerosis, Alzheimer's dementia, Parkinson's disease, Huntington's disease, or amyotrophic lateral sclerosis.

* * * * *